US006972323B1

(12) United States Patent
Serizawa et al.

(10) Patent No.: US 6,972,323 B1
(45) Date of Patent: Dec. 6, 2005

(54) ANTI-FAS ANTIBODIES

(75) Inventors: Nobufusa Serizawa, Yokohama (JP); Kimihisa Ichikawa, Yokohama (JP); Jun Ohsumi, Kawasaki (JP); Masahiko Ohtsuki, Yokohama (JP); Hideyuki Haruyama, Kawagoe (JP); Tohru Takahashi, Tokyo (JP); Hiroko Yoshida, Tokyo (JP); Akio Shiraishi, Tokyo (JP); Shin Yonehara, Kyoto (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/499,662

(22) Filed: Feb. 9, 2000

Related U.S. Application Data

(63) Continuation-in-part of application No. 09/408,646, filed on Sep. 30, 1999, now abandoned, and a continuation-in-part of application No. 09/053,583, filed on Apr. 1, 1998, now abandoned.

(30) Foreign Application Priority Data

| Apr. 1, 1997 | (JP) | ............................................. | 9-82953 |
| Jun. 25, 1997 | (JP) | ............................................. | 9-169088 |
| Oct. 8, 1997 | (JP) | ............................................. | 9-276064 |
| Sep. 30, 1998 | (JP) | ......................................... | 10-276881 |
| Sep. 30, 1998 | (JP) | ......................................... | 10-276882 |

(51) Int. Cl.$^7$ ............................................. C07K 16/28
(52) U.S. Cl. .......................... 530/388.15; 530/388.1; 530/387.1; 530/387.3; 530/387.9
(58) Field of Search .......................... 530/387.3, 387.1, 530/387.9, 388.1, 388.2, 388.15; 435/70.1, 328, 331, 379; 424/130.1, 133.1, 134.1, 138.1, 139.1, 141.1, 142.1, 143.1

(56) References Cited

U.S. PATENT DOCUMENTS 5,620,889 A * 4/1997 Lynch et al. .............. 424/144.1

FOREIGN PATENT DOCUMENTS

| EP | 0799891 A1 | 10/1997 |
| EP | 0842948 A1 | 5/1998 |
| EP | 0909816 A1 | 4/1999 |
| EP | 0866131 A2 | 9/1999 |
| JP | 10-165178 A | 6/1998 |
| JP | 10-194989 A | 7/1998 |
| WO | WO 90/07861 | 7/1990 |
| WO | WO 95/10540 | 4/1995 |
| WO | WO 95/18819 | 7/1995 |
| WO | WO-9620206 | * 7/1996 |
| WO | WO 96/40041 | 12/1996 |
| WO | WO 97/18307 | 5/1997 |

OTHER PUBLICATIONS

Hartwig et., Blood vol. 99, pp. 3041–3049.*
Freshney (Culture of Animal Cells, A Manual of Basic Technique, Alan R. Liss, Inc., 1983, New York, p. 4).*
Green et al (May 1994, Nature Genetics, vol. 7, pp. 13–21.*
Watanabe–Fukunaga et al (Feb. 15, 1992, The Journal of Immunology, vol. 148, p. 1274–1279).*
Forre et al (2000, Scand J Rheumatol vol. 29, pp. 73–84).*
T. Sumida et al, "3. Rheumatoid Arthritis and Apoptosis", *Internal Medicine,* vol. 37, No. 2, pp. 184–188 (Feb. 1998).
K. Fujisawa et al, "Therapeutic Effect of the Anti–Fas Antibody on Arthritis in HTLV–I tax Transgenic Mice", *J. Clin. Invest.,* vol. 98, No. 2, pp. 271–278 (Jul. 1996).
Y. Nishimura–Morita et al, "Amelioration of Systemic Autoimmune Disease by the Stimulation of Apoptosis–promoting Receptor Fas with Anti–Fas mAb", *International Immunology,* vol. 9, No. 12, pp. 1793–1799 (1997).
U.S. Appl. No. 10/785,806, filed Feb. 24, 2004.
U.S. Department of Health and Human Services, Public Health Service, National Institutes of Health, "Sequences of Proteins of Immunological Interest", vol. 1, Fifth Edition (1991), 118, 310.
Eiji Mita, Norio Hayashi, Sadaharu Iio, Tetsuo Takehara, Taizo Hijioka, Akinori Kasahara, Hideyuki Fusamoto and Takenobu Kamada, "Role of Fas Ligand in Apoptosis Induced by Hepatitis C Virus Infection", *Biochemical and Biophysical Research Communications,* 204, 468–474 (1994).
Toshihiro Nakajima, Hiroyuki Aono, Tomoko Hasunuma, Kazuhiko Yamamoto, Toshikazu Shirai, Kazushi Hirohata and Kusuki Nishioka, "Apoptosis and Functional Fas Antigen in Rheumatoid Arthritis Synoviocytes", *Arthritis & Rheumatism,* 38, 485–491 (1995).
Naoki Hiramatsu, Norio Hayashi, Kazuhiro Katayama, Kiyoshi Mochizuki, Yuko Kawanishi, Akinori Kashara, Hideyuki Fusamoto and Takenobu Kamada, "Immunohistochemical Detection of Fas Antigen in Liver Tissue of Patients with Chronic Hepatitis C", *Hepatology,* 19, 1354–1359 (1994).
Jeffrey M. Isner, Marianne Kearney, Scott Bortman, Jonathan Passeri, "Apoptosis in Human Atherosclerosis and Restenosis", *Circulation, 91,* 2703–2711 (1995).
Shin Yonehara, Ai Ishii, and Minako Yonehara, "A Cell–Killing Monoclonal Antibody (ANTI–Fas) To a Cell Surface Antigen Co–Downregulated with the Receptor of Tumor Necrosis Factor", *J. Exp. Med, 169,* 1747–1756 (1989).

(Continued)

*Primary Examiner*—Larry R. Helms
*Assistant Examiner*—Misook Yu
(74) *Attorney, Agent, or Firm*—Frishauf, Holtz, Goodman & Chick, P.C.

(57) ABSTRACT

Anti-Fas antibodies which are cross-reactive with mouse and human Fas and are useful in the treatment of conditions attributable to abnormalities in the Fas/Fas ligand system.

36 Claims, 69 Drawing Sheets

OTHER PUBLICATIONS

F. Rieux–Laucat, F. Le Deist, C. Hivroz, I.A.G. Roberts, K.M. Debatin, A. Fischer, J.P. de Villartay, "Mutations in Fas Associated with Human Lymphoproliferative Syndrome and Autoimmunity", *Science*, 268, 1347–1349 (1995).

Bruce Richardson, Narendra Lalwani, Kent Johnson and Rory Marks, "Fas Ligation Triggers Apoptosis in Macrophages But Not Endothelial Cells", *Eur. J. Immunol.*, 24, 2640–2645 (1994).

Akira Shimizu, Hiroshi Kitamura, Yukinari Masuda, Masamichi Ishizaki, Yuichi Sugisaki, and Nobuaki Yamanaka, "Apoptosis in the Repair Process of Experimental Proliferative Glomerulonephritis", *Kidney International*, 47, 114–121 (1995).

Jaroslaw Maciejewski, Carmine Selleri, Tadatsugu Sato, Stacie Anderson and Neal Young, "Increased Expression of Fas Antigen on Bone Marrow $CD34^+$ Cells of Patients with Aplastic Anaemia", *British Journal of Haematology*, 91, 245–252 (1995).

Tsukasa Takemura, Katsumi Murakami, Hirofumi Miyazato, Kazuro Yagi, and Kazuo Yoshioka, "Expression of Fas antigen and Bcl–2 in Human Glomerulonephritis", *Kidney International*, 48, 1886–1892 (1995).

Hitoshi Sugiyama, Naoki Kashihara, Hirofumi Makino, Yasushi Yamasaki and Zensuke OTA, "Apoptosis in Glomerular Sclerosis", *Kidney International*, 49, 103–111 (1996).

Jun Ogasawara, Rie Watanabe–Fukunaga, Masashi Adachi, Akio Matsuzawa, Tsutomu Kasugai, Yukihiko Kitamura, Naoto Itoh, Takashi Suda, and Shigekazu Nagata, "Lethal Effect of the Anti–Fas Antibody in Mice", *Nature*, 364, 806–809 (1993).

Laurie Owen–Schaub, Shin Yonehara, William Crump III, and Elizabeth Grimm, "DNA Fragmentation and Cell Death is Selectively Triggered in Activated Human Lymphocytes by Fas Antigen Engagement", *Cellular Immunology*, 140, 197–205 (1992).

Amanda Baker, Andrew Mooney, Jeremy Hughes, Donna Lombardi, Richard Johnson and John Savill, "Mesangial Cell Apoptosis: The Major Mechanism for Resolution of Glomerular Hypercellularity in Experimental Mesangial Proliferative Nephritis", *J. Clin. Invest*, 94, 2105–2116 (1994).

Peter Galle, Walter Hofmann, Hennign Walczak, Heinz Schaller, Gerd Otto, Wolfgang Stremmel, Peter Krammer and Laura Runkel, "Involvement of the CD95 (APO–1/Fas) Receptor and Ligand in Liver Damage", *J. Exp. Med.*, 182, 1223–1230 (1995).

Toru Kondo, Takashi Suda, Hidehiro Fukuyama, Masashi Adachi and Shigekazu Nagata, "Essential Roles of the Fas Ligand in the Development of Hepatitis", *Nature Medicine*, 3, 409–413 (1997).

Andreas Strasser, "Death of a T cell", *Nature*, 373, 385–386 (1995).

Galen Fisher, Fredric Rosenberg, Stephen Straus, Janet Dale, Lindsay Middelton, Albert Lin, Warren Strober, Michael Lenardo, Jennifer Puck, "Dominant Interfering Fas Gene Mutations Impair Apoptosis in a Human Autoimmune Lymphoproliferative Syndrome", *Cell*, 81, 935–946 (1995).

Jia Li Chu, Paula Ramos, Adam Rosendorff, Jako Nikolic-Zugic, Elizabeth Lacy, Akio Matsuzawa and Keith Elkon, "Massive Upregulation of the Fas Ligand in lpr and gld Mice: Implications for Fas Regulation and the Graft–versus–Host Disease–like Wasting Syndrome", *J. Exp. Med.*, 181, 393–398 (1995).

Shogo Tsuyuki, Claude Bertrand, Francois Erard, Alexandre Trifilieff, Junko Tsuyuki, Martin Wesp, Gary Anderson and Anthony Coyle, "Activation of the Fas Receptor on Lung Eosinophils Leads to Apoptosis and the Resolution of Eosinophilic Inflammation of the Airways", *J. Clin. Invest.*, 96, 2924–2931 (1995).

Michael Sneller, Stephen Straus, Elaine Jaffe, Jonathan Jaffe, Thomas Fleisher, Maryalice Stetler–Stevenson and Warren Strober, "A Novel Lymphoproliferative/Autoimmune Syndrome Resembling Murine lpr/gld Disease", *J. Clin. Invest*, 90, 334–341 (1992).

Tran Thi Minh Hoa, Tomoko Hasunuma, Hiroyuki Aono, Kayo Masuko, Tetsuji Kobata, Kazuhiko Yamamoto, Takayuki Sumida and Kusuki Nishioka, "Novel Mechanisms of Selective Apoptosis in Synovial T Cells of Patients with Rheumatoid Arthritis", *The Journal of Rheumatology*, 23, 1332–1337 (1996).

J.F.R. Kerr, A.H. Wyllie and A.R. Currie, "Apoptosis: A Basic Biological Phenomenon with Wide–Ranging Implications in Tissue Kinetics", *Br. J. Cancer*, 26, 239–257 (1972).

R.H.J. Begent et al., "Phase I/II Study of Chimeric B72.3 Antibody in Radioimmunoassay of Colorectal Cancer", *Br. J. Cancer*, 62 474 and 487 (1990).

Sherie Morrison, M. Jacqueline Johnson, Leonard Herzenberg, and Vernon Oi, "Chimeric Human Antibody Molecules: Mouse Antigen–binding Domains with Human Constant Region Domains", *Proc. Natl. Acad. Sci. USA*, 81, 6851–6855 (1984).

Peter Jones, Paul Dear, Jefferson Foote, Michael Neuberger and Greg Winer, "Replacing the Complementarity–determining Regions in a Human Antibody With Those From a Mouse", *Nature*, 321, 522–525 (1986).

Robert Schroff, Kenneth Foon, Shannon Beatty, Robert Oldham and Alton Morgan, Jr., "Human Anti–Murine Immunoglobulin Responses in Patients Receiving Monoclonal Antibody Therapy", *Cancer Research*, 45, 879–885 (1985).

Thomas McCloskey, Naoki Oyaizu, Mark Kaplan, and Savita Pahwa, "Expression of the Fas Antigen in Patients Infected With Human Immunodeficiency Virus", *Cytometry*, 22, 111–114 (1995).

Cyrus Chothia and Arthur Lesk, "Canonical Structures for the Hypervariable Regions of Immunoglobulins", *J. Mol. Biol.*, 196, 901–917 (1987).

B.C. Richardson, N.D. Lalwani, K.J. Johnson and R.M. Marks, "Fas Ligation Triggers Apoptosis in Macrophages but not Endothelial Cells" *Eur. J. Immunol.*, 24, 2643–2645 (1994).

Masato Tanaka, Hiroshi Ito, Susumu Adachi, Hajime Akimoto, Toshio Nishikawa, Takeshi Kasajime, Fumiaki Marumo and Michiaki Hiroe, Hypoxia Induces Apoptosis With Enhanced Expression of Fas Antigen Messenger RNA in Cultured Neonatal Rat Cardiomyocytes, *Circulation Research*, 75, 426–433 (1994).

Mark R. Alderson, et al., "Regulation of apoptosis and T cell activation by Fas–specific mAb", *International Immunology*, 6, No. 11, 1799–1806 (Nov., 1994).

Maria Grazia Cifone, et al., "Apoptotic Signaling through CD95 (Fas/Apo–1) Activates an Acidic Sphingomyelinase", *J. Exp. Med.*, 77, 1547–1552 (Oct., 1993).

Yoshiko Nishimura, et al., "In vivo analysis of Fas antigen-mediated apoptosis: effects of agonistic anti–mouse Fas mAb on thymus, spleen and liver", *International Immunology*, 9, No. 2, 307–316 (Feb., 1997).

C. Mangurian, et al., "Expression of a Fas–like proapoptotic molecule on the lymphocytes of *Xenopus laevis*", *Immunology Letters*, 64, 31–38 (1998)

* cited by examiner .

FRL₁

```
                          1                    5                    10                   15                   20
Mouse HFE7A               Asp Ile Val Leu Thr Gln Ser Pro Ala Ser Leu Ala Val Ser Leu Gly Gln Arg Ala Thr Ile Ser Cys
Humanized HFE7A(8E10)     Asp Ile Val Leu Thr Gln Ser Pro Gly Thr Leu Ser Leu Ser Pro Gly Glu Arg Ala Thr Ile Ser Cys
Human Eu                  Asp Ile Gln Met Thr Gln Ser Pro Ser Thr Leu Ser Ala Ser Val Gly Asp Arg Val Thr Ile Thr Cys
Humanized HFE7A(LEU1)     Asp Ile Val Leu Thr Gln Ser Pro Ser Ser Leu Ser Ala Ser Val Gly Asp Arg Val Thr Ile Thr Cys
Humanized HFE7A(LEU2)     Asp Ile Val Leu Thr Gln Ser Pro Ser Ser Leu Ser Ala Ser Val Gly Asp Arg Val Thr Ile Thr Cys
Humanized HFE7A(LEU3)     Asp Ile Val Leu Thr Gln Ser Pro Ser Ser Leu Ser Ala Ser Val Gly Asp Arg Val Thr Ile Thr Cys
```

FRL₂

```
                          40                   45                   50
Mouse HFE7A               Trp Tyr Gln Gln Lys Pro Gly Gln Pro Pro Lys Leu Leu Ile Tyr
Humanized HFE7A(8E10)     Trp Tyr Gln Gln Lys Pro Gly Gln Xaa Pro Lys Leu Leu Ile Tyr       (Amino acid No. 47: Ala or Pro, No. 49: Lys or Arg)
Human Eu                  Trp Tyr Gln Gln Lys Pro Gly Lys Ala Pro Lys Leu Leu Met Tyr
Humanized HFE7A(LEU1)     Trp Tyr Gln Gln Lys Pro Gly Lys Ala Pro Lys Leu Leu Ile Tyr
Humanized HFE7A(LEU2)     Trp Tyr Gln Gln Lys Pro Gly Gln Ala Pro Lys Leu Leu Ile Tyr
Humanized HFE7A(LEU3)     Trp Tyr Gln Gln Lys Pro Gly Lys Ala Pro Lys Leu Leu Ile Tyr
```

FRL₃

```
                          65                   70                   75                   80                   85                   90
Mouse HFE7A               Gly Ile Pro Ala Arg Phe Ser Gly Ser Gly Thr Asp Phe Thr Leu Asn Ile His Pro Val Glu Glu Glu Asp Ala Ala Thr Tyr Cys
Humanized HFE7A(8E10)     Gly Ile Pro Asp Arg Phe Ser Gly Ser Gly Ser Gly Thr Asp Phe Thr Leu Thr Ile Ser Arg Leu Glu Pro Ala Asp Phe Ala Val Tyr Tyr Cys
Human Eu                  Gly Val Pro Ser Arg Phe Ile Gly Ser Gly Ser Gly Thr Glu Phe Thr Leu Thr Ile Ser Ser Leu Gln Pro Asp Asp Phe Ala Thr Tyr Tyr Cys
Humanized HFE7A(LEU1)     Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys
Humanized HFE7A(LEU2)     Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys
Humanized HFE7A(LEU3)     Gly Ile Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys
```

FRL₄

```
                          105                  110
Mouse HFE7A               Phe Gly Gly Gly Thr Lys Leu Glu Ile Lys Arg Ala
Humanized HFE7A(8E10)     Phe Gly Gln Gly Thr Arg Leu Glu Ile Lys Arg Thr
Human Eu                  Phe Gly Gln Gly Thr Lys Val Glu Val Lys Gly Thr
Humanized HFE7A(LEU1)     Phe Gly Gln Gly Thr Lys Val Glu Ile Lys Arg Thr
Humanized HFE7A(LEU2)     Phe Gly Gln Gly Thr Lys Val Glu Ile Lys Arg Thr
Humanized HFE7A(LEU3)     Phe Gly Gln Gly Thr Lys Val Glu Ile Lys Arg Thr
```

Fig. 48

FRH₁

```
                            1                   5                  10                  15                  20                  25                  30
Mouse HFE7A                Gln Val Gln Leu Gln Gln Pro Gly Ala Glu Leu Val Lys Pro Gly Ala Ser Val Lys Leu Ser Cys Lys Ala Ser Gly Tyr Thr Phe Thr
Humanized HFE7A(8E10)      Gln Val Gln Leu Val Gln Ser Gly Ala Glu Val Lys Lys Pro Gly Ala Ser Val Lys Val Ser Cys Lys Ala Ser Gly Tyr Thr Phe Thr
Human Eu                   Glu Val Gln Leu Val Gln Ser Gly Ala Glu Val Lys Lys Pro Gly Ser Ser Val Lys Val Ser Cys Lys Ala Ser Gly Gly Thr Phe Ser
Humanized HFE7A(HEU1)      Gln Val Gln Leu Val Gln Ser Gly Ala Glu Val Lys Lys Pro Gly Ala Ser Val Lys Val Ser Cys Lys Ala Ser Gly Tyr Thr Phe Thr
Humanized HFE7A(HEU2)      Gln Val Gln Leu Val Gln Ser Gly Ala Glu Val Lys Lys Pro Gly Ala Ser Val Lys Val Ser Cys Lys Ala Ser Gly Tyr Thr Phe Thr
Humanized HFE7A(HEU3)      Gln Val Gln Leu Val Gln Ser Gly Ala Glu Val Lys Lys Pro Gly Ala Ser Val Lys Val Ser Cys Lys Ala Ser Gly Tyr Thr Phe Thr
```

FRH₂

```
                            40                   45
Mouse HFE7A                Trp Val Lys Gln Arg Pro Gly Gln Gly Leu Glu Trp Ile Gly
Humanized HFE7A(8E10)      Trp Val Lys Gln Ala Pro Gly Gln Arg Leu Glu Trp Met Gly
Human Eu                   Trp Val Arg Gln Ala Pro Gly Gln Gly Leu Glu Trp Met Gly
Humanized HFE7A(HEU1)      Trp Val Lys Gln Ala Pro Gly Gln Gly Leu Glu Trp Met Gly
Humanized HFE7A(HEU2)      Trp Val Lys Gln Ala Pro Gly Gln Gly Leu Glu Trp Met Gly
Humanized HFE7A(HEU3)      Trp Val Arg Gln Ala Pro Gly Gln Gly Leu Glu Trp Met Gly
```

FRH₃

```
                            70                  75                  80                  85                  90                  95
Mouse HFE7A                Lys Ala Thr Leu Thr Val Asp Thr Ser Ser Ser Thr Ala Tyr Met Gln Leu Ser Ser Leu Thr Ser Glu Asp Ser Ala Val Tyr Tyr Cys Ala Arg
Humanized HFE7A(8E10)      Lys Ala Thr Leu Thr Val Asp Thr Ser Ala Ser Thr Ala Tyr Met Glu Leu Ser Ser Leu Arg Ser Glu Asp Thr Ala Val Tyr Tyr Cys Ala Arg
Human Eu                   Arg Val Thr Ile Thr Ala Asp Glu Ser Thr Asn Thr Ala Tyr Met Glu Leu Ser Ser Leu Arg Ser Glu Asp Thr Ala Phe Tyr Phe Cys Ala Gly
Humanized HFE7A(HEU1)      Lys Ala Thr Leu Thr Val Asp Thr Ser Thr Ser Thr Ala Tyr Met Glu Leu Ser Ser Leu Arg Ser Glu Asp Thr Ala Val Tyr Tyr Cys Ala Arg
Humanized HFE7A(HEU2)      Lys Ala Thr Ile Thr Val Asp Thr Ser Thr Ser Thr Ala Tyr Met Glu Leu Ser Ser Leu Arg Ser Glu Asp Thr Ala Val Tyr Tyr Cys Ala Arg
Humanized HFE7A(HEU3)      Lys Ala Thr Ile Thr Val Asp Thr Ser Thr Ser Thr Ala Tyr Met Glu Leu Ser Ser Leu Arg Ser Glu Asp Thr Ala Val Tyr Tyr Cys Ala Arg
```

FRH₄

```
                            115                 120
Mouse HFE7A                Trp Gly Thr Gly Thr Thr Val Thr Val Ser Ser
Humanized HFE7A(8E10)      Trp Gly Gln Gly Thr Leu Val Thr Val Ser Ser
Human Eu                   Glu Tyr Asn Gly Gly Thr Leu Val Thr Val Ser Ser
Humanized HFE7A(HEU1)      Trp Gly Gln Gly Thr Leu Val Thr Val Ser Ser
Humanized HFE7A(HEU2)      Trp Gly Gln Gly Thr Leu Val Thr Val Ser Ser
Humanized HFE7A(HEU3)      Trp Gly Gln Gly Thr Leu Val Thr Val Ser Ser
```

Fig. 49

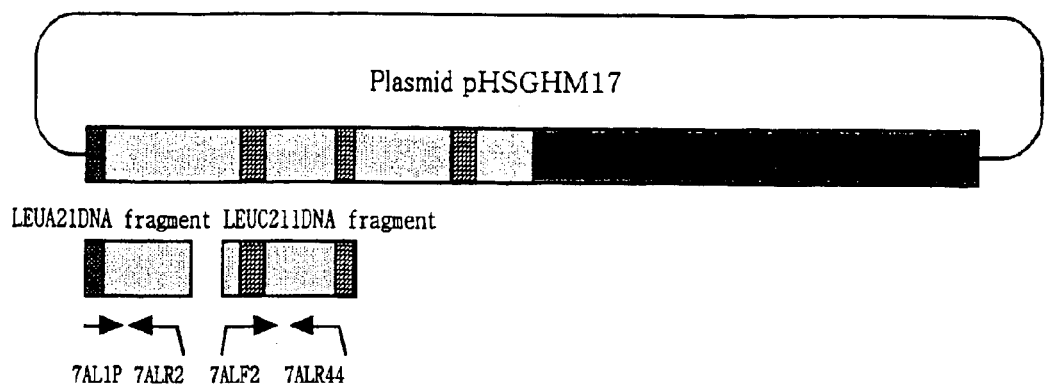
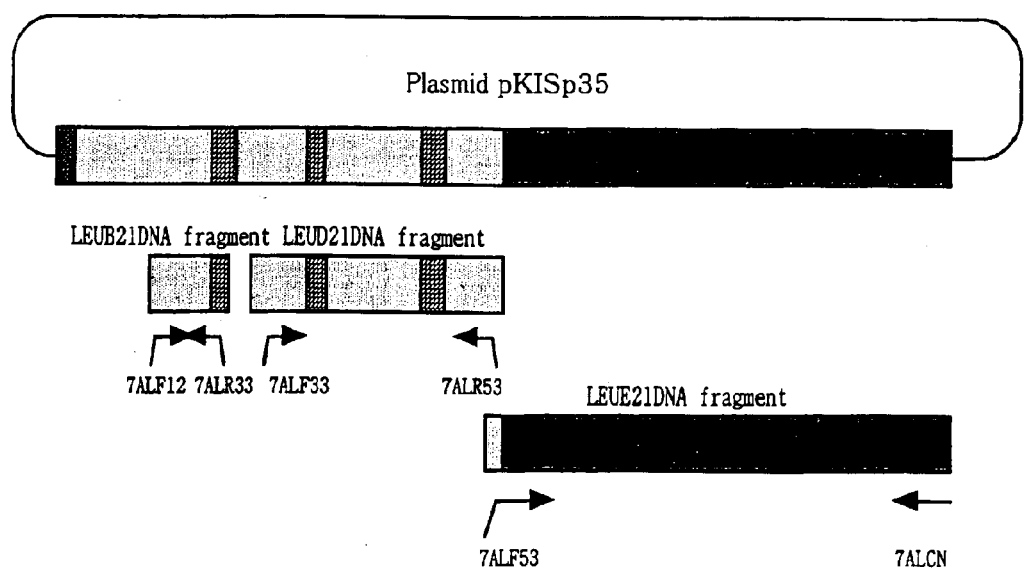
Fig. 52

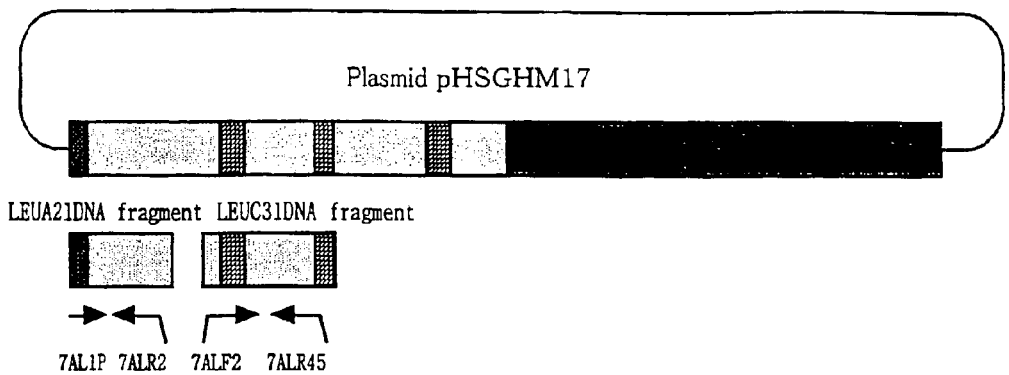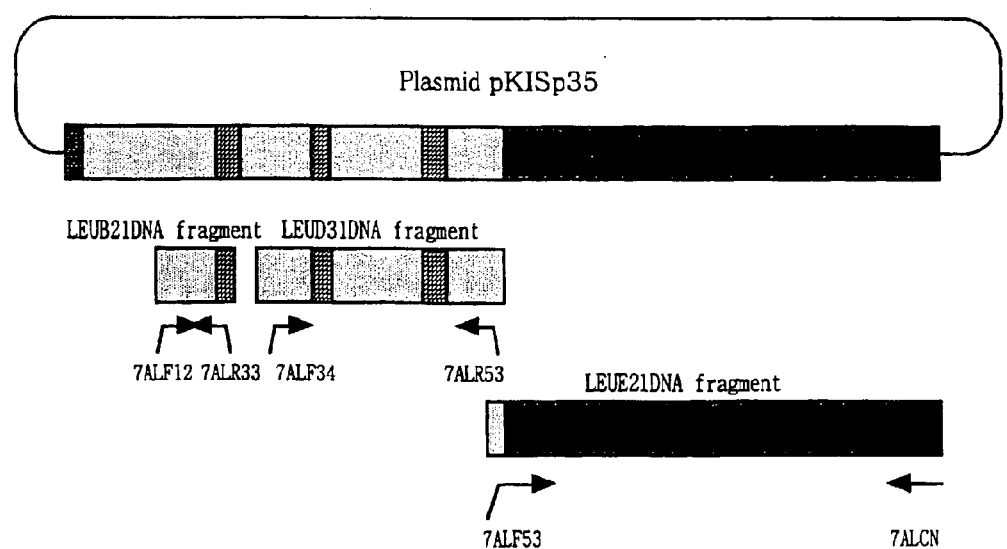
Fig. 54

ANTI-FAS ANTIBODIES

This application is a continuation-in-part application of application Ser. No. 09/053,583, filed Apr. 1, 1998 now abandoned and application Ser. No. 09/408,646, now abandoned filed Sep. 30, 1999; the entire contents of said applications are hereby incorporated by reference herein.

FIELD OF THE INVENTION

The present invention relates to antibodies and fragments thereof, especially humanized antibodies, recognizing the Fas antigen, to DNA encoding all or part of such an antibody, and to agents, comprising such antibodies, for the prophylaxis and/or treatment of conditions arising from abnormalities in the Fas/Fas ligand system.

BACKGROUND OF THE INVENTION

The physiological death of cells in a living organism in the natural course of events is known as apoptosis, and is distinguished from the pathological death of cells, i.e. necrosis [c.f. Kerr et al., (1972), Br. J. Cancer, 26, 239 et seq.]. Apoptosis is an example of programmed cell death, which is where certain cells are programmed, in advance, to die in a living organism in the natural course of events, such as when the cell in question has performed a pre-determined function. Apoptosis is characterised by such morphological changes as curved cell surface, condensed nuclear chromatin and fragmented chromosomal DNA, amongst others.

Apoptosis plays a role in the differentiation of lymphocytes (T cells and B cells) by eliminating cells that recognize an autoantigen. In this respect, it has been demonstrated that 95%, or even more, cells, such as those which react with autoantigens, are eliminated in the thymus during the maturation of T lymphocytes [c.f. Shigekazu Nagata, Tanpakushitsu Kakusan Koso, (1993), 38, 2208–2218]. When such cells are not eliminated by apoptosis, then it is believed that this is a cause of autoimmune disease, due to the presence of mature, auto-reactive lymphocyte in the system [c.f. Nakayama et al., (1995), Mebio, 12 (10), 79–86].

Various molecules have been identified as being involved in apoptosis, including: Fas [c.f. Yonehara, S., et al., (1989), J. Exp. Med., 169, 1747–1756]; tumor necrosis factor receptor [c.f. Loetscher, H., et al., (1990), Cell, 61, 351–359]; CD40 [c.f. Tsubata, T., et al., (1993), Nature, 364, 645–648]; and perforin/granzyme A [c.f. Jenne, D. E., et al., (1988), Immunol. Rev. 103, 53–71].

Fas is a transmembrane protein, present on the cellular surface, and binding of its extracellular domain to a protein generally known as "Fas ligand", expressed on the surface of other cells, induces apoptosis in the cell expressing Fas. Abnormalities in the Fas/Fas ligand system result in various disorders, by failing to delete cells which could be detrimental to homeostasis, and which should have been eliminated by apoptosis, or, alternatively, by inducing apoptosis in cells not otherwise scheduled for elimination and which could be essential for maintaining homeostasis. Such disorders are those referred to herein as being conditions arising from abnormalities in the Fas/Fas ligand system.

In the development, or progression, of diseases arising from abnormalities of the Fas/Fas ligand, it is often the case that abnormal cells, which express Fas but which, nevertheless, remain undeleted (abnormal cells), either attack normal tissues or cells, or else proliferate abnormally, thereby causing disorders in the tissues or cells which, in turn, lead to the respective disease symptoms. In some cases, these disorders may arise from, or be exacerbated by, the expression of Fas on the abnormal cells, thereby stimulating apoptosis in normal tissues or cells. Specific examples of diseases attributable to abnormalities of the Fas/Fas ligand system are as follows.

Autoimmune Diseases.

Links between various human autoimmune diseases (Hashimoto disease, systemic lupus erythematosus, Sjögren syndrome, pernicious anemia. Addison disease, insulin dependent diabetes mellitus, scleroderma, Goodpasture's syndrome, Crohn's disease, autoimmune hemolytic anemia, sterility, myasthenia gravis, multiple sclerosis, Basedow's disease, thrombopenia purpura, rheumatoid arthritis) and abnormalities in the Fas/Fas ligand system have been reported many times.

In the mouse, various genetic abnormalities of the Fas/Fas ligand system are known, including the lpr (lymphoproliferation), gld (generalized lymphoproliferative disease), and lpr$^{cg}$ (where the lpr gene complements the gld gene) mutations. Mice having such genetic abnormalities all exhibit various autoimmune symptoms, accompanied by characteristic systemic swelling of the lymph nodes.

The MRL-lpr/lpr mouse, a mouse model of spontaneous human systemic lupus erythematosus, shows a marked increase in the mass of its lymph nodes and produces autoantibodies causing nephritis owing to the formation of immune complexes. It is speculated that this mouse exhibits this pathology as a result of a mutation in the Fas gene, resulting in a lack of immunological tolerance to autoantigen by failure of Fas induced apoptosis in the peripheral system, as well as by the long-term accumulation of activated autoreactive T cells [c.f. Strasser, A., Nature, 373, 385 (1995)].

In the human, several cases have been reported, including two pediatric cases involving swelling of the lymph nodes, hyper γ-globulinemia and marked increase in CD4$^-$CD8$^-$ T cells [c.f. Sneller, M C., et al., (1992), J. Clin. Invest., 90, 334]. These cases were reported to be based on abnormalities in the Fas gene [c.f. Fisher, G. H., et al., (1995), Cell, 81, 935; and Rieux-Laucat, F., et al., (1995), Science, 268, 1347], and designated autoimmune lymphoproliferative syndrome (ALPS). Based on these findings, it is considered that the apoptosis-inducing system, mediated by Fas, is involved to a large extent in the establishment and maintenance of self-tolerance, not only in the mouse but also in the human, and disorders of this system induce various autoimmune diseases.

It is also known that rheumatoid arthritis has an autoimmune element, based on the fact that the vast majority of T cells invading affected regions of rheumatoid arthritis patients and causing tissue destruction express Fas [c.f. Hoa, T. T. M., et al., (1996), J. Rheumatol., 23, 1332–1337].

Many cases of insulin dependent diabetes mellitus result from a critical shortage of insulin secretion, owing to destruction of pancreatic beta cells by autoreactive T cells. Thus, elimination of autoreactive T cells is important in the radical treatment of certain forms of insulin dependent diabetes mellitus.

In graft versus host disease, such as occurs after a bone marrow transplant, expression of Fas increases in the affected organ, and there is a direct correlation between the degree of increase in Fas expression and damage to the target organ [c.f. Chu, J. L., et al., (1995), J. Exp. Med., 181, 393]. Therefore, the aim in preventing or treating this disease, is to block apoptosis in the cells of the target organ and to decrease the numbers of cells attacking the target organ.

Allergic Diseases

Inflammatory cells involved in allergic diseases are normally activated and invade the lesions. The inflammatory cells accumulate locally in the lesion, and are able to continue to function long term, as their lives are extended by suppression of apoptosis. In an experimental model in which acidophilic inflammation of the air passage is induced in mice, it has been demonstrated that administration of an anti-Fas antibody, having apoptosis-inducing activity, via the air passage, results in the disappearance of invasion of acidophiles under the mucosa normally seen after inhalation of the allergen [c.f. Tsuyuki, S., et al., (1995); J. Clin. Invest., 96, 2924]. Therefore, it is possible to alleviate the symptoms in allergic inflammation by inducing apoptosis in the inflammatory cells.

Rheumatoid Arthritis

Apart from the autoimmune aspect of rheumatoid arthritis described above, abnormally proliferating synovial cells in the lesions are known to express Fas [c.f. Hoa, T. T. M., et al., (1996), J. Rheumatol., 23, 1332]. Apoptosis can be induced by stimulating the synovial cells from such lesions with anti-Fas antibody having apoptosis-inducing activity [c.f. Nakajima, T., et al., (1995), Arthr. Rheum., 38, 485]. In other words, the Fas/Fas ligand system is not functioning properly in the foci of rheumatoid arthritis patients, and neither autoreactive T cells nor abnormally proliferating synovial cells are eliminated, despite both expressing Fas.

Arteriosclerosis Although the final diagnoses of cell deaths at the center of arteriosclerosis lesions is necrosis, involvement of apoptosis in the progression and degeneration processes has been reported [c.f. Kenji Harada (1997), Gendai Iryou, 29, 109]. Electron microscopy of the lesions of arteriosclerosis shows apoptosis of smooth muscle cells, characterized by nucleic condensation [c.f. Isner, J. M., et al., (1995), Circulation, 91, 2703]. Further, it has been reported that foam cells, which are macrophages gathering in the inner layer of the artery and incorporating lipids in early arteriosclerotic lesions, express Fas and are caused to undergo apoptosis with naturally occurring apoptosis-inducing anti-Fas antibodies [c.f. Richardson, B. C., et al., (1994), Eur. J. Immunol., 24, 2640]. Arteriosclerotic lesions of are often associated with lymphocyte infiltration, suggesting a possibility that the Fas ligand of T cells, together with the Fas of macrophages, is responsible for controlling arteriosclerosis [c.f. Kenji Harada (1997), Gendai Iryou, 29, 109].

Myocarditis and Cardiomyopathy

The Fas/Fas ligand system is likely to be involved in the pathogeneses of autoimmune heart diseases, such as ischemic heart disease, viral heart disease, dilated cardiomyopathy and chronic cardiomyopathy. Myocarditis is inflammation of the heart muscle considered to be caused mainly by viruses, such as coxsackie virus, and is typified by chest pain, arrhythmia, heart failure or shock, after cold-like symptoms. Cardiomyopathy is defined as "a disease of the cardiac muscle of unknown cause," although its cause is also considered likely to be as a result of viral infection. In studies of mouse myocarditis models, with heart failure, apoptotic cells (as evidenced by condensation and/or fragmentation of the nuclei), are observed in the mouse heart after viral inoculation. Increase in Fas expression is also observed in the mouse heart, which has led to speculation that the condition was as a result of apoptosis induced by Fas ligand derived from infiltrating inflammatory cells, predominantly lymphocytes [c.f. Takehiko Yamada, et al. Gendai Iryou, (1997), 29, 119]. It is known that apoptosis is induced in cultured rat cardiac muscle cells by ischemia, concurrently with an increase in mRNA coding for Fas in the cells [c.f. Tanaka M., et al., (1994), Circ. Res. 75, 426].

Renal Diseases

In many chronic renal diseases, reconstitution of the tissue within the glomeruli results in the accumulation of extracellular substrates within the glomeruli, thereby promoting sclerosis of the glomeruli, leading to the pathological loss of filtering function and, ultimately, to chronic renal failure. In a model of progressive glomerulosclerosis, the sclerotic regions exhibited typical apoptotic appearances, at electron microscopic levels, and an increase in apoptosis in glomeruli is observed, consistent with a decrease in the number of glomerular cells associated with the progression of sclerosis [c.f. Sugiyama H., et al., (1996), Kidney Int., 49, 103]. In acute glomerular nephritis, it is known that the disease is alleviated by the apoptotic reduction in numbers of abnormally proliferated mesangial cells [c.f. Shimizu A., et al., (1995), Kidney Int., 47, 114 and Baker A. J., et al., (1994), J. Clin. Invest., 94, 2105]. In diseases such as purpura nephritis and lupus nephritis, a marked increase in cells expressing Fas in glomeruli has been reported [c.f. Takemura T., et al., (1995), Kidney Int., 48, 1886].

Hypoplastic Anemia

On the surface of hematopoietic precursor cells of patients with hypoplastic anemia, Fas expression is remarkably elevated compared with that in normal individuals, suggesting the involvement of Fas in the decrease of hematopoietic stem cells in these patients [c.f. Maciejewski, J. P., et al., (1995), Br. J. Haematol., 91, 245].

Hepatitis

In fulminant hepatitis, it is known that apoptosis is induced in many hepatocytes. Extensive hepatocyte death, similar to that observed in fulminant hepatitis, is observed upon intraperitoneal administration of the anti-Fas antibody Jo2 to mice. Thus, it is considered likely that the pathogenesis of fulminant hepatitis involves Fas-induced apoptosis of hepatocytes [c.f. Kamogawa, Y., et al., (1996), Molecular Medicine, 33, 1284; and Ogasawara, J., et al., (1993), Nature, 364, 806]. In immunohistochemical studies, enhanced Fas expression was observed in the cytoplasm of hepatocytes in the regions showing high levels of hepatocyte necrosis, such as within lesions of chronic hepatitis and on the cell membrane of hepatocytes of lesions of hepatic diseases, such as fatty liver [c.f. Hiramatsu, N., et al., (1994), Hepatology, 19, 1354 and Takatani, M., et al., (1996), International Hepatology Commun., 4, 334].

In addition, Fas is expressed in the lesions of chronic persistent hepatitis C and chronic active hepatitis, both of which show dispersed staining of hepatocytes surrounded by infiltrating lymphocytes, which are apparently cytotoxic T cells [c.f. Mita, E., et al., (1994), Biochem. Biophys. Res. Commun., 204, 468]. Cytotoxic T cells have the function of inducing apoptosis in infected cells via the Fas ligand expressed on their surface. They similarly induce apoptosis in the normal cells located near-by. This affect on local, normal cells, called the bystander disorder, results from the fact that many cells in the body express Fas after either their own infection or after infection of neighboring cells. In chronic hepatitis cases, where hepatitis C virus-derived RNA is substantially reduced after the administration of interferon, Fas expression in the hepatic tissue decreases markedly.

Hepatocytes of patients with acute hepatic failure have increased amounts of Fas on the cell surface, and undergo apoptosis when exposed to apoptosis-inducing, anti-Fas antibodies. Further, in alcoholic hepatitis, Fas ligand is expressed on the hepatocytes themselves within the pseudoacinus [c.f. Galle, P. R., et al., (1995), J. Exp. Med., 182, 1223]. In studies involving in situ hybridization of Fas ligand gene expression, expression was found, both in hepatic infiltrating lymphocytes, in cases of acute hepatic failure, and also in the hepatocytes themselves in the pseudoacinus in cases of alcoholic cirrhosis (as above) Thus, it is speculated that apoptosis is induced by different mechanisms in viral cirrhosis and alcoholic cirrhosis, but in both cases the Fas/Fas ligand system is abnormal. In a mouse model of hepatitis, it is known that hepatic disorder is inhibited by the administration of a substance capable of inhibiting the binding of Fas ligand to Fas [c.f. Kondo, T., et al., (1997), Nature Medicine, 3, 409].

Acquired Immunodeficiency Syndrome

Immunodeficiency in patients infected with the human immunodeficiency virus (HIV) results, at least partially, from the apoptotic cell deaths of numerous immune cells not infected with HIV. Helper T cells die on contact with HIV. Since growth factor from helper T cells is essential for the suppression of apoptosis in cytotoxic T cells, depletion of helper T cells results in the apoptosis of cytotoxic T cells. It is also considered likely that apoptosis of immune cells in HIV-infected patients is due to abnormalities of the Fas/Fas ligand system, based on observations that expression of Fas in the peripheral blood lymphocytes of HIV-infected patients correlates well with the pathological progression of the disease [c.f. Dhein, J., et al., (1995), Behring Inst. Mitt., 96, 13 and McCloskey, T. W., et al., (1995), Cytometry, 22, 111]. Fas-positive peripheral blood lymphocytes from non-infected individuals do not readily undergo apoptosis by Fas stimulation, whereas peripheral blood lymphocytes from infected patients undergo Fas-induced apoptosis within a short period [c.f. Owen-Schaub, L. B., et al., (1992), Cell Immunol., 140, 197].

Rejection after Organ Transplantation

Rejection after organ transplantation shares certain similarities with autoimmune diseases, except that the transplanted organ is being attacked by cytotoxic T cells from a donor. Thus, alleviation of the symptoms can be expected if the functions of cytotoxic T cells can be suppressed.

For the diseases listed above, effective means for their treatment is by the elimination of abnormal cells (e.g., autoreactive T cells in autoimmune diseases, foam cells in arteriosclerosis, mesangial cells in acute glomerular nephritis, infected cells in viral infections, and synovial cells in rheumatoid arthritis) and/or by the protection of normal tissues or cells.

The problem lies in the fact that agents which are only capable of inducing Fas-mediated apoptosis, are highly likely to cause disorders in normal tissues, even though abnormal cells are eliminated. On the other hand, agents only capable of inhibiting Fas-mediated apoptosis cannot eliminate abnormal cells, even though they may be able to protect normal cells. For example, the anti-mouse Fas monoclonal antibody Jo2 has apoptosis-inducing activity but causes fulminant hepatitis in mice [c.f. Ogasawara, J., et al., (1993), Nature, 364, 806–809].

To date, an anti-Fas antibody which can be used in the treatment and/or prophylaxis of any of the above diseases, but which is not associated with any undesirable side effects, is not known.

Immunoglobulin G (IgG) is composed of two light polypeptide chains (L chains), each having a molecular weight of about 23,000 kD, and two heavy polypeptide chains (H chains), each having a molecular weight of about 50,000 kD. Both H and L chains consist of a repeated region of conserved amino acids consisting of about 110 residues. This region is referred to herein as a "domain", and constitutes the basic three-dimensional structural unit of the of IgG. The H and L chains consist of four and two consecutive domains, respectively.

When antibody amino acid sequences are compared, the amino-terminal domain of both H and L chains is found to be more variable than the other domains. It is, therefore, referred to as the 'variable' domain (V domain). The V domains of H and L chains associate with each other by their complementary nature to form variable regions in the amino-termini of IgG molecules. The other domains associate to form constant regions. The constant region sequences are characteristic for a given species. For example, the constant regions of mouse IgG differ from those of human IgG, and a mouse IgG molecule is recognized as a foreign protein by the human immune system. Administration of a mouse IgG molecule into a human subject results in the production of a human anti-mouse antibody (hereinafter referred to as "HAMA") response [Schroff et al., (1985), Cancer Res., 45, 879–885]. Accordingly, a mouse antibody cannot be repeatedly administered to a human subject. For effective administration, the antibody must be modified to avoid inducing the HAMA response, while maintaining the antibody specificity.

Data from X-ray crystallography analysis indicates that the immunoglobulin fold generally forms a long cylindrical structure comprising two layers of antiparallel β-sheets, each consisting of three or four β-chains. In a variable region, three loops from each of the V domains of H and L chains cluster together to form an antigen-binding site. Each of these loops is termed a complementarity determining region (CDR). The CDR's have the highest variability in amino acid sequence. The portions of the variable region that are not part of a CDR are called "framework regions" ("FR" regions) and generally play a role in maintaining the structure of CDR's.

Kabat and co-workers compared the primary sequences of a number of variable regions of H and L chains and identified putative CDR's or framework regions, based an sequence conservation (E. A. Kabat et al., Sequences of immunological interest, 5th edition, NIH Publication, No. 91-3242). Further, they classified the framework regions into several subgroups which share common amino acid sequences. They also identified framework regions that correspond between mouse and human sequences.

Studies on the structural characteristics of IgG molecules have led to the development of methods for preparing humanized antibodies, which do not provoke a HAMA response, as described below.

Initial suggestions were directed towards the preparation of a chimaeric antibody, by joining the variable region of a mouse antibody to the constant regions of human origin [Morrison, S. L., et al., (1984), Proc. Natl. Acad. Sci. USA, 81, p6851–6855]. Such a chimeric antibody, however, still contains many non-human amino acid residues, and thus can cause a HAMA response, especially when administered for a prolonged period [Begent et al., (1990), Br. J. Cancer, 62, p487 et seq.].

The grafting of CDR segments alone into a human antibody was then proposed, in order to further reduce the number of non-human amino acid sequences causing the HAMA response [Jones, P. T. et al., (1986), Nature, 321, 522–525]. However, the grafting of the CDR portions alone was generally found to be insufficient to maintain the activity of the immunoglobulin against an antigen.

Based on data from X-ray crystallography, Chothia and co-workers [Chothia et al., (1987), J. Mol. Biol., 196, 901–917] determined that:

1) A CDR has a region involved in antigen binding and a region involved in maintaining the structure of the CDR itself. Possible three-dimensional structures for CDR's can be classified into several classes with characteristic patterns (canonical structures); and
2) The classes of canonical structures are determined not only by the CDR sequences but also by the nature of amino acids in specific positions in the framework regions.

As a result, it has been suggested that the CDR-grafting technique should also involve the grafting of certain amino acid residues from the framework regions into the human antibody backbone [Queen et al., International Patent Publication No. WO90/07861].

In the context of the above, an antibody from a non-human mammal from which the CDR's are obtained for grafting is hereinafter termed a 'donor' molecule. A human antibody into which the CDR's are grafted is hereinafter termed an 'acceptor' molecule.

In performing CDR-grafting, the structures of the CDR region should ideally be conserved and the activity of the immunoglobulin molecule should be maintained. The following factors may, therefore, be relevant:

1) the subgroup of the acceptor; and
2) the nature of the amino acid residues that are transferred from the framework regions of the donor.

Queen et. al [International Patent Publication No. WO90/07861] proposed a method for deciding whether an amino acid residue from the donor FR was to be grafted along with the CDR sequence. According to this method, an amino acid residue from a FR region is grafted onto the acceptor, together with the CDR sequence, if the residue meets at lease one of the following criteria:

1) The amino acid in the human framework region of the acceptor is rarely found at that position in the acceptor, whereas the corresponding amino acid in the donor is commonly found at that position in the acceptor
2) the amino acid is closely located to one of the CDR's; and
3) the amino acid has a side-chain atom within approximately 3 Å of a CDR, as judged by a three-dimensional model of the immunoglobulin, and is potentially able to interact with an antigen or a CDR of a humanized antibody.

However, no one has successfully obtained a humanized, anti-Fas, IgG type antibody which has apoptosis-inducing activity.

OBJECTS OF THE INVENTION

It is an object of the present invention to provide an anti-Fas antibody, or similar molecule, which can be evaluated in an animal model of a human Fas-related disease condition.

It is a further object of the present invention to provide a humanized anti-Fas antibody, or similar molecule, useful in the treatment and/or prophylaxis of conditions arising from abnormalities in the Fas/Fas ligand system.

It is a further object of the present invention to provide a humanized antibody having apoptosis-inducing activity.

Monoclonal antibodies that specifically bind to human Fas and which also have apoptosis-inducing activity are known, but none of them is capable of binding mouse Fas. Likewise, monoclonal antibodies that bind mouse Fas are known, but none binds human Fas. Thus, so far, it has not been possible to establish a mouse model to evaluate the pharmaceutical efficacy of anti-human Fas monoclonal antibodies.

SUMMARY OF THE INVENTION

Thus, in a first aspect, the present invention provides a molecule having a binding region specific for a Fas epitope, the epitope being conserved between a primate and a non-primate animal.

In a second aspect, the present invention provides a molecule having a binding region specific for a common, mammalian, Fas epitope.

The present invention further provides an antibody as produced by the hybridoma HFE7A having the accession number FERM BP-5828, as well as a molecule having at least six antibody CDR's, the antibody being specific for human Fas, wherein the CDR's have identity with the CDR's of the antibody as produced by the hybridoma HFE7A having the accession number FERM BP-5828.

Thus, in a further aspect, the present invention provides a humanized anti-Fas antibody capable of
a) inducing apoptosis in abnormal cells, especially as described above, by binding Fas antigen on the cell surface, and
b) preventing apoptosis in normal cells which would otherwise be induced as a result of the binding of Fas ligand to Fas antigen.

More preferably, the present invention provides an anti-Fas antibody comprising one or more heavy chain heavy chain subunits substantially having an amino acid sequence selected from the group consisting of:
the amino acid sequence 1 to 451 of SEQ ID No. 143;
the amino acid sequence 1 to 451 of SEQ ID No. 145;
the amino acid sequence 1 to 451 of SEQ ID No. 147; and
the amino acid sequence 1 to 451 of SEQ ID No. 157
of the Sequence Listing.

More preferably, the antibody has one or more light chain subunits substantially having an amino acid sequence selected from the group consisting of:
the amino acid sequence 1 to 218 of SEQ ID No. 107;
the amino acid sequence 1 to 218 of SEQ ID No. 127;
the amino acid sequence 1 to 218 of SEQ ID No. 129; and
the amino acid sequence 1 to 218 of SEQ ID No. 131
of the Sequence Listing.

Of the above preferred antibodies, a preferred group are those wherein the heavy chain consists essentially of the amino acid sequence 1 to 451 of SEQ ID No. 157 of the Sequence Listing, it being then further preferred that the light chain consists essentially of the amino acid sequence 1 to 218 of SEQ ID No. 107 of the Sequence Listing.

Another preferred category are those antibodies wherein one or more light chain subunits substantially have an amino acid sequence selected from the group consisting of:
the amino acid sequence 1 to 218 of SEQ ID No. 127;
the amino acid sequence 1 to 218 of SEQ ID No. 129; and
the amino acid sequence 1 to 218 of SEQ ID No. 131
of the Sequence Listing, and one or more heavy chain heavy chain subunits substantially have an amino acid sequence selected from the group consisting of:
the amino acid sequence 1 to 451 of SEQ ID No. 143;
the amino acid sequence 1 to 451 of SEQ ID No. 145; and
the amino acid sequence 1 to 451 of SEQ ID No. 147;
of the Sequence Listing.

It will be appreciated that the term "substantially" is used herein to refer to the possibility of altering the sequences referred to. Such alteration may be by substitution, deletion, insertion or inversion, for example, but will generally be restricted in scope, in order to retain the characteristics of the sequence in question.

In an alternative aspect, the present invention provides a humanized anti-Fas antibody which is capable of binding both human and mouse Fas antigen.

There is further provided an agent for the prophylaxis and/or treatment of conditions involving a Fas disorder, comprising an anti-Fas antibody, or molecules similar thereto, as active ingredient.

Methods of treatment of conditions involving Fas disorders are further provided, such methods involving the administration of non-toxic, or substantially non-toxic, doses of antibodies of the invention to an animal, especially a human, in need thereof.

Other objects, aims, aspects and embodiments of the present invention will become apparent hereinbelow.

BRIEF DESCRIPTION OF THE DRAWINGS

FIG. 30 shows the cytotoxicity of the humanized HFE7A to WR19L12a.

FIG. 48 shows a comparison of FR-amino acid sequences of HFE7A, each human acceptor and light chain of each humanized antibody;

FIG. 49 shows a comparison of FR-amino acid sequences of HFE7A, each human acceptor and heavy chain of each humanized antibody;

FIG. 52 is a summary of the first step PCR for the production of LEU2-DNA;

FIG. 54 is a summary of the first step PCR for the production of LEU3-DNA;

DETAILED DESCRIPTION OF THE INVENTION

Figure 1:
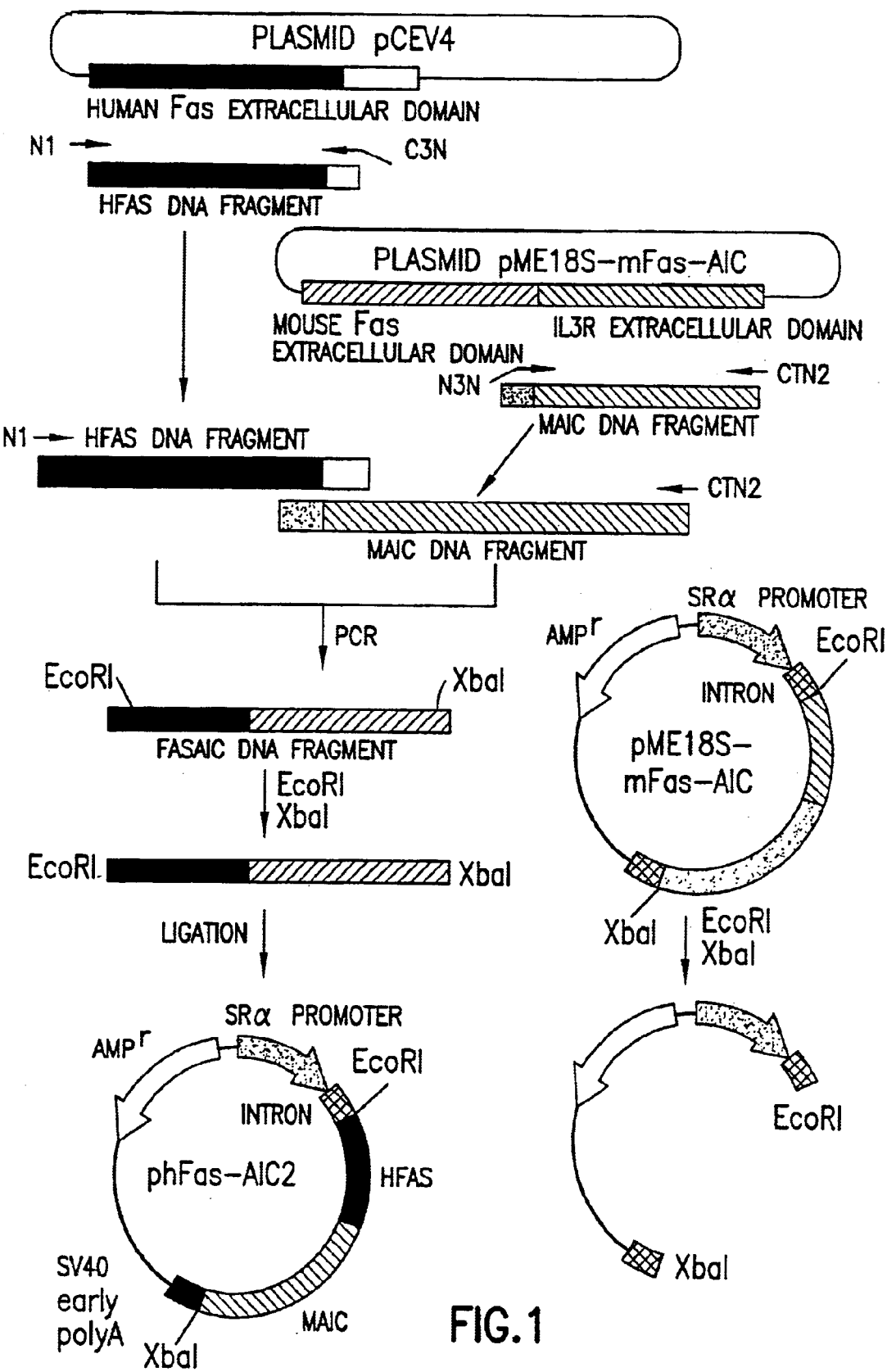
FIG. 1 is a diagram depicting the construction of phFas-AIC2.
Figure 2:
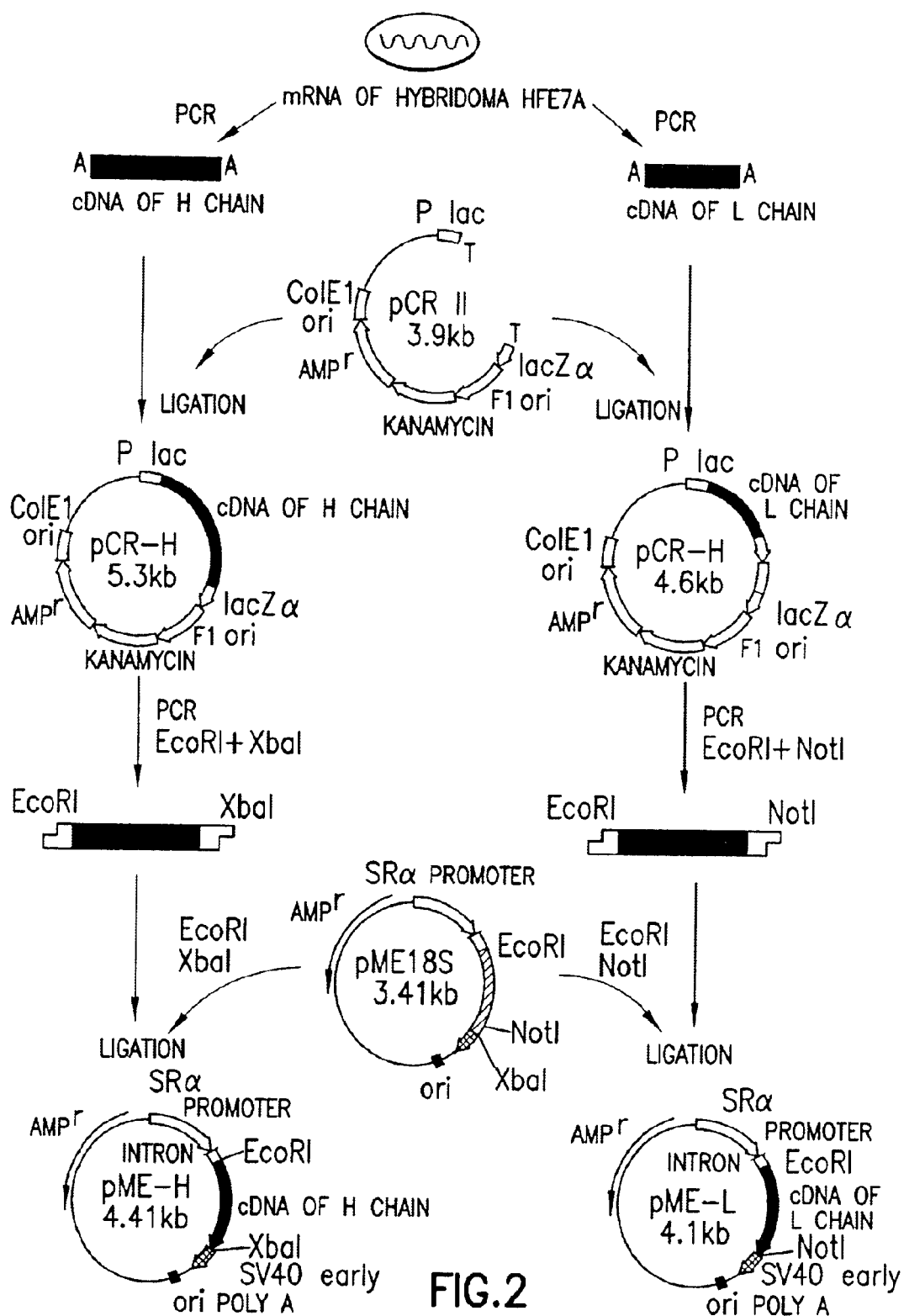
FIG. 2 is a diagram depicting the construction of pME-H and pME-L.

A particular advantage of the antibodies of the present invention (including the HFE7A antibody) is that they are not only able to induce apoptosis in abnormal cells expressing Fas, but that they are also able to inhibit apoptosis in normal cells.

No known monoclonal antibody which binds human Fas and which has apoptosis-inducing activity is capable of binding mouse Fas. Monoclonal antibodies that bind mouse Fas are known, but none of them binds human Fas. Thus, no known anti-Fas antibody can be evaluated in disease model mice. By contrast, the antibodies of the present invention (including the HFE7A antibodies) are able to be evaluated in disease mice models, thereby both providing means for ensuring pharmaceutical efficacy and also establishing a model for the investigation of the role of Fas, in general.

It is believed that the advantages of the antibodies of the present invention arise from their ability to recognize a conserved epitope on the Fas antigen. Fas is a common molecule, but varies from species to species. Without being bound by theory, it is believed that there is at least one conserved region of Fas, which is common to all mammals, and which is necessary for the Fas apoptosis-inducing function. The molecules of the present invention recognize a conserved Fas epitope. In this respect, when comparing murine and human Fas, for example, the epitope in question need not necessarily be absolutely identical in the two molecules, provided that the epitope binding region of the molecule is able to recognize both. However, in general, the epitope will be exactly the same.

Many antibodies directed against Fas are known, including those capable of inducing apoptosis, but none has previously been obtained which bound any kind of consensus sequence. The antibodies of the present invention, by way of contrast, do bind a consensus sequence. Accordingly, as an extension of the theory, instead of merely acting to incapacitate or interfere by generalized binding to Fas, which can have dangerous and unpredictable effects, such as with Jo2 and fulminant hepatitis in mice (supra), the antibodies of the present invention actually act at the Fas active site, thereby mimicking a natural ligand, rather than merely non-specifically binding the Fas antigen.

If a normal laboratory mouse, such as a BALB/c mouse, is immunized with human Fas, cells producing antibodies which bind both human Fas and mouse Fas will be eliminated in the thymus, in the usual course of eliminating autoreactive antibodies. Thus, in order to obtain a mouse monoclonal antibody which is directed to an epitope conserved between human and mouse and which, accordingly, binds both human Fas and mouse Fas, it is necessary to use a mouse in which such elimination has been partially or completely disabled.

It has been speculated that the Fas/Fas ligand system is involved in this elimination process of auto-reactive T cells in the thymus [c.f Shin Yonehara (1994) Nikkei Science Bessatsu, 110, 66–77]. Therefore, by immunizing a mouse having a mutation in the Fas/Fas ligand system (such a mouse is hereinafter referred to as a "Fas knock-out mouse" or "Fas/Fas ligand deficient mouse"), for example, one that is unable to express the gene coding for Fas, antibodies which bind mouse Fas as well as human Fas can be obtained.

Antibodies against Fas may generally be obtained by administering an immunogenically effective amount of a substance comprising an immunogenic epitope of heterologous Fas to a non-human animal, which is at least partially deficient in the apoptotic elimination of autoreactive T cells, and selecting antibodies from the animal thereafter.

The substance carrying the Fas epitope may be Fas itself, or may be another suitable substance, such as a fusion protein.

Selection of appropriate antibodies is within the skill of those in the art, and is exemplified below. In particular, it is preferred to use the immunized animal of the method of the invention to obtain at least one monoclonal antibody, which is readily obtainable using methods well known in the art.

It will also be appreciated that, for ease of manipulation, it is preferred that the non-human animal is a mouse, although other rodent species, such as rabbits, and other mammals, in general, such as goats and macaques, may also be used, although such systems are not quite so well characterised as the mouse. It will also be appreciated that it is preferred that the Fas used for administration be human, although, if desired, antibodies of the invention may be obtained for other mammals. However, it is generally envisaged that, owing to the sharing of a common epitope, the antibodies of the present invention have universal application.

Using the above method, a hybridoma was prepared which produces a novel anti-Fas monoclonal antibody binding both human and mouse Fas. A Fas knock-out mouse was immunized with human Fas and then the spleen cells were fused with mouse myeloma cells, and monoclonal antibodies were then purified from the culture supernatant.

The novel anti-Fas monoclonal antibodies of the present invention induced apoptosis in T-cells of mice and other non-human primates which express Fas. Thus, the present invention demonstrates that there is a common epitope, at least in primate (including human) and rodent (at least murine) Fas, which can be recognized by the antibody of the present invention, and which is able to induce apoptosis when the antibody of the present invention binds thereto.

The novel anti-Fas monoclonal antibody thus recovered has proved to be efficacious in alleviating the severity of the symptoms of autoimmune disease model mice. Moreover, it has been demonstrated that this anti-Fas monoclonal antibody does not induce hepatic disorders, which has previously been a problem.

The respective genes for both chains of the new antibody were also cloned and sequenced, in order to obtain the amino acid sequences of the CDR's. Expression vectors, comprising the respective genes for the heavy and light chains, were constructed in order to produce a recombinant anti-Fas antibody. These recombinant antibodies, obtained in culture supernatant fluids of animal cells co-transfected with these vectors, was demonstrated to react with Fas.

The anti-Fas antibodies thus obtained, and their recombinant antibody clones, are able to protect the liver from Fas-induced fulminant hepatitis, and are also effective in the prevention and treatment of rheumatoid arthritis.

Accordingly, it has now been demonstrated that it is readily possible to provide antibodies which are able both to induce apoptosis via Fas in abnormal cells and to inhibit Fas-induced apoptosis in normal cells, and are, therefore, effective in the prevention, treatment and/or prophylaxis of diseases attributable to abnormalities of the Fas/Fas ligand system.

The method for obtaining the antibodies of the invention involved grafting of the CDR amino acid sequences of the mouse-derived anti-Fas monoclonal antibodies into a human antibody. Recombinant antibodies, which were not immunogenic to human subjects, but still had Fas-binding activity, were successfully obtained.

The present invention allows the construction of humanized antibodies which have a minimal risk of inducing a response, whilst still having an effective antibody effector function.

Homology of a binding region, or epitope, refers to the sequence of the region. Indeed, in general, amino acid sequences surrounding an epitope are often conserved, in different animals, for antigens bound by a common monoclonal antibody which recognizes homologous proteins. Homology of the amino acid sequence in the region is high in many cases. The epitope to which the antibody of the present invention is bound is not limited to such a region. Homology in the primary structure is not conserved but, rather, homology in a higher-order structure is conserved. Thus, epitopes which are conserved between primates and non-primates includes reference to regions having high homology in the higher-order structure of the proteins, particularly those that can be recognized by one monoclonal antibody.

As used herein, the terms "human" and "humanized", in relation to antibodies, relate to any antibody which is expected to elicit little, or no, immunogenic response in a human subject, the subject in question being an individual or a group.

It will be appreciated that, in general, it is preferred that all of the CDR's from a given antibody be grafted into an acceptor antibody, in order to preserve the binding region for the Fas epitope, or epitope binding region, as it is generally referred to herein. However, there may be occasions when it is appropriate or desirable for less than the total amount of CDR's to be grafted into the donor, and these are envisaged by the present invention. It will also be understood that grafting generally entails the replacement, residue for residue, of one amino acid or region, for another. However, occasionally, especially with the transfer of a region, one or more residues may be added or omitted, as desired, and that such deletions and insertions, as well as appropriate replacements and invertions, are within the skill of those in the art.

The epitope binding region of the present invention is a region of the molecule which corresponds to an epitope binding site of an antibody. The epitope binding region need not be derived directly from any particular antibody, or pair of antibodies, and may not resemble any particular epitope binding region. The only requirement is that the epitope binding region resemble the recognition site of an antibody insofar as it is able to bind an antigen, in this case, a Fas epitope. Even though the epitope binding region may be designed using the CDR's from a known antibody, if these are then grafted into a human antibody, the resulting epitope binding region may not necessarily resemble that from the known antibody, although a large degree of similarity is desirable, from the point of view of maintaining binding specificity.

We particularly prefer that all of the CDR's from the non-human antibody be grafted into the human antibody. Further, we prefer that certain areas of the framework regions be incorporated into the acceptor antibody (also referred to as the human antibody, herein) in order to maintain the 3-dimensional structure of the non-human binding site. Such areas of the framework regions typically comprise individual amino acid residues selected for their importance (significant residues), in accordance with the guidelines below. In particular, those residues which are rare in human, but common in the relevant non-human antibody, and those residues having a high probability of interacting directly with the epitope or the recognition site, are preferred to be grafted together with the CDR's.

When grafting the CDR's into the human antibody, it will normally be the case that the non-human CDR replaces a relevant human CDR in its entirety, particularly where both are of the same length. However, it may also be the case that only a part of a human CDR is replaced, or only a part of the non-human CDR is grafted, the two usually going hand-in-hand.

It will also be appreciated that the CDR's from the non-human antibody should generally be used to replace the corresponding CDR's in the human antibody. In the situation where a skeleton human light or heavy chain is used, which only has positions for insertion of CDR's, rather than actually having CDR's, then similar considerations apply.

It will also be understood that the human heavy and light chains need not necessarily come from the same human antibody, nor even from the same class. What is important is that the sequence of the selected donor matches, as closely as possible, the sequence of the non-human antibody. The importance of matching the two chains (light/light or heavy/heavy) is that the resulting antibody should have a epitope binding region as closely resembling that of the original non-human antibody as possible, to ensure the best binding. Thus, the present invention also envisages the possibility of using matches which are not the closest possible, where there is a reasonable expectation that the resulting recombinant antibody will serve the required purpose.

The molecules of the present invention are preferably antibodies, although this is not necessary, provided that the epitope binding region binds a Fas epitope. Thus, isolated and stabilized binding sites, for example, may be attached to an affinity purification column support, or an administration method may comprise an adjuvant carrier molecule, for example, to which are attached epitope binding regions of the invention. For ease of reference, the molecules of the present invention will generally be termed antibodies herein, but such reference encompasses all molecules of the invention, unless otherwise indicated.

Where the molecule of the invention is an antibody, it will be appreciated that any appropriate antibody type may be emulated, or employed, such as IgG, IgA, IgE and IgM, with IgG being generally preferred.

Where molecules and antibodies are discussed herein, it will also be understood that similar considerations apply, mutatis mutandis, to any nucleic acid sequences encoding them, as appropriate.

Certain preferred embodiments of the present invention are as follows.

It is preferred that the antibody of the invention binds a peptide comprising the amino acid sequence of SEQ ID No. 1 of the Sequence Listing.

The antibody is preferably IgG and, more preferably, comprises a light chain polypeptide protein selected individually from the amino acid sequence 1 to 218 of SEQ ID No. 50, the amino acid sequence 1 to 218 of SEQ ID No. 52, the amino acid sequence 1 to 218 of SEQ ID No. 54, the amino acid sequence 1 to 218 of SEQ ID No. 107, and the amino acid sequence 1 to 218 of SEQ ID No. 109 of the Sequence Listing, and wherein the heavy chain polypeptide protein preferably comprises the amino acid sequence 1 to 451 of SEQ ID No. 89 or the amino acid sequence 1 to 451 of SEQ ID No. 117 of the Sequence Listing.

An antibody of the invention, in a preferred embodiment, has a light chain and a heavy chain, the heavy chain having the following general formula (I):

-FRH$_1$-CDRH$_1$-FRH$_2$-CDRH$_2$-FRH$_3$-CDRH$_3$-FRH$_4$-  (I)

wherein FRH$_1$ represents any amino acid sequence consisting of 18 to 30 amino acids, CDRH$_1$ represents the sequence as defined in SEQ ID No. 2 of the Sequence Listing, FRH$_2$ represents any amino acid sequence consisting of 14 amino acids, CDRH$_2$ represents the sequence as defined in SEQ ID No. 3 of the Sequence Listing, FRH$_3$ represents any amino acid sequence consisting of 32 amino acids, CDRH$_3$ represents the sequence as defined in SEQ ID No. 4 of the Sequence Listing, FRH$_4$ represents any amino acid sequence consisting of 11 amino acids, and each amino acid binds another via a peptide bond, and the light chain having the following general formula (II):

-FRL$_1$-CDRL$_1$-FRL$_2$-CDRL$_2$-FRL$_3$-CDRL$_3$-FRL$_4$-  (II)

wherein FRL$_1$ represents any amino acid sequence consisting of 23 amino acids, CDRL$_1$ represents the sequence as defined in SEQ ID No. 5 of the Sequence Listing, FRL$_2$ represents any amino acid sequence consisting of 15 amino acids, CDRL$_2$ represents the sequence as defined in SEQ ID No. 6 of the Sequence Listing, FRL$_3$ represents any amino acid sequence consisting of 32 amino acids, CDRL$_3$ represents the sequence as defined in SEQ ID No. 7 of the Sequence Listing, FRL$_4$ represents any amino acid sequence consisting of 10 amino acids, and each amino acid binds another via a peptide bond.

The invention also provides DNA and RNA encoding any one of the light or heavy chain polypeptide proteins described above. More preferred is DNA comprising the nucleotide sequence 100 to 753 of SEQ ID No. 49, DNA comprising the nucleotide sequence 100 to 753 of SEQ ID No. 51, DNA comprising the nucleotide sequence 100 to 753 of SEQ ID No. 53 and/or DNA comprising the nucleotide sequence 84 to 2042 of SEQ ID No. 88 of the Sequence Listing.

DNA encoding the antibodies of the present invention is also provided, as are recombinant DNA vectors comprising such DNA, and host cells transformed with such vectors. The host is preferably transformed with a separate vector for each heavy and light chain encoded, so will usually contain two vectors, although the present invention also envisages a host transformed with only one expression vector encoding all sequences to be expressed. Such a host cell is preferably mammalian.

Each of the following transformed strains incorporate particularly preferred plasmids of the present invention and are each preferred: (light chains) E. coli pHSGMM6 SANK73697 (FERM BP-6071), E. coli pHSGHM17 SANK73597 (FERM BP-6072), E. coli pHSGHH7 SANK73497 (FERM BP-6073), E. coli pHSHM2 SANK 70198 and E. coli pHSHH5 SANK 70398 (FERM BP-6272); (heavy chains) E. coli pgHSL7A62 (FERM BP-6274) SANK73397 (FERM BP-6074) and E. coli pgH-PDHV3 SANK 70298 (FERM BP-6273).

The present invention also provides a method for producing a humanized anti-Fas antibody comprising culturing the above host cells, and then recovering the humanized anti-Fas antibody from the culture.

Further provided is an agent for the prophylaxis or treatment of diseases attributable to abnormalities of the Fas/Fas ligand system comprising as an active ingredient the antibody of the present invention, especially where the diseases are as defined above. Targeted diseases are autoimmune diseases (systemic lupus erythematosus, Hashimoto disease, rheumatoid arthritis, graft versus host disease, Sjögren syndrome, pernicious anemia, Addison's disease, scleroderma, Goodpasture syndrome, Crohn's disease, autoimmune hemolytic anemia, sterility, myasthenia gravis, multiple sclerosis, Basedow disease, thrombopenia purpura, or insulin dependent diabetes mellitus) Separate preparations are also envisaged for: allergy; rheumatoid arthritis; arteriosclerosis; myocarditis or cardiomyopathy; glomerular nephritis; hypoplastic anemia; hepatitis (fulminant hepatitis, chronic hepatitis, viral hepatitis (hepatitis C, hepatitis B, hepatitis D) or alcoholic hepatitis); and rejection after organ transplantation.

The framework regions (FR's) are present in the variable region of an H or L chain subunit of an immunoglobulin molecule. For instance, $FRH_1$ refers to the framework region located at the most N-terminal position in the variable region of an H chain subunit, and $FRL_4$ refers to the fourth framework region from the N-terminus of the variable region of an L chain subunit. Similarly, $CDRH_1$, for example, refers to the CDR present at the most N-terminal position in the variable region of an H chain subunit, and $CDRL_3$ refers to the third CDR from the N-terminus of the variable region of an L chain subunit. The FRs flank the CDR regions in any light or heavy chain.

It will be appreciated that the antibodies of the present invention can be obtained by, for example, grafting each CDR of the L chain and H chain subunit of the anti-Fas monoclonal antibody HFE7A into a corresponding CDR region of a human antibody, thereby humanizing it.

In one embodiment, an anti-Fas monoclonal antibody, suitable to prepare a humanized anti-Fas antibody according to the present invention, may be obtained by culturing a suitable hybridoma which, in turn, may be obtained by immunizing a Fas knock-out mouse with human Fas and subsequently fusing the spleen cells from the mouse with mouse myeloma cells.

Preparation of a monoclonal antibody typically involves the following steps:
a) purification of a biomacromolecule for use as the immunizing antigen;
b) preparation of antibody producing cells, after first immunizing an appropriate animal using injections of the antigen, bleeding the animal and assaying the antibody titer, in order to determine when to remove the spleen;
c) preparation of myeloma cells;
d) fusing the antibody producing cells and myeloma cells;
e) selecting a hybridoma producing an antibody of interest;
f) preparing a single cell clone (cloning);
g) optionally, culturing the hybridoma cells, or growing animals into which the hybridoma cells have been transplanted, for large scale preparation of the monoclonal antibody; and
h) testing the biological activities and the specificity, or assaying marker agent properties, of the monoclonal antibody thus prepared.

The general procedure followed for the preparation of an anti-Fas monoclonal antibody is herein below described in more detail, in line with the above described steps. However, it will be appreciated that the method described below only represents one way of preparing a suitable antibody, and other procedures may be followed, as desired, such as for instance, using cells other antibody producing cells than spleen cells and other cell lines than myeloma.

a) Preparation of Antigen

A recombinant protein (hereinafter referred to as "recombinant human Fas"), effective as the Fas antigen, can be obtained by transfecting the monkey cell line COS-1 with the expression vector pME18S-mFas-AIC, which encodes a fusion protein comprising the extracellular domain of human Fas and the extracellular domain of the mouse interleukin-3 receptor [IL3R—c.f. Nishimura, Y., et al., (1995), J. Immunol., 154, 4395–4403], and collecting and partially purifying the expression product. The plasmid phFas-AIC2 was constructed by inserting DNA encoding a human Fas and mouse IL3R fusion protein into pME18S, which is an expression vector for animal cells. As noted above, the materials used, such as the DNA encoding Fas, the vector and the host, are not restricted to those mentioned.

The resulting human Fas and IL3R fusion protein, referred to herein as recombinant human Fas, collected from the culture supernatant of the transformed COS-1 cells may be partially purified by a suitable method, such as ion-exchange chromatography using a Resource Q column (tradename; Pharmacia).

As a suitable alternative, purified Fas obtained from the cell membranes of human cell lines can be used as the antigen. Further, since the primary structure of Fas is known [c.f Itoh, N. , et al., (1991), Cell, 66, 233–243], a peptide comprising a suitable portion of the amino acid sequence of human Fas, such as that of SEQ ID No. 1 of the Sequence Listing, may be chemically synthesized by any suitable method and used as the antigen.

b) Preparation of Antibody Producing Cells

An experimental animal is immunized with the immunogen produced in step a), suitably mixed with an adjuvant, such as Freund's complete, or incomplete, adjuvant and alum. In the present instance, a suitable experimental animal is a Fas knock-out mouse, which may be produced by the method of Senju et al. [Senju, S., et al., (1996), International Immunology, 8, 423].

Suitable administration routes to immunize the mouse include the subcutaneous, intraperitoneal, intravenous, intradermal and intramuscular injection routes, with subcutaneous and intraperitoneal injections being preferred.

Immunization can be by a single dose or, more preferably, by several repeated doses at appropriate intervals (preferably 1 to 5 weeks). Immunized mice are monitored for anti-Fas antibody activity in their sera, and an animal with a sufficiently high antibody titer is selected as the source of antibody producing cells. Selecting an animal with a high titer makes the subsequent process more efficient. Cells for the subsequent fusion are generally harvested from the animal 3 to 5 days after the final immunization.

Methods for assaying antibody titer include various well known techniques such as radioimmunoassay (RIA), solid-phase enzyme immunoassay (ELISA), fluorescent antibody assay and passive hemagglutination assay, with RIA and ELISA preferred for reasons of detection sensitivity, rapidity, accuracy and potential for automation.

Determination of antibody titer may be performed, for example, by ELISA, as follows. First, purified or partially purified Fas is adsorbed onto the surface of a solid phase, such as a 96-well ELISA plate, followed by blocking any remaining surface, to which Fas has not bound, with a protein unrelated to the antigen, such as bovine serum albumin (BSA). After washing, the well surfaces are contacted with serially diluted samples of the antibody preparations to be tested (for example, mouse serum) to enable binding of the anti-Fas antibody in the samples to the antigen. An enzyme-labelled, anti-mouse antibody, as the secondary antibody, is added to bind the mouse antibody. After washing, the substrate for the enzyme is added, and anti-Fas binding activity can then be assayed by determining a suitable change, such as absorbance change due to color development.

c) Preparation of Myeloma Cells

In general, cells from established mouse cell lines serve as the source of myeloma cells. Suitable cell lines include: 8-azaguanine resistant mouse (derived from BALB/c) myeloma strains, P3X63Ag8U.1 (P3-U1) [Yelton, D. E., et al., Current Topics in Microbiology and Immunology, 81, 1–7, (1978)], P3/NSI/1-Ag4-1(NS-1) [Kohler, G., et al., European J. Immunology, 6, 511–519 (1976)], Sp2/O-Ag14 (SP-2) [Shulman, M., et al., Nature, 276, 269–270 (1978)], P3X63Ag8.653 (653) [Kearney, J. F., et al., J. Immunology, 123, 1548–1550 (1979)] and P3X63Ag8 (X63) [Horibata, K. and Harris, A. W., Nature, 256, 495–497 (1975)]. The cell line selected is serially transferred into an appropriate medium, such as 8-azaguanine medium [RPMI-1640 medium supplemented with glutamine, 2-mercaptoethanol, gentamicin, fetal calf serum (FCS), and 8-azaguanine], Iscove's Modified Dulbecco's Medium (IMDM) or Dulbecco's Modified Eagle Medium (DMEM). The cells are then transferred to a normal medium, such as ASF104 medium (Ajinomoto, K. K.) containing 10% w/v FCS, 3 to 4 days prior to fusion, in order to ensure that at least $2 \times 10^7$ cells are available on the day of fusion.

d) Cell Fusion

The antibody producing cells used in fusion are plasma cells and their precursor cells, lymphocytes, which may be obtained from any suitable part of the animal. Typical areas are the spleen, lymph nodes, peripheral blood, or any appropriate combination thereof, spleen cells most commonly being used.

After the last booster injection, tissue in which antibody producing cells are present, such as the spleen, is removed from a mouse having the predetermined antibody titer to prepare antibody producing cells. The currently favored technique for fusion of the spleen cells with the myeloma cells prepared in step c), employs polyethylene glycol, which has relatively low cytotoxicity and the fusion procedure using it is simple. An example of this technique is as follows.

The spleen and myelcma cells are washed well with serum-free medium (such as RPMI 1640) or phosphate buffered saline (PBS), and then mixed, so that the number ratio of spleen cells to myeloma cells is approximately between 5:1 and 10:1, and then centrifuged. After the supernatant has been discarded and the pelleted cells sufficiently loosened, a suitable amount, generally 1 ml, of serum-free medium containing 50%(w/v) polyethylene glycol (m.w. 1,000 to 4,000) is added dropwise with mixing. Subsequently, 10 ml of serum-free medium is slowly added and then the mixture centrifuged. The supernatant is discarded again, and the pelleted cells are suspended in an appropriate amount of HAT medium [a solution of hypoxanthin, aminopterin and thymidine (these three compounds, together, are also known as "HAT") and mouse interleukin-2 (IL-2)]. The suspension is then dispensed into the wells of culture plates (also referred herein simply as "plates") and incubated in the presence of 5% v/V $CO_3$ at 37° C. for about 2 weeks, with the supplementary addition of HAT medium as appropriate.

e) Selection of Hybridomas

When the myeloma strain used is resistant to 8-azaguanine, i.e., it is deficient in the hypoxanthin guanine phosphoribosyl transferase (HGPRT) enzyme, any unfused myeloma cells and any myeloma-myeloma fusions are unable to survive in HAT medium. On the other hand, fusions of antibody producing cells with each other, as well as hybridomas of antibody producing cells with myeloma cells can survive, the former only having a limited life. Accordingly, continued incubation in HAT medium results in selection of only the desired hybridomas.

The resulting hybridomas are then grown up into colonies in HAT medium lacking aminopterin (HT medium). Thereafter, aliquots of the culture supernatant are removed to determine anti-Fas antibody titer by, for example, ELISA. When the above recombinant human Fas fusion protein is used as the ELISA antigen, it is also necessary to eliminate clones producing an antibody which specifically binds the extracellular domain of the mouse IL3 receptor. The presence or absence of such a clone may be verified, for example, by ELISA using mouse IL3 receptor, or its extracellular domain, as the antigen.

Although the above selection procedure is exemplified using an 8-azaguanine resistant cell line is used, it will be appreciated that other cell lines may be used with appropriate selection markers and with appropriate modifications to the media used.

f) Cloning

Hybridomas which have been shown to produce anti-Fas specific antibodies, using a method similar to that described in the step b) to determine antibody titer, are then transferred to another place for cloning. Suitable cloning methods include: the limiting dilution method, in which hybridomas are diluted to contain 1 cell per well of a plate and then cultured; the soft agar method, in which colonies are recovered after culturing in soft agar medium; using a micromanipulator to separate a single cell for culture; and "sort-a-clone", in which single cells are separated by a cell sorter. Limiting dilution is generally the most simple and is commonly used.

Whichever cloning procedure is selected is repeated 2 to 4 times for each well demonstrating an antibody titer, and clones having stable antibody titers are selected as anti-Fas monoclonal antibody producing hybridomas. Hybridomas producing an anti mouse Fas antibody are selected by a similar method to obtain an anti-Fas monoclonal antibody producing cell line. A suitable mouse Fas useful for this purpose, for example, is the fusion protein expressed by cultured animal cells transfected with the expression vector pME18S-mFas-AIC. This plasmid has DNA encoding a fusion protein comprising the extracellular domain of mouse Fas and the extracellular domain of the mouse IL3 receptor [c.f. Nishimura, Y., et al., (1995), J. Immunol., 154, 4395–4403, incorporated herein by reference]. Other sources of murine Fas include purified mouse Fas and cells which expressing mouse Fas on their surface.

The mouse-mouse hybridoma HFE7A was selected by the above methodology. Its specific preparation is described in the accompanying Examples. HFE7A is a cell line producing an anti-Fas monoclonal antibody suitable as the base in preparing a humanized anti-Fas antibody of the present invention, and was deposited with the Kogyo Gijutsuin Seimei-Kogaku Kogyo Gijutsu Kenkyujo on Feb. 19, 1997, in accordance with the Budapest Treaty on the Deposition of Microorganisms, and was accorded the accession number FERM BP-5828. Accordingly, when preparing an antibody using the mouse-mouse hybridoma HFE7A, the preparation may be performed by following a procedure starting from step g) below, with steps a) to f), above, omitted.

g) Culture of Hybridoma to Prepare Monoclonal Antibody

The hybridoma obtained by the preceding steps is then cultured in normal medium, rather than HT medium. Large-scale culture can be performed by roller bottle culture, using large culture bottles, or by spinner culture. The supernatant from the large-scale culture is then harvested and purified by a suitable method, such as gel filtration, which is well known to those skilled in the art, to obtain an anti-Fas monoclonal antibody. The hybridoma may also be grown intraperitoneally in a syngeneic mouse, such as a BALB/c mouse or a Nu/Nu mouse, to obtain ascitic fluid containing an anti-Fas monoclonal antibody in large quantities. Commercially available monoclonal antibody purification kits (for example, MAbTrap GII Kit; Pharmacia) may conveniently be used to purify the harvested antibodies.

Monoclonal antibodies prepared as above, and which have been selected for specificity for human and mouse Fas, have a high specificity to human and mouse Fas.

h) Assay of Monoclonal Antibody

Determination of the isotype and the subclass of the monoclonal antibody thus obtained may be performed as follows. Suitable identification methods include the Ouchterlony method, ELISA and RIA. The Ouchterlony method is simple, but requires concentration of the solutions used when the concentration of the monoclonal antibody is low. By contrast, when ELISA or RIA is used, the culture supernatant can be reacted directly with an antigen adsorbed on a solid phase and with secondary antibodies having specificities for the various immunoglobulin isotypes and subclasses to identify the isotype and subclass of the monoclonal antibody. However, in general, it is preferred co use a commercial kit for identification, such as a Mouse Typer Kit (tradename; BioRad).

Quantification of protein may be performed by the Folin-Lowry method, for example, or by calculation based on the absorbance at 280 nm [1.4 ($OD_{280}$)=Immunoglobulin 1 mg/ml].

Identification of the Fas epitope that the monoclonal antibody recognizes may be performed as follows. First, various partial Fas structures are prepared. The partial structures may be prepared synthetically, such as by oligopeptide synthesis, or in vivo by using a suitable host, such as E. coli, which has been transformed by a suitable vector incorporating DNA encoding the desired fragments. Both methods are frequently used in combination for the identification of the epitope recognized by the epitope binding region. For example, a series of polypeptides having appropriately reduced lengths, working from the C- or N-terminus of the antigen protein, can be prepared by genetic engineering techniques well known to those skilled in the art. By establishing which fragments react with the antibody, an approximate idea of the epitopic site can be obtained.

The epitope can be more closely identified by synthesizing a variety of smaller oligopeptides corresponding to portions or mutants of the peptide, or peptides, recognized by the antibody. Oligopeptide synthesis is generally used for the preparation of these smaller fragments. Identification of the epitope may then be established by binding studies or by competitive inhibition studies with the recombinant human Fas fusion protein in ELISA, for example. Commercially available kits, such as the SPOTs Kit (Genosys Biotechnologies, Inc.) and a series of multipin peptide synthesis kits based on the multipin synthesis method (Chiron Corp.) may be conveniently used to obtain a large variety of oligopeptides.

DNA encoding the heavy and light chains of the anti-Fas monoclonal antibody prepared above may be obtained by preparing mRNA from hybridoma cells producing the anti-Fas monoclonal antibody, converting the mRNA into cDNA by reverse transcription, and then isolating the DNA encoding the heavy and or light chains of the antibody, respectively. This DNA may then be used to generate the humanized anti-Fas antibody of the present invention.

Extraction of mRNA can be performed by the guanidinium thiocyanate-hot phenol method or by the guanidinium thiocyanate-guanidinium HCl method, for example, but the guanidinium thiocyanate-cesium chloride method is preferred. Preparation of mRNA from cells is generally performed by first preparing total RNA and then purifying mRNA from the total RNA by using a poly(A)$^+$ RNA purification matrix, such as oligo(dT) cellulose and oligo (dT) latex beads. Alternatively, mRNA may be prepared directly from a cell lysate using such a matrix. Methods for preparing total RNA include: alkaline sucrose density gradient centrifugation [c.f. Dougherty, W. G. and Hiebert, E., (1980), Virology, 101, 466–474]; the guanidinium thiocyanate-phenol method; the guanidinium thiocyanate-trifluorocesium method; and the phenol-SDS method. The currently preferred method uses guanidinium thiocyarate and cesium chloride [c.f. Chirgwin, J. M., et al., (1979), Biochemistry, 18, 5294–5299].

The thus obtained poly(A)$^+$ RNA can be used as the template in a reverse transcriptase reaction to prepare single-strand cDNA [(ss) cDNA]. The (ss) cDNA obtained by the use of reverse transcriptase, as described above, can then be converted to double stranded (ds) cDNA. Suitable methods for obtaining the ds cDNA include the S1 nuclease method [c.f. Efstratiadis, A., et al., (1976), Cell, 7, 279–288], the Gubler-Hoffman method [c.f. Gubler, U. and Hoffman, B. J., (1983), Gene, 25, 263–269] and the Okayama-Berg method [c.f. Okayama, H. and Berg, P., (1982), Mol. Cell. Biol., 2, 161–170]. However, the currently preferred method involves the polymerase chain reaction [PCR—c.f. Saiki, R. K., et al., (1988), Science, 239, 487–491, incorporated herein by reference] using single-strand cDNA as the template. Thus the preferred procedure is labelled "RT-PCR", as it involves reverse transcription and PCR.

The ds cDNA obtained above may then be integrated into a cloning vector and the resulting recombinant vector can then be used to transform a suitable micro-organism, such as E. coli. The transformant can be selected using a standard method, such as by selecting for tetracycline resistance or ampicillin resistance encoded by the recombinant vector. If E. coli is used, then transformation may be effected by the Hanahan method [c.f. Hanahan, D., (1983), J. Mol. Biol., 166, 557–580, incorporated herein by reference]. Alternatively, the recombinant vector may be introduced into competent cells prepared by co-exposure to calcium chloride and either magnesium chloride or rubidium chloride. If a plasmid is used as a vector, then it is highly desirable that the plasmid harbours a drug-resistant gene, such as mentioned above, in order to facilitate selection. Brute force selection is possible, but not preferred. Although plasmids have been discussed, it will be appreciated that other cloning vehicles, such as lambda phages, may be used.

To select transformants for those which carry cDNA encoding a subunit of an anti-human Fas antibody of interest, various methods, such as those described below, can be used. When the cDNA of interest is specifically amplified by RT-PCR, these steps may be omitted.

(1) Screening by Polymerase Chain Reaction

If all or part of the amino acid sequence of the desired protein has been elucidated, then sense and antisense oligonucleotide primers corresponding to separate non-contiguous parts of the amino acid sequence can be synthesised. These primers can then be used in the polymerase chain reaction technique [c.f. Saiki, R. K., et al. (1988), Science, 239, 487–491] to amplify the desired DNA fragment coding for the mouse anti-human Fas monoclonal antibody subunit. The template DNA used in the PCR may be, for example, cDNA synthesized by reverse transcription from mRNA of the hybridoma producing the anti-human Fas monoclonal antibody HFE7A (FERM BP-5828).

The DNA fragment thus synthesised may either be directly integrated into a plasmid vector, such as by using a commercial kit, or may be labelled with, for example, $^{32}$P, $^{35}$S or biotin, and then used as a probe for colony hybridization or plaque hybridization to obtain the desired clone.

Harvesting of DNA encoding each subunit of anti-human Fas monoclonal antibody from the appropriate transformants obtained above may be performed by well known techniques, such as those described by Maniatis, T., et al. [in "Molecular Cloning A Laboratory Manual" Cold Spring Harbor Laboratory, NY, (1982), incorporated herein by reference]. For example, the region of DNA coding for the desired subunit may be excised from plasmid DNA after separating the fraction corresponding to the vector DNA from a transformant which has been determined to possess the necessary plasmid.

(2) Screening Using a Synthetic Oligonucleotide Probe

If all or part of the amino acid sequence of the desired protein has been elucidated, then a short contiguous sequence, which is also representative of the desired protein, may be used to construct an oligonucleotide probe. The probe encodes the amino acid sequence but, owing to the degeneracy of the genetic code, there may be a large number of probes that can be prepared. Thus, an amino acid sequence will normally be selected which can only be encoded by a limited number of oligonucleotides. The number of oligonucleotides which it is necessary to produce can be further reduced by the substitution of inosine where any of the four normal bases can be used. The probe is then suitably labelled, such as with $^{32}P$, $^{35}S$ or biotin, and is then hybridized with denatured, transformed DNA from the transformant which has been immobilised on a nitrocellulose filter. Positive strains show up by detection of the label on the probe.

Wherever appropriate, DNA sequences may be sequenced by various well known methods in the art including, for example, the Maxam-Gilbert chemical modification technique [c.f. Maxam, A. M. and Gilbert, W. (1980) in "Methods in Enzymology" 65, 499–276] and the dideoxy chain termination method using M13 phage [c.f. Messing, J. and Vieira, J. (1982), Gene, 19, 269–276]. In recent years, a further method for sequencing DNA has gained wide acceptance, and involves the use of a fluorogenic dye in place of the conventional radioisotope in the dideoxy method. The whole process is computerised, including the reading of the nucleotide sequence after electrophoresis. Suitable machinery for the process is, for example, the Perkin-Elmer Sequence robot "CATALYST 800" and the Perkin-Elmer model 373A DNA Sequencer. The use of this technique renders the determination of DNA nucleotide sequences both efficient and safe.

By using techniques such as those described above, determination of the DNA sequence can be performed efficiently and safely. Based on the data of the thus determined respective nucleotide sequences of the DNA of the present invention and the respective N-terminal amino acid sequences of the heavy and light chains, the entire amino acid sequences of the heavy and light chains of a monoclonal antibody of the present invention can be determined.

For example, the HFE7A monoclonal antibody of the present invention, which is suitable to provide CDR's for grafting into a humanized antibody of the present invention, is an immunoglobulin G1 (IgG1) molecule and is, thus, a complex composed of γ1 heavy chain and κ light chain subunits. Preferred methods for determining partial amino acid sequences of these respective subunits include, for example, isolating the respective subunits by a suitable technique, such as electrophoresis or column chromatography, and then analyzing the N-terminal amino acid sequences of the respective subunits using, for example, an automated protein sequencer (for example, PPSQ-10, Shimadzu Seisakusyo, K. K.).

The heavy and light chains of an imnmunoglobulin each consist of a variable region and a constant region, the variable region of each chain further consisting of three CDR's and four framework regions flanking the CDR's.

The amino acid sequence of the constant region is constant within any given subclass, regardless of the antigen recognized. On the other hand, the amino acid sequence of the variable region, at least for the CDR's, is specific for each antibody. However, it has been established by comparison studies, using data on amino acid sequences of numerous antibodies, that that both the locations of CDR's and the lengths of framework sequences are roughly similar among antibody subunits belonging to the same subgroup [c.f. Kabat, E. A., et al., (1991), in "Sequences of Proteins of Immunological Interest Vol. II," U.S. Department of Health and Human Services, incorporated herein by reference]. Therefore, by comparing the amino acid sequences of the heavy and light chains of the anti-Fas monoclonal antibody HFE7A with those known amino acid sequence data, for example, the CDR's and the framework regions, as well as the location of the constant region, in each of the amino acid sequences determined above, can be established.

The length of $FRH_1$, i.e., the most N-terminal framework region of heavy chains, has been occasionally found to be shorter than the normal length of 30 amino acids. For example, the shortest known $FRH_1$ in mouse IgG1, of the same subtype as HFE7A, is only 18 amino acids [c.f. Kabat et al., ibid.). Accordingly, in the antibody of the present invention, it will be appreciated that the length of that part of the overall molecule corresponding to $FRH_1$ may be of appropriate length, typically between 18 and 30 amino acids, but preferably about 30 amino acids, provided that the necessary Fas binding activity is not lost. In fact, we have established that activity can be retained, even without grafting the FR into the humanized antibody.

The three-dimensional structure of the Fas binding region is mainly determined by the sequences in the variable regions, with support being provided by the constant regions. The framework regions provide structure to the CDR's which are chemically and structurally configured to interact with the antigen. Accordingly, an existing antibody, or a portion thereof, which recognizes an antigen other than Fas can be selected and modified to recognize Fas by suitable alteration of the CDR's, in accordance with the guidelines above (see, for example, U.S. Pat. No. 5,331, 573). In order to conserve as much binding activity as possible, it is generally preferred to select acceptor chains which have the greatest similarity to the donor chains. Such modified peptides thus modified are useful in the present invention, such as in prevention or treatment of diseases attributable to abnormalities of the Fas/Fas ligand system.

Construction of a mutant wherein one or more amino acids in an amino acid sequence is deleted may be performed, for example, by cassette mutagenesis (c.f. Toshimitsu Kishimoto, "Shin-Seikagaku Jikken Kouza 2. Kakusan III Kumikae DNA Gijutsu," 242–251).

DNA sequences may be prepared by any appropriate method and many are known. A suitable method, especially for shorter sequences, is chemical synthesis using a conventional method, such as the phosphite triester method [c.f. Hunkapiller, M., et al., (1984), Nature, 320, 105–111]. Selection of codons for any amino acid may be from any of the recognized codons corresponding to a desired amino acid, and such selection may be arbitrary, or by taking into account frequency of a given codon in a host, or because it is possible to create a restriction site by appropriate selection, without changing the amino acid sequence, for example. Partial modification of the nucleotide sequence can be accomplished by site specific mutagenesis utilizing synthetic oligonucleotide primers coding for the desired modifications [c.f. Mark, D. F., et al., (1984), Proc. Natl. Acad. Sci. USA, 81, 5662–5666], by conventional techniques.

Hybridization of DNA with DNA encoding the heavy or light chain of an anti-Fas monoclonal antibody of the present invention can be determined, for example, by using an appropriate fragment of DNA of the invention labelled with ($\alpha$-$^{32}$P)dCTP, for example, as a probe by a method such as the random primer method [c.f. Feinberg, A. P. and Vogelstein, B. (1983), Anal. Biochem., 132, 6–13] or by the nick translation method [c.f. Maniatis, T., et al., (1982), in "Molecular Cloning A Laboratory Manual" Cold Spring Harbor Laboratory, NY]. A suitable technique is as follows.

First, the potentially hybridizing DNA is adsorbed onto a nitrocellulose or nylon membrane, for example, being subjected to alkaline treatment if necessary, and then being fixed by heating or UV irradiation. In a preferred method, the membrane is next immersed in prehybridization solution containing 6×SSC (1×SSC is an aqueous solution of 0.15 M NaCl and 0.015 M citric acid tri-sodium), 5% v/v Denhardt solution and 0.1% v/v sodium dodecyl sulfate (SDS), and incubated at 55° C. for 4 hours or more. Then, the probe previously prepared is dissolved in similar prehybridization solution to a final specific activity of 1×10$^6$ cpm/ml, followed by incubation at 60° C. overnight. Subsequently, the membrane is washed at room temperature by repeated washing with 6×SSC for 5 minutes and further with 2×SSC for 20 minutes, and is then subjected to autoradiography.

By using such a method, DNA hybridizable with the DNA coding for the heavy or light chain of an anti-Fas monoclonal antibody which can serve as the basis for a humanized anti-Fas antibody of the present invention is isolatable from any cDNA library or genomic library [c.f. Maniatis, T., et al., (1982), in "Molecular Cloning A Laboratory Manual" Cold Spring Harbor Laboratory, NY]. Such DNA is comprised within the scope of the present invention, the essential features of the hybridization being 6×SSC and 55° C., preferably 60° C. and more preferably 70° C.

Integration of DNA of the present invention thus obtained into an expression vector allows transformation of prokaryotic or eukaryotic host cells. Such expression vectors will typically contain suitable promoters, replication sites and sequences involved in gene expression, thereby allowing the DNA to be expressed in the host cell.

Suitable prokaryotic host cells include, for example, *E. coli* (*Escherichia coli*) and *Bacillus subtilis*. In order to express the gene of interest in such host cells, these host cells may be transformed with a plasmid vector containing a replicon derived from a species compatible with the host, typically having an origin of replication and a promoter sequence, such as lac UV5. These vectors preferably have sequences capable of conferring a selection phenotype on the transformed cell.

A suitable strain of *E. coli* is strain JM109 derived from *E. coli* K12. Suitable vectors include pBR322 and the pUC series plasmids. Suitable promoters include the lactose promoter (lac) the tryptophan lactose promoter (trc), the tryptophan (trp) promoter, the lipoprotein (lpp) promoter, the lambda ($\lambda$) PL promoter derived from bacteriophage $\lambda$, and the polypeptide chain elongation factor Tu (tufB) promoter. In general, it will be appreciated that the present invention is not limited to the use of such hosts, vectors, promoters, etc., as exemplified herein and that any suitable systems may be used, as desired.

A suitable preferred strain of *Bacillus subtilis* is strain 207-25, and a preferred vector is pTUB228 [c.f. Ohmura, K., et al., (1984), J. Biochem., 95, 87–93]. A suitable promoter is the regulatory sequence of the *Bacillus subtilis* a-amylase gene. If desired, the DNA sequence encoding the signal peptide sequence of $\alpha$-amylase may be linked to the DNA of the present invention to enable extracellular secretion.

Eukaryotic hosts include cell hosts from vertebrate and yeast species. An example of vertebrate cells used is the monkey COS-1 cell line [c.f. Gluzman, Y., (1981), Cell, 23, 175–182]. Suitable yeast cell hosts include baker's yeast (*Saccharomyces cerevisiae*), methylotrophic yeast (*Pichia pastoris*) and fission yeast (*Schizosaccharomyces pombe*). It will be appreciated that other hosts may also be used as desired.

In general, the requirements for suitable expression vectors for vertebrate cells are that they comprise: a promoter, usually upstream of the gene to be expressed; an RNA splicing site; a polyadenylation site; and a transcription termination sequence, as well as any other functionalities required, such as an origin of replication. A suitable plasmid is pSV2dhfr containing the SV40 early promoter [c.f. Subramani, S., et. al, (1981), Mol. Cell. Biol., 1, 854–884], but many others are known to those skilled in the art.

Suitable eukaryotic micro-organisms are the yeasts, such as *S. cerevisiae*, and suitable expression vectors for yeasts include pAH301, pAH82 and YEp51. Suitable vectors contain, for example, the promoter of the alcohol dehydrogenase gene [c.f. Bennetzen, J. L. and Hall, B. D., (1982), J. Biol. Chem., 257, 3018–3025] or of the carboxypeptidase Y GAL10 promoter [c.f. Ichikawa, K., et. al, (1993), Biosci. Biotech. Biochem., 57, 1686–1690]. If desired, the DNA sequence encoding the signal peptide sequence of carboxypeptidase Y may be linked, for example, to the DNA to be expressed in order to enable extracellular secretion.

When COS cells are used as hosts, vectors suitably comprise the SV40 replication origin, enabling autonomous replication, a transcription promoter, a transcription termination signal and an RNA splicing site. The expression vectors can be used to transform the cells by any suitable method, such as the DEAE-dextran method [c.f. Luthman, H, and Magnusson, G. (1983), Nucleic Acids Res., 11, 1295–1308], the phosphate calcium-DNA co-precipitation method [c.f. Graham, F. L. and Van der Eb, A. J., (1973), Virology, 52, 456–457] and the electric pulse electroporation method [c.f. Neumann, E., et. al., (1982), EMBO J., 1, 841–845].

In a preferred embodiment, COS cells are co-transfected with two separate expression vectors—one containing DNA encoding a protein comprising at least the variable region of the heavy chain of the HFE7A antibody, preferably as part of a whole humanized heavy chain, and one containing DNA encoding a protein comprising at least the variable region of the light chain of the HFE7A antibody, preferably as part of a whole humanized light chain, these vectors being expressed simultaneously to generate a humanized recombinant anti-human Fas antibody.

Transformants of the present invention may be cultured using conventional methods, the desired proteins being expressed either intra- or extra-cellularly. Suitable culture media include various commonly used media, and will generally be selected according to the host chosen. For example, suitable media for COS cells include RPMI-1640 and Dulbecco's Modified Eagle Minimum Essential medium (DMEM) which can be supplemented with, as desired, fetal bovine serum (FBS).

The culture temperature may be any suitable temperature which does not markedly depress the protein synthesis capability of the cell, and is preferably in the range of 32 to 42° C., most preferably 37° C., especially for mammalian cells. If desired, culture may be effected in an atmosphere containing 1 to 10% (v/v) carbon dioxide.

The transformant strains *E. coli* pME-H and *E. coli* pME-L, each transformed with a recombinant DNA vector for the expression in animal cells of DNA encoding the heavy and light chains, respectively, of an anti-Fas monoclonal antibody useful to prepare humanized anti-Fas antibodies of the present invention, were deposited with the Kogyo Gijutsuin Seimei-Kogaku Kogyo Gijutsu Kenkyujo on Mar. 12, 1997 in accordance with the Budapest Treaty, and the accession numbers FERM BP-5868 and BP-5867, respectively, were accorded them. Therefore, by transforming cultured animal cells such as COS-1 with the recombinant vectors isolated from the deposited strains and culturing the transformant cells, a recombinant anti-Fas antibody can be produced in culture.

The protein expressed by the transformants of the present invention may be isolated and purified by various well known methods of separation according whether the protein is expressed intra- or extra-cellularly and depending on such considerations as the physical and chemical properties of the protein. Suitable specific methods of separation include: treatment with commonly used precipitating agents for protein; various methods of chromatography such as ultrafiltration, molecular sieve chromatography (gel filtration), adsorption chromatography, ion exchange chromatography, affinity chromatography and high performance liquid chromatography (HPLC); dialysis; and combinations thereof.

By the use of such methods as described above, the desired protein can be readily obtained in high yields and high purity.

In order to optimally humanize, in this instance, a mouse anti-Fas monoclonal antibody, it is preferred to graft the variable regions into a human antibody, at least so that the whole of each CDR is incorporated into the human antibody, and preferably also so that significant residues of the FR sequences are grafted into the human antibody in order to maintain as much of the structure of the binding site as possible. This may be accomplished by any one of the following three methods:

1) using heavy and light chains from the same known human antibody; or
2) using heavy and light chains derived from different human antibodies, which have high sequence homology to, or share consensus sequences with, the chains of the donor, while at the same time maintaining the combination of the subgroups of the acceptor chains; or
3) selecting the FR's of heavy and light chains that have the highest homologies with the FR's of the donor from a library of the primary sequences of human antibodies, regardless of the combination of the subgroups.

Such a selection method based upon sequence homology alone, with no other constraints, makes it possible for the donor and the acceptor to share at least 70% amino acid identity in the FR portions. By adopting this approach, it is possible to reduce the number of amino acids grafted from the donor, with respect to known methods, and thus to minimise induction of the HAMA response.

The term 'amino acid sequence homology', as used herein, refers to the similarity of amino acid sequence between two different polypeptides or proteins. Amino acid sequence homology can be assessed by any one of a number of methods, commonly involving the computerised search of sequence databases. These methods are well known to the person skilled in the art. We prefer that the homology is assessed over the length of the framework regions.

It will be appreciated that the role of amino acid residues that occur rarely in the donor subgroup cannot be fully defined, since techniques for predicting the three-dimensional structure of an antibody molecule from its primary sequence (hereinafter referred to as "molecular modelling") have limited accuracy. Known methods, such as the method of Queen and co-workers (Queen et al., supra), do not indicate whether the amino acid residue from the donor or from the acceptor should be selected in such a position. The selection of an acceptor molecule based upon sequence homology alone can significantly reduce the need to make this type of selection.

In the present invention, various humanized antibodies are constructed. Each uses, as a starting point, the HFE7A antibody as a donor. However, the exact nature of the residues transferred to the acceptor molecule and the nature of the acceptor molecule is varied in each case.

In construction of the humanized antibody in which the human monoclonal antibody Eu is used as an acceptor, the above-mentioned method 1) is used, with the FR's being transferred.

In addition, we have discovered a further refinement to this method by the provision of an additional selection procedure, designed to identify amino acids from the donor FR's which are important in the maintenance of the structure and function of the donor CDR regions.

Once the human acceptor molecule has been selected for a given chain, then selection of the amino acid residues to be grafted from a FR of a donor is carried out as follows.

The amino acid sequences of the donor and the acceptor are aligned. If the aligned amino acid residues of the FRs differ at any position, it is necessary to decide which residue should be selected. The residue that is chosen should not interfere with, or only have a minimal effect upon, the three-dimensional structure of the CDRs derived from the donor.

Queen et al. [International Patent Publication No. WO90/07861, incorporated herein by reference] proposed a method for deciding whether an amino acid residue from the donor FR was to be grafted along with the CDR sequence. According to this method, an amino acid residue from a FR region is grafted onto the acceptor, together with the CDR sequence, if the residue meets at least one of the following criteria:

1) The amino acid in the human framework region of the acceptor is rarely found at that position in the acceptor, whereas the corresponding amino acid in the donor is commonly found at that position in the acceptor;
2) the amino acid is closely located to one of the CDR's; and
3) the amino acid has a side-chain atom within approximately 3 Å of a CDR, as judged by a three-dimensional model of the immunoglobulin, and is potentially able to interact with an antigen or a CDR of a humanized antibody.

A residue identified by criterion (2), above, often displays the characteristics of criterion (3). Thus, in the present invention, criterion (2) is omitted and two new criteria are introduced. Accordingly, in the present invention, where an amino acid residue is grafted from a donor FR along with the CDR, it should meet at least one of the following criteria:

a) the amino acid in the human framework region of the acceptor is rarely found at that position in the acceptor, whereas the corresponding amino acid in the donor is commonly found at that position in the acceptor;
b) the amino acid has a side-chain atom within approximately 3 Å of a CDR, as judged by a three-dimensional model of the immunoglobulin, and is potentially able to interact with an antigen or a CDR of a humanized antibody;

c) the amino acid is found in a position which is involved in determining the structure of the canonical class of the CDR;

d) the position of the amino acid is found at the contact surface of the heavy and light chains.

With respect to criterion (a), an amino acid is defined as "common" when it is found at that position in 90% or more of the antibodies of the same subclass [Kabat et al., supra]. An amino acid is defined as "rare" when it is found in less than 10% of antibodies of the same subclass.

With respect to criterion (c), the position of a canonical class determinant residues an be determined unambiguously according to the information provided by Chothia and co-workers [Chothia et al., supra].

With respect to criteria (b) and (d), it is necessary to carry out molecular modeling of the variable regions of the antibody in advance. While any commercially available software for molecular modeling can be used, we prefer that the AbM software is used [Oxford Molecular Limited, Inc.].

Predictions made by molecular modeling have limited accuracy. Therefore, in the present invention, the structure prediction obtained by molecular modeling was assessed by comparing it with X-ray crystallography data from the variable regions of various antibodies.

When using a structural model generated by molecular modeling (such as AbM software), two atoms are presumed to be in contact with each other by Van der Waal's forces when the distance between the two atoms is less than the sum of their Van der Waal's radii plus 0.5 Å. A hydrogen bond is presumed to be present when the distance between polar atoms, such as an amide nitrogen and a carbonyl oxygen of the main and side chains, is shorter than 2.9 Å (the average length for a hydrogen bond) plus 0.5 Å. Furthermore, when the distance between the two oppositely charged atoms is shorter than 2.85 Å plus 0.5 Å, they are presumed to form an ion pair.

The positions of amino acids in the FR which frequently contact a CDR were identified, based upon X-ray crystallography data from the variable regions of various antibodies. These positions were determined irrespective of subgroups. For the light chains, these are positions 1, 2, 3, 4, 5, 23, 35, 36, 46, 48, 49, 58, 69, 71 and 88, and for the heavy chains positions 2, 4, 27, 28, 29, 30, 36, 38, 46, 47, 48, 49, 66, 67, 69, 71, 73, 78, 92, 93, 94 and 103. The above amino acid numbering is defined in accordance with Kabat et al., supra. This numbering system is followed hereinafter. When the same data are analyzed by molecular modeling, the amino acid residues at these positions were shown to be in contact with the amino acid residues of CDR's in two thirds of the antibody variable regions that were examined.

These findings were used to define criterion (b) above. Specifically, if an amino acid position in an FR is predicted both to contact a CDR by molecular modeling and is frequently found experimentally to contact a CDR by X-ray crystallographic analysis, then the grafting of the amino acid residue of the donor is made a priority. In any other case, criterion (b) is not considered.

Similarly, with respect to criterion (d), X-ray crystallography data from the variable regions of a number of antibodies indicates that the amino acid residues at positions 36, 38, 43, 44, 46, 49, 87 and 98 in light chains and those at positions 37, 39, 45, 47, 91, 103 and 104 in heavy chains are frequently involved in the contact between heavy and light chains. If any of these amino acids are predicted to be involved in light and heavy chain contact by molecular modeling, then grafting of the amino acid residue of the donor is given priority. In any other case, criterion (d) is not considered.

In the construction of the humanized antibody based upon the acceptor 8E10'CL in Examples 9–15, both of the heavy chain and the light chain of the antibody of the present invention are designed so that only CDR's from HFE7A as a donor may be grafted. Accordingly, the requirements a) to d) described above are not taken into consideration.

DNA encoding the variable regions of the H and L chains of a humanized anti-human Fas antibody of the present invention may be prepared in a number of ways.

In one method, polynucleotide fragments of between 60 and 70 nucleotides in length may be synthesized which represent partial nucleotide sequences of the desired DNA. The synthesis process is arranged such that the ends of fragments of the sense strand alternate with those of the antisense strand. The resulting polynuclectide fragments can be annealed to one another and ligated by DNA ligase. In this way the desired DNA fragment encoding the variable regions of the H and L chains of the humanized anti-human Fas antibody may be obtained.

Alternatively, DNA coding for the entire variable region of the acceptor may be isolated from human lymphocytes. Site directed mutagenesis, for example, may be used to introduce restriction sites into the regions encoding the CDR's of the donor. The CDR's may then be excised from the acceptor using the relevant restriction enzyme. DNA encoding the CDR's of the donor can then be synthesized and ligated into the acceptor molecule, using DNA ligase.

We prefer that DNA encoding the variable regions of the heavy and light chains of a desired humanized anti-human Fas antibody is obtained by the technique of overlap extension PCR [Horton, et al., (1989), Gene, 77, 61–68, incorporated herein by reference].

Overlap extension PCR allows two DNA fragments, each coding for a desired amino acid sequence, to be joined. For the sake of example, the two fragments are herein designated as (A) and (B). A sense primer (C) of 20 to 40 nucleotides which anneals with a 5'-region of (A) is synthesized, along with an antisense primer of 20 to 40 nucleotides (D), which anneals with a 3'-region of (B). Two further primers are required. First, a chimaeric sense primer (E), which comprises 20 to 30 nucleotides from a 3'-region of (A) joined to 20 to 30 nucleotides from a 5'-region of (B). Secondly, an antisense primer (F) is required, complementary to the sense primer.

A PCR reaction may be carried out using primers (C) and (F), in combination with a DNA template containing fragment A. This allows a DNA product to be produced comprising 20 to 30 nucleotides of the 5'-region of (B) joined to the 3'-end of (A). This fragment is termed fragment (G).

Similarly, PCR may be carried out using primers (D) and (E), in combination with a DNA template containing fragment B. This allows a DNA product to be produced comprising 20 to 30 nucleotides of the 3'-region of (A) joined to the 5'-end of (B). This fragment is termed fragment (H).

The (G) and (H) fragments carry complementary sequences of 40 to 60 nucleotides in the 3'-region of (G) and 40 to 60 nucleotides in the 5'-region of (H), respectively. A PCR reaction may be carried out using a mixture of the (G) and (H) fragments as a template. In the first denaturation step, the DNA becomes single stranded. Most of the DNA returns to the original form in the subsequent annealing step. However, a part of the DNA forms a heterologous DNA duplex, due to the annealing of (G) and (H) fragments in the region of sequence overlap. In the subsequent extension step, the protruding single-stranded portions are repaired to result in chimaeric DNA which represents a ligation of (A) and (B). This DNA fragment is hereinafter referred to as (I). Fragment (I) can be amplified using primer (C) and primer (D).

In embodiments of the present invention, fragments (A) and (B) may represent DNA encoding the CDR regions of the H and L chains of a mouse humanized anti-human Fas monoclonal antibody, DNA coding for the FR regions of human IgG or DNA coding for the secretion signal of human IgG.

The codon or codons which correspond to a desired amino acid are known. When designing a DNA sequence from which to produce a protein, any suitable codon may be selected. For example, a codon can be selected based upon the codon usage of the host. Partial modification of a nucleotide sequence can be accomplished, for example by the standard technique of site directed mutagenesis, utilizing synthetic oligonucleotide primers encoding the desired modifications [Mark, D. F., et al., (1984), Proc. Natl. Acad. Sci. USA, 81, 5662–5666]. By using selected primers to introduce a specific point mutation or mutations, DNA coding for the variable regions of the H and L chains of any desired humanized anti-human Fas antibody can be obtained.

Integration of DNA of the present invention thus obtained into an expression vector allows transformation of prokaryotic or eukaryotic host cells. Such expression vectors will typically contain suitable promoters, replication sites and sequences involved in gene expression, allowing the DNA to be expressed in the host cell.

In general, three transformant strains carrying DNA encoding the variable regions of light chains of humanized anti-Fas antibodies, wherein human monoclonal antibody 8E10 is used as an acceptor, namely *E. coli* pHSGMM6 SANK 73697, *E. coli* pHSGHM17 SANK 73597, *E. coli* PHSGHH7 SANK 73497, as well as a transformant strain carrying DNA encoding the variable region of the heavy chain of the same humanized anti-Fas antibody, namely *E. coli* pgHSL7A62 SANK73397 were deposited in the Kogyo Gijutsuin Seimei-Kogaku Kogyo Gijutsu Kenkyujo on Aug. 22, 1997, in accordance with the Budapest Treaty, and the accession numbers FERM BP-6071, FERM BP-6072, FERM BP-6073, and FERM BP-6074, respectively, were accorded them. Furthermore, two transformant strains carrying DNA encoding the light chains of the same humanized anti-Fas antibodies of the same *E. coli* pHSGHM2 SANK 70198 and *E. coli*pHSHH5 SANK 70398, as well as a transformant strain carrying DNA encoding the heavy chain of the same humanized anti-Fas antibody, namely *E. coli* pgHPDHV3 SANK 70298 were deposited in the Kogyo Gijutsuin Seimei-Kogaku Kogyo Gijutsu Kenkyujo on Feb. 26, 1998, in accordance in the Budapest Treaty, and the accession numbers FERM-6272, FERM-6274 and FERM BP-6273, respectively, were accorded. Therefore, DNA encoding each subunit of the humanized anti-Fas antibody protein can be obtained, for example, by isolating a plasmid from these deposited strains, or by performing PCR using an extract of the deposited strains as a template. The antibody of the present invention can be produced by expressing, in a host cell, DNA obtained by modifying the above mentioned DNA's by, for example, the overlap extension PCR described above.

Three transformant strains carrying DNA encoding the variable regions of the light chains of humanized anti-Fas antibodies of the present invention, namely *E. coli* pHSGLEU15-29-1 SANK 72598, *E. coli* pHSGLEU21-28-8 SANK 72698, *E. coli* pHSGLEU31-6-2 SANK 72798, as well as three transformant strains carrying DNA encoding the variable region of the heavy chain of the same humanized anti-Fas antibody, namely *E. coli* pHSGAB580-3-21 SANK 72898, *E. coli* pHSGHEU222-1-2 SANK 73098, *E. coli* pHSGHEU223-30-1 SANK 72998, were deposited in the Kogyo Gijutsuin Seimei-Kogaku Kogyo Gijutsu Kenkyujo on Sep. 18, 1998, in accordance with the Budapest Treaty, and the accession numbers FERM BP-6512, FERM BP-6511, FERM BP-6513, FERM BP-6515, FERM BP-6514 and FERM BP-6516, were accorded them respectively. Therefore, DNA encoding each subunit of the humanized anti-Fas antibody protein of the present invention can be obtained, for example, by isolating a plasmid from these deposited strains, or by performing PCR using an extract of the deposited strains as the template. A further transformant strain carrying DNA encoding heavy chains of humanized anti-Fas antibodies of the present invention, namely *E. coli* pgHSHHH1 SANK 72198, was deposited in the Kogyo Gijutsuin Seimei-Kogaku Kogyo Gijutsu Kenkyujo on Sep. 18, 1998, in accordance with the Budapest Treaty, and the accession number PERM BP-6510 was accorded thereto.

A high purity, recombinant, anti-Fas antibody can be readily produced in high yields by the methodology described above.

In order to check that a recombinant anti-Fas antibody, prepared as above, specifically binds Fas, ELISA may be performed in a manner similar to that described above for the evaluation of antibody titers in immunized mice.

The HFE7A antibody, and humanized anti-Fas antibodies of the present invention, has the various functional properties a) to f) below, each of which may be verified by, for example, a method described.

Inducing Apoptosis in T Cells Expressing Fas.

Apoptosis-inducing activity in T cells expressing Fas may be assayed by removing the thymus from a mouse which has been given a humanized anti-Fas antibody of the present invention (also referred to hereinbelow as "the antibody"), disrupting the thymus and contacting the cells obtained with T cells and an antibody specific for mouse Fas, and measuring the proportion of the cells to which both antibodies bind by flow cytometry.

Amelioration of the Autoimmune Symptoms of MRL gld/gld Mice.

The antibody is intraperitoneally administered to a MRL gld/gld mouse. These mice carry a mutation in the gene coding for Fas ligand and exhibit symptoms resembling autoimmune diseases [c.f. Shin Yonehara (1994), Nikkei Science Bessatsu, 110, 66–77). The antibody is capable, in many instances, of preventing, or at least ameliorating, swelling of the limbs, which is one of the autoimmune disease-like symptoms.

Failure to Induce Hepatic Disorders.

Peripheral blood is drawn from a BALB/c mouse which has been given the antibody and blood levels of the enzymes glutamic-oxaloacetic transaminase (GOT) and glutamic-pyruvic transaminase (GPT) are measured, using an automated analyzer (for example, Model 7250; Hitachi Seisakusyo, K. K.) together with the reagent for the analyzer (for example, transaminase-HRII; Wako Pure Chemical Industries, Ltd.). Failure to cause elevated blood GOT and GPT levels indicate that the antibody does not induce hepatic disorders upon administration in vivo.

Therapeutic or Prophylactic Effect on Fulminant Hepatitis.

In an experimental system in which fulminant hepatitis is induced in mice by administering the anti-mouse Fas monoclonal antibody Jo2, the effects of administration of the above antibody simultaneously with Jo2 or after administration of Jo2 can be examined. Antibodies of the invention can prevent, to a large degree, all of the effects of Jo2 in mice, thereby demonstrating a protecting effect in the liver.

Preventative Effect on the Onset of Collagen-Induced Arthritis.

The effects of administration of the antibody on a rheumatoid arthritis model elicited by administering to a mouse an emulsion comprising collagen and Freund's complete adjuvant are examined. The antibody has prophylactic properties.

Induction of Apoptosis in Synovial Cells from a Rheumatoid Arthritis Patient.

Synovial cells obtained from an affected region of a patient with rheumatoid arthritis are cultured and the viability of the cells when the above antibody is contained in the culture medium is examined. Surprisingly, proliferation of the synovial cells is inhibited.

Thus, antibodies of the present invention, unlike previous, known, anti-Fas monoclonal antibodies, not only protect normal cells, but also kill abnormal cells. Accordingly, they are useful as prophylactic and therapeutic agents for diseases attributable to abnormalities of the Fas/Fas ligand system.

The ability of the proteins of the present invention to induce apoptosis can be established, for example, by culturing cells such as the human lymphocyte cell line HPB-ALL [Morikawa, S., et al, (1978), Int. J. Cancer, 21, 166–170] or Jurkat (American Type Culture No. TIB-1520) in medium in which the test sample has been or will be added. The survival rate may then be determined by, for example, an MTT assay [Green, L. M., et al., (1984), J. Immunological Methods, 70, 257–268].

Antibodies of the present invention can be used in various pharmaceutical preparations in respect of the various disease conditions connected with abnormalities of the Fas/Fas ligand system, such as those listed above.

Such a prophylactic or therapeutic agent may be administered in any of a variety of forms. Suitable modes of administration include oral administration, such as by tablets, capsules, granules, powders and syrups, or parenteral administration, such as by any suitable form of injection, including intravenous, intramuscular and intradermal, as well as infusions and suppositories. Thus, the present invention also provides methods and therapeutic compositions for treating the conditions referred to above. Such compositions typically comprise a therapeutically effective amount of the protein of the present invention in admixture with a pharmaceutically acceptable carrier therefor, and may be administered in any suitable manner, such as by parenteral, intravenous, subcutaneous or topical administration.

In particular, where the condition to be treated is local, then it is preferred to administer the protein as close as possible to the site. For example, serious rheumatic pain may be experienced in major joints, and the protein may be administered at such locations.

Systemically administered proteins of the present invention are particularly preferably administered in the form of a pyrogen-free, therapeutically, particularly parenterally, acceptable aqueous solution. The preparation of such pharmaceutically acceptable protein solutions with regard to aspects such as pH, isotonicity, stability and the like, is well within the skill of the person skilled in the art. In addition, the compositions of the present invention may comprise such further ingredients as may be deemed appropriate, such as cell growth retardants and other medicaments.

It will be appreciated that the dosage will vary, depending on factors such as the condition, age and body weight of the patient, but usually the dosage for oral administration to an adult ranges between about 0.1 mg and 1,000 mg per day, which may be administered in a single dose or several divided doses. The dosage for parenteral administration typically ranges between 0.1 mg and 1,000 mg, which may be administered by a subcutaneous, intramuscular or intravenous injection (or injections).

A suitable oral administration form of the humanized anti-Fas antibody of the present invention is as an ampoule of a sterile solution or suspension in water or a pharmaceutically acceptable solution. Alternatively, a sterile powder (preferably, prepared by lyophilization of the humanized anti-Fas antibody) may be filled into an ampoule, which may then be diluted with a pharmaceutically acceptable solution for use.

Owing to the fact that the antibodies of the present invention used in human treatment have been humanized, toxicity is very low.

The present invention will now be illustrated by the following Examples. It will be understood that the scope of the present invention is not limited by these Examples.

Any methods, preparations, solutions and such like which are not specifically defined may be found in 'Molecular cloning—A laboratory Handbook' (supra, incorporated herein by reference). All solutions are aqueous and made up in sterile deionised water, unless otherwise specified.

REFERENCE EXAMPLE 1

Preparation of Fas Antigen

In order to obtain a soluble version of human Fas lacking the transmembrane domain, an expression vector was constructed. This vector was designed to encode a fusion protein (the "Fas fusion protein") comprising the extracellular domain of human Fas fused to the extracellular domain of the mouse interleukin 3 (IL3) receptor [c.f. Gorman, D. M. et al., (1990), Proc. Natl. Acad. Sci. USA, 87, 5459–5463]. DNA encoding the human Fas fusion protein was prepared from this vector by PCR. The construction of the vector and preparation of DNA was as follows.

a) Template

The templates used for the PCR to construct the insert encoding the fusion protein were two plasmids. The first plasmid, pME18S-mFas-AIC [c.f. Nishimura, Y. et al., (1995), J. Immunol. 154, 4395–4403], was a DNA expression plasmid vector encoding a fusion protein, comprising the extracellular domain of mouse Fas and the extracellular domain of the mouse IL3 receptor. The second plasmid, pCEV4 [c.f. Itoh, N., et al., (1991), Cell, 66, 233–243], carried cDNA encoding human Fas.

b) PCR Primers

The following oligonucleotide primers were synthesized:

5'-GGGGAATTCC AGTACGGAGT TGGGGAAGCT CTTT-3' (N1: SEQ ID No.12 of the Sequence Listing);

5'-GTTTCTTCTG CCTCTGTCAC CAAGTTAGAT CTGGA-3' (C3N: SEQ ID No.13 of the Sequence Listing);

5'-TCCAGATCTA ACTTGGTGAC AGAGGCAGAA GAAAC-3' (N3N: SEQ ID No.14 of the Sequence Listing); and 5'-CCCTCTAGAC GCGTCACGTG GGCATCAC-3' (CTN2: SEQ ID No.15 of the Sequence Listing).

Unless otherwise specified, all oligonucleotides in these Examples were synthesized using an automated DNA synthesizer (Model 380B; Perkin Elmer Japan, Applied Biosystems Division) following the instructions supplied with the manual [c.f. Matteucci, M. D. and Caruthers, M. H., (1981), J. Am. Chem. Soc., 103, 3185–3191]. After synthesis, each oligonucleotide (primer) was removed from the support, deprotected, and the resulting solution-lyophilized to obtain a powder. This powder was then dissolved in distilled water and stored at −20° C. until required.

c) First Stage of PCR i) A DNA fragment, designated HFAS and encoding the extracellular domain of human Fas, was prepared as follows. PCR was performed using the LA (Long and Accurate) PCR Kit (Takara Shuzo Co., Ltd., Japan).

Composition of the PCR Reaction Solution:
template pCEV4 DNA, 20 ng;
primer N1, 0.5 µg;
primer C3N, 0.5 µg;
10× concentrated LA PCR buffer (provided with the kit), 25 µl;
dNTP's (provided with the kit), 25 µl; and
LA Taq polymerase (provided with the kit), 12.5 units.

Sterile distilled water was added to the solution to a total volume of 250 µl. Unless otherwise specified, dNTP's are provided as an equimolar mixture of dATP, dCTP, dGTP and dTTP.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes (in all PCR reactions described in the Reference Examples, the temperature was regulated using the GeneAmp PCR system 9600; Perkin Elmer, Japan).

ii) A DNA fragment, designated MAIC and encoding the extracellular domain of the mouse IL3 receptor, was prepared as follows.

Composition of the PCR Reaction Solution:
template pME18S-mFas-AIC DNA, 20 ng;
primer N3N, 0.5 µg;
primer CTN2, 0.5 µg;
10-fold concentrated LA PCR buffer, 25 µl;
dNTP's, 25 µl;
LA Taq polymerase, 12.5 units; and
Sterile distilled water to a total volume of 250 µl.

The PCR reaction was conducted as above.

The amplified HFAS and MAIC DNA fragments, thus obtained, were separately first subjected to phenol extraction, then to ethanol precipitation [these two processes are defined in Example 2 (2) 3) a) below], after which the purified fragments were electrophoresed on a 5% w/v polyacrylamide gel. The gel was stained with 1 µg/ml of ethidium bromide to show up DNA under UV light. The bands determined to contain the desired DNA fragments were cut out using a razor blade and the DNA was electroeluted therefrom using an Amicon Centriruter equipped with the centrifuge tube-type ultrafiltration device Centricon-10 (Amicon) After electroelution, the Centricon-10 unit containing the eluate was discarded and centrifuged at 7,500×g for about 1 hour to concentrate the DNA. The DNA was precipitated with ethanol and then dissolved in 20 µl of distilled water.

d) Second Stare of PCR

The FASAIC DNA fragment encoding the human Fas fusion protein (human Fas/murine IL3 receptor) was prepared as follows.

Composition of the PCR Reaction Solution:
template DNA solution HFAS, 20 µl;
template DNA solution MAIC, 20 µl;
primer N1, 0.5 µg;
primer CTN2, 0.5 µg;
10-fold concentrated LA PCR buffer, 25 µl;
dNTP's, 25 µl;
LA Taq polymerase, 12.5 units; and
Sterile distilled water to a total volume of 250 µl.

The PCR reaction was conducted as in c) above.

The amplified FASAIC DNA fragment, thus obtained, was first extracted with phenol, then precipitated with ethanol, after which it was electrophoresed on a 1% w/v polyacrylamide gel. The gel was stained with 1 µg/ml of ethidium bromide to show up DNA under UV light. The band determined to contain the desired DNA fragment was cut out using a razor blade and the DNA was electroeluted therefrom using an Amicon Centriruter equipped with a Centricon-10 device, as described above. After electroelution, the Centricon-10 unit containing the eluate was removed and centrifuged at 7,500×g for about 1 hour to concentrate the DNA, and the DNA was then precipitated with ethanol and finally dissolved in 50 µl of distilled water.

e) Construction of Vectors

The whole of the FASAIC DON, obtained in d) above, was digested with the restriction enzymes EcoRI and XbaI, then extracted with a phenol/chloroform mixture (50% v/v phenol saturated with water, 48% v/v chloroform, 2% v/v isoamyl alcohol), then precipitated with ethanol. The resulting precipitate was suspended in 2 µl of sterile deionized water.

Two micrograms of plasmid pME18S-mFas-AIC were digested with the restriction enzymes EcoRI and XbaI and dephosphorylated [the dephosphorylation process is as defined in Example 2 (2) 3) a) below]. The resulting DNA fragment was then ligated with the restriction-digested FASAIC DNA obtained above using a ligation kit (Takara Shuzo Co., Ltd.). The ligation product was then used in the transformation of E. coli strain DH5α (Gibco BRL) as described by Hanahan [Hanahan, D., (1983), J. Mol. Biol., 166, 557–580]. Plasmid was then obtained from the transformed E. coli by the alkaline-SDS method [c.f. Maniatis, T., et al., (1989), in Molecular Cloning: A Laboratory Manual (2nd Edition), Cold Spring Harbor Laboratory, NY]. The plasmid thus obtained was designated phFas-AIC2.

This plasmid was next further purified using a large scale plasmid preparation kit (MaxiPrep DNA purification system, Promega). 20 µg of purified plasmid DNA was precipitated with ethanol and the precipitate was dissolved in 20 µl of sterile Dulbecco's PBS(−) medium (hereinafter referred to as PBS; Nissui Pharmaceutical Co., Ltd.).

f) Expression

COS-1 cells (American Type Culture Collection No. CRL-1650) were grown to semi-confluence in a culture flask (culture area: 225 $cm^2$; Sumitomo Bakelite, K. K.) containing Dulbecco's modified Eagle medium (DMEM; Nissui Pharmaceutical Co., Ltd., Japan) supplemented with 10% v/v fetal calf serum (FCS; Gibco) at 37° C. under an atmosphere of 5% v/v gaseous $CO_2$. The growth medium was then discarded, and 3 ml of an aqueous solution of 5 g/l trypsin and 2 g/l ethylenediaminetetraacetic acid (trypsin-EDTA solution; Sigma Chemicals, Co.) was added to the flask, which was then incubated at 37° C. for 3 minutes to detach the cells from the flask.

The harvested cells were suspended in PBS, washed twice with PBS, and adjusted to $6 \times 10^7$ cells/ml with PBS. Twenty µl of the resulting cell suspension ($1.2 \times 10^6$ cells) were mixed with 20 µl of the plasmid solution prepared above, and the mixture was introduced into a chamber with electrodes set 2 mm apart (Shimadzu Seisakusyo, K. K.). The chamber was next loaded into gene transfection apparatus (GTE-1; Shimadzu Seisakusyo, K. K.) and pulses of 600 V, duration 30 µsec, were applied twice, 1 second apart. The cell-DNA mixture in the chamber was then introduced into 10 ml of DMEM supplemented with 10% v/v FCS and incubated in a culture flask (culture area: 75 $cm^2$) under 7.5% v/v $CO_2$ at 37° C. for 24 hours. After this time, the culture supernatant was discarded and the cells were washed with serum-free DMEM. Subsequently, 10 ml of serum-free DMEM were added to the washed cells and the mixture was further incubated under 7.5% v/v $CO_2$ at 37° C. for 24 hours, after which time the supernatant was recovered.

The recovered supernatant was dialyzed against 10 mM Tris-HCl (pH 8.0) in a dialysis tube (exclusion m.w. 12,000~14,000; Gibco BRL), and human Fas fusion protein was then further partially purified using FPLC apparatus by Pharmacia under the following conditions:
Column: Resource Q column (trademark; diameter (φ) 6.4× 30 mm; Pharmacia);
Eluent: 10 mM Tris-HCl (pH 8.0);
Flow rate: 5 ml/min;
Elution: NaCl 0.1 M–03 M, linear gradient in 30 minutes.

The eluate was collected in fractions of 5 ml and these were assayed for Fas gene expression product by ELISA (Enzyme-Linked Immunosorbent Assay), as described below. First, 100 μl of each fraction were separately placed into wells of a 96-well microplate (Costar) and incubated at 37° C. for 1 hour. After this time, the solution in the wells was tipped off, and the plate was washed 3 times with 100 μl/well of PBS containing 0.1% v/v Tween 20 (PBS-Tween). After washing, PBS containing 2% w/v bovine serum albumin ("BSA") was added in quantities of 100 μl/well, and the plate was then incubated at 37° C. for 1 hour.

After this time, the wells were washed a further 3 times with 100 μl/well of PBS-Tween, after which 100 μl/well of a solution of anti-mouse IL-3 receptor β subunit monoclonal antibody HC (1 mg/ml; Igaku Seibutsugaku Kenkyujo, K. K.) diluted 100-fold with PBS-Tween was added to each well, and the plate was once again incubated at 37° C. for 1 hour. The wells were then washed 3 times with 100 μl/well of PBS-Tween, and then 100 μl/well of horse radish peroxidase-labeled anti-mouse immunoglobulin antibody (Amersham) diluted 2000-fold with PBS-Tween was added to each well, and the plate was incubated at 37° C. for another 1 hour, after which each well was again washed 3 times with 100 μl PBS-Tween. Horse radish peroxidase substrate (BioRad) was then added in a quantity of 100 μl/well and left for 5 minutes. After this time, the absorbance at 415 nm was measured with a microplate reader (Model 450; Biorad). The 19th to 23rd fractions, inclusive, which had high absorbance values at this wavelength, were collected to prepare the crude human Fas fusion protein sample.

REFERENCE EXAMPLE 2

Immunization of Mice and Preparation of Hybridoma (2-1) Immunization

A sample of 1 ml of the crude human Fas fusion protein solution obtained in Reference Example 1 above (total protein: 100 μg) was taken and, to this, were added 25 μl of 2N HCl. 250 μl of 9% w/v potash alum (final concentration: 1.1% w/v) and 25 μl of 2N NaOH. The resulting mixture was adjusted to a pH of between about 6.5 and 7.0 by the addition of about 120 μl of an aqueous solution of 10%(w/v) sodium hydrogencarbonate and left to stand at room temperature for about 30 minutes. After this time, 200 μl of killed Bordetella pertussis (Wako Pure Chemical Industries, Ltd.; $1.2 \times 10^{11}$ cells/ml) were added to the mixture in order to activate the T cells, and the mixture was administered intraperitoneally to a Fas knock-out mouse. The mouse used was prepared in accordance with the method described by Senju et al. [c.f. Senju, S. et al., (1996), International Immunology, 8, 423]. The mouse was given an intraperitoneal booster injection, after 2 weeks, of crude human Fas fusion protein only (20 μg protein/mouse).

(2—2) Cell Fusion

On the third day after the booster injection, the spleen was removed form the mouse and put into 10 ml of serum-free RPMI 1640 medium (10.4 g/l RPMI 1640 "Nussui" 1; Nissui Pharmaceutical Co., Ltd.) containing 20 mM HEPES buffer (pH 7.3), 350 mg/ml sodium hydrogencarbonate, 0.05 mM β-mercaptoethanol, 50 units/ml penicillin, 50 μg/ml streptomycin and 300 μg/ml L-glutamic acid, and disrupted by passing the organ through a mesh (Cell Strainer; Falcon) using a spatula. The resulting cell suspension was centrifuged to pelletize the spleen cells which were then washed twice with serum-free RPMI medium. The washed cells were then suspended in serum-free RPMI medium and counted.

In the meantime, myeloma NS1 cells (American Type Culture Collection TIB-18) had been grown to a cell density not exceeding $1 \times 10^8$ cells/ml in ASF104 medium (Ajinomoto, K. K.) containing 10% v/v FCS (Gibco BRL) ("ASF medium with serum") at 37° C. under 5% v/v $CO_2$, and these were likewise disrupted, washed, suspended and counted.

An amount of the NS1 cell suspension calculated to contain $3 \times 10^7$ cells was mixed with an amount of the spleen cell suspension calculated to contain $3 \times 10^8$ cells. The resulting mix was centrifuged and the supernatant discarded. The following steps of cell fusion were performed whilst, all the time, keeping the plastic tube containing the pellet at 37° C. in a beaker of warm water.

One ml of 50%(w/v) polyethylene glycol 1500 (Boebringer Manhein) was then slowly added to the tube, all the while stirring the pellet using the tip of a pipette. Subsequently, 1 ml of serum-free RPMI medium, pre-warmed to 37° C., was slowly added in 2 portions, followed by the addition of a further 7 ml of serum-free RPMI medium. The resulting mix was then centrifuged, the supernatant was discarded and 10 ml of hypoxanthin aminopterin thymidine medium ("HAT medium"; Boehringer Manheim) containing 10% v/v FCS were added while stirring gently with the tip of a pipette. A further 20 ml of HAT medium containing 10% v/v FCS was added, and the suspension was dispensed into 96-well cell culture microplates at 100 μl/well and incubated at 37° C. under 5% v/v $CO_2$. After 7 or 8 days, 100 μl/well of fresh HAT medium were used to replace medium in any wells exhibiting a yellowish hue. The fusion cells from these wells were screened by limiting dilution as described below.

(2-3) Limiting Dilution

Thymuses from 4 to 10 week old female BALB/c mice (from Japan SLC, Inc.) were removed, disrupted on a mesh (Cell Strainer; Falcon) as described above, and the disrupted cells were washed twice with hypoxanthin thymidine medium ("HT medium"; Boehringer Manheim) containing 10% v/v FCS. An amount of thymus cells corresponding to those from one mouse were suspended in 30 ml of HT medium containing 10% v/v FCS to produce a feeder cell suspension. The fusion cell preparation obtained above (2—2) was diluted with this feeder cell suspension 10- to 100-fold, and further diluted serially with feeder cell suspension to make suspensions having fusion cell densities of 5, 1 and 0.5 cells/ml. The thus prepared samples were dispensed into wells of 96-well cell culture microplates at 100 μl/well and incubated for 5 days at 37° C. under 5% v/v $CO_2$.

(2-4) Screening

WR19L12a cells [c.f. Itoh, N. et al., (1991), Cell, 66, 233–243] were propagated by incubation in RPMI 1640 medium containing 10% v/v FCS at 37° C. under 5% v/v $CO_2$. WR19L12a cells are derived from mouse T lymphoma WR19L cells (American Type Culture Collection TIB-52) and have been modified to express a gene encoding human Fas. The suspension of propagated WR19L12a cells was adjusted to a cell density of $1 \times 10^7$ cells/ml and aliquots of 50 µl/well were dispensed into the wells of a 96-well microplate, the wells having U-shaped bottoms (Nunc) and the plate was centrifuged (90×g, 4° C., 10 minutes). The supernatant was discarded and 50 µl/well of culture supernatant obtained from the fusion cells cultured in 2-3 above were added to the wells, with mixing.

The resulting mixtures were kept standing on ice for 1 hour and then centrifuged (90×g, 4° C., 10 minutes), and the supernatant removed. The pellets were each washed twice with 100 µl/well of flow cytometry buffer [PBS containing 5% v/v FCS and 0.04%(w/v) sodium azide]. A secondary antibody (50 µl of fluorescein-5-iscthiocyanate (FITC) labeled goat anti-mouse IgG antibody IgG fraction (Organon Technika) diluted 500-fold) was added to the washed cells, and the mixture was kept standing on ice for 1 hour. After further centrifugation (90×g, 4° C., 10 minutes), and removal of the supernatant, the pellet was washed twice with 100 µl/weLl of flow cytometry buffer, and the cells were fixed by adding 50 µl of 3.7% v/v formaldehyde solution and standing on ice for 10 minutes. After centrifugation (90×g, 4° C., 10 minutes) and removal of the supernatant, the pellets were again washed with 100 µl/well of flow cytometry buffer, and suspended in a further 100 µl/well of flow cytometry buffer to produce the flow cytometry samples.

The intensity of FITC fluorescence of the cells in each sample was measured with a flow cytometer (Epics Elite; Coulter; excitation wave length: 488 nm; detection wave length: 530 nm) and fusion cells were selected from samples which had FITC fluorescence intensities clearly higher (FITC fluorescence intensities of about 100 to 1,000) than those for control WR19L12a cells to which no fusion cell supernatant had been added (FITC fluorescence intensity of about 0.3).

(2-5) Cloning

The steps described in (2-3) and (2-4) above were repeated 5 times for the cells selected in (2-4), thereby enabling the selection of several hybridoma clones which each produced a single antibody binding WR19L12a but not binding WR19L. Binding of these antibodies to mouse Fas was examined by using an assay similar to the one described in (2-4), but using L5178YA1 cells. The L5178YA1 cell line expresses murine Fas. L5178YA1 is a cell line produced by transfecting L5178Y cells with a mouse Fas expression vector. L5178Y cells (American Type Culture Collection No. CRL-1722) express almost no Fas.

As a result of this selection procedure, a mouse-mouse hybridoma, designated HFE7A and producing an antibody binding to L5178YA1 cells, but not L5178Y cells, was obtained. This hybridoma, HFE7A, was deposited with Kogyo Gijutsuin Seimei Kogaku Kogyo Gijutsu Kenkyujo on Feb. 20, 1997, in accordance with the Budapest Treaty for the Deposit of Microorganisms, and has been assigned accession No. FERM BP-5828.

The subclass of the antibody produced by the mouse-mouse hybridoma HFE7A (hereinafter referred to simply as "HFE7A") was demonstrated to be IgG1, κ, after testing with a monoclonal antibody isotyping kit (Pierce).

REFERENCE EXAMPLE 3

Purification of HFE7A Monoclonal Antibody

The mouse-mouse hybridoma HFE7A obtained in Reference Example 2 (FERM BP-5828) was grown to a cell density of $1 \times 10^6$ cells/ml by incubation in 1 l of ASF medium, containing 10% v/v FCS, at 37° C. under 5% V/v $CO_2$. The culture was then centrifuged (1,000 r.p.m., 2 minutes) and the supernatant discarded. The cell pellet was washed once with serum-free ASF medium, suspended in 1 l of serum-free ASF medium and incubated for 48 hours at 37° C. under 5% v/v $CO_2$. After this time, the culture was centrifuged (1,000 r.p.m. for 2 minutes) to recover the supernatant. This supernatant was then placed in a dialysis tube (exclusion m.w.: 12,000–14,000; Gibco BRL), and dialyzed against 10 volumes of 10 mM sodium phosphate buffer (pH 8.0). Partial purification of IgG from the inner solution was achieved using a high performance liquid chromatography apparatus (FPLC system; Pharmacia) under the following conditions:

column: DEAE-Sepharose CL-6B column (column size 10 ml; Pharmacia);
eluent: 10 mM sodium phosphate buffer (pH 3.0);
flow rate: 1 ml/min;
elution: linear gradient of 1 M NaCl (0 to 50%, 180 min).

The eluate was collected in fractions of 5 ml and each fraction was assayed for anti-Fas antibody titer by ELRSA using the human Fas fusion protein prepared above.

First, 100 µl/well of the crude human Fas fusion protein solution prepared in Reference Example 1 was introduced into the wells of a 96-well ELISA microplate. After incubation at 37° C. for 1 hour, the solution was discarded and the wells were each washed 3 times with 100 µl/well of PBS-Tween. Then, 100 µl/well of PBS containing 2% BSA was added and incubated at 37° C. for 1 hour. After this time, the cells were washed 3 times with 100 µl/well of PBS-Tween, and then 100 µl samples of the fractions to be assayed were added to the wells, and the plate incubated at 37° C. for 1 hour. Next, after washing each of the wells 3 times with 100 µl/well of PBS-Tween, 100 µl/well of horse radish peroxidase labeled anti-mouse immunoglobulin antibody (Amersham), diluted 2000-fold with PBS-Tween, were added and allowed to react at 37° C. for 1 hour. After this time, each well was washed 3 times with 100 µl/well PBS-Tween. Horse radish peroxidase substrate (BioRad) was added in a quantity of 100 µl/well and left for 5 minutes before reading the absorbance of each well at 415 nm with a microplate reader.

The 21st to 30th fractions, inclusive, which had high absorbance values, were pooled and applied to two antibody affinity purification columns (HighTrap Protein G column, column volume 5 ml; Pharmacia) After washing the columns with equilibrium buffer [20 mM sodium phosphate buffer (pH 7.0), 25 ml/column], antibody was eluted with 15 ml per column of elution buffer [0.1 M glycine-HCl (pH 2.7)]. The eluate was collected in tubes each containing 1.125 ml of 1 M Tris-HCl (pH 9.0) and centrifuged at 3,000×g at 4° C. for 2 hours in the top of a centrifuge tube-type ultrafiltration device (CentriPrep 10; Grace Japan, K. K.) immediately after completion of elution. The filtrate recovered in the bottom of the device was discarded, and 15 ml of PBS was added to the top and the preparation was once again centrifuged at 3,000×g at 4° C. for 2 hours. These same steps were repeated five times, in all. The 5th centrifugation was stopped when the volume of the solution remaining in the top reached 0.5 ml, and this was retained as the HFE7A sample.

REFERENCE EXAMPLE 4 cDNA Cloning (4-1) Preparation of Poly(A)$^+$ RNA

Cells of the mouse-mouse hybridoma HFE7A (FERM BP-5828), obtained in Reference Example 2, were grown to a cell density of 1×10$^6$ cells/ml in 1 l of ASF medium supplemented with 10% v/v FCS at 37° C. under 5% v/v $CO_2$. These cells were harvested by centrifugation and lyzed in the presence of guanidinium thiocyanate solution [4 M guanidinium thiocyanate, 1% v/v Sarcosyl, 20 mM EDTA, 25 mM sodium citrate (pH 7.0), 100 mM 2-mercaptoethanol, 0.1% v/v Antifoam A] and the lysate was recovered. Isolation of poly(A)$^+$ RNA was performed essentially as described in "Molecular Cloning A Laboratory Manual" [c.f. Maniatis, T., et al., (1982), pp. 196–198]. More specifically, the procedure was as follows.

The recovered cell lysate was sucked into and exhausted from a 10 ml-syringe equipped with a 21-gauge needle, several times. The cell lysate was layered over 3 ml of an aqueous solution of 5.7 M cesium chloride, 0.1 M EDTA solution (pH 7.5) in a polyallomer centrifuge tube for the bucket of a RPS-40T rotor (Hitachi Seisakusyo, K. K.). The lysate was then centrifuged at 30,000 r.p.m. at 20° C. for 18 hours, and the resulting pellet was dissolved in 400 µl of distilled water and subjected to ethanol precipitation. The resulting precipitate was again dissolved in 400 µl of distilled water, mixed with an equal volume of a mixture of chloroform and 1-butanol (4:1, v/v), whereafter the aqueous layer was recovered after centrifugation at 5000 r.p.m. for 10 minutes. This aqueous layer was again precipitated with ethanol and the precipitate was dissolved in 600 µl of distilled water. The resulting solution was retained as the total RNA sample.

Poly (A)$^+$ RNA was purified from 600 µg (dry weight) of the total RNA sample, obtained above, by oligo(dT) cellulose chromatography.

More specifically, the total RNA was dissolved in 200 µl of adsorption buffer [0.5 M NaCl, 20 mM Tris-HCl (pH 7.5), 1 mM EDTA, 0.1% v/v sodium dodecyl sulfate (SDS)], then heated at 65° C. for 5 minutes, and then applied to a column of oligo(dt) cellulose (Type 7; Pharmacia) which had been loaded with adsorption buffer. Poly(A)$^+$ RNA was eluted and recovered from the column using elution buffer [10 mM Tris-HCl (pH 7.5), 1 mM EDTA, 0.05% v/v SDS]. A total of 100 µg of poly(A)$^+$ RNA fraction was obtained by this procedure.

(4-2) Determination of the N-Terminal Amino Acid Sequences of the Heavy and Light Chains of HFE7A Ten microliters of the solution containing the anti-human Fas antibody HFE7A, obtained in Reference Example 3, was subjected to SDS-polyacrylamide gel electrophoresis ("SDS-PAGE"), using a gel concentration of 12% w/v, 100 V constant voltage, for 120 minutes. After electrophoresis the gel was immersed in transfer buffer [25 mM Tris-HCl (pH 9.5), 20% methanol, 0.02% v/v SDS] for 5 minutes. After this time, the protein content of the gel was transferred to a polyvinylidene difluoride membrane ("PVDF membrane"; pore size 0.45 µm; Millipore, Japan), presoaked in transfer buffer, using a blotting apparatus (KS-8451; Marysol) under conditions of 10 V constant voltage, 4° C., for 14 hours.

After this time, the PVDF membrane was washed with washing buffer [25 mM NaCl, 10 mM sodium borate buffer (pH 8.0)], then stained in a staining solution (50% v/v methanol, 20% v/v acetic acid and 0.05% w/v Coomassie Brilliant Blue) for 5 minutes to locate the protein bands. The PVDF membrane was then destained with 90% v/v aqueous methanol, and the bands corresponding to the heavy chain (the band with the lower mobility) and light chain (the band with the higher mobility) previously located on the PVDF membrane were excized and washed with deionized water.

The N-terminal amino acid sequences of the heavy and light chains could now be determined by the Edman automated method [c.f. Edman, P., et al., (1967), Eur. J. Biochem., 1, 80] using a gas-phase protein sequencer (PPSQ-10; Shimadzu Seisakusyo, K. K.).

The N-terminal amino acid sequence of the band corresponding to the heavy chain was determined to be:

Gln-Xaa-Gln-Leu-Gln-Gln-Pro-Gly-Ala-Glu-Leu (SEQ ID No. 16 of the Sequence Listing);

and the N-terminal amino acid sequence of the band corresponding to the light chain was determined to be:

Arp-Ile-val-Leu-Thr-Gln-Ser-Pro-Ala-Ser-Leu-Ala-Val-Ser-Leu-Gly-Gln-Arg-Ala-Thr-Ile-Ser (SEQ ID No. 17 of the Sequence Listing).

Comparison of these amino acid sequences with the database of amino acid sequences of antibodies produced by Kabat et al. [c.f. Kabat E. A., et al., (1991), in "Sequences of Proteins of Immunological interest Vol. II," U.S. Department of Health and Human Services] revealed that the heavy chain (γ1 chain) and the light chain (κ chain) of HFE7A belonged to subtypes 2b and 3, respectively. Based on these findings, oligonucleotide primers were synthesized which would be expected to hybridize with portions of the 5'-untranslated regions and the very ends of the 3'-translated regions of the genes belonging to these mouse subtypes [c.f. Kabat et al., ibid.; Matti Kartinen et al., (1988), 25, 859–865; and Heinrich, G., et al., (1984), J. Exp. Med., 159, 417–435]:

5'-GACCTCACCA TGGGATGGA-3' (H1: SEQ ID No. 18 of the Sequence Listing);

5'-TTTACCAGGA GAGTGGGAGA-3' (H2: SEQ ID No. 19 of the Sequence Listing);

5'-AAGAAGCATC CTCTCATCTA-3' (L1: SEQ ID No. 20 of the Sequence Listing); and

5'-ACACTCATTC CTGTTGAAGC-3' (L2: SEQ ID No. 21 of the Sequence Listing).

(4-3) cDNA Cloning cDNA encoding the heavy and light chains of the mouse anti-human Fas monoclonal antibody HFE7A was cloned by a combination of reverse transcription and PCR ("RT-PCR"). Amplification was performed on the poly(A)$^+$ RNA fraction obtained from HFE7A-producing hybridoma cells as described in (4-1) above. The RT-PCR reaction was performed using RNA PCR Kit (AMV) Version 2 (Takara Shuzo Co., Ltd.).

a) The Reverse Transcriptase Reaction

The oligonucleotide primer sets (5'-terminal and 3'-terminal primers), synthesized in (4-2) above, were used as primer pairs for the RT-PCR reaction for the heavy and light chains.

Composition of the Reaction Solution:

poly(A)$^+$ RNA (heavy or light chain, as required), 1 µg;
3'-primer (H2 or L2), 0.3 µg;
Tris-HCl (pH 8.3), 10 mM;
potassium chloride, 50 mM;
dNTP's, 1 mM;
magnesium chloride, 5 mM;
RNase inhibitor (provided with the kit), 0.5 unit;
reverse transcriptase (provided with the kit), 0.25 unit; and redistilled water to a total volume of 20 µl.

The reaction solution was incubated at 55° C. for 30 minutes, 99° C. for 5 minutes and then 5° C. for 5 minutes. The thus treated RT solution was then used in the following PCR stage.

b) PCR

Composition, of the PCR Reaction Solution:
reverse transcriptase reaction solution, 20 µl;
10-fold concentrated RNA PCR buffer (provided with the kit), 10 µl;
magnesium chloride solution (provided with the kit), 10 µl;
Taq polymerase (provided with the kit), 2.5 units;
5'-primer (H1 or L1), final concentration 0.2 µM; and
sterile deionized water to a total volume of 100 µl.

The PCR reaction solution was heated at 94° C. for 2 minutes, then followed by a cycle of 94° C. for 30 seconds, 60° C. for 30 seconds and 72° C. for 1.5 minutes, repeated 28 times.

After the PCR reaction, aliquots of the reaction solutions were electrophoresed on 1.5% w/v agarose gels. Bands of about 1.4 kbp and about 0.7 kbp were found to have been amplified in the reaction solutions, using the primers for the heavy chain and those for the light chain, respectively. This confirmed that cDNA's encoding heavy and light chains had been amplified, as intended. Accordingly, the amplified PCR reaction solutions could be used in the next step of cloning the amplified cDNA's using the TA Cloning kit (Invitrogen). This was performed as follows.

The relevant PCR reaction solution, together with 50 ng of pCRII vector (provided with the TA Cloning kit), was mixed in 1 µl of 10× ligase reaction buffer [6 mM Tris-HCl (pH 7.5), 6 mM magnesium chloride, 5 mM sodium chloride, 7 mM β-mercaptoethanol, 0.1 mM ATP, 2 mM DTT, 1 mM spermidine, and 0.1 mg/ml bovine serum albumin], to which 4 units of T4 DNA ligase (1 µl) had been added. The total volume of the mixture was adjusted to 10 µl with sterile deionized water, and the resulting ligase solution was incubated at 14° C. for 15 hours.

After this time, 2 µl of the ligase reaction solution was added to 50 µl of competent *E. coli* strain TOP10F' (provided with the TA Cloning kit and brought to competence in accordance with the kit's instruction manual) to which 2 µl of 0.5 M β-mercaptoethanol had been added, and the resulting mixture was kept on ice for 30 minutes, then at 42° C. for 30 seconds, and again on ice for 5 minutes. Next, 500 µl of SOC medium (2% v/v tryptone, 0.5% w/v yeast extract, 0.05% w/v sodium chloride, 2.5 mM potassium chloride, 1 mM magnesium chloride, and 20 mM glucose) was added to the culture, and the mixture was incubated for 1 hour at 37° C. with shaking.

After this time, the culture was spread on an L-broth agar plate [1% v/v tryptone, 0.5% w/v yeast extract, 0.5% w/v sodium chloride, 0.1% w/v glucose, and 0.6% w/v bacto-agar (Difco)], containing 100 µg/ml ampicillin, and incubated at 37° C., overnight. Single ampicillin resistant colonies appearing on the plate were selected and scraped off with a platinum transfer loop, and cultured in L-broth medium containing 100 µg/ml ampicillin at 37° C., overnight, with shaking at 200 r.p.m. After incubation, the cells were harvested by centrifugation, from which plasmid DNA was prepared by the alkali method. The thus obtained plasmids were designated as plasmid pCR-H (the plasmid carrying cDNA encoding the heavy chain of HFE7A) or pCR-L (the plasmid carrying cDNA encoding the light chain of HFE7A).

(4—4) Nucleotide Sequence Analysis

The nucleotide sequences of both of the cDNA's encoding the heavy chain of HFE7A (1.4 kbp) and the light chain of HFE7A (0.7 kbp) carried by the plasmids pCR-H and pCR-L, obtained in (4-3) above, were determined by the dideoxy method [c.f. Sanger, F. S., et al., (1977), Proc. Natl. Acad. Sci. USA, 74:5463–5467] using a gene sequence analyzer (Model 310 Genetic Analyzer; Perkin Elmer, Japan).

The cDNA nucleotide sequences of the heavy and light chains of HFE7A, thus determined, are given as SEQ ID Nos. 8 and 10, respectively, in the Sequence Listing. The concomitant, complete amino acid sequences of the heavy and light chains of HFE7A, as coded by the cDNA's, are given as SEQ ID Nos. 9 and 11, respectively, of the Sequence Listing. The N-terminal amino acid sequence of HFE7A heavy chain established in (4-1) above (SEQ ID No. 16 of the Sequence Listing) matched perfectly with the sequence of amino acid Nos. 1 to 11 of SEQ ID No. 9, except for the one uncertain residue. The N-terminal amino acid sequence of the HFE7A light chain (SEQ ID No. 17 of the Sequence Listing) matched exactly the sequence of amino acid Nos. 1 to 22 of SEQ ID No. 11. Thus, the N-termini of the mature heavy and light chain proteins of HFE7A were demonstrated to be amino acids Nos. 1 to 11 and Nos. 1 to 22 in SEQ ID Nos. 9 and 11, respectively.

Furthermore, when the amino acid sequences of the heavy and light chains were compared with the database of amino acid sequences of antibodies [Kabat E. A., et al., (1991), in "Sequences of Proteins of Immunological Interest Vol. II," U.S. Department of Health and Human Services], it was established that, for the heavy chain, amino acid Nos. 1 to 121 of SEQ ID NO. 9 constituted the variable region, while amino acid Nos. 122 to 445 constituted the constant region. For the light chain, amino acid Nos. 1 to 111 of SEQ ID NO. 11 constituted the variable region, while amino acid Nos. 112 to 218 constituted the constant region.

The locations and sequences of the CDR's in the amino acid sequences of the variable regions of the heavy and light chains of HFE7A, as determined above, were also elucidated by comparing the homologies with the same database of amino acid sequences of antibodies [c.f. Kabat E. A., et al., (1991), ibid.]. From this publication, it can be established the lengths of the framework regions in the variable regions are substantially the same, and that the amino acid sequences share common characteristics, among different antibodies of the same subtype. CDR's are unique sequences located between the framework regions. Therefore, by comparing the amino acid sequences of the heavy and light chains of HFE7A with those of the same subtypes in Kabat's work, it was possible to identify the CDR's of HFE7A.

Accordingly, it was established that, in the heavy chain of HFE7A (SEQ ID No. 9 in the Sequence Listing), amino acid Nos. 31 to 35 form $CDRH_1$, amino acid Nos. 50 to 66 form $CDRH_2$ and amino acid Nos. 99 to 110 form $CDRH_3$. The CDR's in the light chain of HFE7A (SEQ ID No. 11 in the Sequence Listing) were identified as amino acid Nos. 24 to 38 ($CDRL_1$), amino acid Nos. 54 to 60 ($CDRL_2$), and amino acid Nos. 93 to 101 ($CDRL_3$).

REFERENCE EXAMPLE 5

Preparation of Recombinant Antibody (5-1) Construction of Expression Plasmid

Recombinant expression vectors for animal cells were constructed by inserting the cDNA's encoding the heavy and light chains of HFE7A (cloned in Reference Example 4) into the expression vector pMS18S [c.f. Hara, T., et al., (1992), EMBO J., 11, 1875]. This was performed as follows.

First, Oligonucleotide Primers:
5'-GGGGAATTCG ACCTCACCAT GGGATGGA-3' (H3: SEQ ID No. 22 of the Sequence Listing) and
5'-GGGTCTAGAC TATTTACCAG GAGAGTGGGA GA-3' (H4: SEQ ID No. 23 of the Sequence Listing)
were synthesized. These primers serve for the introduction of a recognition site for the restriction enzyme EcoRI, for a recognition site for the restriction enzyme XbaI, as well as a termination codon, at the 5'-end and at the 3'-end, respectively, of the heavy chain cDNA carried by plasmid pCR-H.

Oligonucleotide Primers:
5'-GGGGAATTCA AGAAGCATCC TCTCATCTA-3' (L3: SEQ ID No. 24 of the Sequence Listing) and
5'-GGGGCGGCCG CTTACTAACA CTCATTCCTG TTGAAGC-3' (L4: SEQ ID No. 25 of the Sequence Listing)
were also synthesized. These primers serve for the introduction of a recognition site for the restriction enzyme EcoRI, for a recognition site for the restriction enzyme NotI, as well as for a termination codon, at the 5'-end and at the 3'-end, respectively, of the light chain cDNA carried by plasmid pCR-L.

Using these respective primers for the heavy and light chains, PCR was performed as follows.
Composition of the Reaction Solution:
template (pCR-H or pCR-L), 1 μg;
5'-primer (H3 or L3), 40 pmol;
3'-primer (H4 or L4), 40 pmol;
Tris-HCl (pH 8.0), 20 mM;
potassium chloride, 10 mM;
ammonium sulfate, 6 mM;
magnesium chloride, 2 mM;
Triton X-100, 0.1%;
bovine serum albumin, nuclease-free, 10 μg/ml;
dNTP's, 0.25 mM;
native Pfu DNA polymerase (Stratagene), 5 units; and
sterile distilled water to a total volume of 100 μl.
PCR Thermal Conditions:

Initial heating of the reaction solution was at 94° C. for 2 minutes, after which a thermal cycle of 94° C. for 30 seconds, 60° C. for 30 seconds and 75° C. for 1.5 minutes was repeated 28 times.

The resulting amplified DNA was digested with the restriction enzymes EcoRI and XbaI (for the heavy chain) or EcoRI and NotI (for the light chain), and then mixed with the animal cell expression plasmid pME18S [c.f. Hara. T., et al., (1992), EMBO J., 11, 1875] which had either been digested with the restriction enzymes EcoRI and XbaI (for the heavy chain) or EcoRI and NotI (for the light chain) and dephosphorylated using CIP [as described in Example 2 (2) 3) c) below]. One microliter of 4 units of T4 DNA ligase were added to 8 μl of the resulting mixture, and 1 μl of 10× ligase reaction buffer [6 mM Tris-HCl (pH 7.5), 6 mM magnesium chloride, 5 mM sodium chloride, 7 mM β-mercaptoethanol, 0.1 mM ATP, 2 mM DTT, 1 mM spermidine, and 0.1 mg/ml bovine serum albumin] was then also added to the mixture, which was then incubated at 14° C. for 15 hours.

After this time, 2 μl of the incubated ligase reaction solution was mixed with 50 μl of competent *E. coli* strain JM109 at a cell density of 1–2×10⁹ cells/ml (Takara Shuzo Co., Ltd.), and the mixture was kept on ice for 30 minutes, then at 42° C. for 30 seconds, and again on ice for 5 minutes. Then, 500 μl of SOC medium (2% v/v tryptone, 0.5% w/v yeast extract, 0.05% w/v sodium chloride, 2.5 mM w/v potassium chloride, 1 mM magnesium chloride, and 20 mM glucose) was added to the mixture, which was incubated for a further hour, with shaking. Transformant strains were then isolated, and plasmid DNA was prepared from the strains, following the methods described in Reference Example 4 (4-3).

The resulting plasmids were designated pME-H (the expression plasmid vector carrying cDNA encoding the heavy chain of HFE7A) and pME-L (the expression plasmid vector carrying cDNA encoding the light chain of HFE7A).

The transformant *E. coli* strains harboring these plasmids, designated as *E. coli* pME-H and *E. coli* pME-L, were deposited with Kogyo Gijutsuin Seimei-kogaku Gijutsu Kenkyujo on Mar. 12, 1997, in accordance with the Budapest Treaty for the Deposit of Microorganisms, and were accorded the accession numbers FERM BP-5868 and FERM BP-5867, respectively.

(5-2) Expression in COS-7 Cells

Transfection of COS-7 cells with the expression plasmids pME-H and pME-L obtained in (5-1) above was performed by electroporation using a gene transfection apparatus (ECM600; BTX).

COS-7 cells (American Type Culture Collection No. CRL-1651) were grown up to semi-confluence in a culture flask (culture area: 225 cm², Sumitomo Bakelite, K. K.) containing DMEM supplemented with 10% v/v FCS. Subsequently, the medium was discarded and 3 ml of trypsin-EDTA solution (Sigma Chemicals Co.) were added to the cells, followed by incubation at 37° C. for 3 minutes. The cells detached by this process were harvested, washed twice with PBS and then adjusted to a cell density of 5×10⁶ cells/ml with PBS.

Meanwhile, 20 μg each of plasmids pME-H and pME-L, prepared using a large-scale plasmid preparation kit (MaxiPrep DNA Purification System; Promega), were separately precipitated with ethanol and dissolved in 20 μl each of sterile PBS. Where COS-7 cells were cotransfected with both plasmids, 20 μg of each of the plasmids were used and dissolved together in 20 μl of sterile PBS.

Twenty μl of the cell suspension prepared above (1.2×10⁶ cells) and 20 μl of the relevant plasmid solution were mixed and transferred to a chamber with electrodes set at a distance apart of 2 mm (BTX). The chamber was then loaded in the gene transfection apparatus and given a single pulse of 10 msec at 150 V to provide a total charge of 900 μF. The cell-DNA mixture in the chamber was added to 40 ml of DMEM supplemented with 10% v/v FCS and incubated in plastic cell culture dishes under 5% v/v CO₂ at 37° C. for 24 hours. After this time, the culture supernatant was discarded and the cells were washed with serum-free DMEM medium. After that, 40 ml of serum-free DMEM was added to each of the plastic dishes and the supernatant recovered after the cells had been cultured under 5% v/v CO₂ at 37° C. for a further 72 hours.

Using the above method, COS-7 cells were obtained which were transfected with either or both plasmids (as shown below), and the supernatant of each of the transformants was recovered:

(A): pME-H only;
(B): pME-L only; and
(C): cotransfection of pME-H and pME-L.

(5-3) Detection of Anti-Fas Antibody in Transformant Culture Supernatant

Expression of anti-Fas antibody in the culture supernatants obtained in (5-2) above was determined by ELISA, in a manner similar to that described in Reference Example 3, and using the human Fas fusion protein as the antigen. It was established that the production of an antibody reacting with the human Fas antigen fusion protein in the culture supernatant only happened when pME-H and pME-L were both used to cotransfect COS-7 cells [5-2 (C)].

REFERENCE EXAMPLE 6

Epitope Determination (6-1) ELISA

The following peptides were synthesized by Fmoc solid phase synthesis [c.f. Carpino, L. A. and Han, G. Y., (1970), J. Am. Chem. Soc., 92, 5748–5749] using an automated peptide synthesizer (Model 430A; Perkin Elmer, Japan, Applied Biosystems Division):

Arg-Leu-Ser-Ser-Lys-Ser-Val-Asn-Ala-Gln-Val-Thr-Asp-Ile-Asn-Ser-Lys-Gly-Leu (P1: SEQ ID No. 26 of the Sequence Listing);

Val-Thr-Asp-Ile-Asn-Ser-Lys-Gly-Leu-Glu-Leu-Arg-Lys-Thr-Val-Thr-Thr-Val-Glu (P2: SEQ ID No. 27 of the Sequence Listing);

Glu-Leu-Arg-Lys-Thr-Val-Thr-Thr-Val-Glu-Thr-Gln-Asn-Leu-Glu-Gly-Leu-His-His-Asp (P3: SEQ ID No. 28 of the Sequence Listing);

Thr-Gln-Asn-Leu-Glu-Gly-Leu-His-His-Asp-Gly-Gln-Phe-Cys-His-Lys-Pro-Cys-Pro-Pro (P4: SEQ ID No. 29 of the Sequence Listing);

Gly-Gln-Phe-Cys-His-Lys-Pro-Cys-Pro-Pro-Gly-Glu-Arg-Lys-Ala-Arg-Asp-Cys-Thr-Val (P5: SEQ ID No. 30 of the Sequence Listing);

Gly-Glu-Arg-Lys-Ala-Arg-Asp-Cys-Thr-Val-Asn-Gly-Asp-Glu-Pro-Asp-Cys-Val-Pro-Cys-Gln (P6: SEQ ID No. 31 of the Sequence Listing);

Asn-Gly-Asp-Glu-Pro-Asp-Cys-Val-Pro-Cys-Gln-Glu-Gly-Lys-Glu-Tyr-Thr-Asp-Lys-Ala (P7: SEQ ID No. 32 of the Sequence Listing);

Glu-Gly-Lys-Glu-Tyr-Thr-Asp-Lys-Ala-His-Phe-Ser-Ser-Lys-Cys-Arg-Arg-Cys-Arg (P8: SEQ ID No. 33 of the Sequence Listing);

His-Phe-Ser-Ser-Lys-Cys-Arg-Arg-Cys-Arg-Leu-Cys-Asp-Glu-Gly-His-Gly-Leu-Glu-Val (P9: SEQ ID No. 34 of the Sequence Listing);

Leu-Cys-Asp-Glu-Gly-His-Gly-Leu-Glu-Val-Glu-Ile-Asn-Cys-Thr-Arg-Thr-Gln-Asn-Thr (P10: SEQ ID No. 35 of the Sequence Listing);

Glu-Ile-Asn-Cys-Thr-Arg-Thr-Gln-Asn-Thr-Lys-Cys-Arg-Cys-Lys-Pro-Asn-Phe-Phe-Cys (P11: SEQ ID No. 36 of the Sequence Listing);

Lys-Cys-Arg-Cys-Lys-Pro-Asn-Phe-Phe-Cys-Asn-Ser-Thr-Val-Cys-Glu-His-Cys-Asp-Pro (P12: SEQ ID No. 37 of the Sequence Listing);

Asn-Ser-Thr-Val-Cys-Glu-His-Cys-Asp-Pro-Cys-Thr-Lys-Cys-Glu-His-Gly-Ile-Ile-Lys (P13: SEQ ID No. 38 of the Sequence Listing);

Cys-Thr-Lys-Cys-Glu-His-Gly-Ile-Ile-Lys-Glu-Cys-Thr-Leu-Thr-Ser-Asn-Thr-Lys-Cys (P14: SEQ ID No. 39 of the Sequence Listing);

Glu-Cys-Thr-Leu-Thr-Ser-Asn-Thr-Lys-Cys-Lys-Glu-Glu-Gly-Ser-Arg-Ser-Asn (P15: SEQ ID No. 40 of the Sequence Listing); and Ser-Ser-Gly-Lys-Tyr-Glu-Gly-Gly-Asn-Ile-Tyr-Thr-Lys-Lys-Glu-Ala-Phe-Asn-Val-Glu (P16: SEQ ID No. 41 of the Sequence Listing).

P1 to P15 are partial sequences of the amino acid sequence of Nos. 1 to 157 of the extracellular domain of human Fas, with between 9 and 11 amino acid residues overlapping one another. P16 is a negative control having no homology with human Fas.

P1 to P16 were respectively dissolved completely in 48 µl dimethyl sulfoxide (DMSO) and each was then adjusted to adjusted to a final volume of 0.8 ml by the addition of 752 µl PBS containing 1 mM β-mercaptoethanol.

The above peptides each correspond to a portion of the extracellular domain of the human Fas molecule, but with a carboxyl group added to the C-terminus. Each peptide was diluted to 50 µg/ml with 0.05 M carbonate-bicarbonate buffer (pH 9.6), containing 10 mM 2-mercaptoethanol, and 50 µl of each were introduced into a well of a 96-well ELISA microplate (Nunc). The plate was kept standing at 4° C. overnight to allow adsorption of the peptide to the well surface.

After this time, the solution in the wells was discarded and each well was washed 4 times with PBS-Tween. Then, 100 µl of PBS containing 1% (w/v) bovine serum albumin (A3803; Sigma Chemicals Co.) was added to each well and the plate was incubated at 37° C. for 1 hour. The wells were then washed a further 4 times with PBS-Tween, and then 50 µl of HFE7A or CH11 adjusted to 5 µg/ml in PBS was added to each well. The plate was then incubated at 37° C. for 1 hour, and the wells were again washed 4 times with PBS-Tween. After washing, 50 µl of horse radish peroxidase labeled goat anti-mouse immunoglobulin antibody (Amersham), diluted 1000-fold with PBS, was added per well, and the plate was again incubated at 37° C. for 1 hour, after which the wells were washed 4 times with PBS-Tween. Horse radish peroxidase substrate (BioRad) was then added in an amount of 100 µl/well and the plate was allowed to stand at room temperature for 15 minutes before reading the absorbance of each well at 415 nm using a microplate reader (Corona). As a positive control, the human Fas fusion protein prepared in Reference Example 1 was used in place of the synthetic peptides.

Figure 3:
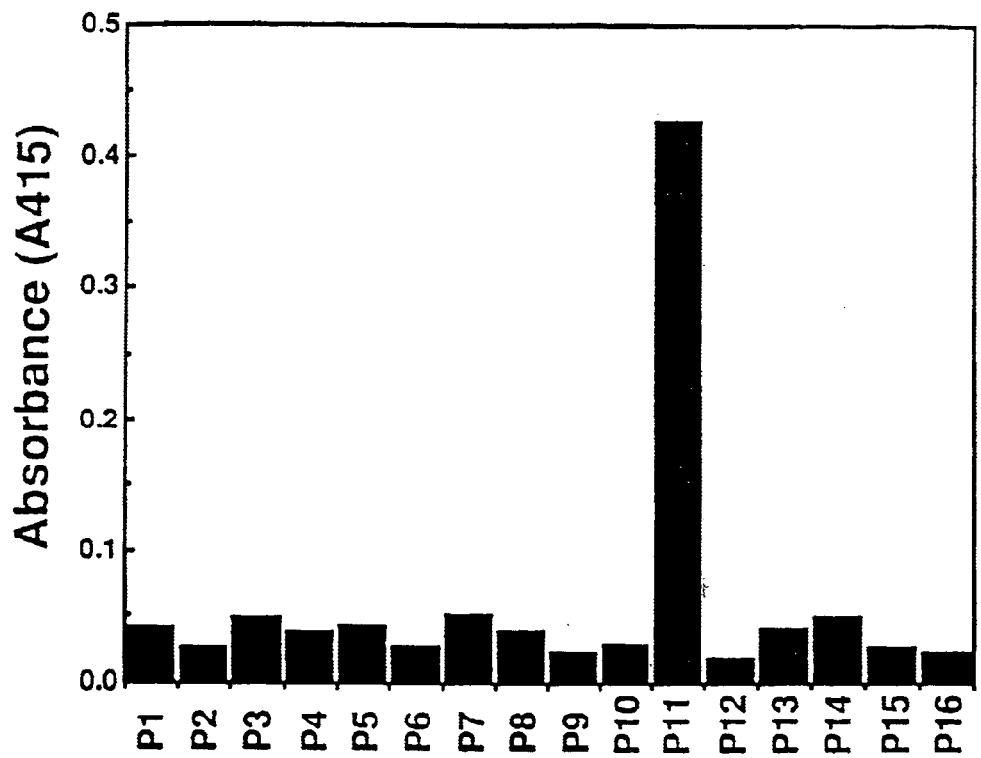
FIG. 3 is a figure showing the results of ELISA for the determination of the epitope recognized by the HFE7A antibody.

Using the above methodology, it was established that only the wells with adsorbed P11 showed high absorbance values, demonstrating that HFE7A specifically binds an amino acid sequence contained in P11 (FIG. 3).

(6-2) Identification of the Epitope Recognized by HFE7A in P11 by Competitive Assay The following peptides were synthesized:

His-Gly-Leu-Glu-Val-Glu-Ile-Asn-Cys-Thr (P95: SEQ ID No. 42 of the Sequence Listing);

Glu-Ile-Asn-Cys-Thr-Arg-Thr-Gln-Asn-Thr (P100: SEQ ID No. 43 of the Sequence Listing);

Arg-Thr-Gln-Asn-Thr-Lys-Cys-Arg-Cys-Lys (P105: SEQ ID No. 1 of the Sequence Listing);

Lys-Cys-Arg-Cys-Lys-Pro-Asn-Phe-Phe-Cys (P110: SEQ ID No. 44 of the Sequence Listing);

Pro-Asn-Phe-Phe-Cys-Asn-Ser-Thr-Val-Cys-Glu-His-Cys-Asp (P115L: SEQ ID No. 45 of the Sequence Listing); and Gly-Lys-Ile-Ala-Ser-Cys-Leu-Asn-Asp-Asn (D355–364: SEQ ID No. 46 of the Sequence Listing).

P95, P100, P105 and P110 are each 10-residue partial sequences of the flanking region (corresponding to amino acids 95 to 128 of the extracellular domain of human Fas) of the amino acid sequence corresponding to P11 in the extracellular domain of human Fas, each having 5 overlapping amino acid residues with the next.

Intended Peptide P115,

Pro-Asn-Phe-Phe-Cys-Asn-Ser-Thr-Val-Cys (P115: amino acid Nos. 1 to 10 of SEQ ID No. 45 of the Sequence Listing) has a 5-residue overlap with a 10-residue peptide P110, but was expected to have poor solubility, So 4 extra residues were added at the C-terminus of P115 to produce P115L.

D355–364 was used as a negative control, this peptide having no homology with human Fas.

Each peptide, except P115L, was dissolved completely in 16 µl DMSO each was then adjusted to a final volume of 0.8 ml by the addition of 784 µl PBS containing 1 mM 2-mercaptoethanol. P115L was dissolved completely in 48 µl DMSO and was then adjusted to a final volume of 0.8 ml by the addition of PBS containing 1 mM 2-mercaptoethanol.

Each of the above peptide solutions (corresponding to 200 µg peptide) were mixed with 0.25 µg of HFE7A in a microtube and adjusted to a total volume of 100 µl with PBS containing 1 mM 2-mercaptoethanol. The mixture was incubated at 37° C. for 2 hours with stirring at 10 to 20 r.p.m., followed by the addition of FCS to a final concentration of 5%, thereby to yield the peptide-antibody mixture.

WR19L12a cells were grown up by a method similar to that described in Reference Example 2. The cells were then recovered by centrifugation and adjusted to a cell density of $1\times10^7$ cells/ml with serum-free RPMI medium. The cell suspension was dispensed into a 96-well plate, with the wells having U-shaped bottoms, at 100 µl/well and centrifuged at 4° C., 1,000 r.p.m. for 3 minutes using a swing rotor for the microplates, and the supernatant was then discarded. Next, 100 µl of peptide-antibody mixture was added to each pellet and mixed by pipetting a few times, as described above. The plate was then allowed to stand at 4° C. for 30 minutes, and was then centrifuged and the supernatant discarded. The pellet was washed 3 times with flow cytometry buffer, and then 50 µl FITC-labeled goat anti-mouse IgG antibody (Kappel), diluted 250-fold with flow cytometry buffer, was added per well, followed by light pipetting to mix the well contents.

The plate was kept in the dark at 4° C. for 30 minutes, then centrifuged and the supernatant discarded. The pellet was washed 3 times with flow cytometry buffer, which contained 10% v/v neutral buffered formaldehyde solution (Wako Pure Chemical Industries, Ltd.) for tissue fixation, this solution being 10-fold diluted with PBS and 50 µl/well was added and mixed with light pipetting. Next, the plate was kept in the dark at 4° C. for at least 12 hours to fix the cells.

After this time, the cells were suspended in 100 µl/well of flow cytometry buffer and centrifuged, in order to remove the supernatant. The pellet was washed 3 times with flow cytometry buffer and suspended in 500 µl/well of flow cytometry buffer, and the resulting suspension was analyzed with a flow cytometer (Cytoace-150; Nippon Bunko, K. K.—excitation wave length: 488 nm; detection wave length: 530 nm) to calculate average intensities of FITC fluorescence per cell. Average intensities of FITC fluorescence for each sample were calculated by taking the value with no peptide-antibody mixture as 0% and the value of the sample containing D355–364 as 100%.

Figure 4:
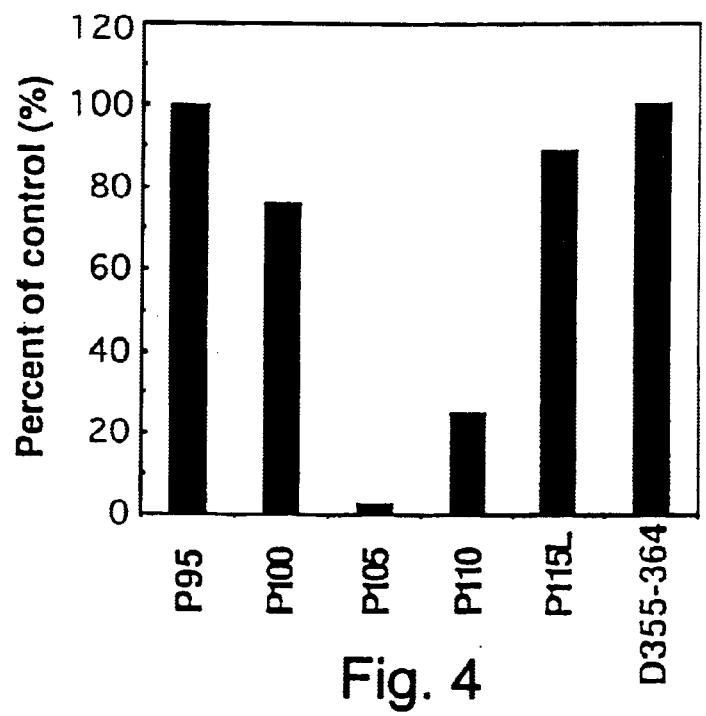
FIG. 4 is a figure showing the results of a competitive assay for the determination of the epitope recognized by the HFE7A antibody.

By the above procedure, it was established that P105 is able to strongly inhibit binding between HFE7A and WR19L12a cells, and that P100 and P110, the amino acid sequence of each of which overlaps 50% with P105, each inhibit binding between HFE7A and WR19L12a cells by about 50% and 60%, respectively. No inhibition was observed with either of P95 and P115L, which also have no overlapping segments shared with P105 (FIG. 4). From these results, it was established that P105 represents an amino acid sequence capable of inhibiting binding between HFE7A and human Fas and that, consequently, the epitope for HFE7A must be located within the amino acid sequence reproduced in P105. This epitopic amino acid sequence is a region which is conserved between human Fas and mouse Fas.

REFERENCE EXAMPLE 7

Binding of HFE7A to Simian Fas

The following test was performed, in order to establish whether HFE7A was able to bind Fas antigen from various primate species.

First, peripheral blood samples were taken from a chimpanzee (Sanwa Kagaku Kenkyujo Kumamoto Primates Park, 40 ml), 20 ml from either a Japanese monkey (*Macaca fuscata*) or from a crab-eating monkey (*Macaca irus*) and 3 ml from a marmoset (of the genus *Hapalide*). The blood samples had 1 ml of heparin (Novoheparin; Novo) added to them and the samples were then slowly layered over an equal volume of Ficol Paque solution [(Pharmacia) specific gravity: 1.077 far all except the crab-eating monkey, which had a specific gravity of 1.072] and centrifuged at 1,700 r.p.m. for 30 minutes in order to obtain a fraction of peripheral blood mononuclear cells. This mononuclear cell fraction was washed twice with Hanks' balanced salt solution and then suspended in RPMI 1640 medium with 10% v/v FCS to a cell density of $1\times10^4$ cells/ml. Phytohemagglutinin-P (Sigma Chemicals, Co.) was added to the resulting suspension to a final concentration of 5 µg/ml and the sample incubated at 37° C. under 5% v/v $CO_2$ for 24 hours. After this time, the cells were recovered by centrifugation, washed and resuspended in RPMI 1640 medium containing 10% v/v FCS. Then, to activate the recovered cells, interleukin-2 (Amersham) was added to the suspension to a final concentration of 10 units/ml, and this was incubated at 37° C. under 5% v/v $CO_2$ for 72 hours.

An amount of the activated preparation calculated to contain $1\times10^6$ activated lymphocyte cells was placed in a test tube and either suspended in 50 µl of 20 µg/ml HFE7A in PBS or 50 µl of PBS alone. The resulting suspension was allowed to stand on ice for 1 hour, after which the cells were washed 3 times with aliquots of 500 µl of PBS and then suspended in 50 µl of 20 µg/ml FITC-labeled anti-mouse IgG antibody (Bioresource) in PBS. This suspension was then placed on ice for 30 minutes, and washed 3 times with aliquots of 500 µl of PBS. Using the cells suspended in 500 µl of PBS as controls, the fluorescence intensities were measured, using a flow cytometer (Cytoace; Nippon Bunko, K. K.).

Distributions of cell numbers by fluorescence intensity were obtained and the proportions of the numbers of the stained cells to those of total cells were calculated. As a result, in the samples without HFE7A, the stained cells constituted less than 3% for all species. However, in the samples treated with HFE7A, at least 17% of the cells were stained, the maximum being 82%. Accordingly, HFE7A is capable of binding a wide range of primate Fas including humans against which HFE7A was originally prepared.

REFERENCE EXAMPLE 8

Apoptosis-Inducing Activity of HFE7A on Murine T Cells In Vivo

Either 500 µl of PBS, alone, or 0.05 or 0.1 mg of HFE7A monoclonal antibody (in 500 µl of PBS) was administered intraperitoneally to the members of groups of three 6-week old female C3H/HeJ mice (from Japan Clea). The mice were anesthetized with ether, 42 hours post administration, and their thymuses removed. These thymuses were washed with RPMI medium containing 10% v/v FCS, and subsequently disrupted, using a spatula on a mesh (Cell Strainer; Falcon). The disrupted cells (which had passed through the mesh) were washed twice with RPMI 1640 medium containing 10% v/v FCS.

Where washing more than once is referred to in any of the Examples herein, it will be understood that the medium with which the washing is performed is replaced with fresh such medium for each wash, unless otherwise required.

The washed cells obtained above were counted and adjusted to $1\times10^6$ cells in 50 µl of RPMI 1640 medium containing 10% v/v FCS. Each of the resulting suspensions was dispensed into a well of a 96-well microplate, the wells having U-shaped bottoms (Nunc) and the plate was then centrifuged (90×g, 4° C., 10 minutes).

The supernatants were discarded and then one of the following two fluorescence-labeled antibody solutions in PBS, (a) or (b), was added to each well:
(a) 10 μl of 0.5 mg/ml of FITC-labeled anti-mouse CD95 (Fas) antibody (Jo2; PharMingen), and 10 μl of 0.5 mg/ml of phycoerythrin (PE) labeled anti-mouse CD90 antibody (Thy-1.2; Cedarlane; CD90 being a cell surface antigen expressed only on T cells);
(b) 10 μl of 0.5 mg/ml of FITC-labeled anti-mouse CD4 antibody (L3T4; PharMingen), and 10 μl of 0.2 mg/ml of PE-labeled anti-mouse CD8 antibody (Ly-2; PharMingen).

After addition of the antibody mixtures, the plate was shaken to mix the contents of the wells and then kept on ice for 1 hour before centrifuging (90×g, 4° C., 10 minutes). After discarding the supernatant and washing the wells twice with 100 μl/well of flow cytometry buffer, cells were fixed by adding 50 μl/well of 3.7% v/v formaldehyde solution and were then stood on ice for 10 minutes. After further centrifugation (90×g, 4° C., 10 minutes) to remove the supernatant, the cell pellets were again washed with 100 μl/well of flow cytometry buffer and suspended in 100 μl/well of flow cytometry buffer. Using the thus obtained cell suspensions from each well as samples, the fluorescence of samples of $1 \times 10^4$ cells was measured, using a flow cytometer (Epics Elite; Coulter) under the following conditions:
excitation wave length: 488 nm;
detection wave length: 530 nm (FITC) or 600 nm (PE).

Fluorescence distributions of FITC and PE for the cell populations of each sample could then be prepared. For the samples to which antibody mixture (a) was added, the proportion of the number of cells that were positive for Fas and CD90 (hereinafter referred to as "Fas$^+$CD90$^+$") relative to the total cell number was calculated. Similarly, for the samples to which antibody mixture (b) was added, the proportion of the number of cells that were positive for CD4 and CD8 (hereinafter referred to as "CD4$^+$CD8$^+$") or those that were positive for CD4 but negative for CD8 (hereinafter referred to as "CD4$^+$CD8$^-$") relative to the total cell number was calculated.

The results are shown as percentages in Table 1, below.

TABLE 1

| Cell | Fas$^+$ CD90$^+$ | CD4$^+$ CD8$^+$ | CD4$^+$ CD8$^-$ |
|---|---|---|---|
| PBS only | 76.2 | 62.6 | 11.7 |
| HFE7A 0.05 mg | 2.3 | 1.9 | 1.2 |
| HFE7A 0.1 mg | 1.7 | 2.8 | 0.7 |

Compared with the group to which PBS only was administered, the proportions of T cells expressing Fas (Fas$^+$CD90$^+$) in the thymus cells of mice from the groups to which HPFE7A was administered were remarkably reduced at both doses. Further, the CD4$^+$CD8$^+$ and CD4$^+$CD8$^-$ cell populations, known for substantial Fas expression, were also markedly reduced in number after HFE7A administration, compared with the PBS only group.

Accordingly, it was deduced that the anti-Fas monoclonal antibody HFE7A had apoptosis-inducing activity, in vivo, on Fas-expressing T cells.

REFERENCE EXAMPLE 9

Effects of HFE7A on an Autoimmune Disease Model

The effects of administration of anti-Fas monoclonal antibody HFE7A on autoimmune disease symptoms were examined using MRL gld/gld mice. These mice carry a mutant of the Fas ligand gene and serve as an animal model of systemic lupus erythematosus-like autoimmune diseases.

18-week old MRL gld/gld mice (from Japan SLC, K. K.), were treated intraperitoneally with a single dose of either 0.2 or 0.5 mg of HFE7A monoclonal antibody prepared in Reference Example 3 (in 500 μl of PBS) or with 500 μl of PBS alone.

Each test mouse was monitored for swelling of the ankles as a symptom of autoimmune disease. The degree of swelling was evaluated and recorded over time for each group [c.f. Shin Yonehara, (1994), Nikkei Science Bessatsu, 110, 66–77]. The degree of swelling of the ankles was observed to markedly decrease with administration of HFE7A.

The thymuses were removed from the test mice and the proportions of T cells which expressed Fas in the thymuses were determined by the method described in Reference Example 8 above. The results showed that the number of Fas-expressing T cells in the thymuses were significantly reduced after the administration of HFE7A, in accordance with the results of Reference Example 8.

REFERENCE EXAMPLE 10

Hepatotoxicity Testing

BALB/c mice were intraperitoneally administered a single dose of one of the following:
i) 0.2 mg HFE7A in 500 μl of PBS;
ii) 0.5 mg HFE7A in 500 μl of PBS;
iii) 0.1 mg Jo2 (PharMingen) in 500 μl of PBS; and
iv) 500 μl of PBS alone.

Figure 5:
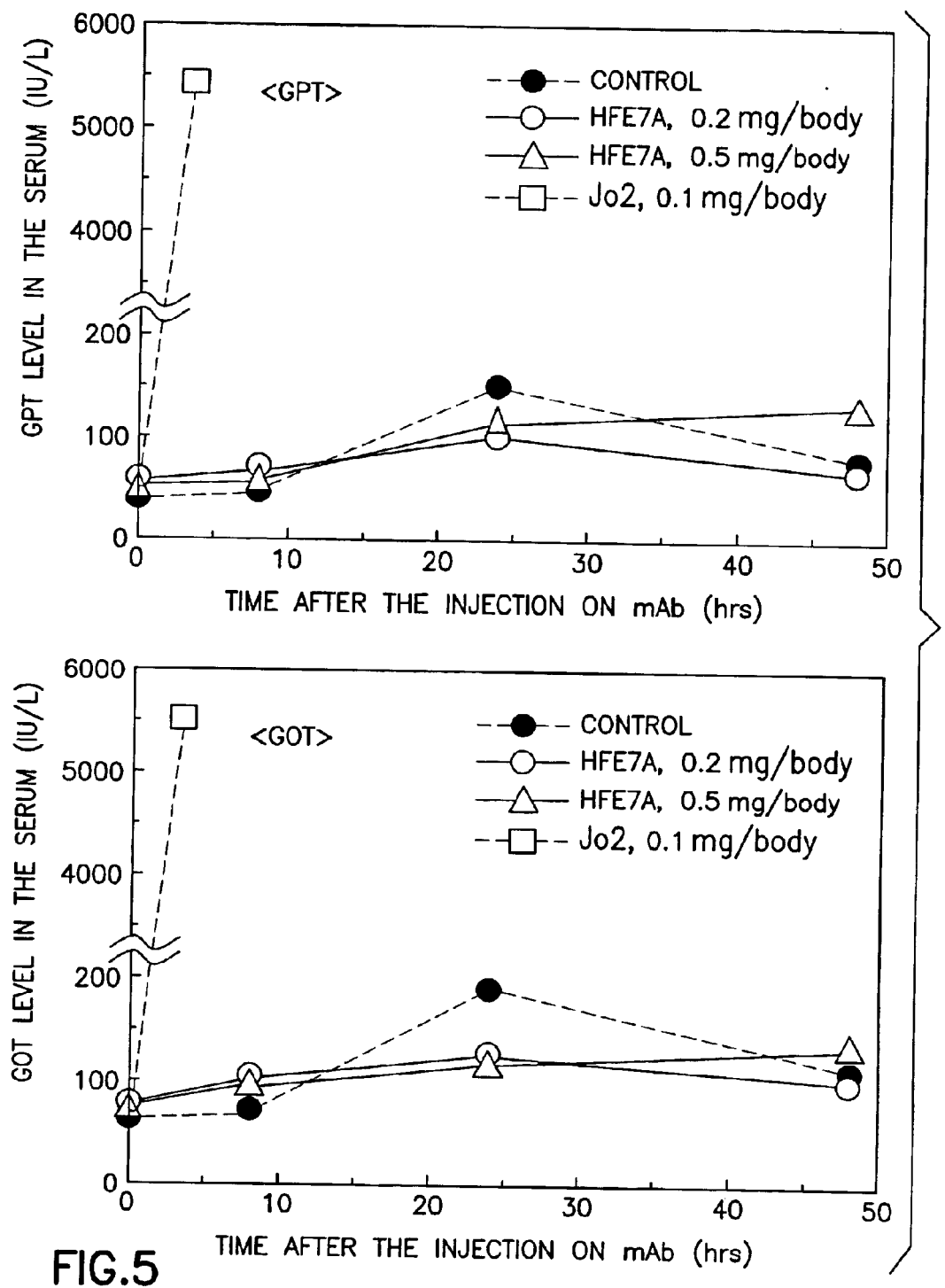
FIG. 5 is a figure showing the results of toxicity testing of HFE7A.

Of the above, Jo2 is a known anti-mouse Fas antibody which has apoptosis-inducing activity. Blood was taken from the posterior aorta of the mice at 8 hours, 24 hours or 72 hours post administration. Blood was taken at 3 hours post administration for the Jo2-treated mice, while they were still alive. All blood was taken under light ether anesthetization. The blood levels of glutamic-oxaloacetic transaminase (GOT) and glutamic-pyruvic transaminase (GPT) were measured for each blood sample, using an automated analyzer (Model 7250; Hitachi Seisakusyo, K. K.) together with the appropriate reagent for the analyzer (Transaminase-HRII; Wako Pure Chemical industries, Ltd.). As a result, the Jo2-treated group showed rapid elevation of GOT and GPT values after 3 hours, whereas the corresponding values for the groups treated with RFE7A showed little change, as with the group treated with PBS only (FIG. 5). From these results, it was could be established that HFE7A did not induce acute hepatic disorders.

REFERENCE EXAMPLE 11

Effects an Fulminant Hepatitis Model

It is known that, upon intraperitoneal administration of the anti-mouse Fas antibody Jo2, a mouse develops fulminant hepatitis and dies within several hours [c.f. Ogasawara, J., et al., (1993), Nature, 364, 806]. Accordingly, in order to evaluate the effects of HFE7A on hepatic disorders induced by Jo2, the viability of mice was tested by administering HFE7A simultaneously with, or subsequently to, Jo2 administration.

Figure 6:
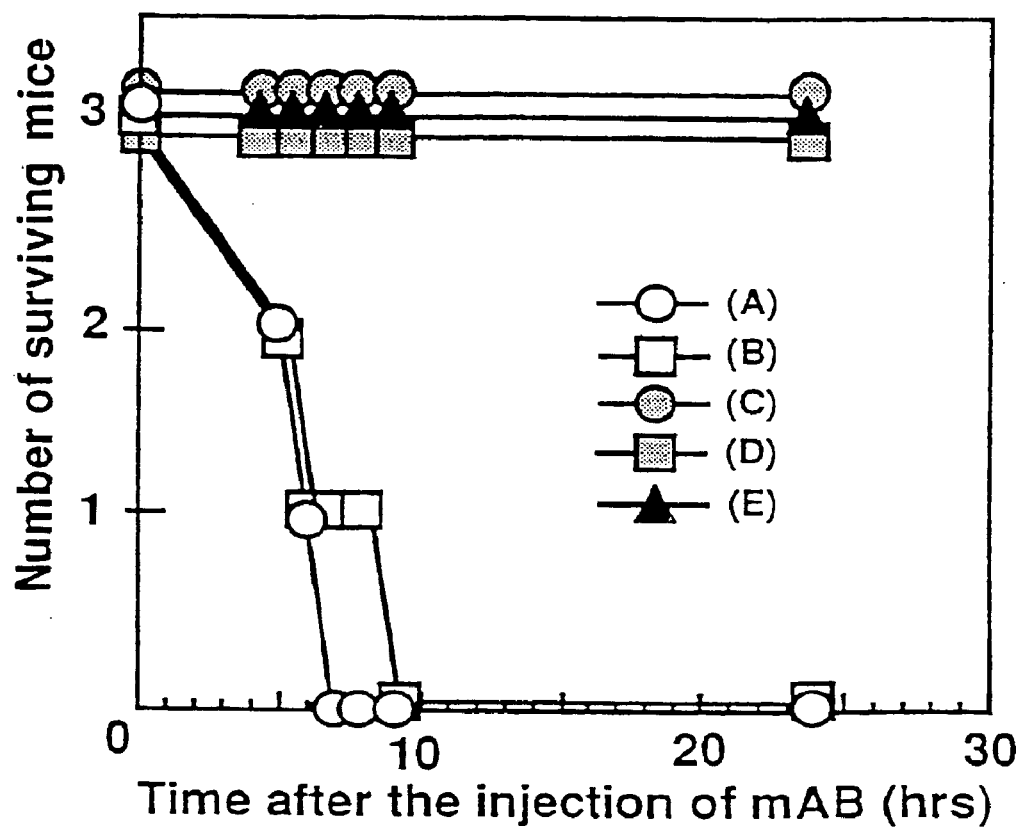
FIG. 6 is a figure showing the results of testing with a fulminant hepatitis model.

Female, 6 week old BALB/c mice (three mice per group; from Japan SLC) received intraperitoneal administration of an antibody preparation as follows:
(A) 0.1 mg of Jo2 in 0.5 ml PBS;
(B) 0.01 mg of Jo2 in 0.5 ml PBS;

(C) 0.1 mg of Jo2 and 0.5 mg of HFE7A together in 0.5 ml PBS (simultaneous administration);
(D) 0.1 mg of Jo2 and 0.05 mg of HFE7A in 0.5 ml PBS (simultaneous administration); and
(E) 0.01 mg of Jo2 in 0.2 ml PBS, followed by 0.1 mg of HFE7A in 0.2 ml PBS after 20 minutes;
and the mice were then observed over time. The results are shown in FIG. 6.

When Jo2 alone was administered, all mice died within 9 hours, regardless of whether they were administered with 0.1 mg or with 0.01 mg Jo2 mouse, i.e., mice of groups (A) and (B) above all died within 9 hours of administration. In contrast, when HFE7A was administered simultaneously with Jo2 (both 0.5 mg/mouse and 0.05 mg/mouse), i.e., groups (C) and (D) above, the mice showed no disorders even for several weeks post administration, demonstrating that HFE7A administration can block the development of fulminant hepatitis. Moreover, mice remained normal, with no apparent symptoms developing, even when HFE7A was administered 20 minutes after Jo2 administration.

Thus, HFE7A has preventive and therapeutic effects on various diseases involving disorders of normal tissues which are mediated by the Fas/Fas ligand system, both in the liver and in other organs.

REFERENCE EXAMPLE 12

Effects on Rheumatoid Arthritis

1) Preventative Effect on the Development of Collagen-Induced Arthritis

F1 mice obtained from the mating of a female BALB/c mouse and a male DBA/1J mouse (CD1F1mice, 6 weeks old, female, from Japan Charles River, K. K.) were tamed for 1 week. After this time, the mice were treated with collagen to induce arthritis.

In more detail, the method was based on one described in the literature [c.f. Phadke, K., (1985), Immunopharmacol., 10, 51–60]. In this method, a 0.3% v/v solution of bovine collagen type II (Collagen Gijutsu Kensyukai, supplied in a 50 mM acetic acid solution) was diluted to 0.2% (2 mg/ml) with further 50 mM acetic acid and then emulsified with an equal volume of Freund's complete adjuvant (Difco). This emulsion was then administered, in an amount of 100 $\mu$l (corresponding to 100 $\mu$g bovine collagen type II), intradermally in the proximal portion of the tail, which was held in a fixing device for intravenous injection, using a 1 ml plastic syringe equipped with a tuberculin needle. An identical booster dose was administered under similar conditions, 1 week after the initial challenge.

At the same time as the booster injection, an injection of 100 $\mu$g of either HFE7A or control mouse IgG in 0.5 ml PBS was administered intraperitoneally (6 mice per group). Starting five weeks after the initial challenge, swelling of the limbs was monitored visually. The degree of swelling of the joints of the limbs was scored based on the method of Wood, F. D., et al. [Int. Arch. Allergy Appl. Immunol., (1969), 35, 456–467]. Accordingly, the following criteria were used in the calculation of the scores for each of the limbs:

Score

0: no symptom;
1: swelling and reddening of only one of the small joints, e.g., of a toe;
2: swelling and reddening of 2 or more small joints, or of one relatively large joint, such as an ankle; and
3: swelling and reddening of a limb in its entirety.

Figure 7:
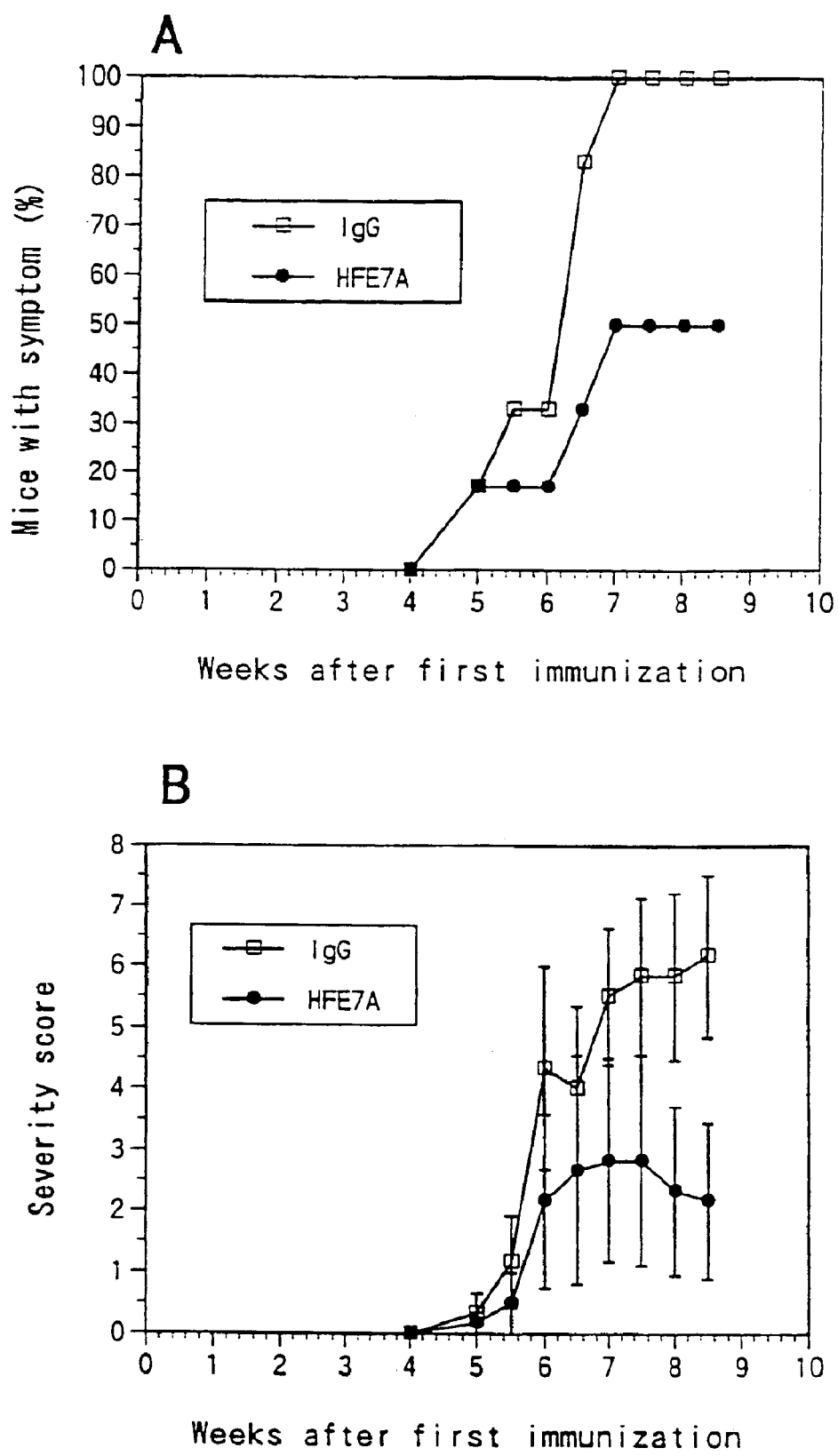
FIG. 7 is a figure showing the results of testing of prevention of collagen-induced arthritis.

Accordingly, the maximum score for one animal is when all 4 limbs swell, and is 12. An animal scoring at least 1 for all four limbs was designated as an "affected mouse." The results are shown in FIG. 7.

In the control group to which non-specific mouse IgG was given, all mice were affected by the 7th week after the initial challenge, whereas in the group to which HFE7A was administered, a half of the mice showed no reddening of any joints at all up to the 8th week (FIG. 7A). In addition, the HFE7A-treated group had a lower average score compared with the control group (FIG. 7B).

2) Apoptosis-Induction in Synovial Cells from Rheumatic Patients

The effects of HFE7A on the viability of synovial cells from patients with rheumatoid arthritis were evaluated. The method was as described below, using the reducing power of the mitochondria as the index.

Synovial tissue obtained from an affected region of a patient with rheumatoid arthritis was cut into small pieces, with scissors, in Dulbecco's modified Eagle medium (Gibco) supplemented with 10% v/v FCS (Summit). The fat was removed and collagenase (Sigma Chemical Co.) was then added to a final concentration of 5 $\mu$g/ml and the mixture was incubated at 37° C. for 90 minutes under 5% v/v $CO_2$. The resulting incubated cells then served as the synovial cells for the remainder of the Experiment.

The thus obtained synovial cells were separated into single cells by treatment with a 0.05% w/v aqueous trypsin solution at 37° C. for 2 minutes, then suspended in Dulbecco's modified Eagle medium containing 10% v/v FCS to a cell density of $1 \times 10^5$/ml. This cell suspension was then dispensed into wells of a 96-well plate at $2 \times 10^4$ cells/200 $\mu$l per well, and incubated at 37° C. under 5% v/v $CO_2$ for 6 days. The culture supernatant was discarded and the cells were washed 3 times with Hank's buffer (Gibco). After washing, 200 $\mu$l of Dulbecco's modified Eagle medium containing lot v/v FCS and between 10 and 1,000 ng/ml of HFE7A (serial 10-fold dilutions) were added to each well and the plate further incubated at 370° C. under 5% v/v $CO_2$ for 20 hours. Next, 50 $\mu$l of an aqueous solution of 1 mg/ml XTT (2,3-bis[2-methoxy-4-nitro-5-sulfophenyl]-2H-tetrazolium-5-carboxanilide inner salt; Sigma Chemical Co.) and 25 $\mu$M PMS (phenazine methosulfate; Sigma Chemical Co.) was added to each well (final concentrations: 250 $\mu$g/ml XTT and 5 $\mu$M PMS). After a further 4 hours of incubation at 37° C. under 5% v/v $CO_2$, the absorbance of each well was read at 450 nm.

The viability of cells in each well was calculated according to the following formula:

$$\text{Viability } (\%) = 100 \times (a-b)/(c-b),$$

wherein "a" is the absorbence of a test well, "b" is the absorbance of a well with no cells, and "c" is the absorbance of a well with no antibody added The result are shown in Table 2. HFE7A inhibited the survival of synovial cells from patient with rheumatism in a dose-dependent manner.

TABLE 2

| HFE7A concentration (ng/ml) | Average viability (%) |
| --- | --- |
| 0 | 100 |
| 10 | 91 |
| 100 | 77 |
| 1000 | 42 |

REFERENCE EXAMPLE 13

Designing a Humanized Version of the HFE7A Antibody (1) Molecular Modeling of the Variable Regions of HFE7A Molecular modeling of the variable regions of HFE7was performed by the method generally known as homology modeling [c.f. Methods in Enzymology, 203, 121–153, (1991)].

The primary sequences of variable regions of human immunoglobulin registered in the Protein Data Bank (hereinafter referred to as the "PDB"; Chemistry Department, Building 555, Brookhaven National Laboratory, P.O. Box 5000, Upton, N.Y. 11973-5000, USA), for which X-ray crystallography had been performed, were compared with the framework regions of HPE7A determined above. As a result, 1GGI and 2HFL were selected as having the highest homologies of the three-dimensional structures of the framework regions for the light and heavy chains, respectively. Three-dimensional structures of the framework regions were generated by combining the properties of 1GGI and 2HFL and by calculating the properties of the regions of HFE7A, as described below, to obtain the "framework model".

Using the classification described by Chothia et al., the CDR's of HFE7A could be classified as follows: $CDRL_2$, $CDRL_3$ and $CDRH_1$ all belong to canonical class 1, while $CDRL_1$, $CDRH_2$ and $CDRH_3$ do not currently appear to belong to any specific canonical class. The CDR loops of $CDRL_2$, $CDRL_3$ and $CDRH_1$ were ascribed the conformations inherent to their respective canonical classes, and then integrated into the framework model. $CDRL_1$ was assigned the conformation of cluster 15B, in accordance with the classification of Thornton et al. [c.f. J. Mol. Biol., 263, 800–815, (1996)]. For $CDRH_2$ and $CDRH_3$, conformations of sequences with high homologies were selected from the PDB and then these were combined with the results of energy calculations. The conformations of the CDR loops with the highest probabilities were then taken and integrated into the framework model.

Finally, energy calculations were carried out to eliminate undesirable contact between inappropriate atoms, in terms of energy, in order to obtain an overall molecular model of HFE7A. The above procedure was performed using the commercially available common molecular modeling system, AbM (Oxford Molecular Limited, Inc.), although any other appropriate system could have been used.

For the molecular model obtained, the accuracy of the structure was further evaluated using the software, PROCHECK [J. Appl. Cryst., (1993), 26, 283–291], and the degree of surface exposure of each residue was calculated to determine which surface atoms and groups interacted.

(2) Selection of the Acceptors

The subgroups of the light and heavy chains of HFE7A shared identities of 79% with the subgroup κIV and also 79% with the subgroup I, respectively, by comparison with the consensus sequences of the respective subgroups of human antibodies. However, there was no human antibody having a combination of a κIV light chain and a sub-group I heavy chain. Thus, 8E10'CL, which has a light chain of subgroup κIII and a heavy chain of subgroup I, having 72% and 77% sequence identities with the light and heavy chains of HFE7A, respectively, was selected as the single human antibody which had light and heavy chains which both had an identity of greater than 70% with the light and heavy chains of HFE7A.

(3) Selection of Donor Residues to be Grafted onto the Acceptors

Using the software, Cameleon (Oxford Molecular Limited, Inc.), the amino acid sequence of each of the light and heavy chains of HPE7A was aligned with that of the relevant chain of 8E10'CL, and humanized sequences of the variable regions were made as described in the following Examples in accordance with the general guidelines set out in a) to e) above. Plasmids were constructed which could serve as recombinant vectors comprising DNA nucleotide sequences encoding humanized anti-human Fas antibodies.

REFERENCE EXAMPLE 14

Preparation of DNA Encoding Humanized Light Chain (1) Cloning of cDNA Encoding a Full-Length Human Light Chain (κ Chain)

Prior to humanization of the light chain amino acid sequence of the mouse anti-human Fas antibody HFE7A, cDNA cloning of a human immunoglobulin light chain comprising the constant region was first performed.

1) Synthesis of Primers

Separation of cDNA encoding a human light chain was carried out by PCR. For the PCR, the following two primers were synthesized:

5'-GCGAATTCTG CCTTGACTGA TCAGAGTTTC CTCA-3' (HVKII5-4: SEQ ID No. 47 of the Sequence Listing); and 5'-GCTCTAGATG AGGTGAAAGA TGAGCTGGAG GA-3' (HKCL3-3: SEQ ID No. 48 of the Sequence Listing).

2) Construction of a Plasmid Containing Human Immunoglobulin Light Chain cDNA cDNA encoding a full-length human immunoglobulin light chain was prepared by PCR, inserted into a plasmid and cloned into *E. coli*.

The HL-DNA fragment encoding a full-length human immunoglobulin light chain was prepared under the following conditions:

Composition of the PCR Reaction Solution:
human lymphocyte cDNA library (Life Technologies), 25 ng;
oligonucleotide primer HVKII5-4, 50 pmol;
oligonucleotide primer HKCL3-3, 50 pmol;
25 mM dNTP cocktail, 10 µl;
100 mM Tris-HCl buffer (pH 8.5), 10 µl;
1 M potassium chloride [KCl], 5 µl;
25 mm magnesium chloride [$MgCl_2$], 10 µl;
Taq DNA polymerase (Perkin Elmer Japan), 1 unit;
Redistilled water to a total volume of 100 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The thus prepared HL-DNA (human light chain DNA) fragment was inserted into plasmid pCR3DNA using a eukaryote TA Cloning Kit (Invitrogen), following the manufacturer's protocol, and introduced into competent *E. coli* TOP10F' contained in the kit, and following the instructions in the kit. Plasmid pHL15-27 carrying the HL-DNA fragment, i.e., cDNA for a human immunoglobulin light chain, was thereby obtained.

(2) Construction of Expression Vectors for the Light Chains of Humanized Versions of the HFE7A Antibody 1) Construction of Expression Plasmid Vectors for Humanized HFE7A Light Chain Humanization of the amino acid sequence of the light chain of the mouse anti-human Fas antibody HFE7A entailed replacing the 47th amino acid (proline) and the 49th amino acid (lysine) from the N-terminus of the amino acid sequence of the light chain (hereinafter referred to as "region I") with alanine and arginine, respectively. Alanine (47) and arginine (49) are conserved in the human light chain (κ chain). Further humanization was also performed, and entailed replacing the 80th amino acid (histidine), the 81st amino acid (proline), the 82nd amino acid (valine), the 84th amino acid (glutamic acid), the 85th amino acid (glutamic acid), the 87th amino acid (alanine) and the 89th amino acid (threonine) (hereinafter referred to as "region II") with serine, arginine, leucine, proline, alanine, phenylalanine and valine, respectively, as these are also conserved in the human light chain (κ chain).

Where both regions I and II were humanized, the sequence was designated as "HH type."

Where only region I was humanized, the sequence was designated as "HM type."

Where neither region was humanized, the sequence was designated as "MM type."

Expression plasmids, respectively carrying these 3 types of humanized light chain amino acid sequences from the anti-human Fas antibody HFE7A, were constructed as follows.

2) Synthesis of Primers for Preparing the Variable and Constant Regions of the Light Chain of Humanized HFE7A PCR was used to construct the following DNA sequences, each of which comprised one of the HH, HM or MM sequences described above, together with the constant region of the human immunoglobulin light chain (κ chain):

DNA (SEQ ID No. 49 of the Sequence Listing) encoding the HH type polypeptide chain (SEQ ID No. 50 of the Sequence Listing);

DNA (SEQ ID No. 51 of the Sequence Listing) encoding the HM type polypeptide chain (SEQ ID No. 52 of the Sequence Listing); and DNA (SEQ ID No. 53 of the Sequence Listing) encoding the MM type polypeptide chain (SEQ ID No. 54 of the Sequence Listing).

The following 13 oligonucleotide PCR primers were synthesized:

5'-CCCAAGCTTA AGAAGCATCC TCTCATCTAG TTCT-3' (7AL1P; SEQ ID No. 55);

5'-GAGAGGGTGG CCCTCTCCCC TGGAGACAGA GACAAAGTAC CTGG-3' (7AL1N; SEQ ID No. 56);

5'-CCAGGTACTT TGTCTCTGTC TCCAGGGGAG AGGGCCACCC TCTC-3' (7AL2P; SEQ ID No. 57);

5'-GATTCGAGAT TGGATGCAGC ATAGATGAGG AGTCTGGGTG CCTG-3' (7AL2N; SEQ ID No. 58);

5'-GCTGCATCCA ATCTCGAATC TGGBATCCCA GACAGGTTTA GTGGC-3' (7AL3PA; SEQ ID No. 59);

5'-AAAATCCGCC GGCTCCAGAC GAGAGATGGT GAGGGTGAAG TCTGTCCCAG AC-3' (7AL3N; SEQ ID No. 60);

5'-CTCGTCTGGA GCCGGCGGAT TTGCAGTCT ATTACTGTCA GCRAAGTAAT GAGGATCC-3' (7AL4P; SEQ ID No. 61);

5'-TGAAGACAGA TGGTGCAGCC ACAGTCCGTT TGATTTCCAG CCTGGTGCCT TGACC-3' (7AL4N; SEQ ID No 62);

5'-GGTCAAGGCA CCAGGCRGGA AATCAAACGG ACTGTGGCTG CACCATCTGT CTTCA-3' (7ALCP; SEQ ID No. 63);

5'-CCCGAATTCT TACTAACACT CRCCCCTGTT GAAGCTCTTT GTGAC-3' (7ALCN; SEQ ID No. 64);

5'-TCTGTCCCAG ACCCACTGCC ACTAAACCTG TCTGGGATCC CAGATTCGAG ATTGG-3' (M7AL2N; SEQ ID No. 65);

5'-GTTTAGTGGC AGTGGGTCTG GGACAGACTT CACCTCTACC ATCCATCCTG TGGAG-3' (M7AL3PA; SEQ ID No. 66); and 5'-ATGGTGCAGC CACAGTCCGT TTGATTTCCA GCCTGGTGCC TTGACCGAAC GTCCG-3' (7AL4NA; SEQ ID No. 67).

3) Construction of Plasmid p7AL-HH (Expression Plasmid for Humanized HH Type HPE7A Light Chain)

The VHH-DNA fragment (SEQ ID No. 49 of the Sequence Listing) encoding the amino acid sequence of SEQ ID No. 50 of the Sequence Listing was prepared by performing 3-stage PCR, and then inserted into a plasmid vector and cloned into E. coli.

a) First Stage PCR

Figure 8:
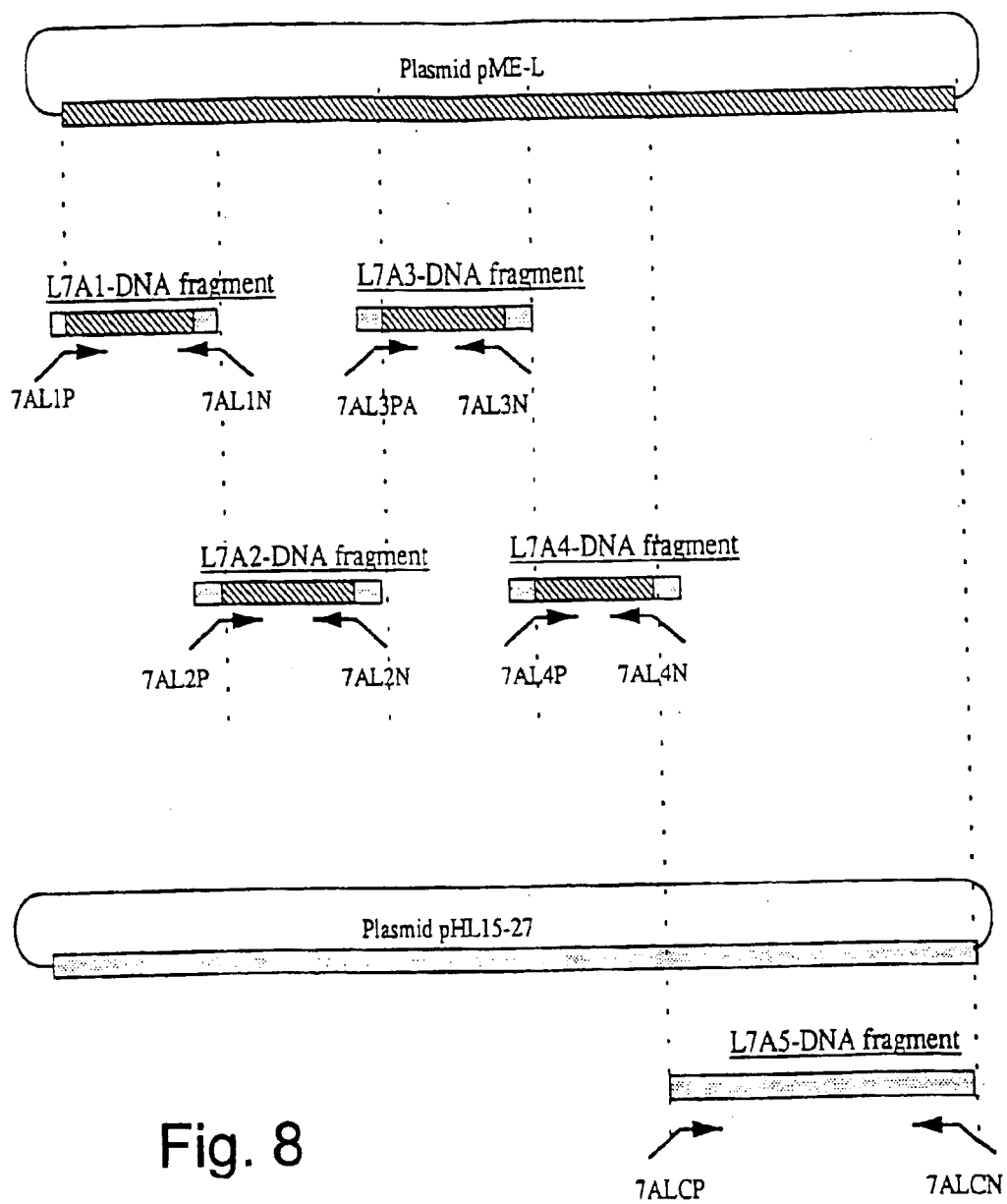
FIG. 8 is a summary of the first step PCR for the production of VHH-DNA.

The outline of the first stage PCR for the preparation of VHH-DNA is shown in FIG. 8.

The L7A1-DNA fragment, encoding a secretion signal sequence and a portion of the FRL, region altered to contain a Hind III restriction enzyme cleavage site at the 5'-end, was prepared as follows.

Composition of the PCR Reaction Solution:
plasmid pME-L DNA, 200 ng;
oligonucleotide primer 7AL1P, 80 pmol;
oligonucleotide primer 7AL1N, 80 pmol;
dNTP cocktail, 20 μl;
10×Pfu buffer, 20 μl;
Pfu DNA polymerase (Stratagene), 10 units; and
redistilled water to a final volume of 200 μl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The L7A2-DNA fragment, encoding a portion of the $FRL_1$, $CDRL_1$, $FRL_2$ and a portion of the $CDRL_2$ region, was prepared as follows.

Composition of the PCR Reaction Solution:
plasmid pME-L DNA, 200 ng;
oligonucleotide primer 7AL2P, 80 pmol;
oligonucleotide primer M7AL2N, 80 pmol;
dNTP cocktail, 20 μl;
10×Pfu buffer, 20 μl;
Pfu DNA polymerase, 10 units; and
redistilled water to a final volume of 200 μl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The L7A3-DNA fragment, encoding the $CDRL_2$ and a portion of the FRL, was prepared as follows.

Composition of the PCR Reaction Solution:
plasmid PME-L DNA, 200 ng;
oligonucleotide primer 7AL3PA, 80 pmol;
oligonucleotide primer 7AL3N, 80 pmol;
dNTP cocktail, 20 μl;
10×Pfu buffer, 20 μl;
Pfu DNA polymerase, 10 units; and
redistilled water to a final volume of 200 μl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The L7A4-DNA fragment, encoding a portion of the $FRL_3$, $CDRL_3$, $FRL_4$ and a portion of the constant region was prepared as follows.
Composition of the PCR Reaction Solution:
plasmid pME-L DNA, 200 ng;
oligonucleotide primer 7AL4P, 80 pmol;
oligonucleotide primer 7ALAN, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The L7A5-DNA fragment, encoding a portion of the $FRL_4$ and the constant region altered to have an EcoRI restriction enzyme cleavage site at the 3'-end, was prepared as follows.
Composition of the PCR Reaction Solution:
plasmid pHL15-27 DNA, 200 ng;
oligonucleotide primer 7ALCP, 80 pmol;
oligonucleotide primer 7ALCN, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

An equal volume of phenol-chloroform (50% v/v phenol saturated with water, 48% v/v chloroform, 2% v/v isoamyl alcohol) was added to 200 µl of each of the PCR products, and vigorously mixed for 1 minute. After this time, the mixture was centrifuged at 10,000×g, and the aqueous layer was recovered and mixed with an equal volume of chloroform-isoamyl alcohol (96% v/v chloroform and 4% v/v isoamyl alcohol), which was again vigorously mixed for 1 minute. The resulting mixture was centrifuged at 10,000×g and the aqueous layer was recovered (the series of steps recited in this paragraph is referred to, herein, as "phenol extraction").

Ethanol precipitation was then performed on the recovered aqueous layer. As used and referred to herein, "ethanol precipitation" consists of adding, with mixing, a one tenth volume of 3M sodium acetate (pH 5.2) and 2.5 volumes of 100% ethanol to the solution to be treated, and freezing the mixture using dry ice. The resulting mixture is then centrifuged at 10,000×g to recover DNA as a precipitate.

After phenol extraction and ethanol precipitation, the resulting DNA precipitate was vacuum-dried, dissolved in a minimum of redistilled water, and separated by 5% w/v polyacrylamide gel electrophoresis. After electrophoresis, the gel was stained with a 1 µg/ml aqueous solution of ethidium bromide to allow detection of DNA under UV light. The DNA bands corresponding to L7A1-DNA, L7A2-DNA, L7A3-DNA, L7A4-DNA and L7A5-DNA were cut out using a razor blade and eluted from the gel using Centriruter and Centricon-10, as described above. The eluted DNA was then concentrated by centrifugation at 7,500×g, followed by ethanol precipitation, and finally dissolved in 50 µl of distilled water.

b) Second Stage PCR

Figure 9:
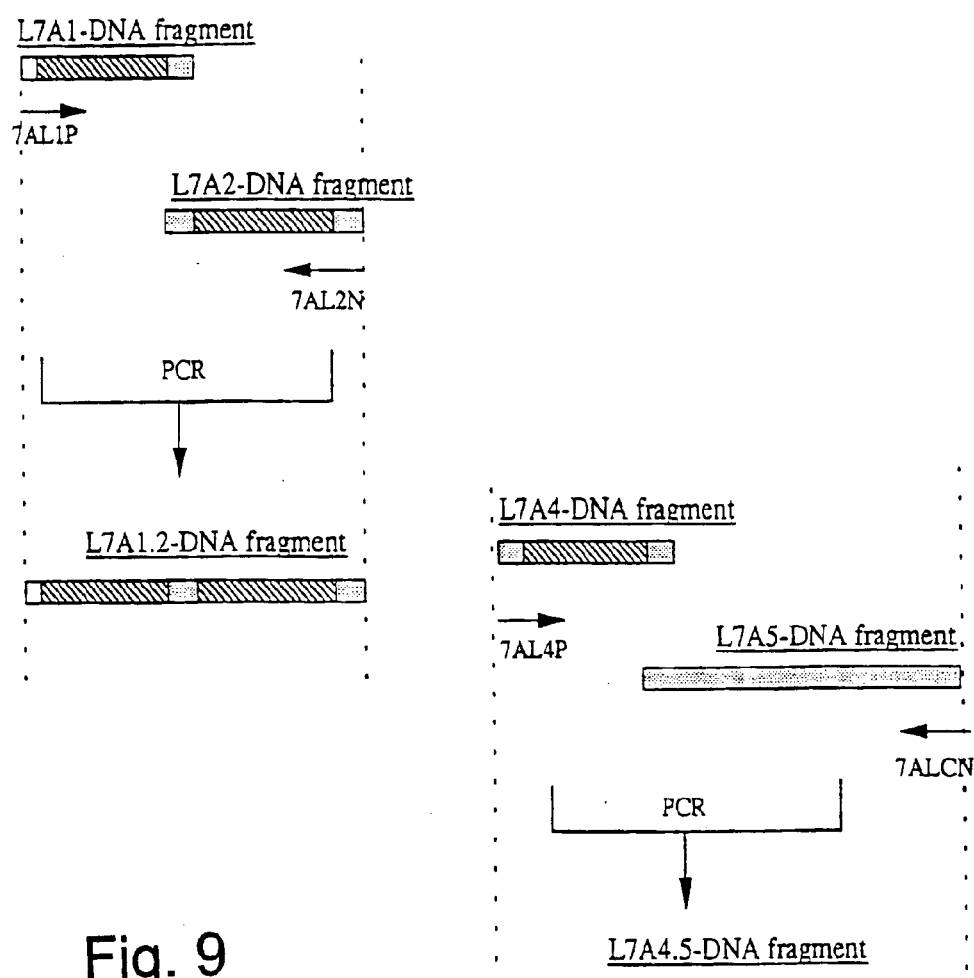
FIG. 9 is a summary of the second step PCR for the production of VHH-DNA.

The outline of the second stage PCR for the production of VHH-DNA is shown in FIG. 9.

L7A1.2-DNA, in which the L7A1-DNA and L7A2-DNA fragments, described above, were fused, was prepared as follows.
Composition of the PCR Reaction Solution:
L7A1-DNA solution prepared in the first stage PCR, 10 µl;
L7A2-DNA solution prepared in the first stage PCR, 10 µl;
oligonucleotide primer 7AL1P, 80 pmol;
oligonucleotide primer 7AL2N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

L7A4.5-DNA, in which the L7A4-DNA and L7A5-DNA fragments described above were fused, was prepared as follows.
Composition of the Reaction Solution:
L7A4-DNA solution prepared in the first stage PCR, 10 µl;
L7A5-DNA solution prepared in the first stage PCR, 10 µl;
oligonucleotide primer 7AL4P, 80 pmol;
oligonucleotide primer 7ALCN, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

First, phenol extraction and then ethanol precipitation were performed on the amplified PCR L7A1.2-DNA and L7A4.5-DNA fragments, and these fragments were then separated by 5% w/v polyacrylamide gel electrophoresis. After electrophoresis, the gel was stained with 1 µg/ml of ethidium bromide, and the bands detected under UV light were cut out using a razor blade and eluted from the gel using a Centriruter and Centricon-10, as described above. The eluted DNA was concentrated first by centrifugation at 7,500×g, then by ethanol precipitation, and then dissolved in 50 µl of distilled water.

c) Third Stage PCR

Figure 10:
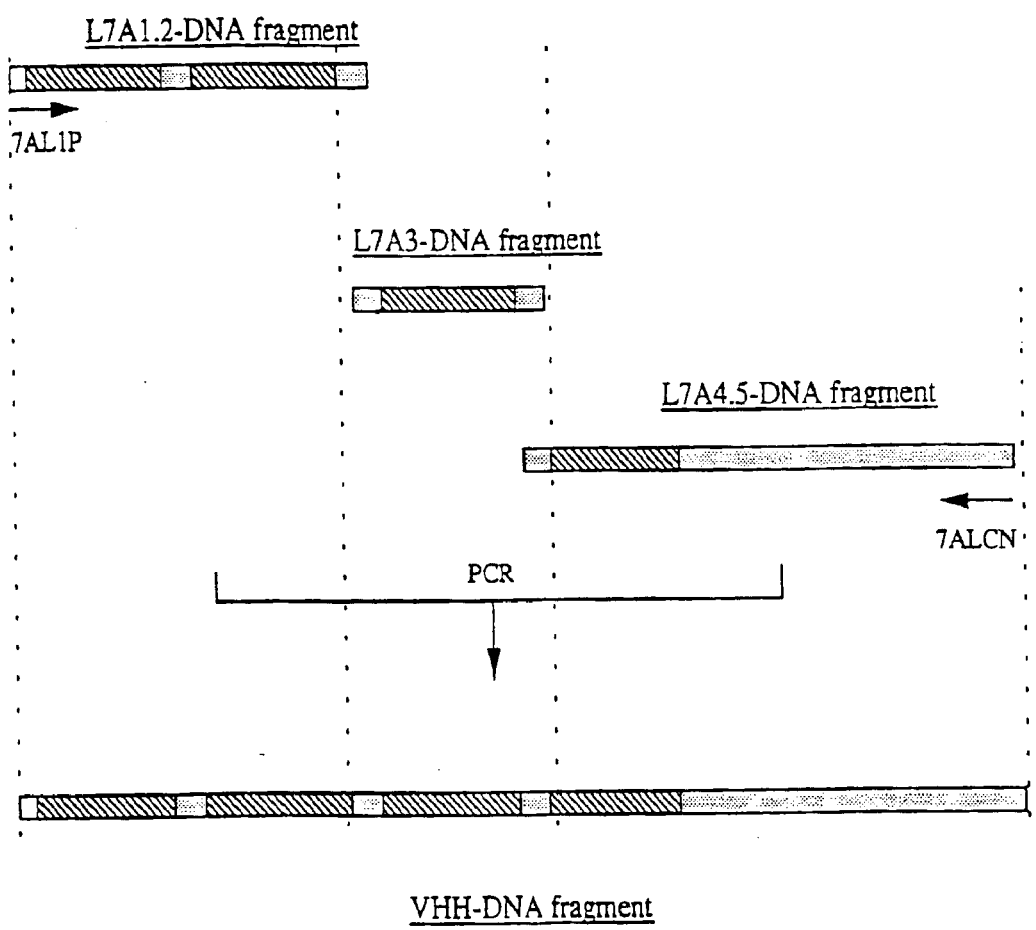
FIG. 10 is a summary of the third step PCR for the production of VHH-DNA.

The outline of the third stage PCR for the production of VHH-DNA is shown in FIG. 10.

The VHH-DNA fragment in which the above described L7A1.2-DNA and L7A4.5-DNA fragments and L7A3-DNA were fused was prepared as follows.
Composition of the PCR Reaction Solution:
L7A1.2-DNA solution prepared in the second stage PCR, 10 µl;
L7A4.5-DNA solution prepared in the second stage PCR, 10 µl;
L7A3-DNA solution prepared in the first stage PCR, 10 µl;
oligonucleotide primer 7AL1P, 80 pmol;
oligonucleotide primer 7ALCN, 80 pmol;

dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The amplified PCR VHH-DNA fragment was subjected first to phenol extraction and then to ethanol precipitation, before separation on a 5% w/v polyacrylamide electrophoresis gel. After electrophoresis, the gel was stained with 1 µg/ml of ethidium bromide and the VHH-DNA band detected under UV light was cut out using a razor blade and eluted from the gel using a Centriruter and Centricon-10, as described above. The eluted DNA was then concentrated by centrifugation at 7,500×g, followed by ethanol precipitation, and finally dissolved in 50 µl of distilled water.

Figure 11:
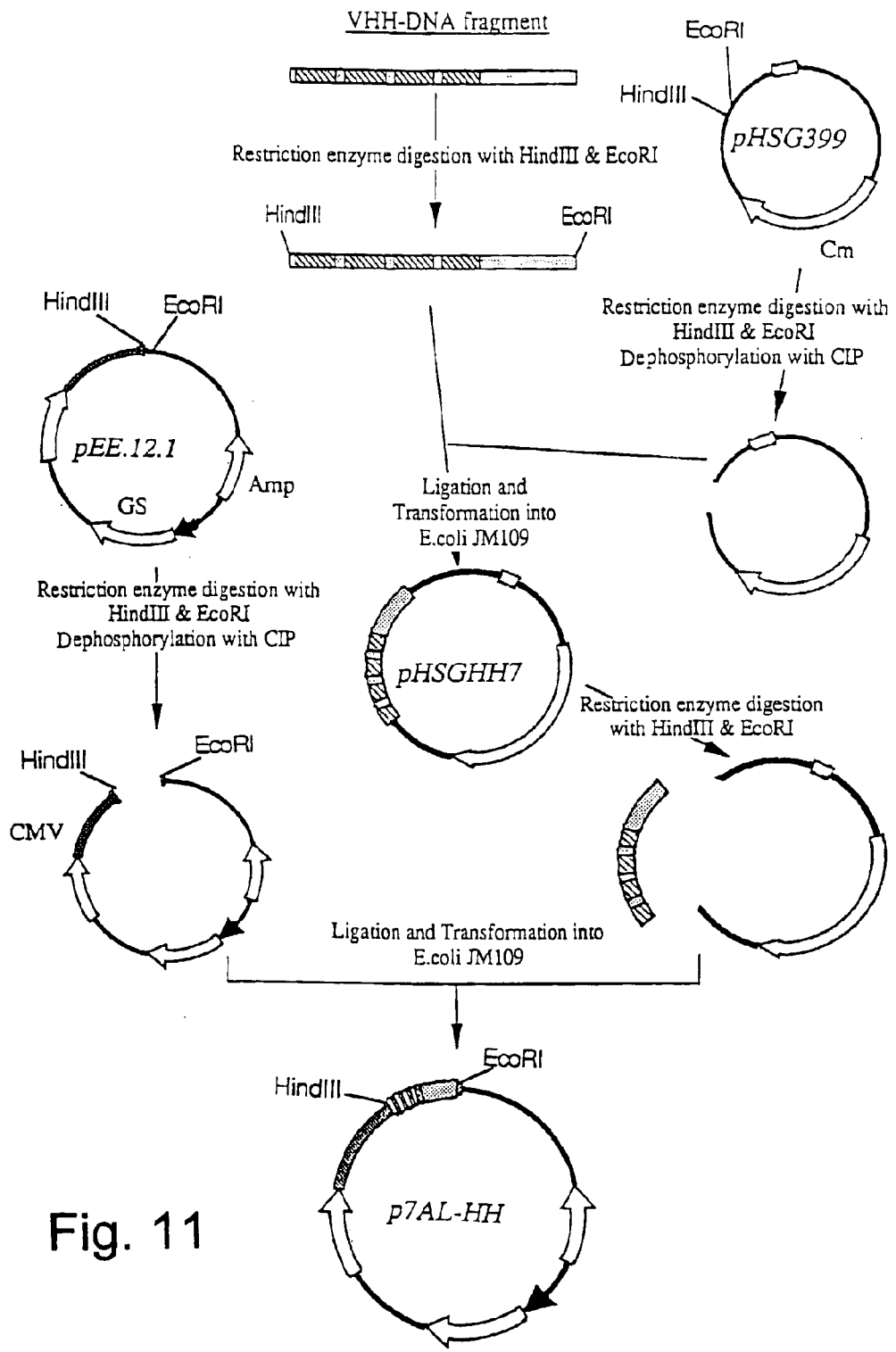
FIG. 11 is a summary of the construction of the expression plasmid carrying VHH-DNA fragment.

The construction of an expression plasmid carrying VHH-DNA fragment is outlined in FIG. 11.

The VHH-DNA fragment obtained above was further purified by phenol extraction followed by ethanol precipitation, and it was then digested with the restriction enzymes Hind III and EcoRI.

One µg of cloning plasmid pHSG399 DNA (Takara Shuzo Co., Ltd.) was digested with the restriction enzymes Hind III and EcoRI, and then dephosphorylated with alkaline phosphatase (derived from calf intestine; hereinafter abbreviated as CIP). The resulting, dephosphorylated plasmid pHSG399 DNA and the digested VHH-DNA fragment were ligated using a DNA Ligation Kit Version 2.0 (Takara Shuzo Co., Ltd.) using the manufacturer's protocol.

The ligated DNA was recovered by ethanol precipitation, dissolved in 5 µl of redistilled water, and then mixed with E. coli JM109 Electro-Cell (Takara Shuzo Co., Ltd.). The mixture was transferred to a Gene Pulser/E. coli Pulser Cuvette, 0.1 cm (BioRad) and the ligated mix was then used to transform the E. coli JM 109 using Gene Pulser II (BioRad) by the manufacturer's protocol (the series of steps in this paragraph is referred to herein as "transformation").

After transformation, the cells were plated onto LB agar medium [Bacto-tryptone (Difco) 10 g, Bacto-yeast extract (Difco) 5 g, NaCl 10 g, Bacto-agar (Difco) 15 g; dissolved in distilled water, q.s. to 1l] containing final concentrations of 1 mM IPTG (isopropylthio-β-D-galactoside; Takara Shuzo Co., Ltd.), 0.1% w/v X-Gal (5-bromo-4-chloro-3-indolyl-β-D-galactoside; Takara Shuzo Co., Ltd.) and 50 µg/ml chloramphenicol, and the plates were incubated at 37° C. overnight to obtain E. coli transformants.

Any white transformants obtained were cultured in 2 ml of liquid LB medium at 37° C. overnight, and plasmid DNA was extracted from the resulting culture by the alkaline-SDS method [Sambrook, J., et al., (1989), in "Molecular Cloning: A Laboratory Manual (2nd Edition)", Cold Spring Harbor Laboratory Press].

The resulting, extracted plasmid DNA was digested with the restriction enzymes Hind III and EcoRI, and a clone carrying the VHH-DNA fragment was then selected by 1% w/v agarose gel electrophoresis.

Plasmid pHSGHH7 carrying a fusion fragment of the variable region of the humanized HH type HPE7A light chain and DNA encoding the constant region of human immunoglobulin κ chain was obtained accordingly. The transformant E. coli pHSGHH7 SANK 73497 harboring plasmid pHSGHH7 was deposited with the Kogyo Gijutsuin Seimei-Kogaku Kogyo Gijutsu Kenkyujo on Aug. 22, 1997, in accordance with the Budapest Treaty, and was accorded the accession number FERM BP-6073.

Using above described plasmid pHSGHH7, it was then possible to construct the expression vector plasmid p7AL-HH, carrying the DNA of SEQ ID No. 49 of the Sequence Listing and which encodes the humanized HH type HFE7A light chain polypeptide of SEQ ID No. 50 of the Sequence Listing.

One µg of pEE.12.1 DNA (Lonza), an expression vector for mammalian cells, was digested with the restriction enzymes Hind III and EcoRI, and then dephosphorylated using CIP. The resulting digested, dephosphorylated plasmid DNA (100 ng) was ligated with 10 µg of the pHSGHH7 DNA fragment which had also been digested with Hind III and EcoRI, using a DNA Ligation Kit Version 2.0 (Takara Shuzo Co., Ltd.). The ligation mix was then used to transform E. coli JM109 (as described above), which was then plated on LB agar plates containing 50 µg/ml ampicillin.

The transformants obtained by this method were cultured in 2 ml of liquid LB medium containing 50 µg/ml ampicillin at 37° C. overnight, and plasmid DNA was subsequently extracted from the resulting culture by the alkaline-SDS method.

The extracted plasmid DNA was digested with Hind III and EcoRI, and subjected to 1% w/v agarose gel electrophoresis to confirm the presence or absence of the insert of interest. This enabled the isolation of the plasmid p7AL-HH, which contains a fusion fragment having the variable region of the humanized HH type HFE7A light chain together with DNA encoding the constant region of the human immunoglobulin κ chain. The fusion fragment was found to be located downstream of the cytomegalovirus (CMV) promoter in the correct orientation.

4) Construction of Plasmid p7AL-HM (Expression Plasmid for Humanized HM Type HFE7A Light Chain)

The VHM-DNA fragment of SEQ ID No. 51 of the Sequence Listing encoding the amino acid sequence of SEQ ID No. 52 of the Sequence Listing was produced by performing a 3-stage PCR, inserted into a plasmid vector and then cloned into E. coli.

a) First Stage PCR

Figure 12:
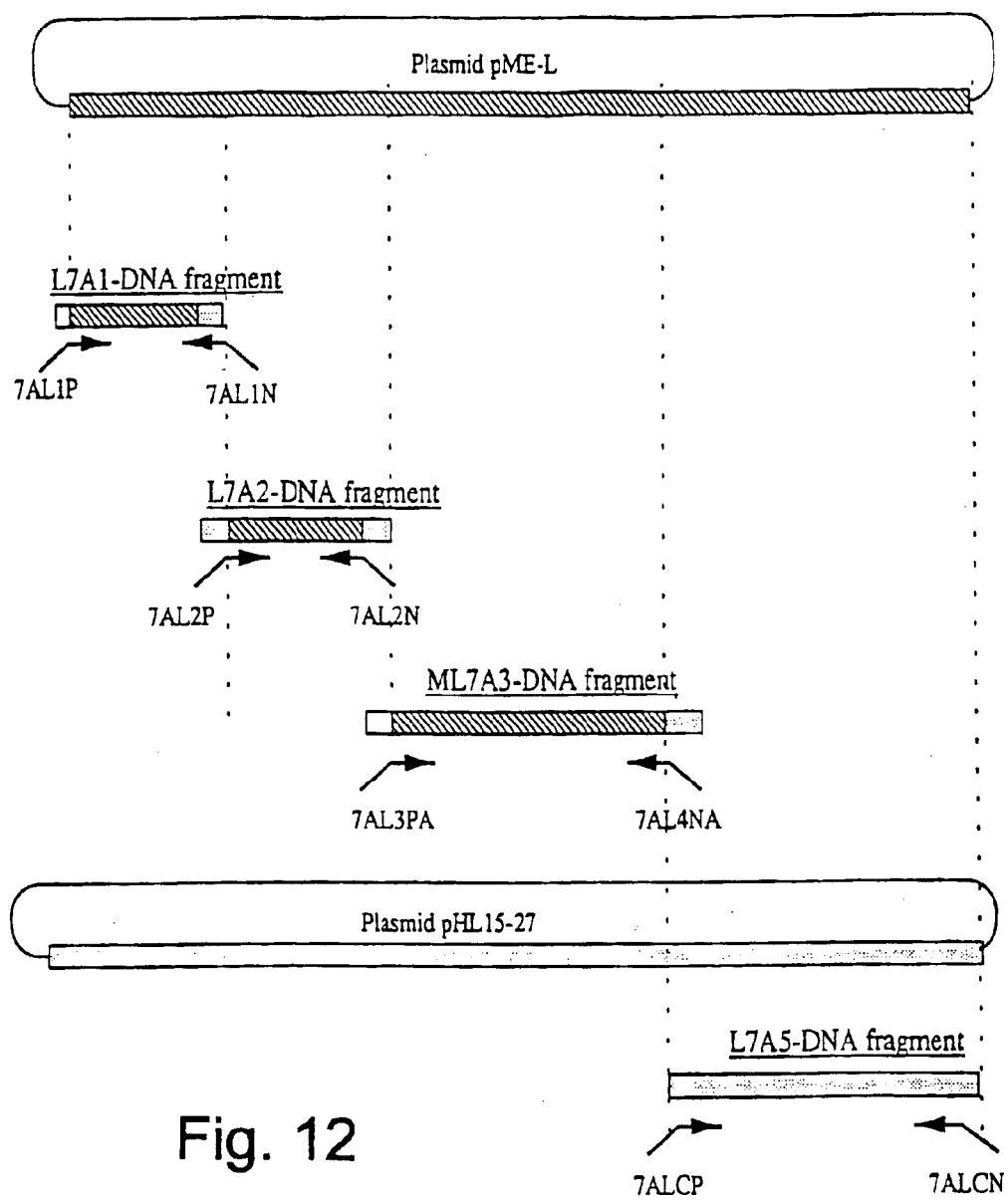
FIG. 12 is a summary of the first step PCR for the production of VHM-DNA.

The outline of the first stage PCR for the preparation of the VHM-DNA fragment is shown in FIG. 12.

The L7A1-DNA fragment, encoding a secretion signal sequence and a portion of $FRL_1$ having a Hind III restriction enzyme cleavage site added at the 5'-end, the L7A2-DNA fragment, encoding a portion of $FRL_1$, $CDRL_1$, $FRL_2$ and a portion of $CDRL_2$, and the L7A5-DNA fragment, encoding a portion of $FRL_4$ and the constant region having an EcoRI site added at the 3'-end, were used in this process, and were those obtained in the preparation of the VHH-DNA fragment in 2) above.

An ML7A3-DNA fragment, encoding $CDRL_2$, $FRL_3$, $CDRL_3$, $FRL_4$ and a portion of the constant region, was prepared as follows.

Composition of the PCR Reaction Solution:
plasmid pME-L DNA, 200 ng;
oligonucleotide primer 7AL3PA, 80 pmol;
oligonucleotide primer 7AL4NA, 80 pmol;
DNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The PCR products were subjected first to phenol extraction and then to ethanol precipitation, and then separated by 5% w/v polyacrylamide gel electrophoresis. After electrophoresis, the gel was stained with 1 µg/ml of ethidium bromide and the DNA band detected under UV light, corresponding to ML7A3-DNA, was cut out using a razor blade and eluted from the gel using a Centriruter and Centricon-10, as described above. The eluted DNA was then concentrated by centrifugation at 7,500×g followed by ethanol precipitation, and then dissolved in 50 µl of distilled water.

b) Second Stage PCR

Figure 13:
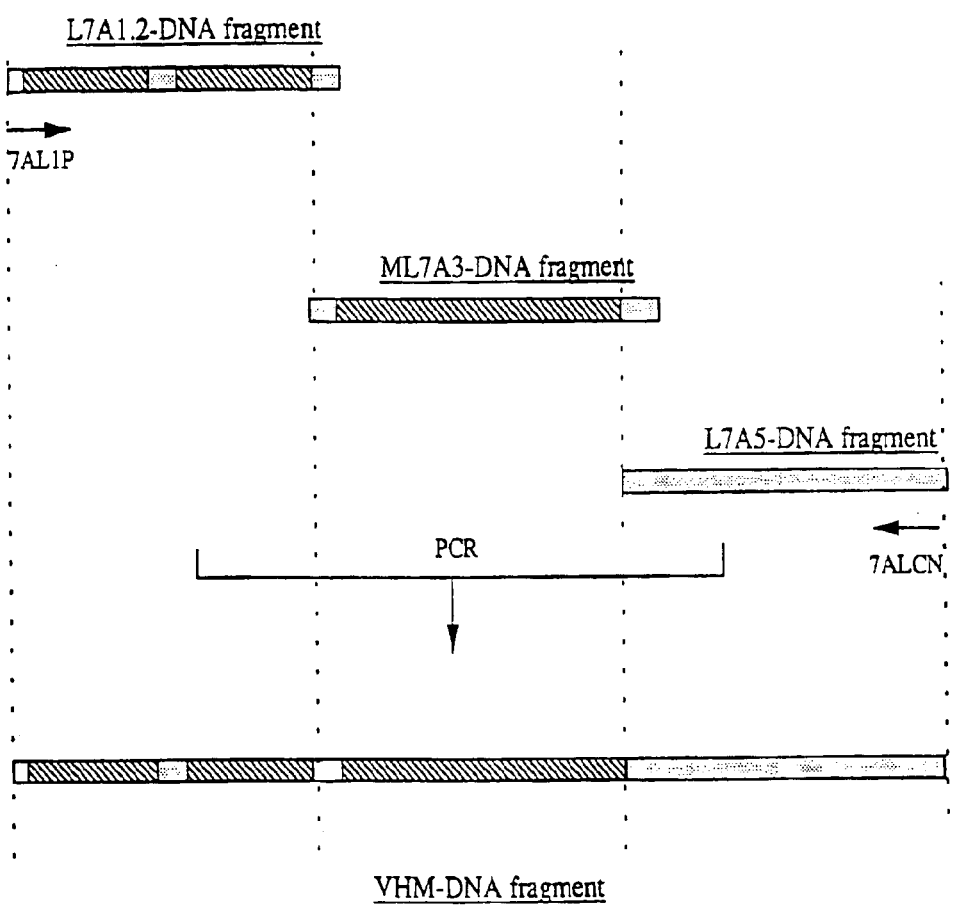
FIG. 13 is a summary of the second step PCR for the production of VHM-DNA.

The outline of the second stage PCR for the preparation of VHM-DNA is shown in FIG. 13.

A VHM-DNA fusion fragment comprising the L7A1.2-DNA, the ML7A3-DNA and the L7A5-DNA fragment above was prepared as follows.

Composition of the PCR Reaction Solution:
L7A1.2-DNA solution prepared in the second stage PCR, 10 µl;
ML7A3-DNA solution prepared in the first stage PCR, 10 µl;
L7A5-DNA solution prepared in the first stage PCR, 10 µl;
oligonucleotide primer 7AL1P, 80 pmol;
oligonucleotide primer 7ALCN, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The resulting, amplified VHM-DNA fragment was subjected first to phenol extraction and then to ethanol precipitation, and then separated by 5% w/v polyacrylamide gel electrophoresis. After electrophoresis, the gel was stained with 1 µg/ml of ethidium bromide and the VHM-DNA band thus detected was cut out using a razor blade and eluted from the gel using a Centriruter and Centricon-10, as described above. The eluted DNA was concentrated by centrifugation at 7,500×g, followed by ethanol precipitation, and dissolved in 50 µl of distilled water.

Figure 14:
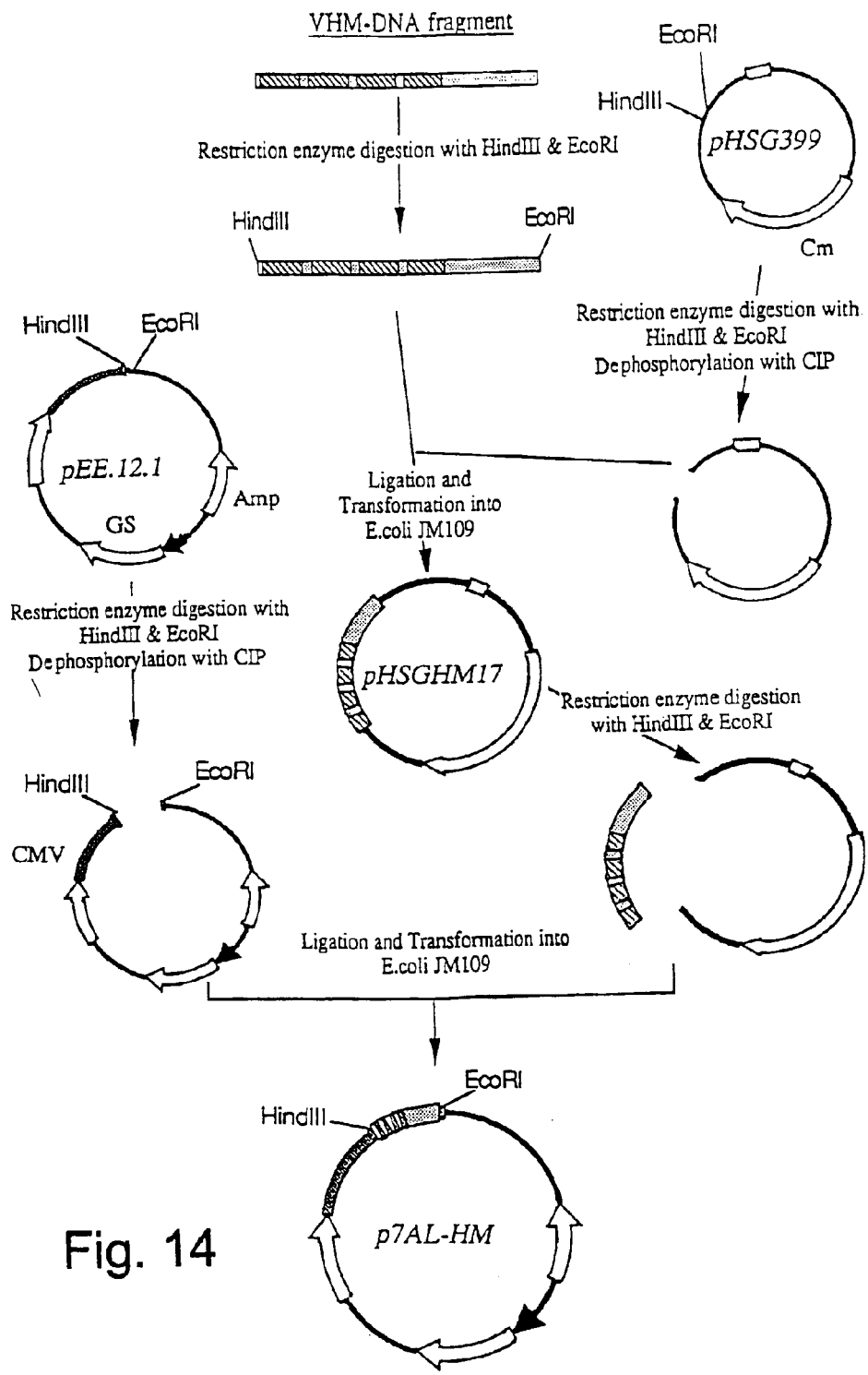
FIG. 14 is a summary of the construction of the expression plasmid carrying VHM-DNA fragment.

The construction of an expression plasmid carrying VHM-DNA fragment is outlined in FIG. 14.

The VHM-DNA obtained above was further purified by phenol extraction followed by ethanol precipitation, and then digested with the restriction enzymes Hind III and EcoRI.

One pg of the cloning plasmid pHSG399 DNA (Takara Shuzo Co., Ltd.) was digested with the restriction enzymes Hind III and EcoRI, and then dephosphorylated using CIP. The resulting dephosphorylated pHSG399 DNA was then ligated with VHM-DNA, which had also been digested with Hind III and EcoRI, using a DNA Ligation Kit Version 2.0 (Takara Shuzo Co., Ltd.). E. coli JM109 was then transformed with the ligated DNA and spread onto LB agar medium containing final concentrations of 1 mM IPTG, 0.1% w/v X-Gal and 50 µg/ml chloramphenicol. The white transformants obtained were cultured in 2 ml liquid LB medium containing 50 µg/ml chloramphenicol at 37° C. overnight, and plasmid DNA was extracted from the resulting culture by the alkaline-SDS method. The extracted plasmid DNA was then digested with Hind III and EcoRI, and a clone carrying VHM-DNA fragment was selected using 1% w/v agarose gel electrophoresis.

Accordingly, plasmid pHSGHM17, carrying a fusion fragment of the variable region of the humanized HM type HFE7A light chain and DNA encoding the constant region of human Igκ chain, was obtained. The transformant E. coli pHSGHM17 SANK 73597 harboring plasmid pHSGHM17 was deposited with the Kogyo Gijutsuin Seimei-Kogaku Kogyo Gijutsu Kenkyujo on Aug. 22, 1997, in accordance with the Budapest Treaty, and was accorded the accession number FERM BP-6072.

Using the above described plasmid pHSGHM17, an expression vector plasmid p7AL-HM was constructed that carried the DNA of SEQ ID No. 51 of the Sequence Listing, encoding the humanized HM type HFE7A light chain polypeptide of SEQ ID No. 52 of the Sequence Listing.

One µg of pEE.12.1 DNA (Lonza), an expression vector for mammalian cells, was digested with the restriction enzymes Hind III and EcoRI, and then dephosphorylated using CIP. The resulting digested, dephosphorylated plasmid DNA (100 ng) was ligated with 10 µg of the pHSGHM17-DNA fragment which had also been digested with Hind III and EcoRI, using a DNA Ligation Kit Version 2.0 (Takara Shuzo Co., Ltd.). The ligation mix was then used to transform E. coli JM109 (as described above), which was then plated on LB agar plates containing 50 µg/ml ampicillin.

The transformants obtained by this method were cultured in 2 ml of liquid LB medium containing 50 µg/ml ampicillin at 37° C. overnight, and plasmid DNA was subsequently extracted from the resulting culture by the alkaline-SDS method.

The extracted plasmid DNA was digested with Hind III and EcoRI, and subjected to 1% w/v agarose gel electrophoresis to confirm the presence or absence of the insert of interest. This enabled the isolation of the plasmid p7AL-HM, which contains a fusion fragment having the variable region of the humanized HM type HFE7A light chain together with DNA encoding the constant region of the human immunoglobulin κ chain. The fusion fragment was found to be located downstream of the cytomegalovirus (CMV) promoter in the correct orientation.

5) Construction of Plasmid p7AL-MM (Expression Plasmid for Humanized MM Type HFE7A Light Chain)

The VMM-DNA fragment of SEQ ID No. 53 of the Sequence Listing encoding the amino acid sequence of SEQ ID No. 54 of the Sequence Listing was produced by performing 3-stage PCR, inserted into a plasmid vector, and then cloned into E. coli.

a) First Stage PCR

Figure 15:
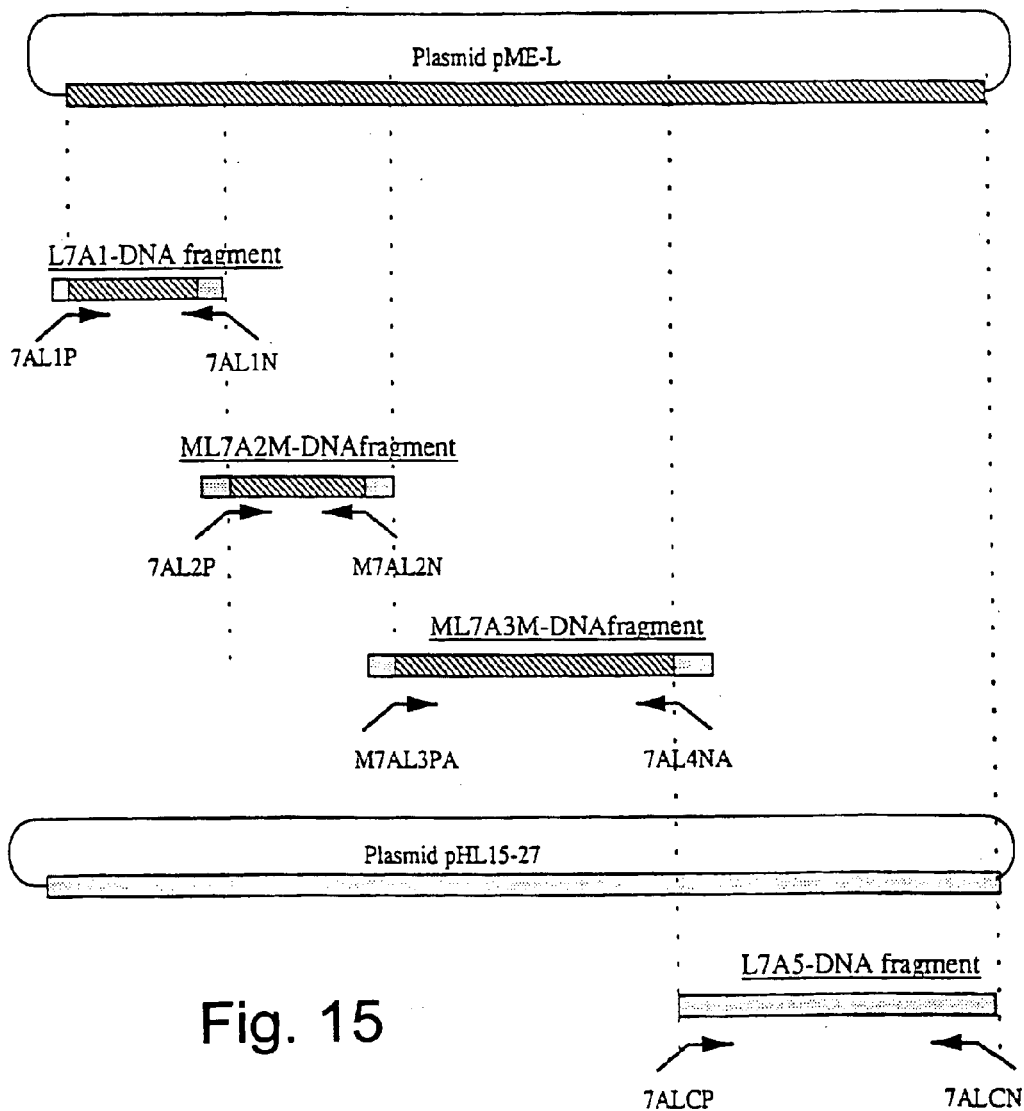
FIG. 15 is a summary of the first step PCR for the production of VMM-DNA.

The outline of the first stage PCR for the preparation of VMM-DNA is shown in FIG. 15.

The L7A1-DNA fragment, encoding a secretion signal sequence and a portion of $FRL_1$, and having a HindIII restriction enzyme cleavage site added at the 5'-end, and the L7A5-DNA fragment encoding a portion of $FRL_4$ and the constant region having an EcoRI restriction site added at the 3'-end, were as obtained in the preparation of the VHH-DNA fragment in (2) above. These fragments were used in the first stage PCR construction of VMM-DNA.

The ML7A2M-DNA fragment, encoding a portion of $FRL_1$, $CDRL_1$, $FRL_2$, $CDRL_2$ and a portion of $FRL_3$, was prepared as follows.

Composition of the PCR Reaction Solution:
plasmid pME-L DNA, 200 ng;
oligonucleotide primer 7AL2P, 80 pmol;
oligonucleotide primer M7AL2N, 80 pmol;
dNTP cocktail, 20 µl;

10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The ML7A3M-DNA fragment, encoding a portion of $FRL_3$, $CDRL_3$, $FRL_4$ and a portion of the constant region, was prepared as follows.
Composition of the PCR Reaction Solution:
plasmid pME-L DNA, 200 ng;
oligonucleotide primer M7AL3PA, 80 pmol;
oligonucleotide primer 7AL4NA, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The PCR products were subjected first to phenol extraction and then to ethanol precipitation, and then separated by 5% w/v polyacrylamide gel electrophoresis. After electrophoresis, the gel was stained with 1 µg/ml of ethidium bromide and the DNA bands corresponding to ML7A2M-DNA and ML7A3M-DNA, as detected by UV light, were cut out using a razor blade and eluted from the gel using a Centriruter and Centricon-10, as described above. The eluted DNA's were concentrated by centrifugation at 7,500×g, followed by ethanol precipitation, and dissolved in 50 µl of distilled water.

b) Second Stage PCR

Figure 16:
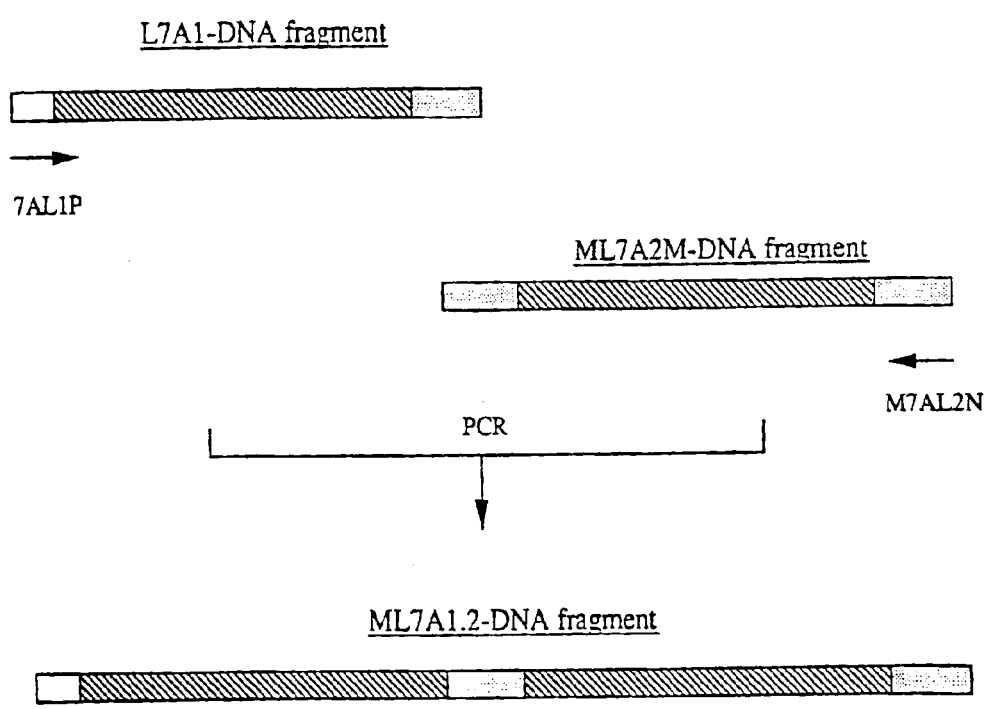
FIG. 16 is a summary of the second step PCR for the production of VMM-DNA.

The outline of the second stage PCR for the preparation of the VMM-DNA is shown in FIG. 16.

The ML7A1.2-DNA fragment, comprising a fusion of the above ML7A1-DNA and ML7A2M-DNA fragmentsm, was prepared as follows.
Composition of the PCR Reaction Solution:
L7A1-DNA solution prepared in the first stage PCR, 10 µl;
ML7A2M-DNA solution prepared in the first stage PCR, 10 µl;
oligonucleotide primer 7AL1P, 80 pmol;
oligonucleotide primer 7AL2N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The resulting, amplified ML7A1.2-DNA fragment was subjected first to phenol extraction and then to ethanol precipitation, and separated by 5% w/v polyacrylamide gel electrophoresis. After electrophoresis, the gel was stained with 1 µg/ml of ethidium bromide and the fusion-DNA band thus detected was cut out using a razor blade and eluted from the gel using a Centriruter and Centricon-10, as described above. The eluted DNA was concentrated by centrifugation at 7,500×g, followed by ethanol precipitation, and dissolved in 50 µl of distilled water.

c) Third Stage PCR

Figure 17:
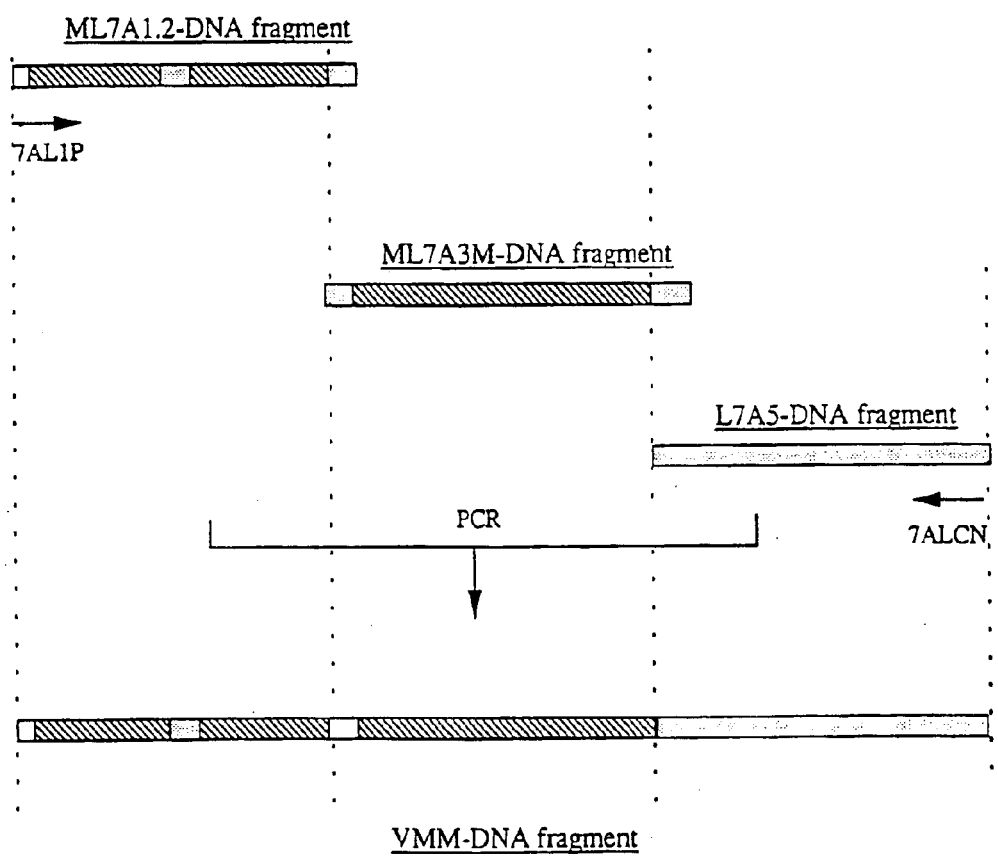
FIG. 17 is a summary of the third step PCR for the production of VMM-DNA.

The outline of the third stage PCR for the preparation of the VMM-DNA is shown in FIG. 17.

The VMM-DNA fragment, comprising a fusion of the above ML7A1.2-DNA, ML7A3M-DNA and the L7A5-DNA fragment, was prepared as follows.
Composition of the PCR Reaction Solution:
ML7A1.2-DNA solution prepared in the second stage PCR, 10 µl;
ML7A3M-DNA solution prepared in the first stage PCR, 10 µl;
L7A5-DNA solution prepared in the first stage PCR, 10 µl;
oligonucleotide primer 7AL1P, 80 pmol;
oligonucleotide primer 7ALCN, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The resulting, amplified VMM-DNA fragment was subjected first to phenol extraction and then to ethanol precipitation, and separated by 5% w/v polyacrylamide gel electrophoresis. After electrophoresis, the gel was stained with 1 µg/ml of ethidium bromide and the VMM-DNA band thus detected was cut out using a razor blade and eluted from the gel using a Centriruter and Centricon-10, as described above. The eluted DNA was concentrated by centrifugation at 7,500×g, followed by ethanol precipitation, and dissolved in 50 µl of distilled water.

Figure 18:
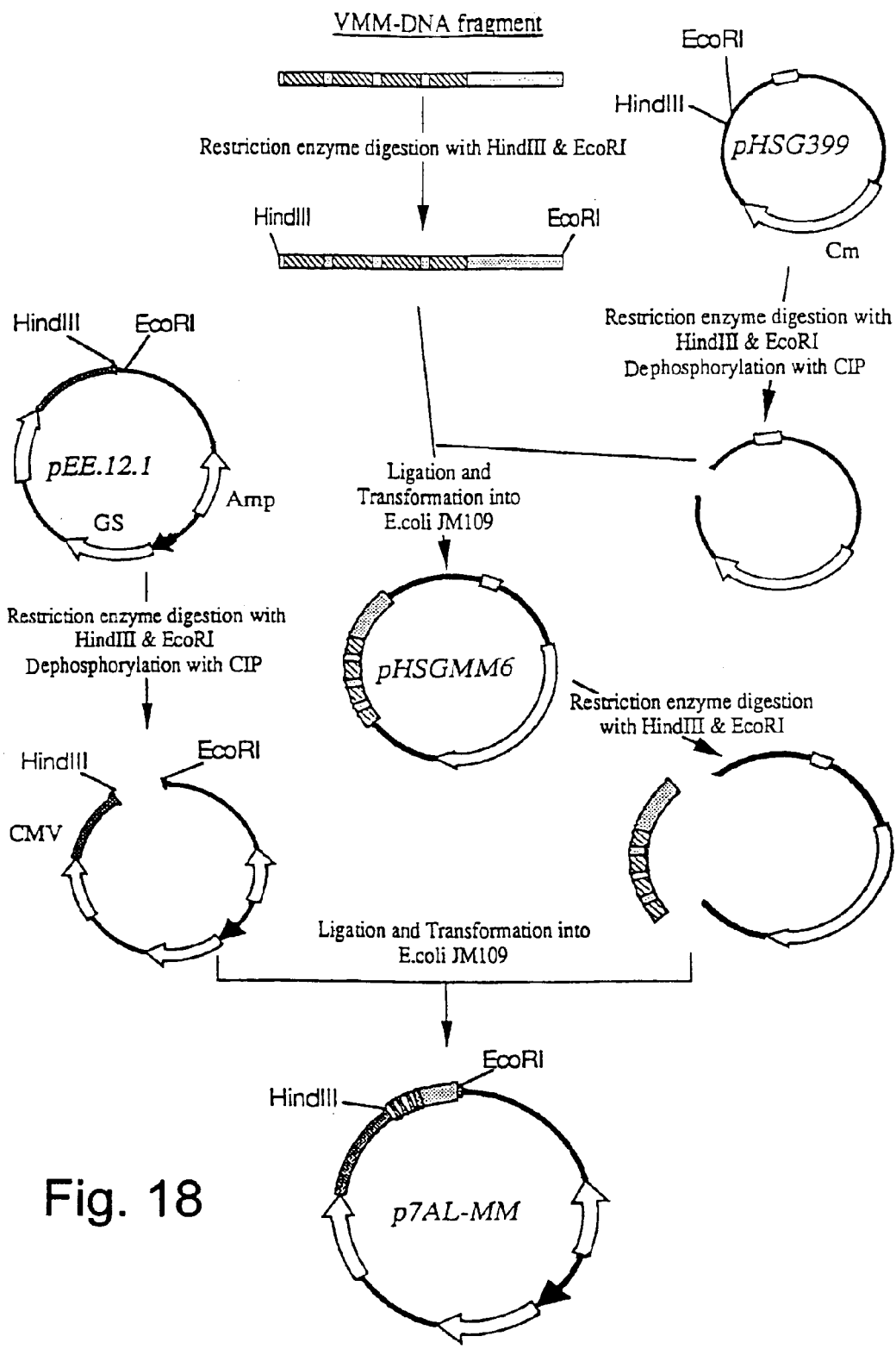
FIG. 18 is a summary of the construction of the expression plasmid carrying VMM-DNA fragment.

The construction of a plasmid carrying the VMM-DNA fragment is outlined in FIG. 18.

The VMM-DNA obtained above was further purified by phenol extraction followed by ethanol precipitation, and then digested with the restriction enzymes Hind III and EcoRI.

One µg of the cloning plasmid pHSG399 DNA (Takara Shuzo Co., Ltd.) was digested with the restriction enzymes Hind III and EcoRI, and then dephosphorylated using CIP. The resulting dephosphorylated pHSG399 DNA was then ligated with VMM-DNA, which had also been digested with Hind III and EcoRI, using a DNA Ligation Kit Version 2.0 (Takara Shuzo Co., Ltd.). *E. coli* JM109 was then transformed with the ligated DNA and spread onto LB agar medium containing final concentrations of 1 mM IPTG, 0.1% w/v X-Gal and 50 µ/ml chloramphenicol. The white transformants obtained were cultured in 2 ml liquid LB medium containing 50 µg/ml chloramphenicol at 37° C. overnight, and plasmid DNA was extracted from the resulting culture by the alkaline-SDS method. The extracted plasmid DNA was then digested with Hind III and EcoRI, and a clone carrying VMM-DNA fragment was selected using 1% w/v agarose gel electrophoresis.

Accordingly, plasmid pHSGMM6, carrying a fusion fragment of the variable region of the MM type HFE7A light chain and DNA encoding the constant region of human immunoglobulin κ chain was obtained. The transformant *E. coli* pHSGM6 SANK 73697 harboring plasmid pHSGM6 was deposited with the Kogyo Gijutsuin Seimei-Kogaku Kogyo Gijutsu Kenkyujo on Aug. 22, 1997, in accordance with the Budapest Treaty, and was accorded the accession number FERM BP-6071.

The expression vector plasmid p7AL-MM was constructed using the above described plasmid pHSGM6, and carries the DNA of SEQ ID No. 53 of the Sequence Listing encoding the MM type HFE7A light chain polypeptide of SEQ ID NO. 54 of the Sequence Listing.

One µg of pEE.12.1 DNA (Lonza), an expression vector for mammalian cells, was digested with the restriction enzymes Hind III and EcoRI, and then dephosphorylated using CIP. The resulting digested, dephosphorylated plasmid DNA (100 ng) was ligated with 10 µg of the pHSGM6-DNA fragment which had also been digested with Hind III and EcoRI, using a DNA Ligation Kit Version 2.0 (Takara Shuzo Co., Ltd.). The ligation mix was then used to transform *E. coli* JM109 (as described above), which was then plated on LB agar plates containing 50 µg/ml ampicillin.

The transformants obtained by this method were cultured in 2 ml of liquid LB medium containing 50 µg/ml ampicillin at 37° C. overnight, and plasmid DNA was subsequently extracted from the resulting culture by the alkaline-SDS method.

The extracted plasmid DNA was digested with Hind III and EcoRI, and subjected to 1% w/v agarose gel electrophoresis to confirm the presence or absence of the insert of interest. This enabled the isolation of the plasmid p7AL-MM, which contains a fusion fragment having the variable region of the MM type HFE7A light chain together with DNA encoding the constant region of the human immunoglobulin κ chain. The fusion fragment was found to be located downstream of the cytomegalovirus (CMV) promoter in the correct orientation.

6) Verification of the Nucleotide Sequences

To verify that the DNA inserts of plasmids p7AL-HH, p7AL-HM and p7AL-MM have the desired nucleotide sequences, their DNA inserts were analyzed to determine the nucleotide sequences. The oligonucleotide primers prepared for nucleotide sequencing were as follows:

5'-CCCAAGCTTA AGAAGCATCC-3' (SP1; SEQ ID No. 68);
5'-ATCTATGCTG CATCCAATCT-3' (SP2; SEQ ID No. 69);
5'-GTTGTGTGCC TGCTGAATAA-3' (SP3; SEQ ID No. 70);
5'-CCCGAATTCT TACTAACACT-3' (SP4; SEQ ID No. 71);
5'-TTATTCAGCA GGCACACAAC-3' (SP5; SEQ ID No. 72); and
5'-AGATTGGATG CAGCATAGAT-3' (SP6; SEQ ID No. 73).

Figure 19:
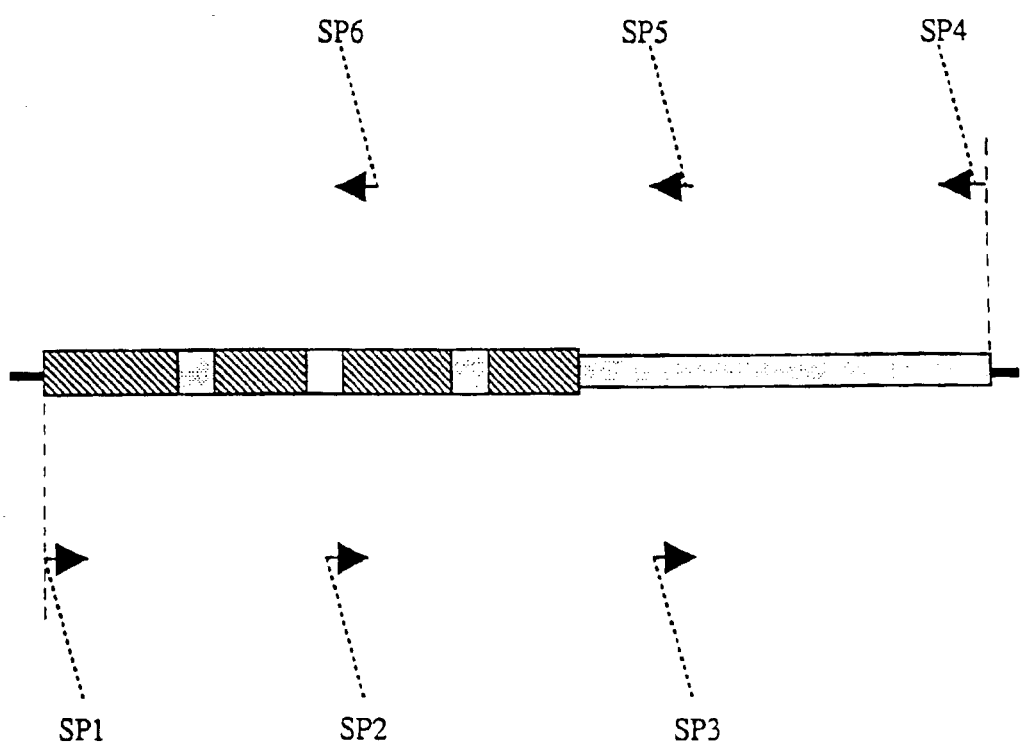
FIG. 19 shows the positions to which the light chain sequencing primers bind.

The positions to which each primer binds are shown in FIG. 19. The determination of the nucleotide sequences was performed by the dideoxynucleotide chain termination method [Sanger, F. S. et al., (1977), Proc. Ratl. Acad. Sci. USA, 74, 5463]. The templates used were the respective plasmid DNA's purified by the alkaline-SDS method and by the cesium chloride method [c.f. Sambrook, J. et al. (1989), in "Molecular Cloning: A Laboratory Manual, Second Edition" Cold Spring Harbor Laboratory Press, for both methods].

More specifically, 3 µg of purified plasmid DNA were dissolved in 13 µl of redistilled water, followed by the addition of 2 µl each of 2 mM EDTA and 2 N NaOH, and the mixture was then allowed to stand at room temperature for 5 minutes. Next, 4 µl of 10 M ammonium acetate solution and 100 µl of 100 µl ethanol were added and mixed in, and the mixture was placed on dry ice for 10 minutes. After this time, the mixture was centrifuged at 15,000×g, and the pellet obtained was washed with 80% v/v aqueous ethanol and then vacuum-dried. The resulting, dried DNA was dissolved in 7 µl of redistilled water and used for nucleotide sequencing.

The nucleotide sequencing reaction was performed using a 7-Deaza-Sequenase, Version 2.0 Kit (for dCTP; Amersham). A mixture of 7 µl of the above described plasmid solution, 1 pmol of a primer, which had been synthesized in advance, and 1 µl of reaction buffer (provided with the kit) was made up, and this mixture was then incubated at 65° C. for 2 minutes. Subsequently, the DNA was annealed with the primer by gradually cooling to room temperature, followed by labeling with [α-$^{32}$P]dCTP (Amersham). The reaction product was then subjected to gel electrophoresis on a 5% w/v polyacrylamide gel containing 8 M urea in 1×TBE buffer (100 mM Tris, 100 mM boric acid, 1 mM EDTA, pH8.3). After drying, the sequences on the gel were read by autoradiography. As used herein, all nucleotide sequencing was performed as above, unless otherwise specified.

As a result, it was established that the DNA inserts of plasmids p7AL-HH, p7AL-HM and p7AL-MM had the expected nucleotide sequences, that is:
SEQ ID No. 49 encoding the polypeptide sequence of SEQ ID No. 50; SEQ ID No. 51 encoding the polypeptide sequence of SEQ ID No. 52; and
SEQ ID No. 53 encoding the polypeptide sequence of SEQ ID No. 54; respectively, of the Sequence Listing.

REFERENCE EXAMPLE 15

Construction of an Expression Vector for the Heavy Chain of the Humanized Version of the HPE7A Antibody (1) Construction of a Plasmid Carrying the Heavy Chain Variable Region DNA of Humanized HFE7A 1) Synthesis of Primers for Preparing the Variable Region of the Humanized Heavy Chain The synthesis of DNA (SEQ ID No. 74 of the Sequence Listing) encoding a polypeptide chain comprising the variable region of humanized anti-Fas antibody HFE7A heavy chain and the 5 amino acid residues at the N-terminus of the IgG-CH1 region (SEQ ID No. 75 of the Sequence Listing) was performed using a combination of PCR.

The following 8 PCR primers were synthesized as described above:
5'-GGGAAGCTTG GCTTGACCTC ACCATGGGAT GGAGCTGTAT-3' (7AH1P; SEQ ID No. 76);
5'-TGAAGCCCCA GGCTTCTTGA CCTCAGCCCC AGACTGCACC AGTTGGAC-3' (7AH1NNEW; SEQ ID No. 77);
5'-TCCACTCAAG CCTCTGTCCA GGGGCCTGTT TTACCC-3' (7AH2N; SEQ ID No. 78);
5'-GTCTGGGGCT GAGGTCAAGA TTCAGTGAAG GTGTCCTGCA AG-3' (7AH2PNEW; SEQ ID No. 79);
5'-CAGGCCCCTG GACAGAGGCT TGAGTGGATG GGAGAGATT-3' (7AH3P; SEQ ID No. 80);
5'-TCAGATCTCA GGCRGCTGAG CTCCATGTAG GCTGTGCTAG CGGATGTGTC-3' (7AH3N; SEQ ID No. 81),
5'-TGGAGCTCAG CAGCCTGAGA TCTGAGGACA CGGCGGTCTA TTAC-3' (7AH4P; SEQ ID No. 82); and
5'-GATGGGCCCT TGGTGGAGGC TGAGGAGACG GTGACCAGGG TCCCTTCGCC CCAGT-3' (7AH4N; SEQ ID No. 83).

2) Construction of Plasmid pBL7A27

The VD-DNA fragment (SEQ ID No. 74 of the Sequence Listing) encoding the amino acid sequence of SEQ ID No. 75 of the Sequence Listing, was prepared by performing 3-stage PCR, then inserted into a plasmid and cloned into *E. coli.* a) First Stage PCR

Figure 20:
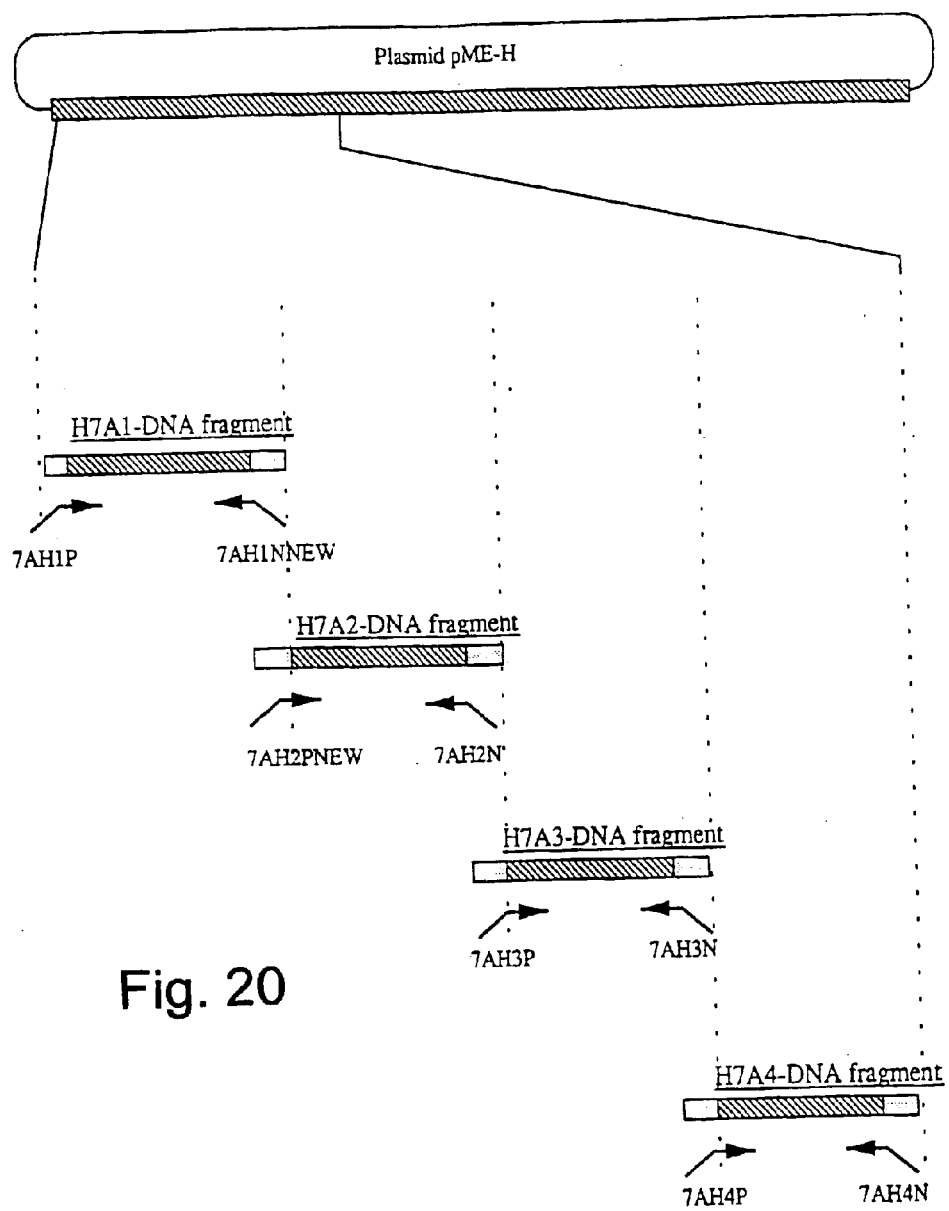
FIG. 20 is a summary of the first step PCR for the production of VD-DNA.

The outline of the first stage PCR for the preparation of VD-DNA is shown in FIG. 20.

The H7A1-DNA fragment, encoding a secretion signal sequence and an N-terminal portion of $FRH_1$ and having a Hind III restriction enzyme cleavage site added at the 5'-end, was prepared as follows.
Composition of the PCR Reaction Solution:
plasmid pME-H DNA, 200 ng;
oligonucleotide primer 7AH1P, 80 pmol;
oligonucleotide primer 7AH1NNEW, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The H7A2-DNA fragment, encoding a portion of $FRH_1$, $CDRH_1$ and a portion of $FRH_2$, was prepared as follows.
Composition of the PCR Reaction Solution:
plasmid pME-H DNA, 200 ng;
oligonucleotide primer 7AH2N, 80 pmol;
oligonucleotide primer 7AH2PNEW, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The H7A3-DNA fragment, encoding a portion of $FRH_2$, $CDRH_2$ and a portion of $FRH_2$, was prepared as follows.
Composition of the PCR Reaction Solution:
plasmid pME-H DNA, 200 ng;
oligonucleotide primer 7AH3P, 80 pmol;
oligonucleotide primer 7AH3N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The H7A4-DNA fragment, encoding a portion of $FRH_1$, $CDRH_3$, $FRH_4$ and the 5 N-terminal amino acid residues of the CH1 region, was prepared as follows.
Composition of the PCR Reaction Solution:
plasmid pME-H DNA, 200 ng;
oligonucleotide primer 7AH4P, 80 pmol;
oligonucleotide primer 7AH4N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The respective PCR products were first subjected to phenol extraction and then to ethanol precipitation, and then separated by 5% w/v polyacrylamide gel electrophoresis. After electrophoresis, the gel was stained with 1 µg/ml of ethidium bromide and the DNA bands corresponding to H7A1-DNA, H7A2-DNA, H7A3-DNA and H7A4-DNA, detected under UV light, were cut out using a razor blade and eluted from the gel using a Centriruter and Centricon-10, as described above. The eluted DNA was concentrated by centrifugation at 7,500×g, followed by ethanol precipitation, and dissolved in 50 µl of distilled water.

b) Second Stage PCR

Figure 21:
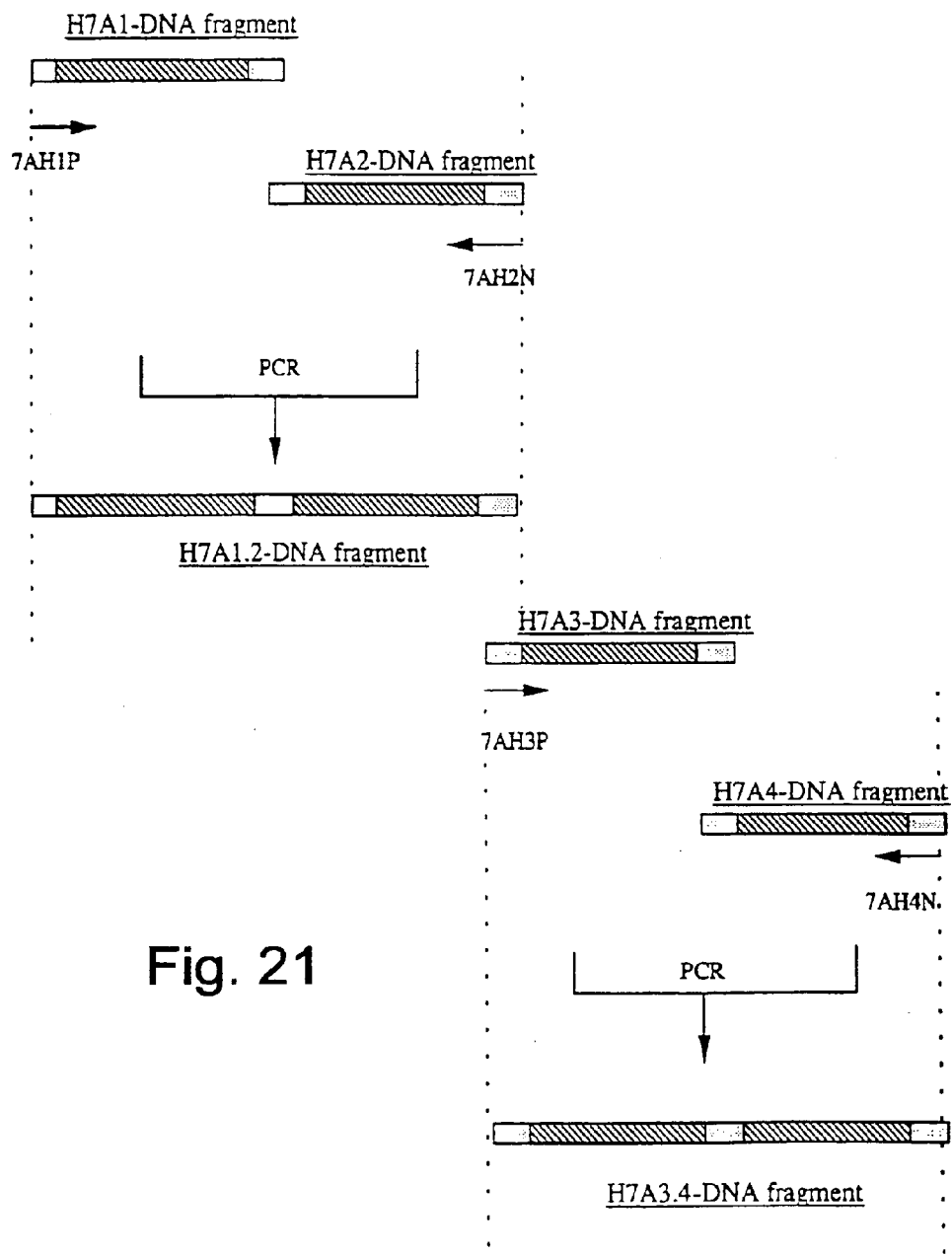
FIG. 21 is a summary of the second step PCR for the production of VD-DNA.

The outline of the second stage PCR for the preparation of VD-DNA is shown in FIG. 21.

The H7A1.2-DNA fragment, in which the above described H7A1-DNA and H7A2-DNA fragments were fused, was prepared as follows.
Composition of the PCR Reaction Solution:
H7A1-DNA solution prepared in the first stage PCR, 10 µl;
H7A2-DNA solution prepared in the first stage PCR, 10 µl;
oligonucleotide primer 7AH1P, 80 pmol;
oligonucleotide primer 7AH2N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The H7A3.4-DNA fragment, in which the above described H7A3-DNA and H7A4-DNA fragments were fused, was prepared as follows.
Composition of the PCR reaction solution:
H7A3-DNA solution prepared in the first stage PCR, 10 µl;
H7A4-DNA solution prepared in the first stage PCR, 10 µl;
oligonucleotide primer 7AH3P, 80 pmol;
oligonucleotide primer 7AH4N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The resulting, amplified H7A1.2-DNA and H7A3.4-DNA fragments were subjected first to phenol extraction and then to ethanol precipitation, and then separated by 5% w/v polyacrylamide gel electrophoresis. After electrophoresis, the gels were stained with 1 µg/ml of ethidium bromide and the relevant bands thus detected were cut out using a razor blade and eluted from the gel using a Centriruter and Centricon-10, as described above. The eluted DNA was concentrated by centrifugation at 7,500×g, followed by ethanol precipitation, and dissolved in 50 µl of distilled water.

c) Third Stage PCR

Figure 22:
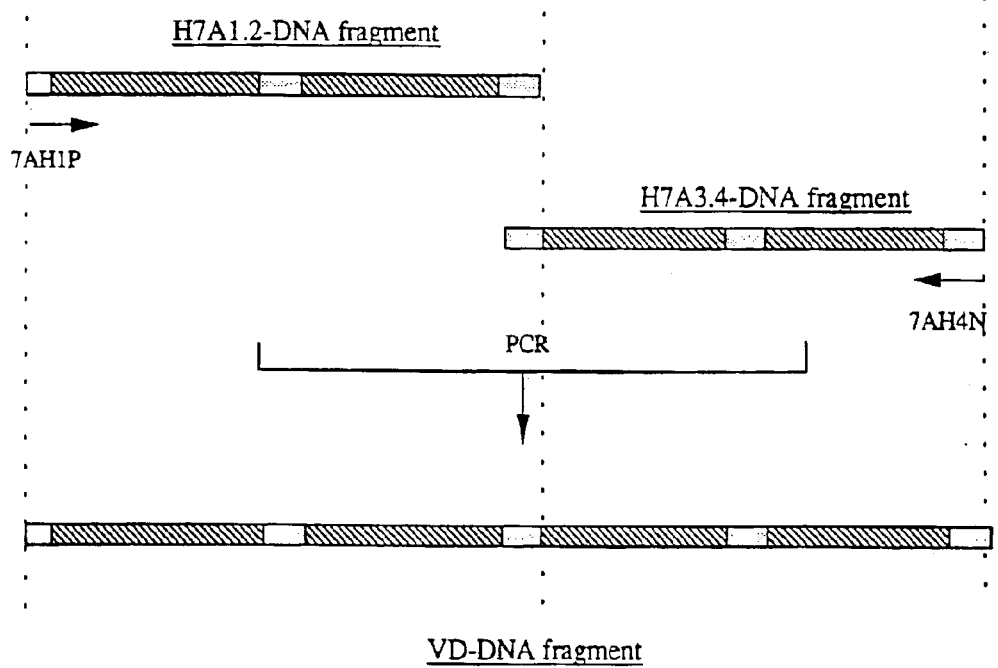
FIG. 22 is a summary of the third step PCR for the production of VD-DNA.

The outline of the third stage PCR for the preparation of VD-DNA is shown in FIG. 22.

The VD-DNA fragment, in which above described H7A1.2-DNA and H7A3.4-DNA fragments were fused, was prepared as follows.

Composition of the PCR Reaction Solution:

H7A1.2-DNA solution prepared in the second stage PCR, 10 µl;
H7A3.4-DNA solution prepared in the second stage PCR, 10 µl;
oligonucleotide primer 7AH1P, 80 pmol;
oligonucleotide primer 7AH4N, 80 pmol;
DNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The resulting, amplified VD-DNA fragment was subjected first to phenol extraction and then to ethanol precipitation, and then separated by 5% w/v polyacrylamide gel electrophoresis. After electrophoresis, the gel was stained with 1 µg/ml of ethidium bromide and the VD-DNA band thus detected was cut out using a razor blade and eluted from the gel using a Centriruter and Centricon-10, as described above. The eluted DNA was concentrated by centrifugation at 7,500×g, followed by ethanol precipitation, and dissolved in 50 µl of distilled water.

Figure 23:
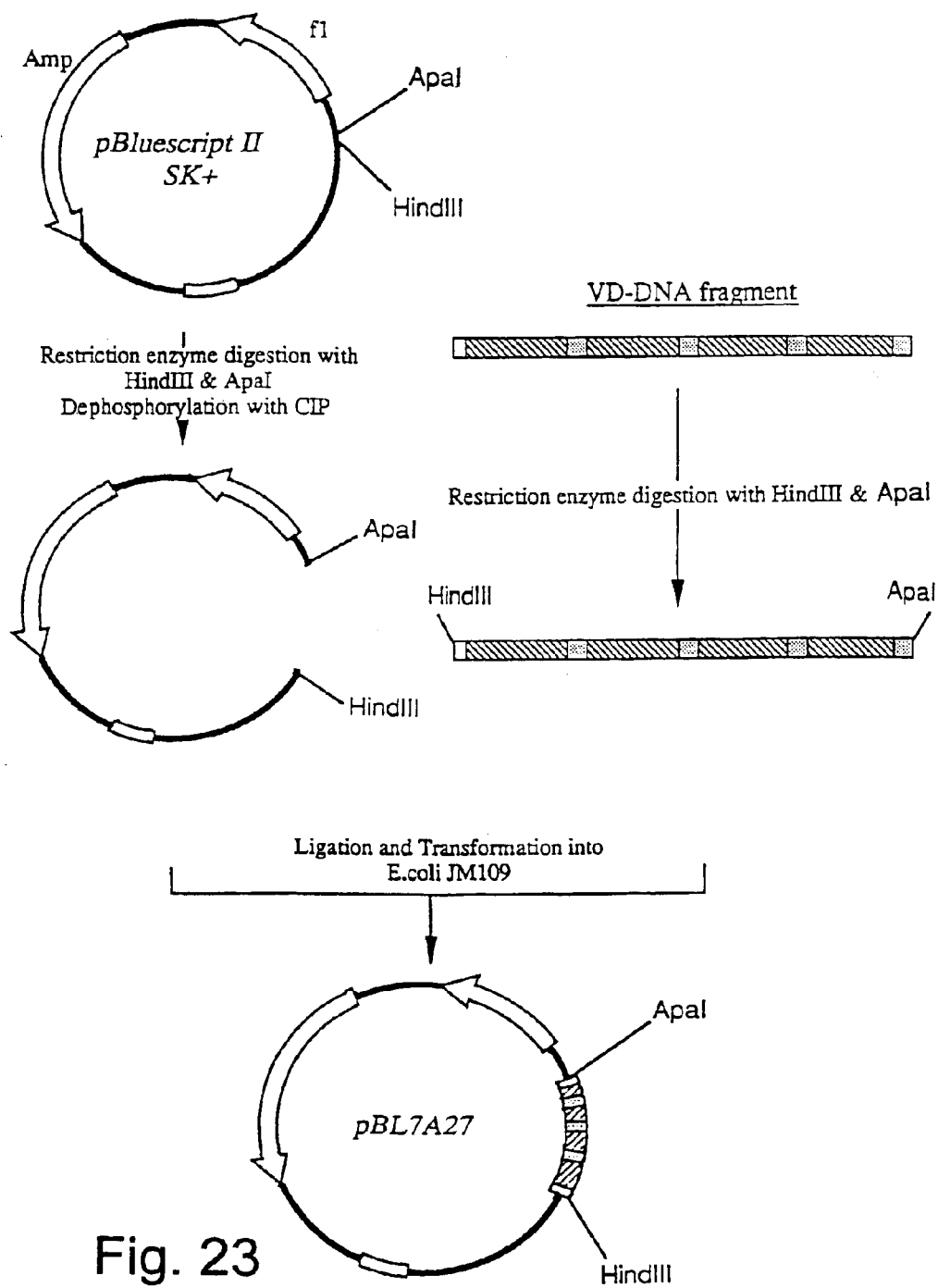
FIG. 23 is a summary of the construction of the expression plasmid carrying VD-DNA fragment.

The construction of a plasmid carrying the VD-DNA fragment is outlined in FIG. 23.

The VD-DNA fragment obtained above was further purified by phenol extraction followed by ethanol precipitation, and then digested with the restriction enzymes Hind III and ApaI.

One µg of the plasmid vector pBLUESCRIPT-II SK+ DNA (Stratagene) was digested with Hind III and Apa I, and then dephosphorylated using CIP. The resulting, dephosphorylated plasmid DNA and 100 ng of the VD-DNA fragment, which had also been digested with Hind III and Apa I, were ligated using a DNA Ligation Kit Version 2.0 (Takara Shuzo Co., Ltd.). The resulting ligation mix was then used to transform E. coli JM109, which was then plated on LB agar plates containing final concentrations of 1 mM IPTG, 0.1% w/v X-Gal and 50 µg/ml ampicillin. Any resulting white transformants were cultured in 2 ml liquid LB medium containing 50 µg/ml ampicillin at 37° C. overnight, and plasmid DNA was then extracted from the culture by the alkaline-SDS method. The resulting plasmid was digested with Hind III and Apa I and subjected to agarose gel electrophoresis to confirm the presence or absence of the insert of interest. Accordingly, the plasmid pBL7A27 with a VD-DNA insert was obtained.

(2) Construction of a Plasmid Carrying Human IgG1 Constant Region Genomic DNA

1) Synthesis of Primers for Preparing 5'-Terminal Human Genomic DNA Fragment

A 5'-terminal human IgG1 genomic DNA fragment was synthesized by PCR. For this, the following 2 oligonucleotide primers were prepared:

5'-GGGAAGCTTC CGCGGTCACA TGGCACCACC TCTCTTGCA-3' (5'Hind: SEQ ID No. 84 of the Sequence Listing); and 5'-GCTCTGCAGA GAGAAGATTG GGAGTTACTG GAATC-3' (IGGCPSTN: SEQ ID No. 85 of the Sequence Listing).

2) Construction of Plasmid pIG5'03

Figure 24:
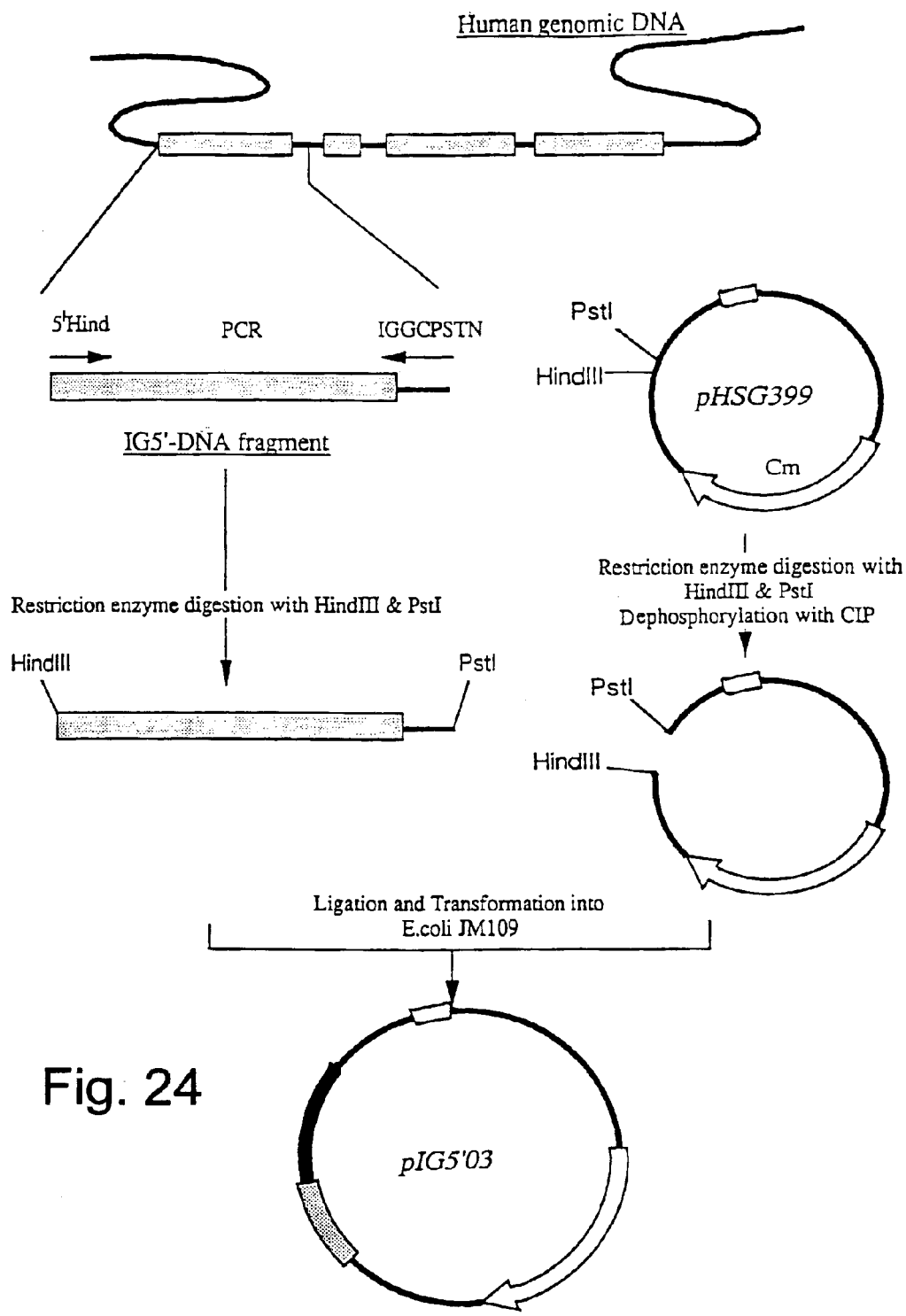
FIG. 24 is a summary of the construction of the DNA (IG5'-DNA) fragment comprising CH1 region of human IgG1 and an intron.

Genomic DNA, comprising the CH1 region of human IgG1 together with an intron following a Hind III cleavage sequence, was separated and amplified by PCR using human genomic DNA as the template, and then inserted into the plasmid pHSG399 (Takara Shuzo Co., Ltd.) and cloned into E. coli. The preparation of this DNA (hereinafter referred to as "IG5'-DNA") is outlined in FIG. 24.

An IG5'-DNA fragment was prepared as follows.

Composition of the PCR Reaction Solution:

human genomic DNA (Clonetech), 2 µg;
oligonucleotide primer 5'Hind, 80 pmol;
oligonucleotide primer IGGCPSTN, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The resulting, amplified IG5'-DNA fragment was subjected first to phenol extraction and then to ethanol precipitation, and separated by 5% w/v polyacrylamide gel electrophoresis. After electrophoresis, the gel was stained with 1 µg/ml of ethidium bromide and the IG5'-DNA band thus detected was cut out using a razor blade and eluted from the gel using a Centriruter and Centricon-10, as described above. The eluted DNA was concentrated by centrifugation at 7,500×g, followed by ethanol precipitation, and dissolved in 50 µl of distilled water.

The IG5'-DNA fragment thus obtained was further purified by phenol extraction and then ethanol precipitation, and was then digested with the restriction enzymes Hind III and Pst I.

One µg of plasmid pHSG399 DNA (Takara Shuzo Co., Ltd.) was digested with the restriction enzymes Hind III and Pst I, and then dephosphorylated using CIP. The resulting dephosphorylated plasmid DNA and 100 ng of the IG5'-DNA fragment, which had also been digested with Hind III and Pst I, were ligated using a DNA Ligation Kit Version 2.0 (Takara Shuzo Co., Ltd.). The ligation mix was then used to transform E. coli JM109, which was then plated onto LB agar medium containing final concentrations of 1 MM IPTG, 0.1% w/v X-Gal and 50 µg/ml chloramphenicol. Any white transformants obtained were cultured in 2 ml liquid LB medium containing 50 µg/ml chloramphenicol at 37° C. overnight, and plasmid DNA was extracted from the resulting culture by the alkaline-SDS method. The extracted plasmid DNA was then digested with Hind III and Pst I, and subjected to 1% w/v agarose gel electrophoresis to confirm the presence or absence of the insert of interest. Accordingly, the plasmid pIG5'03, containing a IG5'-DNA fragment insert, was obtained.

(3) Construction of a Plasmid Carrying Human IgG1 Constant Region Genomic DNA

1) Synthesis of Primers for Preparing 3'-Terminal Human IgG1 Genomic DNA Fragment A 3'-terminal human IgG1 genomic DNA fragment was synthesized by PCR. For this, the following 2 primers were prepared:

5'-TCTCTGCAGA GCCCAAATCT TGTGACAAAA CTCAC-3' (IGGCPSTP: SEQ ID No. 86 of the Sequence Listing); and 5'-GGGGAATTCG GGAGCGGGGC TTGCCGGCCG TCGCACTCA-3' (Eco3': SEQ ID No. 87 of the Sequence Listing).

2) Construction of Plasmid pIG3'08

Figure 25:
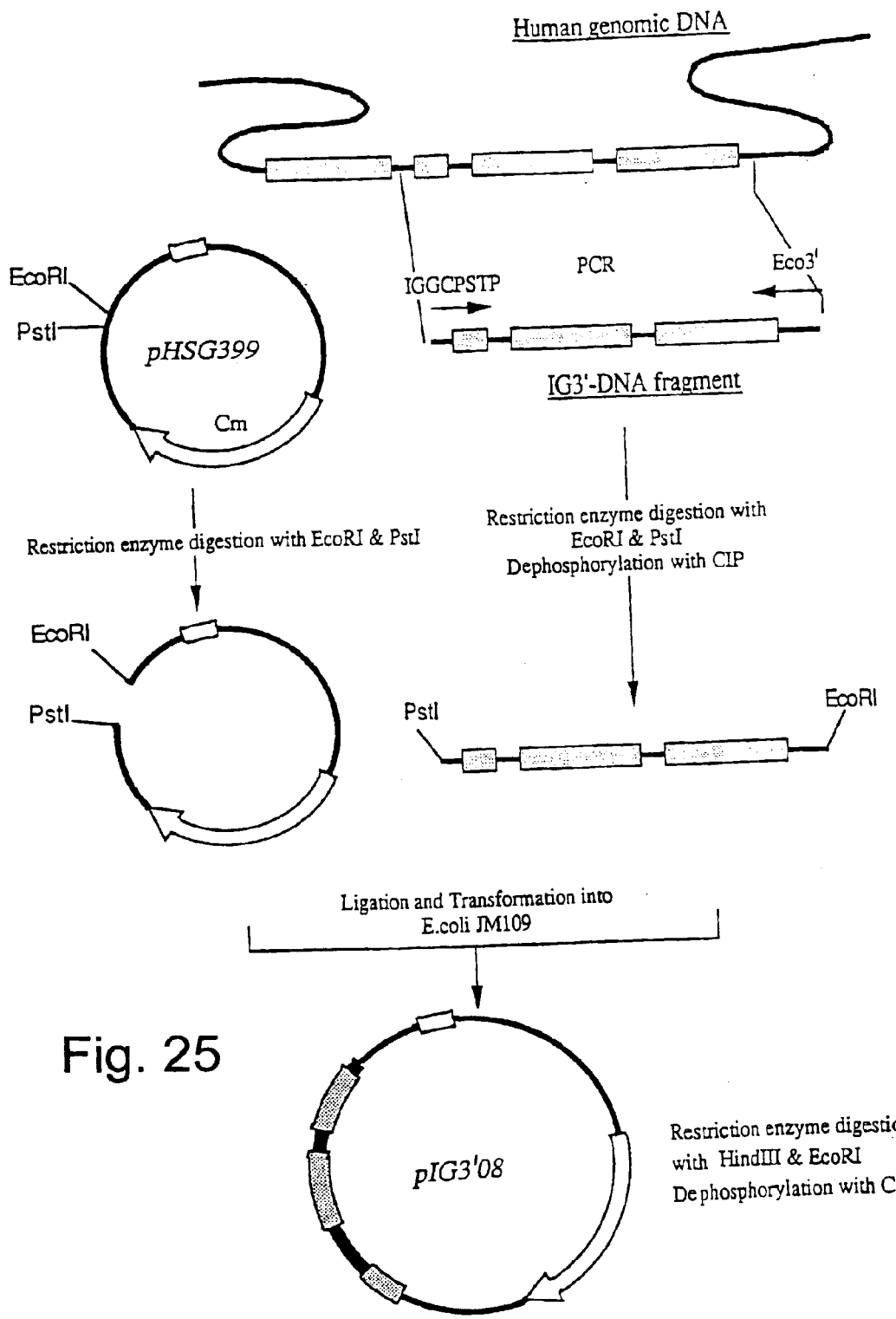
FIG. 25 is a summary of the construction of the genomic DNA(IG3'-DNA) fragment comprising hinge region, CH2 region, CH3 region and introns of human IgG1.

DNA comprising the sequence: intron from human IgG1; hinge region; intron from human IgG1; CH2 region; intron from human IgG1; CH3 region; and an EcoRI cleavage sequence, was separated and amplified by PCR using human genomic DNA as the template, and then inserted into the plasmid pHSG399 (Takara Shuzo Co., Ltd.) and cloned into E. coli. The preparation of the above DNA (hereinafter referred to as "IG3'-DNA") is outlined in FIG. 25.

IG3'-DNA was prepared as follows.
Composition of the PCR reaction solution:
human genomic DNA (Clonetech), 2 μg;
oligonucleotide primer IGGCPSTP, 80 pmol;
oligonucleotide primer Eco3', 80 pmol;
dNTP cocktail, 20 μl;
10×Pfu buffer, 20 μl;
Pfu DNA polymerase, 10 units; and
redistilled water to a final volume of 200 μl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The resulting, amplified IG3'-DNA fragment was subjected first to phenol extraction and then to ethanol precipitation, and then separated by 5% w/v polyacrylamide gel electrophoresis. After electrophoresis, the gel was stained with 1 μg/ml of ethidium bromide and the IG3'-DNA band thus detected was cut out using a razor blade and eluted from the gel using a Centriruter and Centricon-10, as described above. The eluted DNA was concentrated by centrifugation at 7,500×g, followed by ethanol precipitation, and dissolved in 50 μl of distilled water.

The IG3'-DNA fragment thus obtained was further purified by phenol extraction and then ethanol precipitation, and was then digested with the restriction enzymes EcoRI and Pst I.

One μg of plasmid pHSG399 DNA (Takara Shuzo Co., Ltd.) was digested with EcoRI and Pst I, and then dephosphorylated using CIP. The resulting dephosphorylated plasmid DNA was then ligated with 100 ng of the IG3'-DNA fragment, which had also been digested with EcoRI and Pst I, using a DNA Ligation Kit Version 2.0 (Takara Shuzo Co., Ltd.). The ligation mix was then used to transform E. coli JM109, which was plated onto LB agar medium containing final concentrations of 1 mM IPTG, 0.1% w/v X-Gal and 50 μg/ml chloramphenicol. Any white colonies were selected and the plasmid pIG3'08, containing an IG3'-DNA insert, was obtained.

(4) Construction of Expression Vector Plasmid for Humanized HFE7A Heavy Chain

Figure 26:
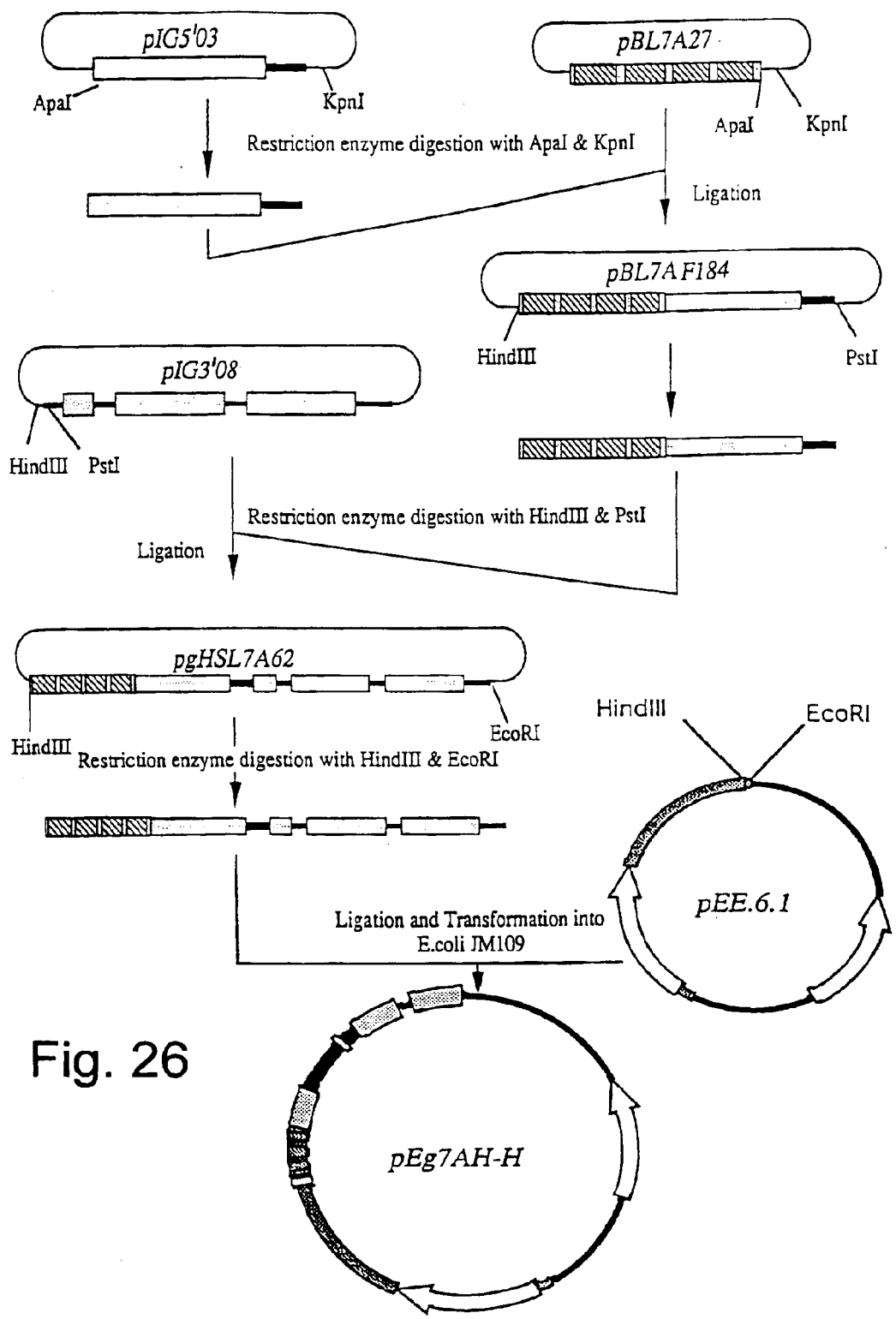
FIG. 26 is a summary of the construction of the expression plasmid pEg7AH-H.

The expression plasmid vector pEg7AH-H, carrying the DNA of SEQ ID No. 88 of the Sequence Listing and encoding the humanized HFE7A heavy chain polypeptide of SEQ ID No. 89 of the Sequence Listing, was constructed using the above described plasmids pBL7A27, pIG3'03 and pIG3'8. The procedure is outlined in FIG. 26.

Ten μg of plasmid pIG5'03 DNA, comprising the CH1 region of human IgG1 heavy chain and an intron, was digested with the restriction enzymes ApaI and Kpn I. In addition, 1 μg of pBL7A27 DNA above was also digested with the restriction enzymes Apa I and Kpn I, and then dephosphorylated using CIP. The resulting dephosphorylated pBL7A27 DNA (100 ng) was ligated with 10 μg of the digested and dephosphorylated pIG5'03 DNA, using a DNA Ligation Kit Version 2.0 (Takara Shuzo Co., Ltd.). The ligation mix was then used to transform E. coli JM109, which was plated on LB medium containing 50 μg/ml ampicillin. Resulting transformants were cultured in 2 ml liquid LB medium containing 50 μg/ml ampicillin at 37° C. overnight, and plasmid DNA was extracted from the culture by the alkaline-SDS method. The plasmid was digested with Apa I and Kpn I, or with Hind III and Pst I, to confirm the presence or absence of the insert of interest by 1% w/v agarose gel electrophoresis. Thus, the plasmid pBL7AF184, containing a VD-DNA fragment of humanized HFE7A connected with the IG5'-DNA fragment, was obtained.

Next, 10 μg of the thus obtained plasmid pBL7AF184 was digested with the restriction enzymes Hind III and Pst I, and 1 μg of the plasmid pIG3'08 DNA above was likewise digested with Hind III and Pst I, and dephosphorylated using CIP. The resulting dephosphorylated pIG3'08 DNA (100 ng) was ligated with 10 μg of the digested pBL7AF184 DNA, using a DNA Ligation Kit Version 2.0 (Takara Shuzo Co., Ltd.). E. coli JM109 was transformed with the ligation mix and plated onto LB medium containing 50 μg/ml ampicillin. Any resulting transformants were cultured in 2 ml liquid LB medium containing 50 μg/ml chloramphenicol at 37° C. overnight, and plasmid DNA was extracted from the culture by the alkaline-SDS method. The plasmid was digested with Hind III and Pst I, or with Hind III and EcoRI, to confirm the presence or absence of the insert of interest by 1% w/v agarose gel electrophoresis.

Plasmid pgHSL7A62, containing a VD-DNA fragment of humanized HFE7A connected to a genomic DNA fragment encoding human IgG1 constant region, was obtained. The transformant E. coli pgHSL7A62 SANK 73397 harboring plasmid pgHSL7A62 was deposited with the Kogyo Gijutsuin Seimei-Kogaku Kogyo Gijutsu Kenkyujo on Aug. 22, 1997, in accordance with the Budapest Treaty, and was accorded the accession number FERM BP-6074.

Ten micrograms of the thus obtained plasmid pgHSL7A62 DNA were digested with the restriction enzymes Hind III and EcoRI and, likewise, 1 μg of the expression plasmid pEE.6.1 DNA was digested with Hind III and EcoRI, and dephosphorylated using CIP. The resulting dephosphorylated pEE.6.1 DNA (100 ng) was ligated with 10 μg of the digested pgHSL7A62 DNA, using a DNA Ligation Kit Version 2.0 (Takara Shuzo Co., Ltd.). E. coli JM109 was transformed with the ligation mix and plated onto LB medium containing 50 μg/ml ampicillin. Any resulting transformants were cultured in 2 ml liquid LB medium containing 50 μg/ml ampicillin at 37° C. overnight, and plasmid DNA was extracted from the culture by the alkaline-SDS method. The plasmid was digested with Hind III and EcoRI, to confirm the presence or absence of the insert of interest by 1% w/v agarose gel electrophoresis.

The resulting plasmid, pEg7AH-H, contained a fusion fragment comprising a VD-DNA fragment of humanized HFE7A and a genomic DNA fragment encoding human IgG1 constant region in connection and inserted downstream of the CMV promoter in the correct orientation.

(5) Verification of Nucleotide Sequence

To verify that the DNA insert of the pEg7AH-H had the expected nucleotide sequence, the DNA insert was analyzed to determine the nucleotide sequence. For this, the following primers were synthesized:

5'-ACAGCCGGGA AGGTGTGCAC-3' (IG01: SEQ ID No. 90);

5'-AGACACCCTC CCTCCCTGTG-3' (IG02: SEQ ID No. 91);

5'-GTGCAGGGCC TGGGTTAGGG-3' (IG03: SEQ ID No. 92);
5'-GCACGGTGGG CATGTGTGAG-3' (IG04: SEQ ID No. 93);
5'-GTTTTGGGGG GAAGAGGAAG-3' (IG05: SEQ ID No. 94);
5'-CCAGTCCTGG TGCAGGACGG-3' (IG06: SEQ ID No. 95);
5'-CCTGTGGTTC TCGGGGCTGC-3' (IG07: SEQ ID No. 96);
5'-CGTGGTCTTG TAGTTGTTCT-3' (IG08: SEQ ID No. 97);
5'-CTTCCTCTTC CCCCCAAAAC-3' (IGP5: SEQ ID No. 98);
5'-CCGTCCTGCA CCAGGACTGG-3' (IGP6: SEQ ID No. 99);
5'-GCAGCCCCGA GAACCACAGG-3' (IGP7: SEQ ID No. 100);
5'-AGAACAACTA CAAGACCACG-3' (IGP8: SEQ ID No. 101);
5'-GCCTGACATC TGAGGACTC-3' (H5+: SEQ ID No. 102);
5'-GAGTCCTCAG ATGTCAGGC-3' (H5−: SEQ ID No. 103);
5'-GAGCAGTACT CGTTGCTGCC GCGCGCGCCA CCAG-3' (PEEF: SEQ ID No. 104); and
5'-GGTATGGCTG ATTAATGATC AATG-3' (PEEB: SEQ ID No. 105).

Figure 27:
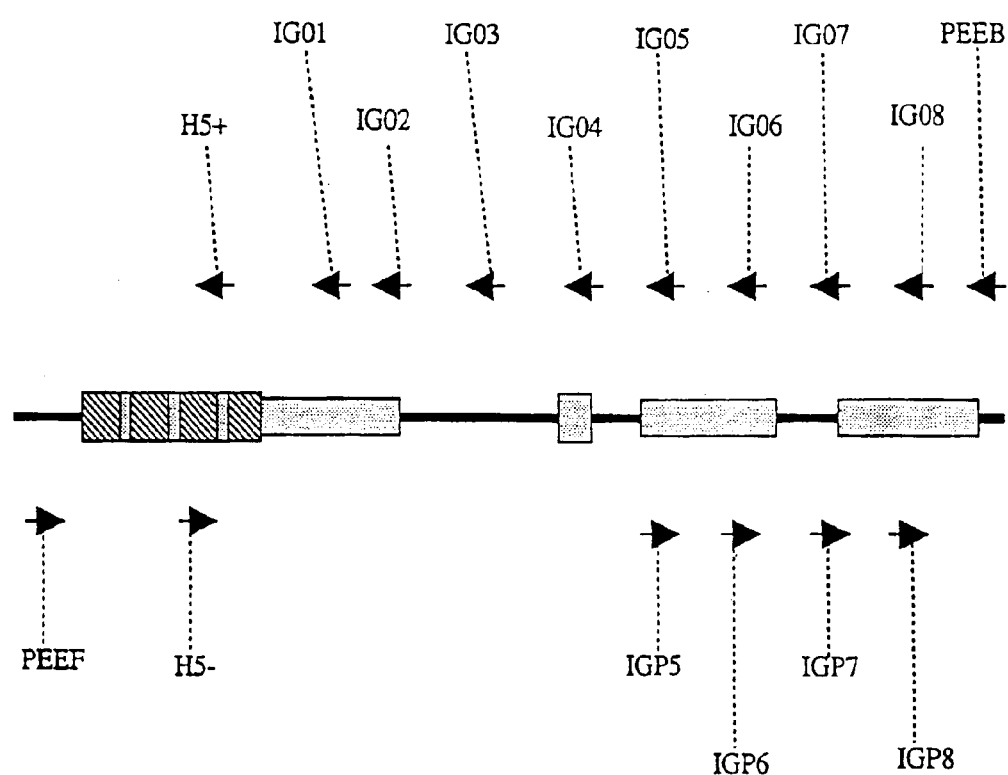
FIG. 27 shows the positions to which the heavy chain sequencing primers bind.

The positions to which each primer binds are shown in FIG. 27. The determination of the nucleotide sequence was performed by the dideoxynucleotide chain termination method (ibid.) using, as templates, the respective plasmids purified by the alkaline-SDS method and the cesium chloride method (ibid.). It was confirmed that pEg7AH-H had the nucleotide sequence of SEQ ID No. 88 of the Sequence Listing, encoding the polypeptide of SEQ ID No. 89 of the Sequence Listing.

REFERENCE EXAMPLE 16

Expression in COS-1 Cells

COS-1 cells (derived from a monkey kidney) were transfected with the expression plasmids for the humanized HPE7A heavy chain and with the expression plasmids for each of the humanized HFE7A light chains obtained above. Transfection was performed by electroporation using the gene transfection apparatus GTE-1 (Shimadzu Seisakusyo, K. K.) equipped with an FCT-13 chamber having electrodes separated by 2 mm (Shimadzu Seisakusyo, K. K.).

COS-1 cells (American Type Culture Collection No. CRL-1650) were grown to semi-confluence in a culture flask (culture area: 225 cm$^2$; Sumitomo Bakelite) containing Minimal Essential α medium ["α(+)MEM"; Gibco BRL] supplemented with 10% v/v FCS (Moregate). Subsequently, the medium was discarded and the COS-1 cells were detached from the flask by treatment with 3 ml of trypsin-EDTA solution (Sigma Chemicals Co.) at 37° C. for 3 minutes. The detached cells were then harvested by centrifugation at 800 r.p.m. for 2 minutes, discarding the supernatant and washing twice with phosphate buffer (0.02% w/v potassium chloride [KCl], 0.02% w/v potassium dihydrogenphoshate [$KH_2PO_4$], 0.8% w/v sodium chloride [NaCl], 1.15% w/v disodium hydrogenphosphate [$Na_2HPO_4$]; hereinafter referred to as "PBS(−) buffer"; Nissui Pharmaceutical Co., Ltd.). The washed COS-1 cells were then suspended to a cell density of 1×10$^8$ cells/ml in PBS(−) buffer.

In parallel, 4 μg of humanized HFE7A heavy chain expression plasmid DNA were mixed with 4 μg of humanized HFE7A light chain expression plasmid DNA, each purified by the alkaline-SDS method and cesium chloride density gradient centrifugation. The resulting mixture was subjected to ethanol precipitation and then suspended in 20 μl of PBS(−) buffer. These mixing, precipitation and resuspension steps were all performed in the same tube. The whole of the resulting plasmid suspension (20 μl) was mixed with 20 μl of the previously prepared COS-1 cell suspension (2×10$^6$ cells) and the mixture was transferred to an FCT-13 electroporation chamber (Shimadzu Seisakusyo, K. K.) having electrodes set 2 mm apart, which was then loaded into gene transfection apparatus GTE-1 (Shimadzu Seisakusyo, K. K.). Pulses of 600 V, each of 50 μF were applied twice with a 1 second interval, in order transform the COS-1 cells with the plasmid DNA. After electroporation, the cell-DNA mixture in the chamber was suspended in 20 μl of α(+)MEM supplemented with 10% v/v FCS and transferred to a culture flask (culture area 75 cm$^2$; Sumitomo Bakelite). After incubating under 5% v/v $CO_2$ at 37° C. for 72 hours, the culture supernatant was recovered, and analysis was performed on the supernatants to determine what expression products were present.

Using the above method, but modified as appropriate, COS-1 cells were variously transfected with each of the following plasmid or plasmid combinations:

(A): no plasmid DNA
(B): cotransfection with pEg7AH-H and p7AL-MM
(C): cotransfection with pEg7AH-H and p7AL-HM
(D): cotransfection with pEg7AH-H and p7AL-HH

REFERENCE EXAMPLE 17

Quantification of Expression Products by ELISA

Verification and quantitative assay of the expression of humanized antibodies as expression products in the culture supernatant fluids prepared in Reference Example 16 were performed by ELISA, using an anti-human IgG antibody.

Goat anti-human IgG Fc specific polyclonal antibody (Kappel) was dissolved to a final concentration of 1 μg/ml in adsorption buffer (0.05 M sodium hydrogencarbonate, 0.02% w/v sodium azide, pH 9.6) and 100 μl aliquots were added to each well of a 96-well plate (MaxiSorb, Nunc), and the plate was incubated at 37° C. for 2 hours to encourage adsorption of the antibody. Next, each well was washed with 350 μl of PBS-T [PBS(−) containing 0.05% w/v Tween-20 (BioRad)] four times. After washing, culture supernatant diluted with α(+)MEM containing 10% v/v FCS was added to the wells, and the plate was further incubated at 37° C. for 2 hours.

After this time, the wells were again washed four times with PBS-T, and then 100 μl of alkaline phosphatase-labeled goat anti-human IgG Fc specific polyclonal antibody (Caltag Lab.) diluted 5,000-fold with PBS-T were added to each well and the plate was incubated at 37° C. for 2 hours. Each well was then again washed four times with PBS-T, and 100 μl of a substrate solution of 1 mg/ml p-nitrophenyl phosphate, prepared in 10% v/v diethanol amine (pH 9.8), was added to each well. After a subsequent incubation at 37° C. for 0.5 to 1 hour, absorbance at 405 nm was measured.

In the present experiments, human plasma IgG subclass 1 (IgG1; Biopure AG) diluted with α(+)MEM containing 10% v/v FCS to certain desired concentrations was used to provide concentration reference samples of the humanized HFE7A antibodies contained in the culture supernatant fluids.

As expected, each supernatants of transformants (B), (C) and (D) was determined to express human antibody, as detected by anti-human IgG antibody. The negative control, (A), showed no expression of human antibody.

REFERENCE EXAMPLE 18

Assay for Fas-Binding Activity

The assay for Fas-binding activity in the cell culture supernatants prepared in Reference Example 16 was performed by ELISA as follows.

Culture supernatant from COS-1 cells expressing the human Fas fusion protein, as obtained in Reference Example 1 above, diluted 5-fold with adsorption buffer, was dispensed into wells of a 96-well plate (MaxiSorb; Nunc) at 50 µl per well and the plate was incubated at 4° C. overnight to allow adsorption of the human Fas fusion protein to the surface of the wells. Next, each of the wells was washed 4 times with 350 µl of PBS-T. After washing, PBS-T containing 5% v/v BSA (bovine serum albumin; Wako Pure Chemical Industries, Ltd.) was added to the wells at 50 µl per well and the plate was incubated at 37° C. for 1 hour to block the remainder of the surface of each well. The wells were then again washed four times with PBS-T.

The culture supernatants obtained in Reference Example 16 were adjusted to have a final concentration of the product of interest of 100 ng/ml in α(+)MEM containing 10% v/v PCS. Concentrations were estimated by the method described in Reference Example 17. Each of the resulting 100 ng/ml solutions was then used to produce serial dilutions by serial 2-fold dilution with α(+)MEM containing 10% v/v FCS. Next, 50 µl of each of the resulting serial dilutions of each expression product was added to a well prepared as above, and the plate was incubated at 37° C. for 2 hours to allow reaction.

After this time, the wells were again washed four times with PBS-T, and then 50 µl of alkaline phosphatase-labeled goat anti-human IgG Fc specific polyclonal antibody (Caltag Lab.), diluted 10,000-fold with PBS-T, were dispensed into each well and reaction was allowed to proceed at 37° C. for 2 hours.

HFE7A purified from mouse hybridoma HPE7A was used as a control (IgG1), and was detected using alkaline phosphatase-labeled goat anti-mouse IgG+IgA+IgM (Gibco BRL), diluted 5,000-fold with PBS-T, in place of the alkaline phosphatase-labeled goat anti-human IgG Fc specific polyclonal antibody.

The wells were again washed four times with PBS-T, and then 50 µl of substrate solution [1 mg/ml p-nitrophenyl phosphate in 10% v/v diethanol amine (pH9.8)] was dispensed into each well and the plate was incubated at 37° C. for 0.5 to 1 hour. Binding activity of the expression product contained in each culture supernatant fluid with the human Fas fusion protein was evaluated by reading the absorbance of each well at 405 nm.

Figure 28:
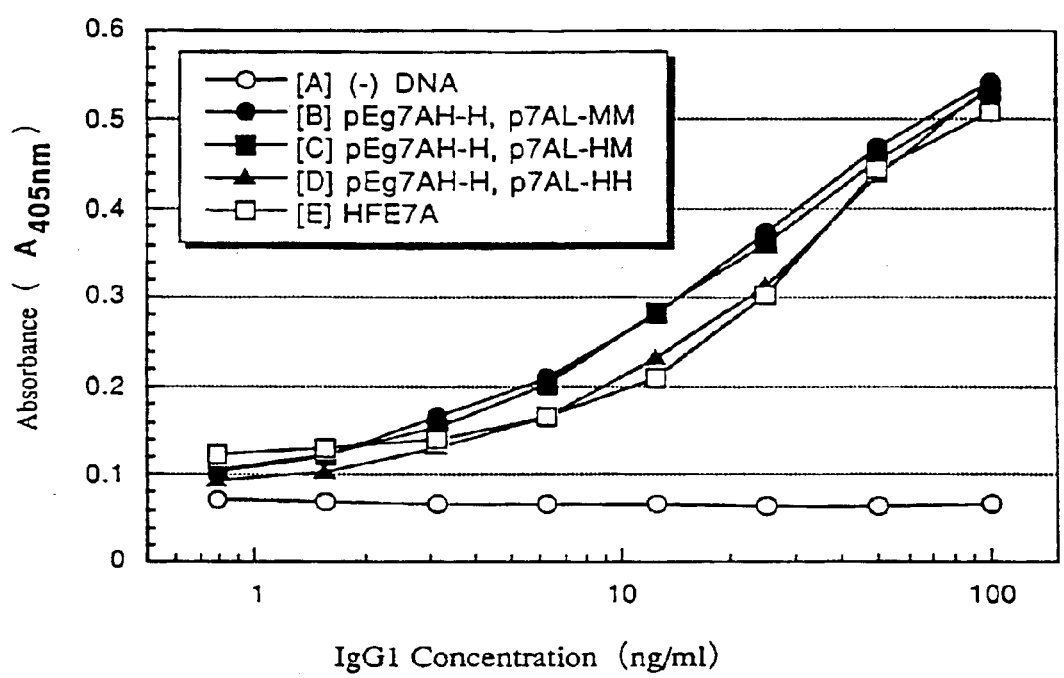
FIG. 28 is a graph depicting the binding activity of the humanized anti-Fas antibodies to the human Fas fusion protein.

As expected, binding activity to the human Fas fusion protein was demonstrated for supernatants (B), (C) and (D) above (FIG. 28).

REFERENCE EXAMPLE 19

Competitively Inhibiting Binding of HFE7A to Fas

The humanized anti-Fas antibodies of the Examples should inhibit the binding of HFE7A to Fas, as the antibodies of the Examples were derived from HFE7A. Therefore, the ability of the expression products obtained in Reference Example 16 to competitively inhibit the binding of HFB7A to the human Fas fusion protein was measured.

One mg of the purified monoclonal antibody HPE7A obtained in Reference Example 3 was labeled using a commercially available alkaline phosphatase labeling kit (Immuno-Link AP and APL Labeling Kit; Genosis), using the protocol supplied with the kit. The resulting, labeled antibody is also referred to herein as "AP-HPE7A".

The COS-1 cell culture supernatant containing the human Fas fusion protein, as obtained in Reference Example 1, was diluted 5-fold with adsorption buffer, and dispensed into the wells of a 96-well plate for luminescence detection (Luminescent Solid Assay Plate, high binding property; Costar) at 50 µl per well. The plate was then incubated at 40° C. overnight to allow adsorption of the human Fas fusion protein to the surface of the wells.

After this time, each well was washed 4 times with 350 µl of PBS-T, and then 100 µl PBS-T containing 5% v/v BSA was added to each well and the plate was incubated at 37° C. for 1 hour to block the remainder of the surface of each well. The wells were then again washed four times with PBS-T.

The culture supernatants obtained in Reference Example 16 were adjusted to final concentrations of antibody of 1 µg/ml in α(+)MEM containing 10% v/v FCS by the method of Reference Example 17. Each of the resulting solutions of the expression products was used to produce serial dilutions by serial 2-fold dilution with α(+)MEM containing 10% v/v FCS. AP-HFE7A was diluted to 50 ng/ml with α(+)MEM containing 10% v/v PCS, and 25 µl of the resulting solution was mixed with an equal volume of each of the prepared serial dilutions.

Each of the wells was again washed four times with PBS-T, and then 50 µl of each of the resulting antibody mixtures were added to individual wells, and the plate was allowed to stand at at room temperature overnight. Subsequently, after washing each well with PBS-T again four times, 100 µl of CDP-star buffer (9.58 ml diethanol amine, 0.2 g magnesium chloride, 0.25 g sodium azide, pH8.5) was dispensed into each well and the plate was allowed to stand at room temperature for 10 minutes. After this time, the CDP-star buffer was discarded and CDP-star substrate [1.2 ml sapphire II (Tropix), 200 µl CDP-star (Tropix), q.s. to 12 ml with CDP-star buffer] was added at 50 µl per well, and the plate was then allowed to stand at room temperature for a further 40 minutes.

Competitive inhibition of the expression products of Reference Example 16 of the binding of HFE7A to the human Fas fusion protein was evaluated by measuring the intensity of the luminescence with Luminoscan (Titertech).

Figure 29:
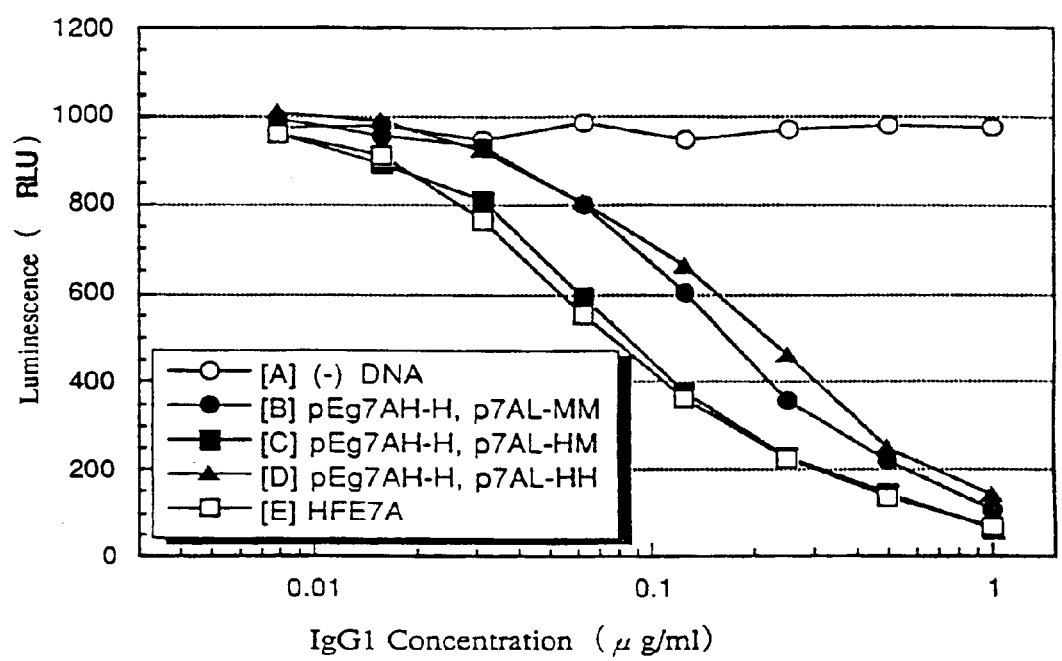
FIG. 29 shows competitive inhibition of HFE7A and the humanized anti-Fas antibodies for the human Fas fusion protein.

As a result, it was verified that the expression products prepared in Reference Example 16 specifically inhibited the binding of HFE7A to the human Fas fusion protein (FIG. 29).

REFERENCE EXAMPLE 20

Apoptosis-Inducing Activity

WR19L12a cells (c.f. Itoh, N. et al., ibid.) were used to examine the apoptosis-inducing activity of the COS-1 cell culture supernatant of Reference Example 16.

WR19L12a cells were cultured in RPMI 1640 medium with 10% v/v FCS (Gibco BRL) at 37° C. for 3 days under 5% v/v $CO_2$, and 50 µl ($1\times10^5$ cells) of the resulting culture were then dispensed into each well of a 96-well microplate (Sumitomo Bakelite). The culture supernatants obtained in Reference Example 16 were adjusted to a final concentration of antibody of 100 ng/ml in RPMI 1640 medium containing 10% v/v FCS. Concentrations were estimated by the method of Reference Example 17. Each of the adjusted solutions of the expression products was used to produce serial dilutions by serial 2-fold dilution with RPMI 1640 containing 10% v/v FCS. Each of the resulting dilutions of each expression product solution was added to individual wells, at 50 µl per well, and the plate was incubated at 37° C. for 1 hour. After this time, the cells in each well were washed four times with RPMI 1640 containing 10% v/v FCS and then the washed cells were suspended in 75 µl per well of RPMI 1640 containing 10% v/v FCS.

Subsequently, 75 µl of 1.25 µg/ml goat anti-human IgG Fc specific polyclonal antibody (Kappel) in RPMI 1640 medium containing 10% v/v FCS was added to each well, as secondary antibody. The plate was allowed to stand at 37° C. for 12 hours, and then 50 µl of 25 µM PMS (phenazine methosulfate; Sigma Chemical Co.), containing 1 mg/ml XTT [2,3-bis(2-methoxy-4-nitro-5-sulfophenyl)-2H-tetrazolium-5-carboxyanilide inner salt; Sigma Chemical Co.] to final concentrations of 250 µg/ml for XTT and 5 µM for PMS, were added to each well. The plate was then incubated for 3 hours at 37° C., and the absorbance at 450 nm of each well was measured, to calculate cell viability, using the reducing power of the mitochondria as the index.

The viability of the cells in each well was calculated according to the following formula:

Viability (%)=100×(a−b)/(c−b)

wherein "a" is the absorbance of a test well, "b" is the absorbance of a well with no cells, and "c" is the absorbance of a well with no antibody added.

Figure 30:
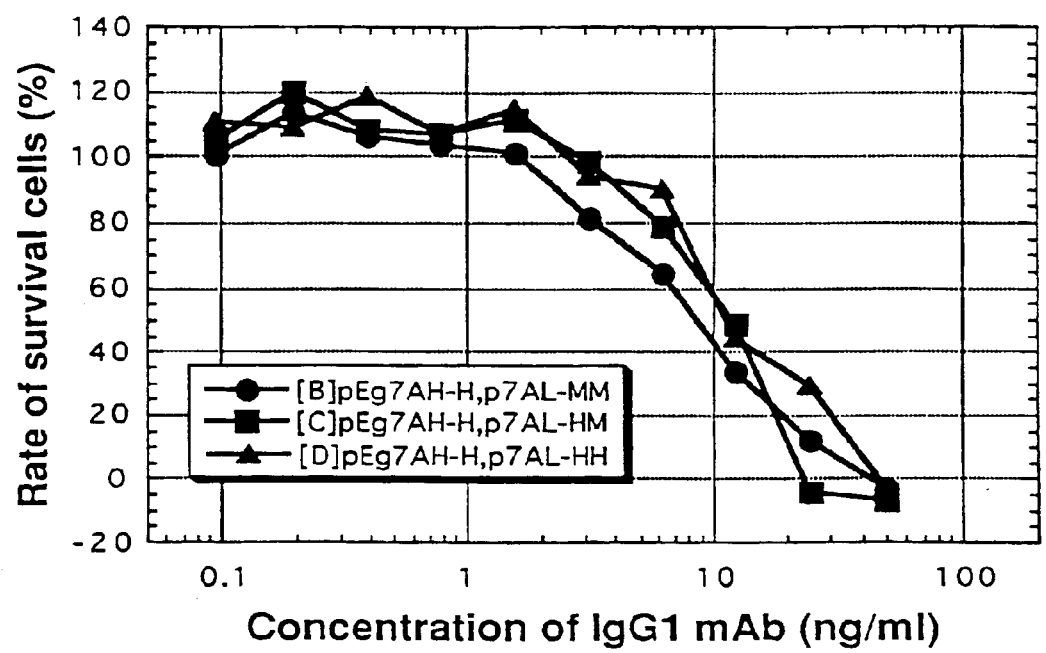

As expected, each of the expression products (B), (C) and (D) of Reference Example 16, were demonstrated to induce apoptosis in T cells expressing the human Fas antigen (FIG. 30).

REFERENCE EXAMPLE 21

Preparation of DNA Encoding Humanized Light Chain (1) Construction of Vectors for the Light Chains of Humanized Versions of HFE7A Antibody In order to humanize the amino acid sequence of the light chain of the mouse anti-human Fas antibody HFE7A, the 1st amino acid (aspartic acid), the 85th amino acid (alanine) and the 107th amino acid (arginine) from the N-terminus of the amino acid sequence of the HR type light chain were replaced with glutamic acid, glutamic acid and lysine, respectively. These replacement residues are conserved in the human light chain (κ chain). The resulting sequence was designated as "PDHH type." For the HM light chain sequence, the 1st amino acid (aspartic acid) and the 107th amino acid (arginine) from the N-terminus of the amino acid sequence were replaced with the conserved glutamic acid and lysine residues, respectively. The resulting sequence was designated as "PDHM type."

Expression plasmids separately carrying these 2 types of humanized light chain amino acid sequences (PDHH and PFHM) were constructed as follows.

1) Synthesis of Primers for Preparing the Variable and Constant Regions of the Light Chain of Humanized HFE7A DNA (SEQ ID No. 106 of the Sequence Listing) encoding the PDHH type polypeptide chain (SEQ ID No. 107 of the Sequence Listing) and DNA (SEQ ID No. 108 of the Sequence Listing) encoding the PDHM type polypeptide chain (SEQ ID No. 109 of the Sequence Listing) were prepared by PCR. Each of these sequences is a fusion of one the humanized versions of the variable region of the HFE7A light chain with the constant region of the human Ig light chain (κ chain). 7AL1P (SEQ ID No. 55) and 7ALCN (SEQ ID No. 64) had already been synthesized [Reference Example 2 (2) 2) above], and the following oligonucleotide primers were also synthesized for PCR:
5'-GGTGAGATTG TGCTCACCCA ATCTCCAGG-3' (LPD1P; SEQ ID No. 110);
5'-CCTGGAGATT GGGTGAGCAC AATCTCACC-3' (LPD1N; SEQ ID No. 111);
5'-CCATCTCTCG TCTGGAGCCG GAGGATTTTG C-3' (LPD2P; SEQ ID No. 112);
5'-GCAAAATCCT CCGGCRCCAG ACGAGAGATG G-3' (LPD2N; SEQ ID No. 113);
5'-CAAGGCACCAAGCTGGAAAT CAAACGGACT G-3' (LPD3P; SEQ ID No. 114); and
5'-CAGTCCGTTT GATTTCCAGC TTGGTGCCTT G -3' (LPD3M; SEQ ID No. 115).

2) Construction of Plasmid pLPDHH75 (Expression Plasmid for Humanized PDHH Type HFE7A Light Chain)

LPDHH-DNA (light chain constant region fused with PDHH DNA), as defined in SEQ ID No. 106 of the Sequence Listing, and encoding the amino acid sequence of SEQ ID No. 107 of the Sequence Listing, was prepared by performing 3-stage PCR, inserted into a plasmid vector, and cloned into E. coli.

a) First Stage PCR

Figure 31:
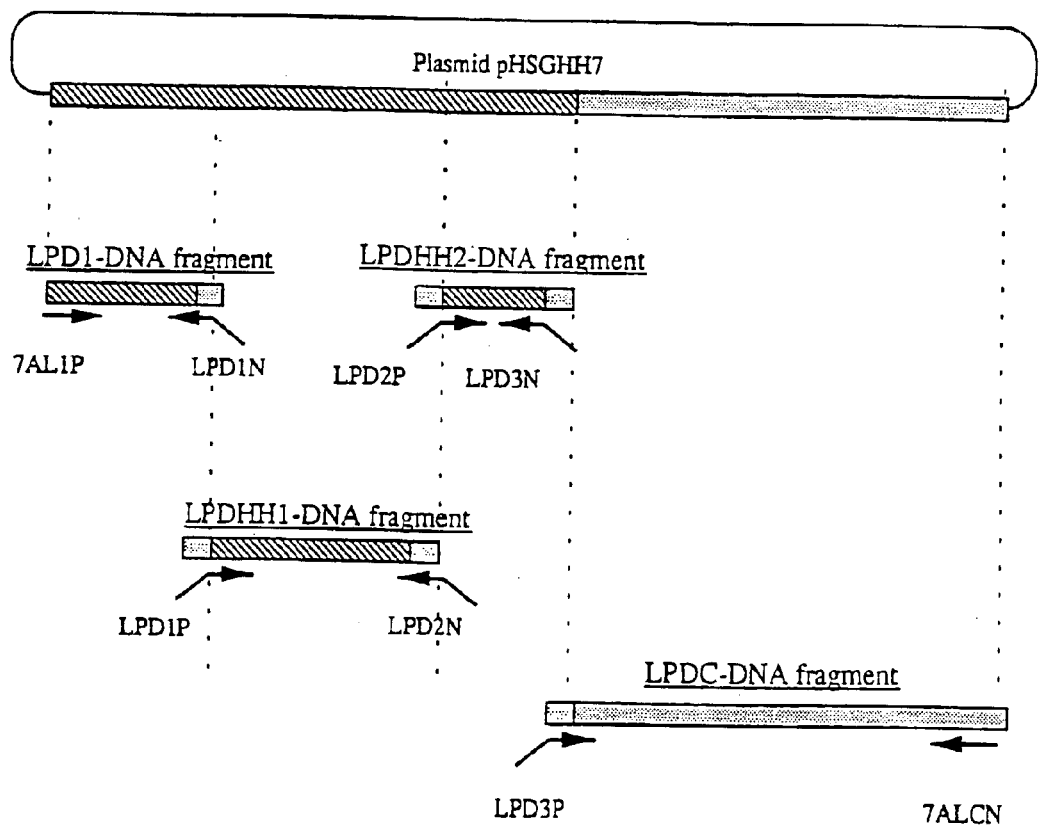
FIG. 31 shows the outline of the first stage PCR for the preparation of LPDHH-DNA.

The outline of the first stage PCR for the preparation of LPDHH-DNA is shown in FIG. 31.

The LPD1-DNA fragment, encoding a secretion signal sequence and a portion of FRL$_1$, but having an added HindIII restriction enzyme cleavage site at the 5'-end, was prepared as follows.
Composition of the PCR Reaction Solution:
plasmid pHSGHH7 DNA, 200 ng;
oligonucleotide primer 7AL1P, 80 pmol;
oligonucleotide primer LPD1N, 80 pmol;
dNTP cocktail, 20 µl;
10×Pfu buffer, 20 µl;
Pfu DNA polymerase (Stratagene), 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The LPDHH1-DNA fragment, encoding a portion of FRL$_1$, CDRL$_1$, FRL$_2$, CDRL$_2$ and a portion of the FRL$_3$ region, was prepared as follows.
Composition of the PCR Reaction Solution:
plasmid pHSGHH7 DNA, 200 ng;
oligonucleotide primer LPD1P, 80 pmol;
oligonucleotide primer LPD2N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The LPDHH2-DNA fragment, encoding a portion of FRL$_3$, CDRL$_3$ and FRL$_4$, was prepared as follows.

Composition of the PCR Reaction Solution:
plasmid pHSGHH7 DNA, 200 ng;
oligonucleotide primer LPD2P, 80 pmol;
oligonucleotide primer LPD3N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The LPDC-DNA fragment, encoding a portion of FRL$_4$ and the HFE7A light chain constant region, but having an EcoRI restriction enzyme cleavage site added at the 3'-end, was prepared as follows.

Composition of the PCR Reaction Solution:
plasmid pHSGHH7 DNA, 200 ng;
oligonucleotide primer LPD3P, 80 pmol;
oligonucleotide primer 7ALCN, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified DNA fragments were subjected first to phenol extraction and then to ethanol precipitation, and then separated by 5% w/v polyacrylamide gel electrophoresis. After electrophoresis, the gel was stained with 1 µg/ml of ethidium bromide, and the DNA bands thus detected, under UV light, were cut out with a razor blade and eluted from the gel using a Centriruter and a Centricon-10, as described above. The eluted DNA was concentrated by centrifugation at 7,500×g, followed by ethanol precipitation, and was finally dissolved in 50 µl of distilled water.

b) Second Stage PCR

Figure 32:
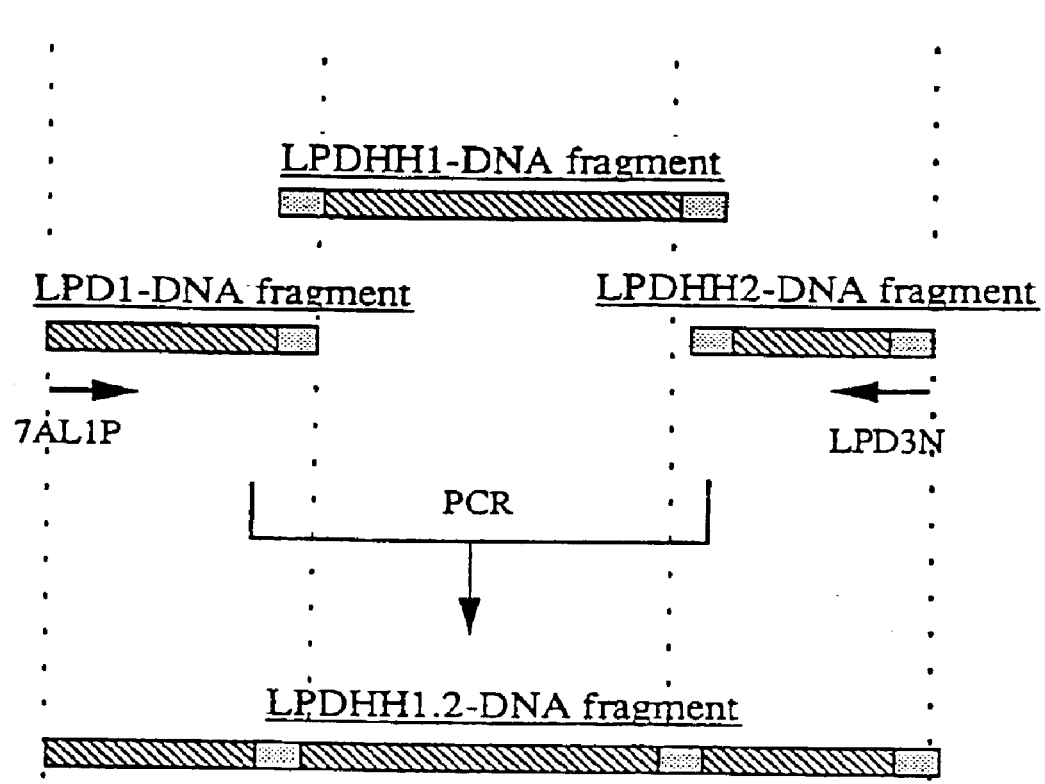
FIG. 32 shows the outline of the second stage PCR for the production of LPDHH-DNA.

The outline of the second stage PCR for the production of LPDHH-DNA is shown in FIG. 32.

LPDHH1.2-DNA, in which the above described LPD1-DNA, LPDHH1-DNA and LPDHH2-DNA fragments are fused, was prepared as follows.

Composition of the PCR Reaction Solution:
LPD1-DNA solution (from the first stage PCR), 10 µl;
LPDHH1-DNA solution (from the first stage PCR), 10 µl;
LPDHH2-DNA solution (from the first stage PCR), 10 µl;
oligonucleotide primer 7AL1P, 80 pmol;
oligonucleotide primer LPD3N, 80 pmol;
dNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified LPDHH1.2 fragment was subjected first to phenol extraction and then to ethanol precipitation, and then separated by 5% w/v polyacrylamide gel electrophoresis. After electrophoresis, the gel was stained with 1 µg/ml of ethidium bromide, and the fusion DNA band thus detected, under UV light, was cut out with a razor blade and eluted from the gel using a Centriruter and a Centricon-10, as described above. The eluted DNA was concentrated by centrifugation at 7,500×g, followed by ethanol precipitation, and was finally dissolved in 50 µl of distilled water.

c) Third Stage PCR

Figure 33:
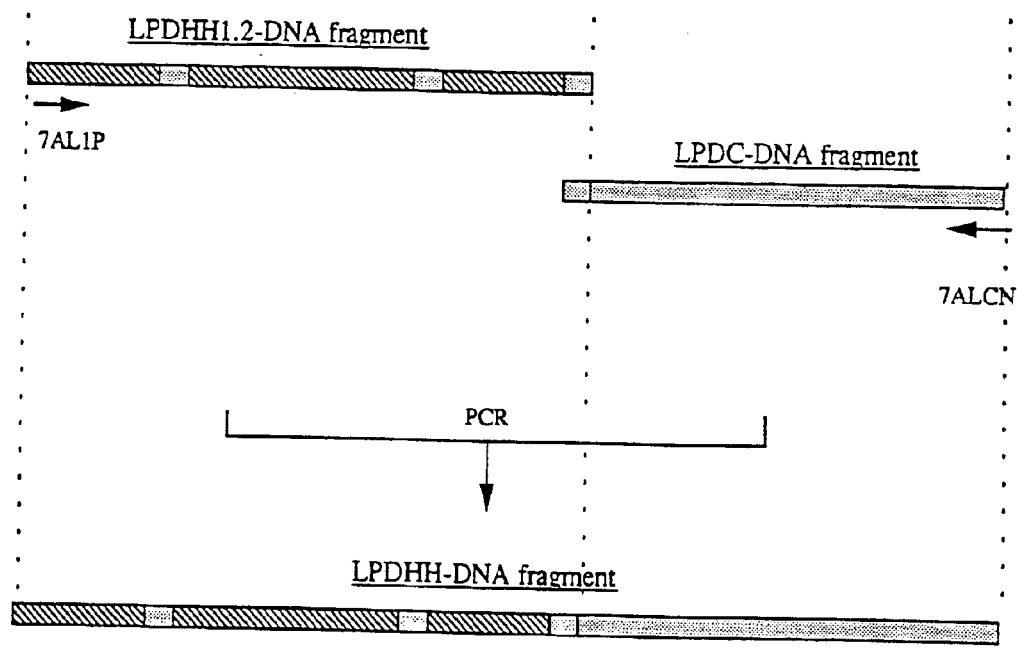
FIG. 33 shows the outline of the third stage PCR for the production of LPDHH-DNA.

The outline of the third stage PCR for the production of LPDHH-DNA is shown in FIG. 33.

The LPDHH-DNA fragment, in which the above described LPDHH1.2-DNA and LPDC-DNA fragments were fused, was prepared as follows.

Composition of the PCR Reaction Solution:
LPDHH1.2-DNA solution (from second stage PCR), 10 µl;
LPDC-DNA solution (from first stage PCR), 10 µl;
oligonucleotide primer 7AL1P, 80 pmol;
oligonucleotide primer 7ALCN, 80 pmol;
DNTP cocktail, 20 µl;
10×Pfu buffer, 20 µl;
Pfu DNA polymerase, 10 units; and
redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified LPDHH-DNA fragment was subjected first to phenol extraction and then to ethanol precipitation, and then separated by 5% w/v polyacrylamide gel electrophoresis. After electrophoresis, the gel was stained with 1 µg/ml of ethidium bromide, and the DNA band thus detected, under UV light, was cut out with a razor blade and eluted from the gel using a Centriruter and a Centricon-10, as described above. The eluted DNA was concentrated by centrifugation at 7,500×g, followed by ethanol precipitation, and was finally dissolved in 50 µl of distilled water.

Figure 34:
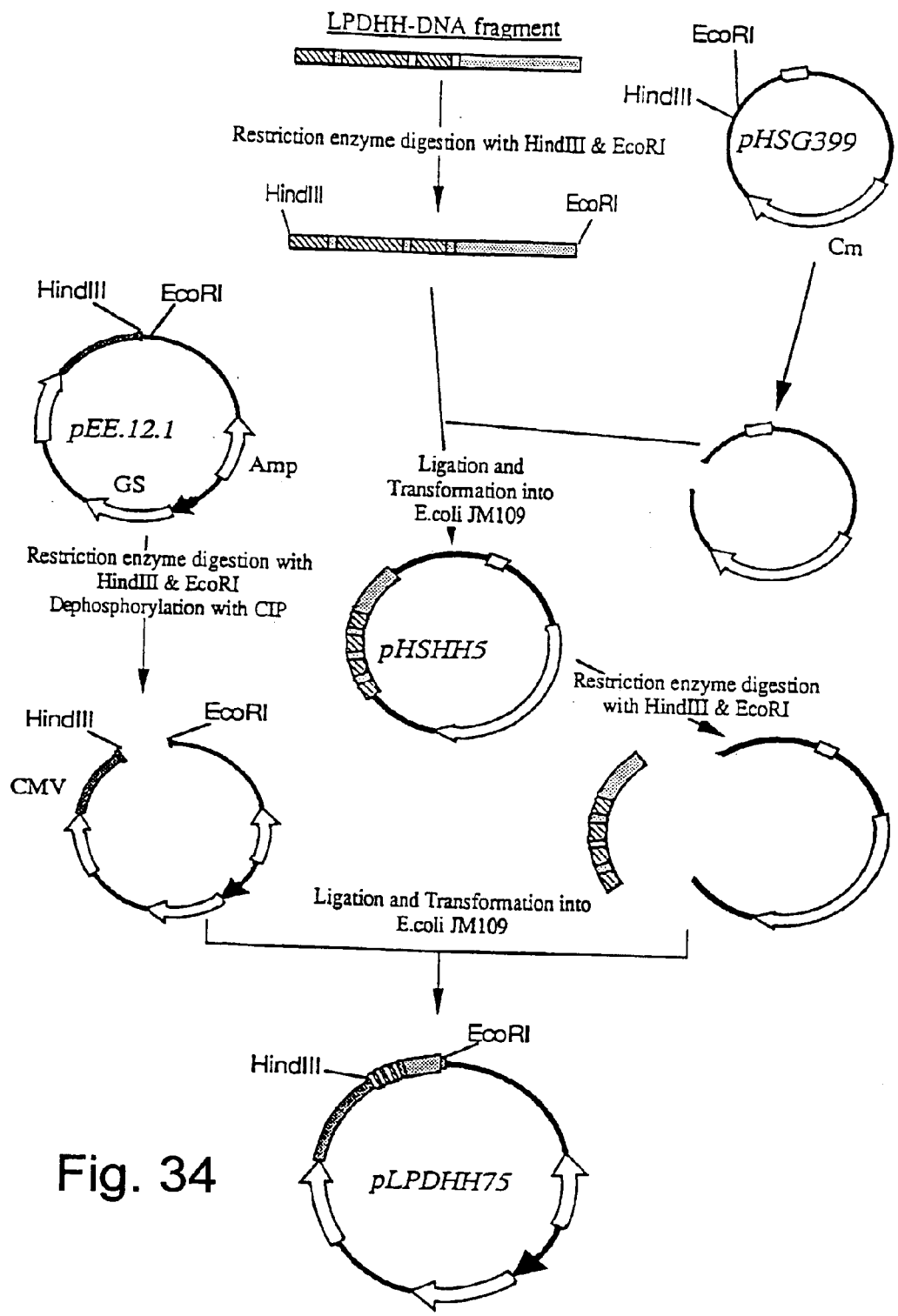
FIG. 34 shows the outline of the construction of an expression plasmid carrying the LPDHH-DNA fragment.

Construction of an expression plasmid carrying the LPDHH-DNA fragment is outlined in FIG. 34.

The LPDHH-DNA fragment, obtained above, was further purified by phenol extraction followed by ethanol precipitation, and then digested with the restriction enzymes HindIII and EcoRI.

One µg of the cloning plasmid pHSG399 DNA was digested with the restriction enzymes HindIII and EcoRI, and then dephosphorylated with CIP. The resulting dephosphorylated pHSG399 DNA was then ligated with the LPDHH-DNA fragment, which had previously also been digested with HindIII and EcoRI, using a DNA Ligation Kit Version 2.0 (Takara Shuzo, Co. Ltd.). *E. coli* JM109 was then transformed with the ligation mix and plated onto LB agar medium containing final concentrations of 1 mM IPTG, 0.1% w/v X-Gal and 50 µg/ml chloramphenicol. Any white transformants obtained were cultured in 2 ml liquid LB medium containing 50 µg/ml chloramphenicol at 37° C. overnight, and plasmid DNA was extracted from the resulting culture by the alkaline-SDS method. The extracted plasmid DNA was digested with HindIII and EcoRI, and a clone carrying the LPDHH-DNA fragment was then selected by 1% w/v agarose gel electrophoresis.

Accordingly, plasmid pHSHH5, carring a fusion insert comprising the variable region of the humanized LPDHH DNA and DNA encoding the constant region of human immunoglobulin κ chain, was isolated. The transformant *E. coli* pHSHH5SANK 70398, harboring plasmid pHSHH5, was deposited with the Kogyo Gijutsuin Seimei-Kogaku Kogyo Gijutsu Kenkyujo on Feb. 26, 1998, in accordance with the Budapest Treaty on the Deposit of microorganisms, and was accorded the accession number FERM BP-6274.

The expression vector plasmid pLPDHH75 carrying the DNA fragment of SEQ ID No. 106 of the Sequence Listing, encoding the humanized PDHH type HFE7A light chain polypeptide of SEQ ID No. 107 of the Sequence Listing, was then prepared using the plasmid pHSHH5.

One μg of pEE.12.1 DNA (Lonza), an expression vector for mammalian cells, was digested with the restriction enzymes HindIII and EcoRI, and then dephosphorylated using CIP. The resulting digested, dephosphorylated plasmid DNA (100 ng) was ligated with 10 μg of the pHSHH5 DNA fragment which had also been digested with Hind III and EcoRI, using a DNA Ligation Kit Version 2.0 (Takara Shuzo Co., Ltd.). The ligation mix was then used to transform *E. coli* JM109 (as described above), which was th en plated on LB agar plates containing 50 μg/ml ampicillin.

The transformants obtained by this method were cultured in 2 ml of liquid LB medium containing 50 μg/ml ampicillin at 37° C. overnight, and plasmid DNA was subsequently extracted from the resulting culture by the alkaline-SDS method.

The extracted plasmid DNA was digested with HindIII and EcoRI, a nd subjected to 1% w/v agarose gel electrophoresis to confirm the presence or absence of the insert of interest. This enabled the isolation of the plasmid pLPDHH75, which contains a fusion fragment having the variable region of the humanized PDHH type HFE7A light chain together with DNA encoding the constant region of the human immunoglobulin κ chain. The fusion fragment was found to be located downstream of the cytomegalovirus (CMV) promoter in the correct orientation.

3) Construction of Plasmid pLPDHM32 (Expression Plasmid for Humanized PDHM Type HPE7A Light Chain)

The LPDHM-DNA fragment (SEQ ID No. 108 of the Sequence Listing, encoding the amino acid sequence of SEQ ID No. 109 thereof) was produced by performing 3-stage PCR, the fragment then being inserted into a plasmid vector and cloned into *E. coli*.

a) First Stage PCR

Figure 35:
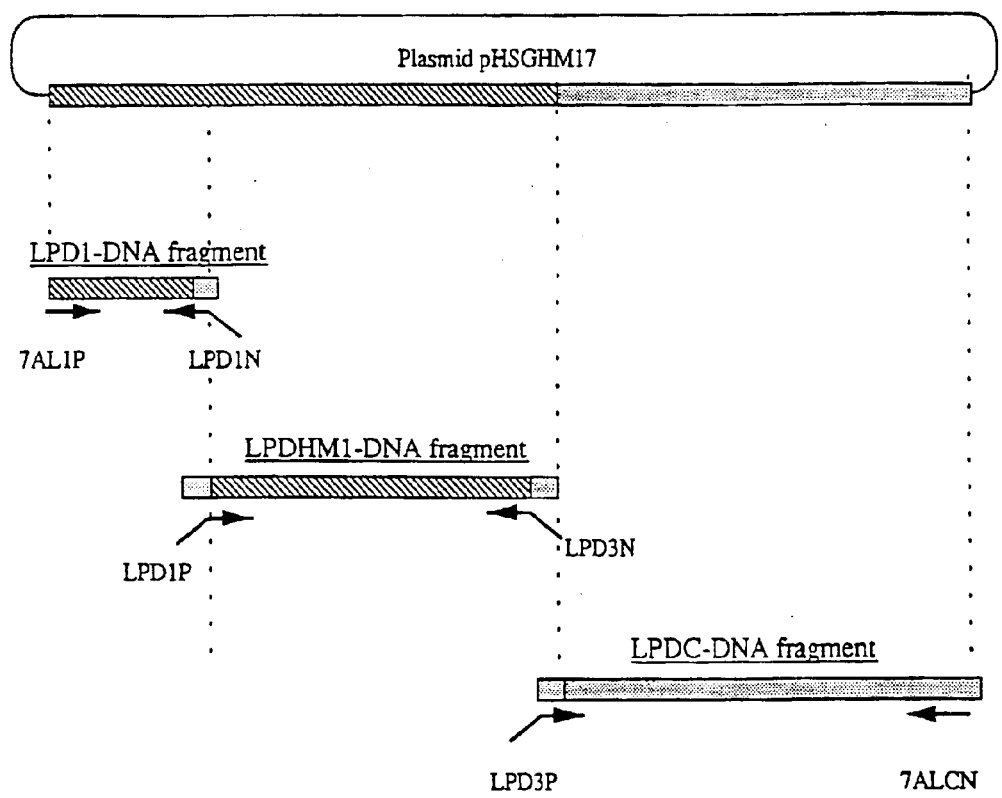
FIG. 35 shows the outline of the first stage PCR for the preparation of LPDHM-DNA.

The outline of the first stage PCR for the preparation of LPDHM-DNA is shown in FIG. 35.

The LPD1-DNA fragment, encoding a secretion signal sequence and a portion of $FRL_1$ having a HindIII restriction enzyme cleavage site added at the 5'-end, and the LPDC-DNA fragment, encoding a portion of $FRL_4$ and the constant region having an EcoRI restriction enzyme cleavage site added at the 3'-end, were those obtained in the preparation of the LPDHH-DNA fragment [see "2) Construction of plasmid pLPDHH75 (expression plasmid for humanized PDHH type HFE7A light chain)" and "a) First Stage PCR"].

The LPDHM1-DNA fragment, encoding a portion of $CDRL_1$, $FRL_2$, $CDRL_2$, $FRL_3$, $CDRL_3$ and $FRL_4$, was prepared as follows.

Composition of the PCR Reaction Solution:
plasmid pHSGHM17 DNA, 200 ng;
oligonucleotide primer LPDLP, 80 pmol;
oligonucleotide primer LPD3N, 80 pmol;
dNTP cocktail, 20 μl;
10×Pfu buffer, 20 μl;
Pfu DNA polymerase, 10 units; and
redistilled water to a final volume of 200 μl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified LPD1, LPDHM1 and LPDC-DNA fragments were subjected first to phenol extraction and then to ethanol precipitation, and then separated by 5% w/v polyacrylamide gel electrophoresis. After electrophoresis, the gel was stained with 1 μg/ml of ethidium bromide, and the fusion DNA bands thus detected, under UV light, were cut out with a razor blade and eluted from the gel using a Centriruter and a Centricon-10, as described above. The eluted DNA was concentrated by centrifugation at 7,500×g, followed by ethanol precipitation, and was finally dissolved in 50 μl of distilled water.

b) Second Stage PCR

Figure 36:
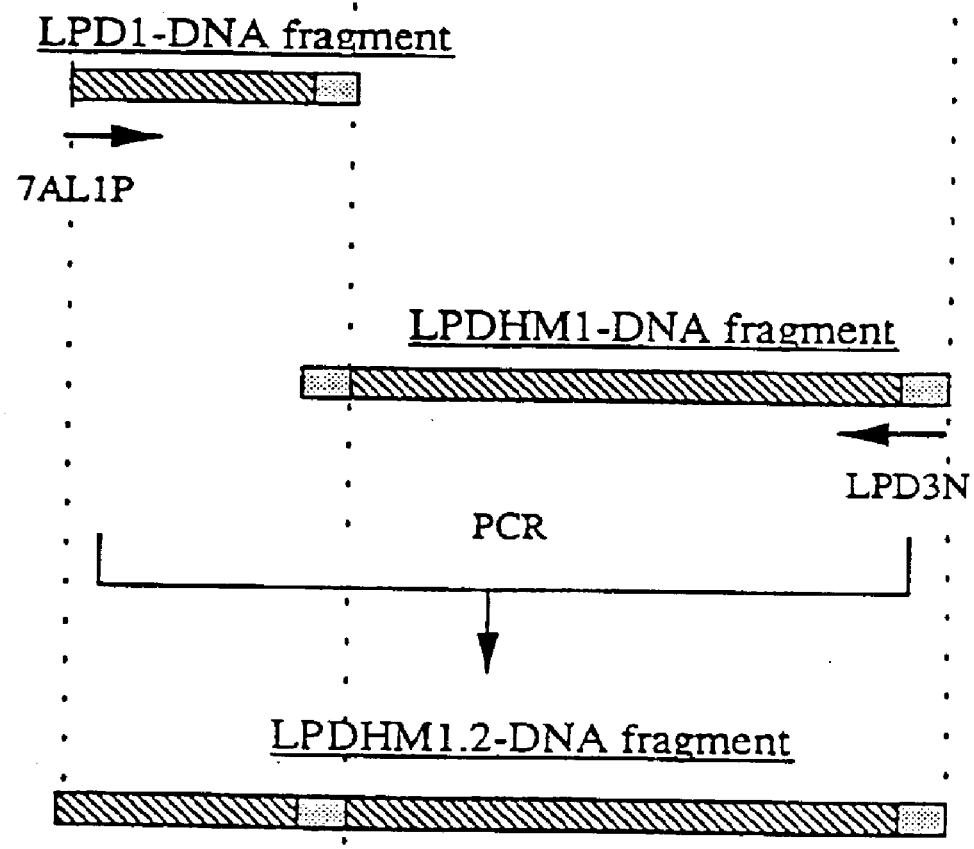
FIG. 36 shows the outline of the second stage PCR for the production of PDHM-DNA.

The outline of the second stage PCR for the production of PDHM-DNA is shown in FIG. 36.

LPDHM1.2-DNA, in which the above LPD1-DNA and LPDHM1-DNA fragments were fused, was prepared as follows.

Composition of the PCR Reaction Solution:
LPD1-DNA solution (from the first stage PCR), 10 μl;
LPDHM1-DNA solution (from the first stage PCR), 10 μl;
oligonucleotide primer 7AL1P, 80 pmol;
oligonucleotide primer LPD3N, 80 pmol;
dNTP cocktail, 20 μl;
10×Pfu buffer, 20 μl;
Pfu DNA polymerase, 10 units; and
redistilled water to a final volume of 200 μl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified LPDHM1.2-DNA fragment was subjected first to phenol extraction and then to ethanol precipitation, and then separated by 5% w/v polyacrylamide gel electrophoresis. After electrophoresis, the gel was stained with 1 μg/ml of ethidium bromide, and the DNA band thus detected, under UV light, was cut out with a razor blade and eluted from the gel using a Centriruter and a Centricon-10, as described above. The eluted DNA was concentrated by centrifugation at 7,500×g, followed by ethanol precipitation, and was finally dissolved in 50 μl of distilled water.

c) Third Stage PCR

Figure 37:
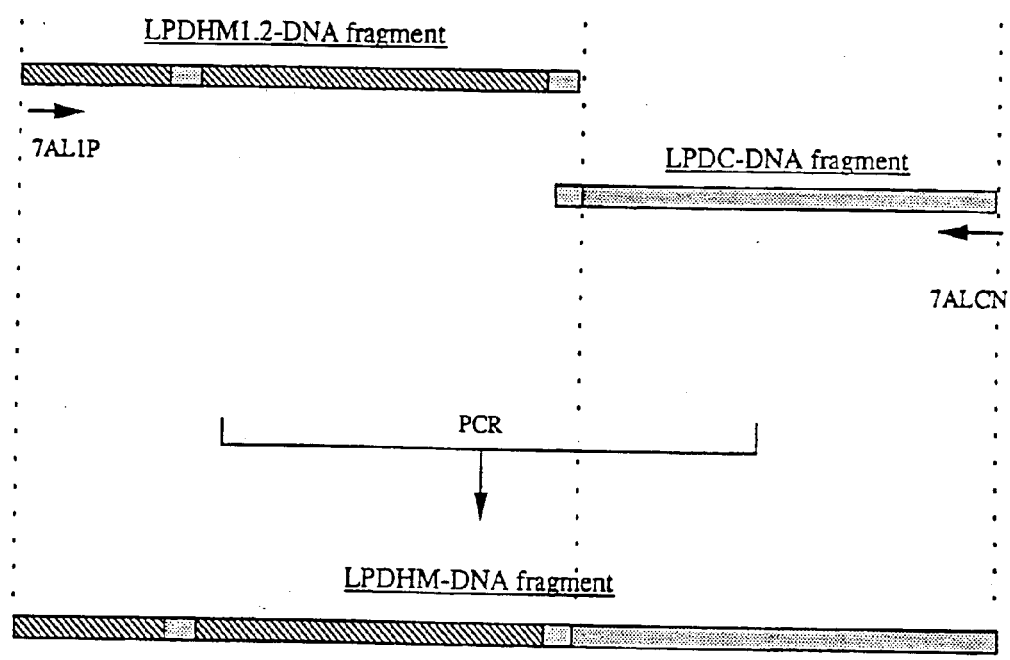
FIG. 37 shows the outline of the third stage PCR for the preparation of LPDHM-DNA.

The outline of the third stage PCR for the preparation of LPDHM-DNA is shown in FIG. 37.

The LPDHM-DNA fragment, comprising a fusion of the LPDHM1.2-DNA and LPDC-DNA fragments above, was prepared as follows.

Composition of the PCR Reaction Solution:
LPDHM1.2-DNA solution (from the second stage PCR), 10 μl;
LPDC-DNA solution (from the first stage PCR), 10 μl;
oligonucleotide primer 7AL1P, 80 pmol;
oligonucleotide primer 7ALCN, 80 pmol;
dNTP cocktail, 20 μl;
10×Pfu buffer, 20 μl;
Pfu DNA polymerase, 10 units; and
redistilled water to a final volume of 200 μl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified LPDHM-DNA fragment was subjected first to phenol extraction and then to ethanol precipitation, and then separated by 5% w/v polyacrylamide gel electrophoresis. After electrophoresis, the gel was stained with 1 µg/ml of ethidium bromide, and the DNA band thus detected, under UV light, was cut out with a razor blade and eluted from the gel using a Centriruter and a Centricon-10, as described above. The eluted DNA was concentrated by centrifugation at 7,500×g, followed by ethanol precipitation, and was finally dissolved in 50 µl of distilled water.

Figure 38:
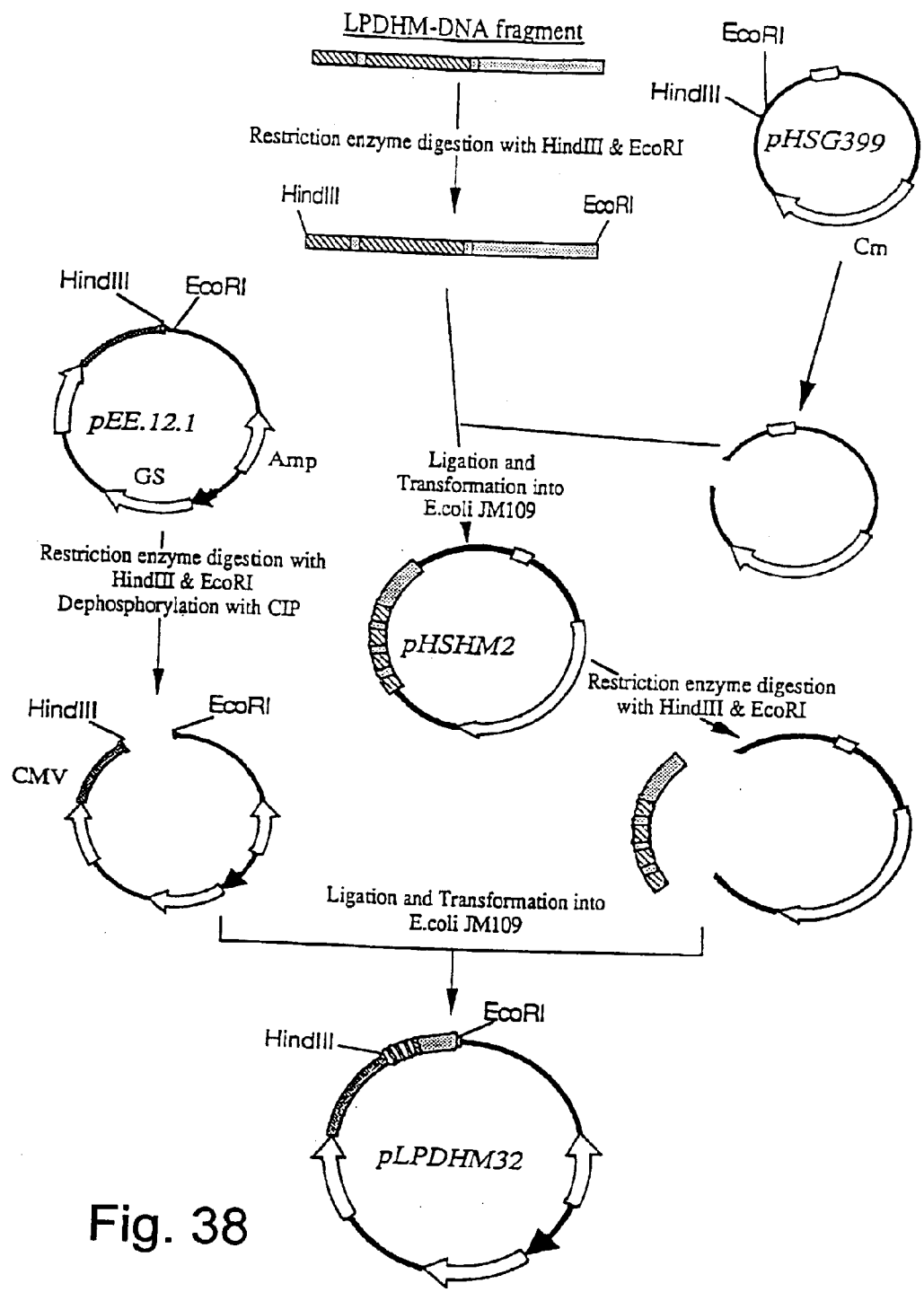
FIG. 38 shows the outline of the construction of a plasmid carrying the LPDHM-DNA fragment.

The construction of a plasmid carrying the LPDHM-DNA fragment is outlined in FIG. 38.

The LPDHM-DNA obtained above was further purified by phenol extraction followed by ethanol precipitation, and then digested with the restriction enzymes HindIII and EcoRI.

One µg of the cloning plasmid pHSG399 DNA was digested with the restriction enzymes HindIII and EcoRI, and then dephosphorylated with CIP. The resulting dephosphorylated pHSG399 DNA and was then ligated with the LPDHM-DNA fragment, which had previously also been digested with HindIII and EcoRI, using a DNA Ligation Kit Version 2.0 (Takara Shuzo, Co. Ltd.). *E. coli* JM109 was then transformed with the ligation mix and plated onto LB agar medium containing final concentrations of 1 mM IPTG, 0.1% w/v X-Gal and 50 µg/ml chloramphenicol. Any white transformants obtained were cultured in 2 ml liquid LB medium containing 50 µg/ml chloramphenicol at 37° C. overnight, and plasmid DNA was extracted from the resulting culture by the alkaline-SDS method. The extracted plasmid DNA was digested with HindIII and EcoRI, and a clone carrying the LPDHM-DNA fragment was then selected by 1% w/v agarose gel electrophoresis.

As a result of the above procedure, plasmid pHSHM2 carrying a fusion insert comprising the variable region of the humanized PDMM type HFE7A light chain and DNA encoding the constant region of the human Ig κ chain, was obtained. The transformant *E. coli* pHSHM2 SANK 70198, harboring plasmid pHSHM2, was deposited with the Kogyo Gijutsuin Seimei-Kogaku Kogyo Gijutsu Kenkyujo on Feb. 26, 1998, in accordance with the Budapest Treaty on the Deposit of Microorganisms, and was accorded the accession number FERM BP-6272.

The expression vector plasmid pLPDHM32 was constructed, carrying the DNA of SEQ ID No. 108 of the Sequence Listing encoding the humanized PDHM type HFE7A light chain polypeptide of SEQ ID No. 109, using plasmid pHSHM2 obtained above.

One µg of pEE.12.1 DNA (Lonza), an expression vector for mammalian cells, was digested with the restriction enzymes Hind III and EcoRI, and then dephosphorylated using CIP. The resulting digested, dephosphorylated plasmid DNA (100 ng) was ligated with 10 µg of the pHSHM2 DNA fragment which had also been digested with Hind III and EcoRI, using a DNA Ligation Kit Version 2.0 (Takara Shuzo Co., Ltd.). The ligation mix was then used to transform *E. coli* JM109 (as described above), which was then plated on LB agar plates containing 50 µg/ml ampicillin.

The transformants obtained by this method were cultured in 2 ml of liquid LB medium containing 50 µg/ml ampicillin at 37° C. overnight, and plasmid DNA was subsequently extracted from the resulting culture by the alkaline-SDS method.

The extracted plasmid DNA was digested with HindIII and EcoRI, and subjected to 1% w/v agarose gel electrophoresis to confirm the presence or absence of the insert of interest. This enabled the isolation of the plasmid pLPDHM32, which contains a fusion fragment having the variable region of the humanized PDHM type HFE7A light chain together with DNA encoding the constant region of the human immunoglobulin κ chain. The fusion fragment was found to be located downstream of the cytomegalovirus (CMV) promoter in the correct orientation.

(4) Verification of Nucleotide Sequences

To verify that the DNA inserts of plasmids pLPDHH75 and pLPDHM32 have the desired nucleotide sequences, the DNA inserts were analyzed to determine their nucleotide sequences. The oligonucleotide primers used for nucleotide sequencing were SP1 (SEQ ID No. 68), SP2 (SEQ ID No. 69), SP3 (SEQ ID No. 70), SP4 (SEQ ID No. 71), SP5 (SEQ ID No. 72) and SP6 (SEQ ID No. 73).

The positions to which each primer binds are shown in FIG. 19. The determination of the nucleotide sequence was performed by the dideoxynucleotide chain termination method using, as the templates, the plasmid containing the sequence to be confirmed, the plasmid having been purified by the alkaline-SDS method and the cesium chloride method. As expected pLPDHH75 was confirmed to have the nucleotide sequence of SEQ ID No. 106 of the Sequence Listing, encoding the polypeptide of SEQ ID No. 107, and that pLPDHM32 had the nucleotide sequence of SEQ ID No. 108 of the Sequence Listing, encoding the polypeptide of SEQ ID No. 109.

REFERENCE EXAMPLE 22

Preparation of DNA Encoding Humanized Heavy Chain (1) Construction of Vector for the Heavy Chain of Humanized Version of HFE7A Antibody In further humanizing the amino acid sequence of SEQ ID No. 75 of the Sequence Listing (the humanized heavy chain of the mouse anti-human Fas antibody HFE7A), the 44th amino acid (arginine) and the 76th amino acid (alanine) in the amino acid sequence of SEQ ID No. 75 were replaced with glycine and threonine, respectively, these residues being conserved in the human heavy chain. The resulting sequence was designated as the "HV type."

Expression plasmids carrying the HV type humanized heavy chain amino acid sequences of the anti-human Fas antibody HFE7A were constructed as follows.

(1) Synthesis of Primers for Preparing the Variable Region of the Humanized Heavy Chain The synthesis of DNA (SEQ ID No. 116 of the Sequence Listing) encoding the humanized anti-Fas antibody HFE7A heavy chain (SEQ ID No. 117 of the Sequence Listing) was performed by using a combination of PCR steps.

In addition to 7AH1P (SEQ ID No: 76 above), the following 3 primers were synthesized for PCR:

5'-CAGGCCCCTG GACAGGGCCT TGAGTGGATG-3' (HPD1P; SEQ ID No. 118);

5'-CATCCACTCA AGGCCCTGTC CAGGGGCCTG-3' (HPD1N; SEQ ID No. 119); and

5'-GCTGAGCTCC ATGTAGGCTG TGCTAGTGGA TGTGTCTAC-3' (HPD2N; SEQ ID No. 120).

2) Construction of Plasmid pgHPDHV3

The HPD1.2-DNA fragment, encoding amino acid No's −19−+84 of SEQ ID No. 117 of the Sequence Listing, was prepared by performing 2-stage PCR, inserted into a plasmid and then cloned into *E. coli*.

a) First Stage PCR

Figure 39:
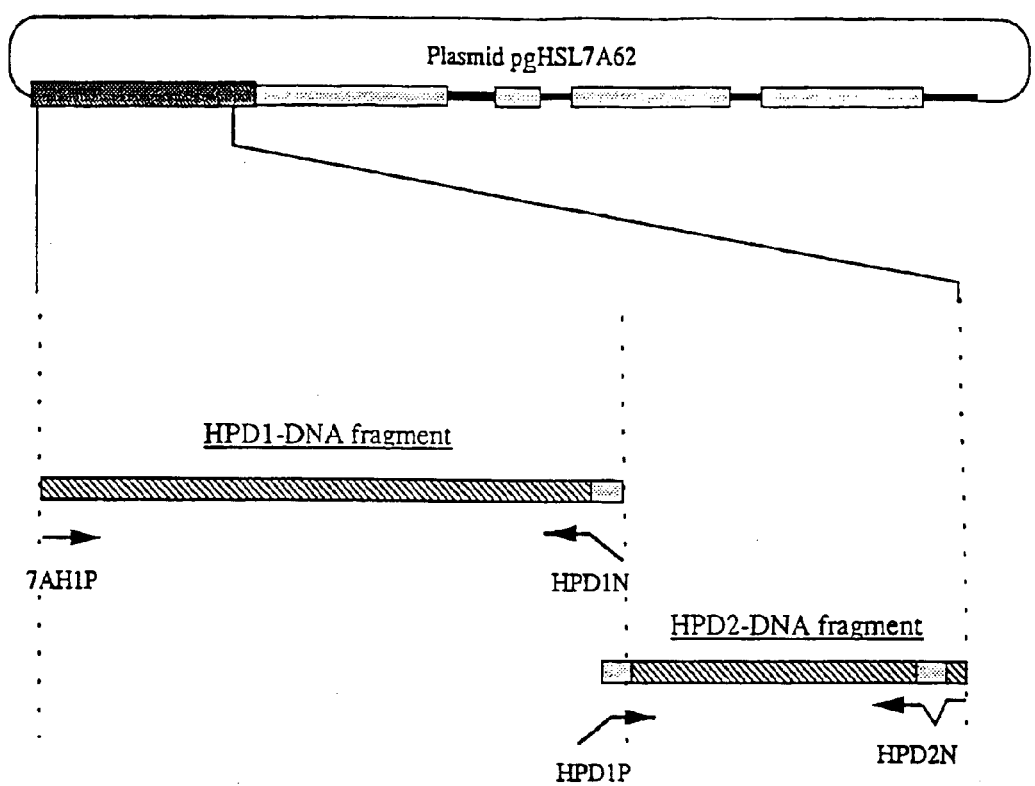
FIG. 39 shows the outline of the first stage PCR for the preparation of HPD1.2-DNA.

The outline of the first stage PCR for the preparation of HPD1.2-DNA is shown in FIG. 39.

The HPD1-DNA fragment, encoding a secretion signal sequence and $FRH_1$, $CDRH_2$ and a portion of $FRH_2$ with an added HindIII restriction enzyme cleavage site added at the 5'-end, was prepared as follows.

Composition of the PCR Reaction Solution:
  plasmid pgHSL7A62 DNA, 200 ng;
  oligonucleotide primer 7AH1P, 80 pmol;
  oligonucleotide primer HPD1N, 80 pmol;
  dNTP cocktail, 20 µl;
  10×Pfu buffer, 20 µl;
  Pfu DNA polymerase, 10 units; and
  redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The HPD2-DNA fragment, encoding a portion of $FRH_2$, $CDRH_3$, and a portion of $FRH_3$, was prepared as follows.
Composition of the PCR Reaction Solution:
  plasmid pgHSL7A62 DNA, 200 ng;
  oligonucleotide primer HPD1P, 80 pmol;
  oligonucleotide primer HPD2N, 80 pmol;
  dNTP cocktail, 20 µl;
  10×Pfu buffer, 20 µl;
  Pfu DNA polymerase, 10 units; and
  redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified HPD1 and HPD2 DNA fragments were subjected first to phenol extraction and then to ethanol precipitation, and then separated by 5% w/v polyacrylamide gel electrophoresis. After electrophoresis, the gel was stained with 1 µg/ml of ethidium bromide, and the DNA bands thus detected, under UV light, were cut out with a razor blade and eluted from the gel using a Centriruter and a Centricon-10, as described above. The eluted DNA was concentrated by centrifugation at 7,500×g, followed by ethanol precipitation, and was finally dissolved in 50 µl of distilled water.

b) Second Stage PCR

Figure 40:
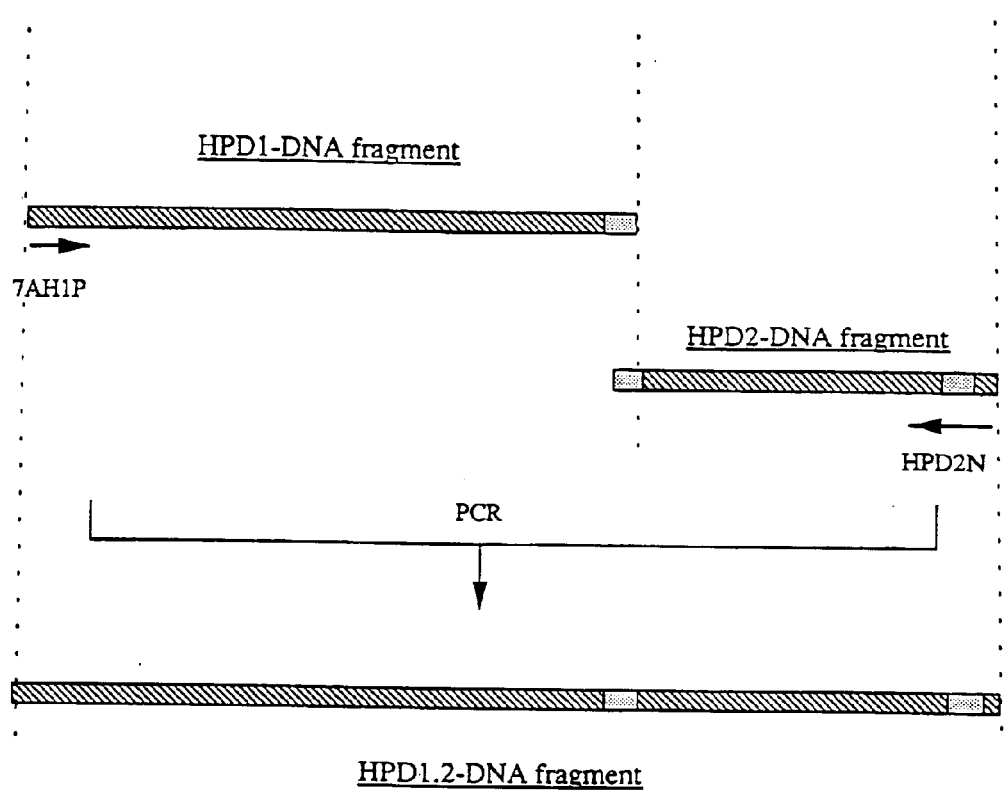
FIG. 40 shows the outline of the second stage PCR for the preparation of HPD1.2-DNA.

The outline of the second stage PCR for the preparation of HPD1.2-DNA is shown in FIG. 40.

The HPD1.2-DNA fragment, in which above described HPD1-DNA and HPD2-DNA fragments are fused, was prepared as follows.
Composition of the PCR Reaction Solution:
  HPD1-DNA solution (from the first stage PCR), 10 µl;
  HPD2-DNA solution (from the first stage PCR), 10 µl;
  oligonucleotide primer 7AH1P, 80 pmol;
  oligonucleotide primer HPD2N, 80 pmol;
  dNTP cocktail, 20 µl;
  10×Pfu buffer, 20 µl;
  Pfu DNA polymerase, 10 units; and
  redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified HPD1.2 DNA fragment was subjected first to phenol extraction and then to ethanol precipitation, and then separated by 5% w/v polyacrylamide gel electrophoresis. After electrophoresis, the gel was stained with 1 µg/ml of ethidium bromide, and the DNA band thus detected, under UV light, was cut out with a razor blade and eluted from the gel using a Centriruter and a Centricon-10, as described above. The eluted DNA was concentrated by centrifugation at 7,500×g, followed by ethanol precipitation, and was finally dissolved in 50 µl of distilled water.

Figure 41:
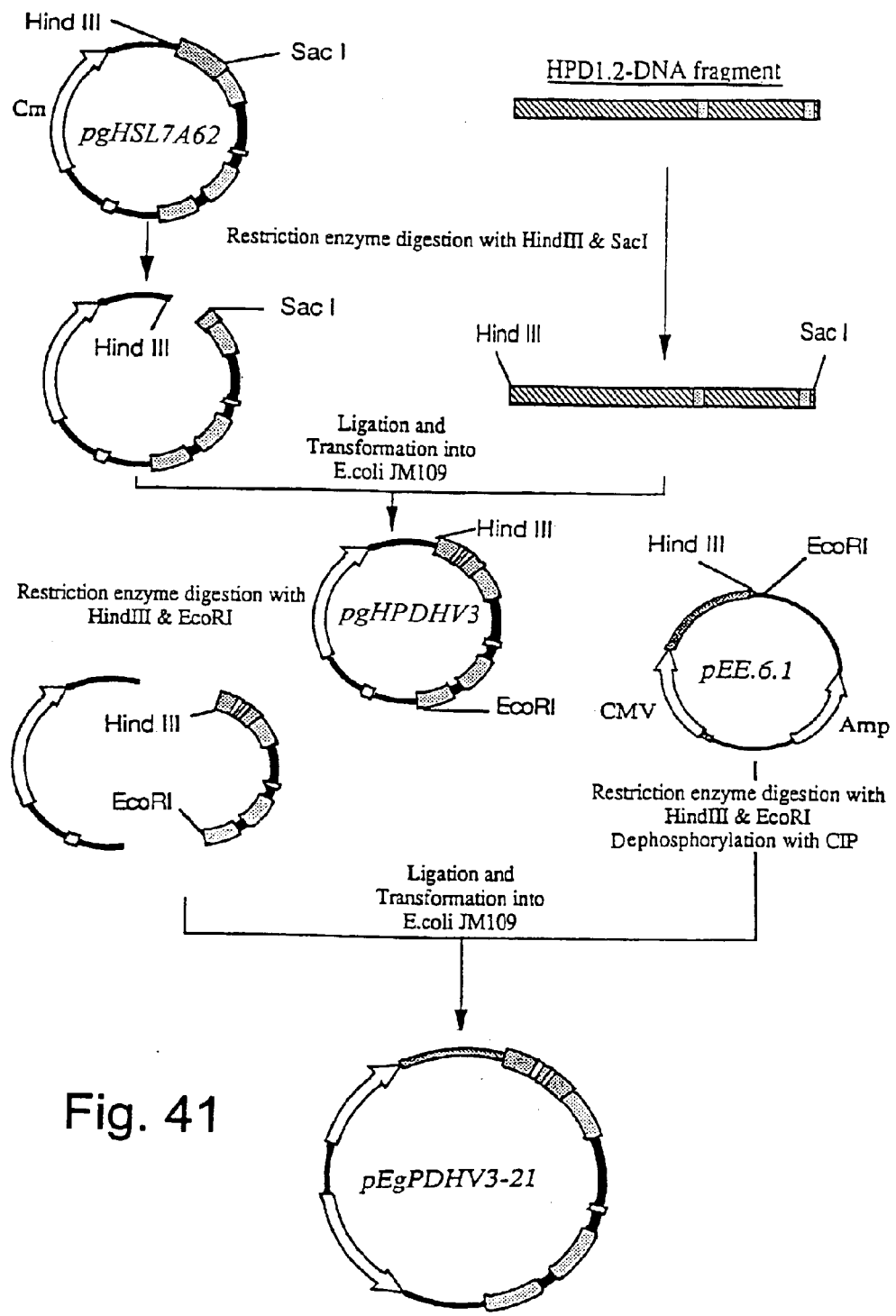
FIG. 41 shows the construction of a plasmid carrying the HPD1.2-DNA fragment.

The construction of a plasmid carrying HPD1.2-DNA fragment is outlined in FIG. 41.

The HPD1.2-DNA fragment obtained above was further purified by phenol extraction followed by ethanol precipitation, and then digested with the restriction enzymes HindIII and SacI.

Next, 10 µg of the plasmid pgHSL7A62 DNA was digested with the restriction enzymes HindIII and SacI and dephosphorylated with CIP. The resulting dephosphorylated pgHSL7A62 DNA (100 ng), was ligated with 10 µg of HPD1.2-DNA, which had previously been digested with HindIII and SacI, using a DNA Ligation Kit Version 2.0 (Takara Shuzo, Co. Ltd.) and the ligation mix was cloned into E. coli JM109. Any resulting transformants were cultured in 2 ml liquid LB medium, containing 50 µg/ml chloramphenicol at 37° C. overnight, and plasmid DNA was extracted from the culture by the alkaline-SDS method.

The extracted plasmid was then digested with HindIII and SacI, in order to confirm the presence or absence of the insert of interest by 1% w/v agarose gel electrophoresis. Thus, the plasmid pgHPDHV3, carrying a fusion insert comprising the DNA fragment encoding the variable region of the humanized HV type HFE7A heavy chain and a genomic DNA fragment encoding the constant region of human IgG1 heavy chain, was obtained. The transformant E. coli pgHPDHV3 SANK 70298, harboring plasmid pgHPDHV3, was deposited with the Kogyo Gijutsuin Seimei-Kogaku Kogyo Gijutsu Kenkyujo on Feb. 26, 1998, in accordance with the Budapest Treaty on the Deposit of Microorganisms, and was accorded the accession number FERM BP-6273.

Ten micrograms of the thus obtained plasmid pgHPDHV3 DNA was digested with the restriction enzymes HindIII and EcoRI. In parallel, 1 µg of the mammalian expression plasmid pEE.6.1 DNA was digested with HindIII and EcoRI, and then dephosphorylated with CIP. The resulting dephosphorylated pEE.6.1 DNA (100 ng) was ligated with 10 µg of digested pgHPDHV3 DNA using a Ligation kit Version 2.0 (Takara Shuzo, Co. Ltd.), and cloned into E. coli JM109. Any resulting transformants were cultured in 2 ml liquid LB medium containing 50 µg/ml ampicillin at 37° C. overnight, and plasmid DNA was extracted from the culture by the alkaline-SDS method. The plasmid was digested with HindIII and EcoRI, to confirm the presence or absence of the insert of interest by 1% w/v agarose gel electrophoresis. Thus, the plasmid pEgPDHV3-21, containing a fusion insert comprising the DNA fragment encoding the variable region of the humanized HV type HFE7A heavy chain and a genomic DNA fragment encoding the constant region of human IgG1 heavy chain downstream of CMV promoter, and in the correct orientation, was obtained.

(3) Verification of Nucleotide Sequence

To verify that the DNA insert of the plasmid pEgPDHV3-21 had the desired nucleotide sequence, the DNA insert was analyzed to determine the nucleotide sequence. For this sequencing, the primers PEEF (SEQ ID No. 104), HPD1P (SEQ ID No. 1118), HPD1N (SEQ ID No. 119) and HPD2N (SEQ ID No. 120) were used.

Figure 42:
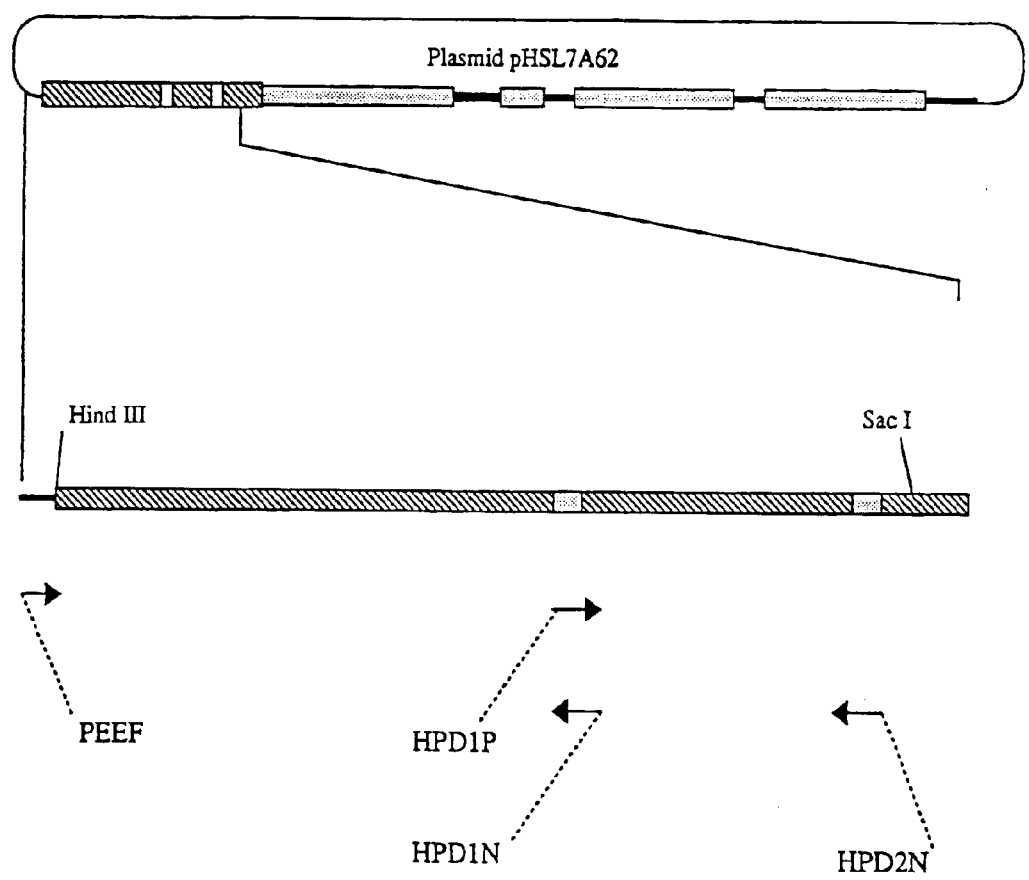
FIG. 42 shows where primers for sequencing pEgPDHV3-21 bind.

The positions, to which the primers bind, are shown in FIG. 42. Determination of nucleotide sequences was performed by the dideoxynucleotide chain termination method using, as templates, the plasmids, purified by the alkaline-SDS method and the cesium chloride method, containing the sequences for confirmation.

As expected, it was verified that pEgPDHV3-21 had the nucleotide sequence of SEQ ID No. 116 of the Sequence Listing, encoding the polypeptide of SEQ ID No. 117.

REFERENCE EXAMPLE 23

Construction of High-Level Expression Vectors Optimized for COS-1 Cells

High-level expression vectors, optimized for COS-1 cells, were constructed, using the above described vectors p7AL-HH, p7AL-HM, p7AL-MM, pLPDHH75, pLPDHM32, pEg7AH-H and pEgPDHV3-21.

(1) High-Level Expression Vectors for Humanized Light Chains

Figure 43:
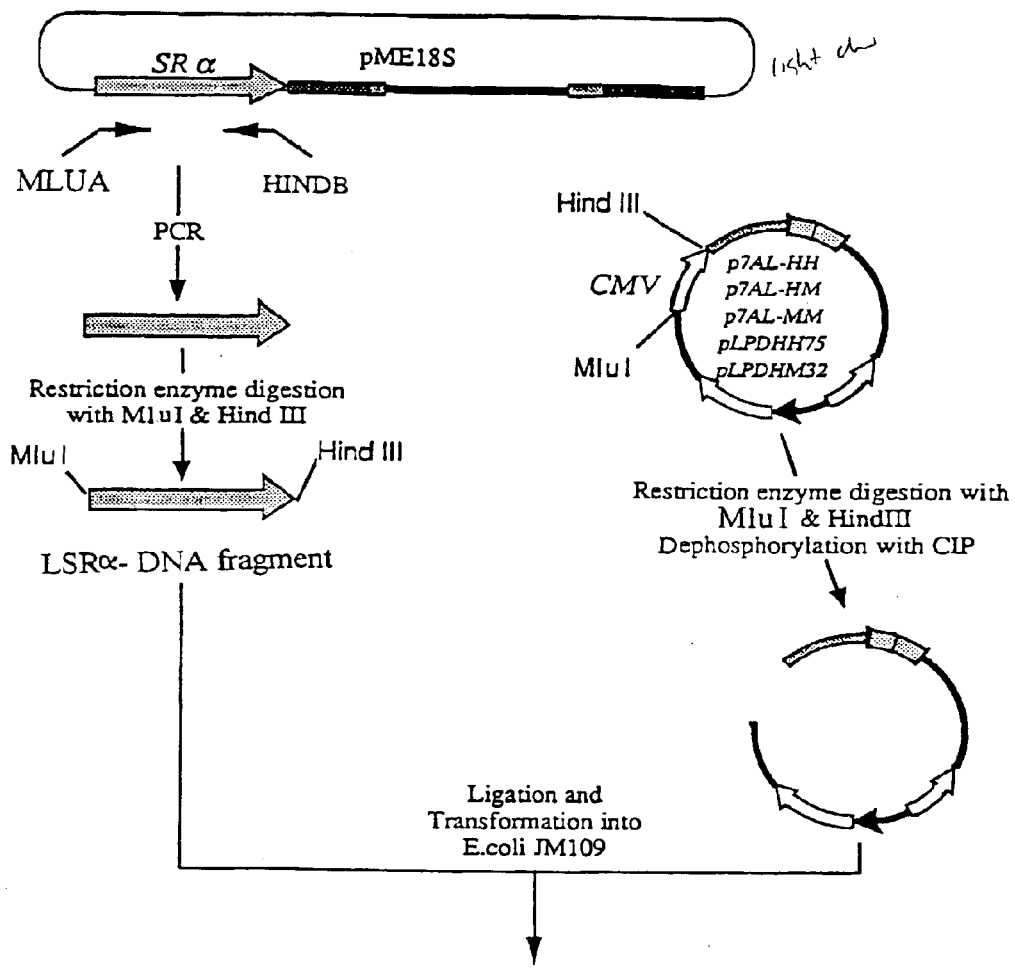
FIG. 43 shows the construction of high-level expression vectors for the humanized light chains.

The construction of high-level expression vectors for the humanized light chains is outlined in FIG. 43.

1) Synthesis of Primers for Preparing the SR α Promoter DNA Fragment

The SR α promoter DNA fragment, for insertion into the expression vectors for humanized light chains, was synthesized using PCR.

The following 2 oligonucleotide primers were synthesized for PCR:

5'-TGCACGCGTG GCTGTGGAAT GTGTGTCAGT TAG -3' (MLUA: SEQ ID No. 121); and
5'-TCCGAAGCTT TTAGAGCAGA AGTAACACTT C -3' (HINDB: SEQ ID No. 122).

2) Construction of Plasmids

After synthesis, the SR α promoter DNA fragment was inserted into the vectors p7AL-HH, p7AL-HM, p7AL-MM, pLPDHH75 or pLPDHM2 and then cloned into E. coli.

An LSR α-DNA fragment, comprising the SR α promoter with a MluI restriction enzyme cleavage site added at the 5'-end and a HindIII restriction enzyme cleavage site added at the 3'-end, was prepared as follows.

Composition of the PCR Reaction Solution:
  plasmid pME18S DNA, 200 ng;
  oligonucleotide primer MLUA, 80 pmol;
  oligonucleotide primer HINDB, 80 pmol;
  dNTP cocktail, 20 µl;
  10×Pfu buffer, 20 µl;
  Pfu DNA polymerase, 10 units; and
  redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified LSR α-DNA fragment was subjected first to phenol extraction and then to ethanol precipitation, and then separated by 5% w/v polyacrylamide gel electrophoresis. After electrophoresis, the gel was stained with 1 µg/ml of ethidium bromide, and the DNA band thus detected, under UV light, was cut out with a razor blade and eluted from the gel using a Centriruter and a Centricon-10, as described above. The eluted DNA was concentrated by centrifugation at 7,500×g, followed by ethanol precipitation, and was finally dissolved in 50 µl of distilled water.

One µg of plasmid p7AL-HH, p7AL-HM, p7AL-MM, pLPDHH75 or pLPDHM32 DNA was digested with the restriction enzymes MluI and HindIII, and then dephosphorylated with CIP. The resulting dephosphorylated plasmid DNA (100 ng) was ligated with 10 µl of the solution containing the LSR α-DNA fragment, which had previously been digested with MluI and HindIII, using a DNA Ligation Kit Version 2.0 (Takara Shuzo, Co. Ltd.). E. coli JM109 was then transformed with the ligation mix and plated onto LB agar medium containing 50 µg/ml ampicillin. The transformants obtained were cultured in 2 ml liquid LB medium containing 50 µg/ml ampicillin at 37° C. overnight, and plasmid DNA was extracted from the resulting culture by the alkaline-SDS method. The extracted plasmid DNA was digested with MluI and HindIII, and a clone carrying LSR α-DNA fragment was selected by 1% w/v agarose gel electrophoresis.

Following the above procedure, the high-level expression vector plasmids pSRHH (HH type), pSRHM (HM type), pSRMM (MM type), PSRPDHH (PDHH type) and pSRP-DHM (PDHM type), were obtained.

(2) High-Level Expression Vectors for Humanized Heavy Chains

Figure 44:
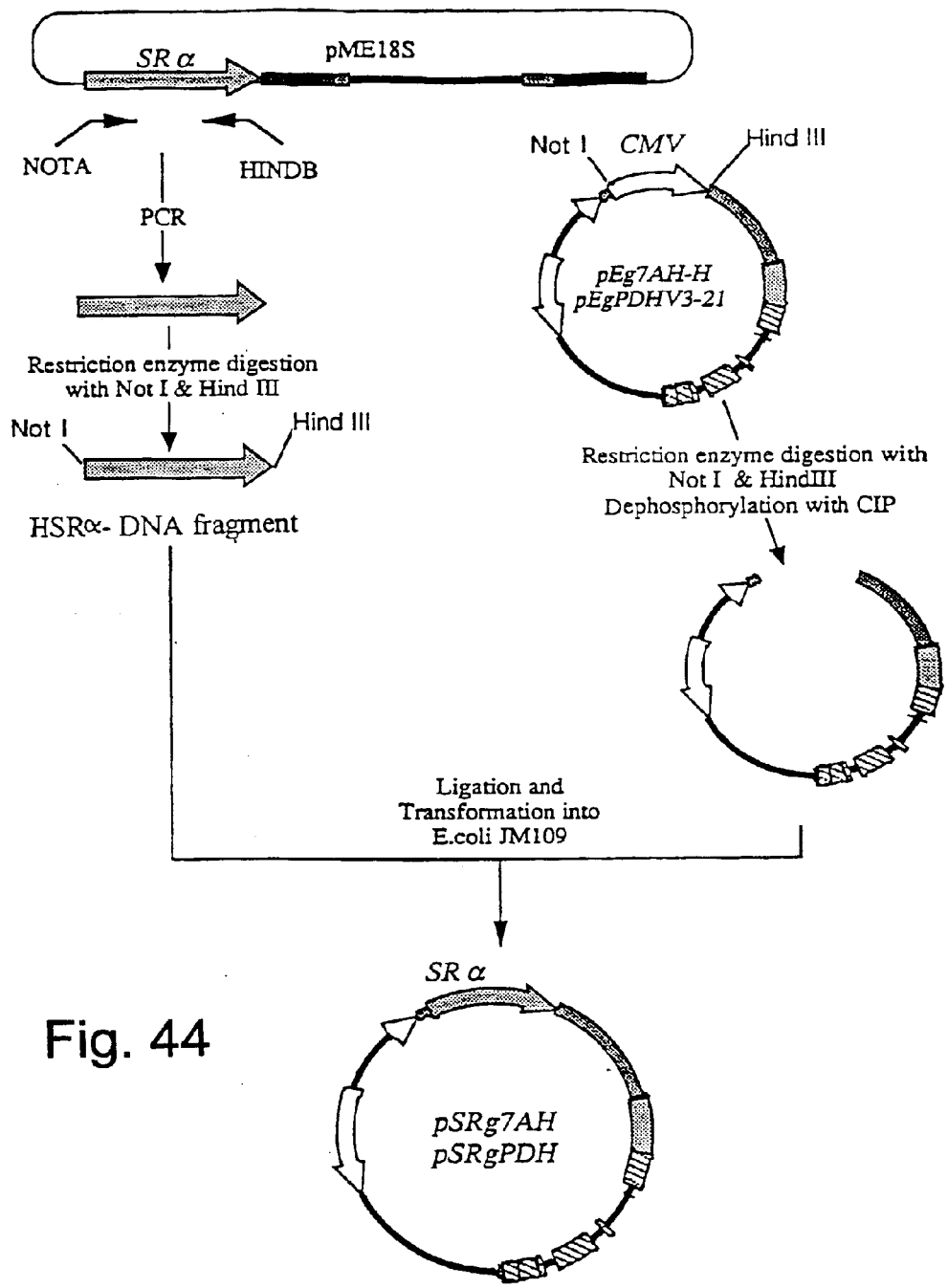
FIG. 44 shows the construction of high-Level expression vectors for humanized heavy chains.

The construction of high-level expression vectors for humanized heavy chains is outlined in FIG. 44.

1) Synthesis of Primers for Preparing SR α promoter DNA Fragment

The SR α promoter DNA fragment, for insertion into the expression vectors for humanized heavy chains, was synthesized using PCR.

In addition to HINDB (SEQ ID No 122), the following oligonucleotide primer was synthesized for PCR:
5'-AAAGCGGCCG CTGCTAGCTT GGCTGTGGAA TGTGTG-3' (NOTA: SEQ ID No. 123).

2) Construction of Plasmids

The SR α promoter DNA fragment was synthesized using PCR, inserted into the above described vector, pEg7AH-H or pEgPDHV3-21, and then cloned into E. coli.

The HSR α-DNA fragment, comprising the SR α promoter with a NotI restriction enzyme cleavage site added at the 5'-end and a HindIII restriction enzyme cleavage site added at the 3'-end, was prepared as follows.

Composition of the PCR Reaction Solution:
  plasmid pMELBS DNA, 200 ng;
  oligonucleotide primer NOTA, 80 pmol;
  oligonucleotide primer HINDB, 80 pmol;
  dNTP cocktail, 20 µl;
  10×Pfu buffer, 20 µl;
  Pfu DNA polymerase, 10 units; and
  redistilled water to a final volume of 200 µl.

The PCR reaction was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After PCR, the amplified HSR α-DNA fragment was subjected first to phenol extraction and then to ethanol precipitation, and then separated by 5% w/v polyacrylamide gel electrophoresis. After electrophoresis, the gel was stained with 1 µg/ml of ethidium bromide, and the DNA band thus detected, under UV light, was cut out with a razor blade and eluted from the gel using a Centriruter and a Centricon-10, as described above. The eluted DNA was concentrated by centrifugation at 7,500×g, followed by ethanol precipitation, and was finally dissolved in 50 µl of distilled water.

One μg of plasmid pEg7AH-H or pEgPDHV3-21 DNA was then digested with the restriction enzymes NotI and HindIII, and then dephosphorylated with CIP. The resulting dephosphorylated plasmid DNA (100 ng) was ligated with 10 μl of the solution containing the HSR α-DNA fragment, which had previously also been digested with NotI and HindIII, using a DNA Ligation Kit Version 2.0 (Takara Shuzo, Co. Ltd.). *E. coli* JM109 was transformed with the ligation mix and plated onto LB agar medium containing final concentrations of 1 mM IPTG, 0.1% w/v X-Gal and 50 μg/ml ampicillin. The white transformants obtained were cultured in 2 ml liquid LB medium containing 50 μg/ml ampicillin at 37° C. overnight, and plasmid DNA was extracted from the resulting culture by the alkaline-SDS method. The extracted plasmid DNA was digested with NotI and HindIII, and a clone carrying then HSR α-DNA fragment was selected by 1% w/v agarose gel electrophoresis.

By following the above procedure, the high-level expression vector plasmids pSRg7AH and pSRgPDH (HV type) were obtained.

REFERENCE EXAMPLE 24

Expression in COS-1 Cells

Transfection of COS-1 cells with the high-level expression plasmids, for each of the humanized HFE7A heavy chains and for each of the humanized HFE7A light chains obtained above, was conducted by electroporation in a manner similar to that described in Reference Example 16.

COS-1 cells were grown to semi-confluence in a culture flask (culture area: 225 $cm_2$), containing α(+)MEM supplemented with 10% v/v FCS. Next, the medium was discarded and the COS-1 cells were detached from the flask by treatment with 3 ml of trypsin-EDTA solution (Sigma Chemicals Co.) at 37° C. for 3 minutes. The detached cells were then harvested by centrifugation at 800 r.p.m. for 2 minutes and then washed twice with PBS(−) buffer. The washed COS-1 cells were then adjusted to $1 \times 10^8$ cells/ml with PBS(−) buffer to produce a COS-1 cell suspension.

In parallel, 4 μg of humanized HFE7A heavy chain expression plasmid DNA and 4 μg of humanized HFE7A light chain expression plasmid DNA, prepared by the alkaline-SDS method and cesium chloride density gradient centrifugation, were mixed and then precipitated with ethanol, before being suspended in 20 μl of PBS(−) buffer, the whole operation being performed in the same tube. The whole of the resulting plasmid suspension (20 μl) was mixed with 20 μl of the previously prepared COS-1 cell suspension ($2 \times 10^6$ cells) and the mixture was transferred to a FCT-13 (Shimadzu Seisakusyo, K. K.) chamber having electrodes set 2 mm apart. This chamber was then loaded into gene transfection apparatus GTE-1 (Shimadzu Seisakusyo, K. K.) and two pulses, each of 600 V, 50 μF, were applied with a one second interval to transform the COS-1 cells with the plasmid DNA of interest.

After electroporation, the cell-DNA mixture in the chamber was suspended in 5 ml of α(+)MEM, supplemented with 10% v/v FCS, in a culture flask (culture area 25 $cm^2$; Sumitomo Bakelite) and incubated under 5% v/v $CO_2$ at 37° C. for 72 hours. After this time, the culture supernatant was taken and analyzed for the expression products.

By following the above method, COS-1 cells transfected with each of the following plasmid combinations were obtained:

(A) no plasmid DNA;
(B) cotransfection of pSRgPDH and pSRPDHH;
(C) cotransfection of pSRgPDH and pSRPDHM;
(D) cotransfection of pSRg7AH and pSRHH;
(E) cotransfection of pSRg7AH and pSRHM; and
(F) cotransfection of pSRg7AH and pSRMM.

REFERENCE EXAMPLE 25

Assay for Fas-Binding Activity

The assay for Fas-binding activity in the cell culture supernatant fluids prepared in Reference Example 24 was performed by ELISA as follows.

Culture supernatant from COS-1 cells expressing the human Fas fusion protein, as obtained in Reference Example 1 above, diluted 5-fold with adsorption buffer, was dispensed into wells of a 96-well plate (MaxiSorb; Nunc) at 50 μl per well and the plate was incubated at 4° C. overnight to allow adsorption of the human Fas fusion protein to the surface of the wells. Next, each of the wells was washed 4 times with 350 μl of PBS-T. After washing, PBS-T containing 5% v/v BSA (bovine serum albumin; Wako Pure Chemical Industries, Ltd.) was added to the wells at 50 μl per well and the plate was incubated at 37° C. for 1 hour to block the remainder of the surface of each well. The wells were then again washed four times with PBS-T.

The culture supernatants obtained in Reference Example 16 were adjusted to have a final concentration of the product of interest of 100 ng/ml in α(+)MEM containing 10% v/v FCS. Concentrations were estimated by the method described in Reference Example 17. Each of the resulting 100 ng/ml solutions was then used to produce serial dilutions by serial 2-fold dilution with α(+)MEM containing 10% v/v FCS. Next, 50 μl of each of the resulting serial dilutions of each expression product was added to a well prepared as above, and the plate was incubated at 37° C. for 2 hours to allow reaction.

After this time, the wells were again washed four times with PBS-T, and then 50 μl of alkaline phosphatase-labeled goat anti-human IgG Fc specific polyclonal antibody (Caltag Lab.), diluted 10,000-fold with PBS-T, were dispensed into each well and reaction was allowed to proceed at 37° C. for 2 hours.

HFE7A purified from mouse hybridoma HFE7A was used as a control (IgG1), and was detected using alkaline phosphatase-labeled goat anti-mouse IgG+IgA+IgM (Gibco BRL), diluted 5,000-fold with PBS-T, in place of the alkaline phosphatase-labeled goat anti-human IgG Fc specific polyclonal antibody.

The wells were again washed four times with PBS-T, and then 50 μl of substrate solution [1 mg/ml p-nitrophenyl phosphate in 10% v/v diethanol amine (pH 9.8)] was dispensed into each well and the plate was incubated at 37° C. for 0.5 to 1 hour. Binding activity of the expression product contained in each culture supernatant fluid with the human Fas fusion protein was evaluated by reading the absorbance of each well at 405 nm.

Figure 45:
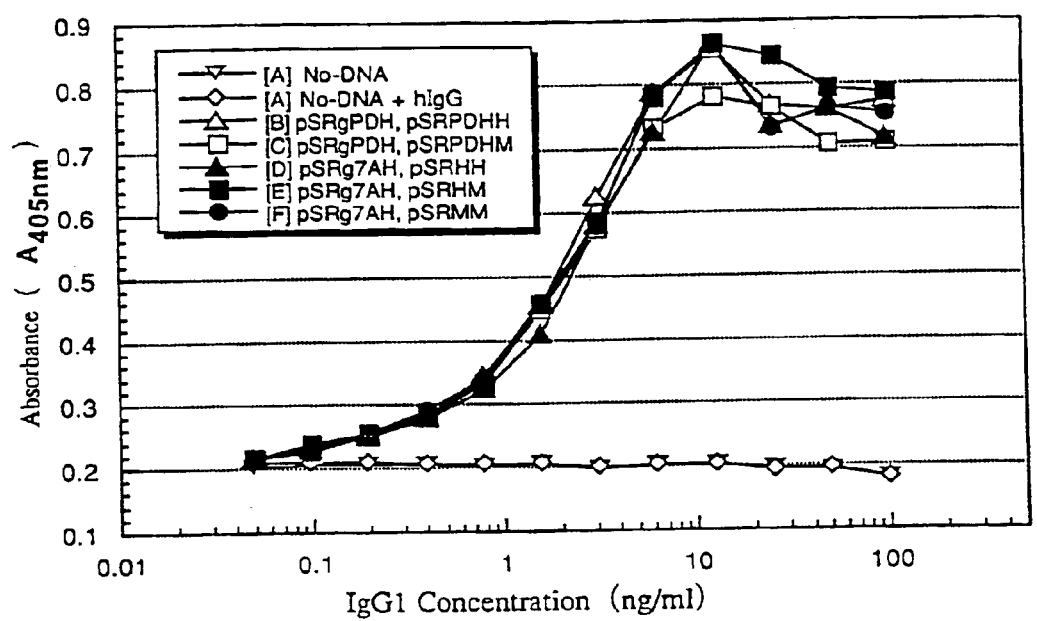
FIG. 45 shows the binding activity for the human Fas fusion protein for the supernatants of Example 12.

As expected, binding activity for the human Fas fusion protein was demonstrated for the supernatants of categories (B), (C), (D), (E) and (F) above of Reference Example 24, and is shown in FIG. 45.

REFERENCE EXAMPLE 26

Competitive Inhibition of Fas-Binding Activity of HFE7A

The humanized anti-Fas antibodies obtained in Reference Example 24 should inhibit the binding of HFE7A to Fas, as the antibodies of this Example were derived from HFE7A. Therefore, the ability of the expression products obtained in Reference Example 24 to competitively inhibit the binding of HFE7A to the human Fas fusion protein was measured.

The COS-1 cell culture supernatant containing the human Fas fusion protein, as obtained in Reference Example 1, was diluted 5-fold with adsorption buffer, and dispensed into the wells of a 96-well plate for luminescence detection (Luminescent Solid Assay Plate, high binding property; Costar) at 50 µl per well. The plate was then incubated at 4° C. overnight to allow adsorption of the human Fas fusion protein to the surface of the wells.

After this time, each well was washed 4 times with 350 µl of PBS-T, and then 100 µl PBS-T containing 5% v/v BSA was added to each well and the plate was incubated at 37° C. for 1 hour to block the remainder of the surface of each well. The wells were then again washed four times with PBS-T.

The culture supernatants obtained in Reference Example 24 were adjusted to final concentrations of antibody of 1 µg/ml in α(+)MEM containing 10% v/v FCS by the method of Reference Example 17. Each of the resulting solutions of the expression products was used to produce serial dilutions by serial 2-fold dilution with α(+)MEM containing 10% v/v FCS. AP-HFE7A was diluted to 50 ng/ml with α(+)MEM containing 10% v/v FCS, and 25 µl of the resulting solution was mixed with an equal volume of each of the prepared serial dilutions.

Each of the wells was again washed four times with PBS-T, and then 50 µl of each of the resulting antibody mixtures were added to individual wells, and the plate was allowed to stand at room temperature overnight. Subsequently, after washing each well with PBS-T again four times, 100 µl of CDP-star buffer (9.58 ml diethanol amine, 0.2 g magnesium chloride, 0.25 g sodium azide, pH8.5) was dispensed into each well and the plate was allowed to stand at room temperature for 10 minutes. After this time, the CDP-star buffer was discarded and CDP-star substrate [1.2 ml sapphire 11 (Tropix), 200 µl CDP-star (Tropix), q.s. to 12 ml with CDP-star buffer] was added at 50 µl per well, and the plate was then allowed to stand at room temperature for a further 40 minutes.

Competitive inhibition of the expression products of Reference Example 24 of the binding of HFE7A to the human Fas fusion protein was evaluated by measuring the intensity of the luminescence with Luminoscan (Titertech).

Figure 46:
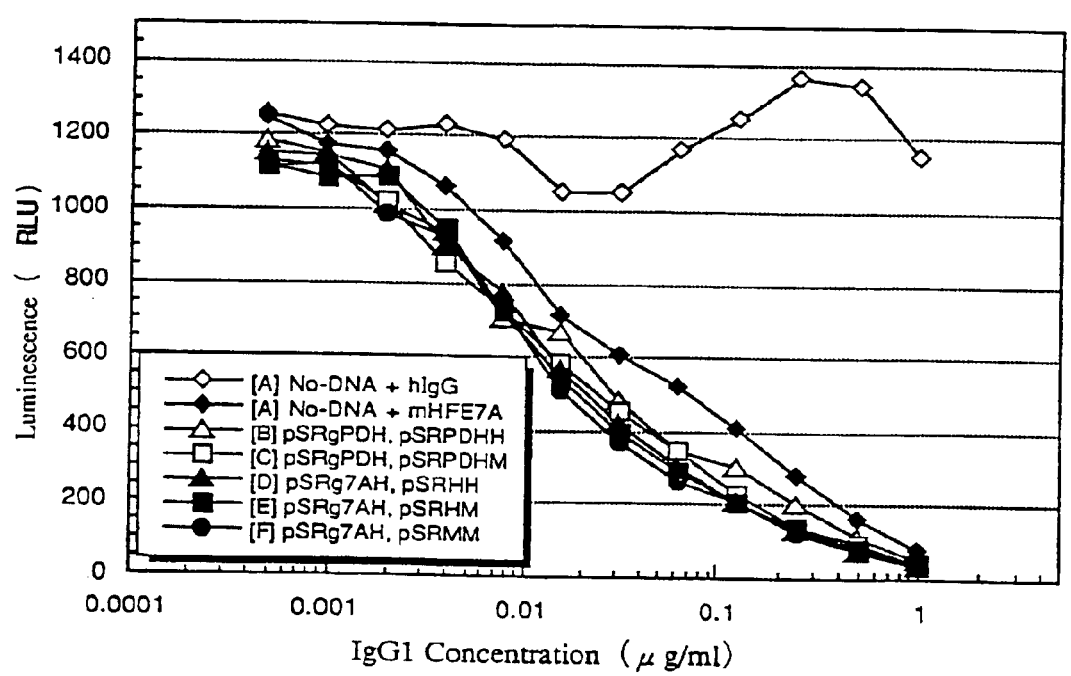
FIG. 46 shows the results of competitive inhibition of HFE7A antibody by the supernatants of Example 12.

As expected, it was verified that each of the expression products of supernatants (B), (C), (D), (E) and (F) obtained in Reference Example 24 above specifically inhibited the binding of HFE7A antibody to the human Fas fusion protein. The results are shown in FIG. 46.

REFERENCE EXAMPLE 27

Apoptosis-Inducing Activity

The apoptosis-inducing activity of the expression products in the culture supernatant fluids obtained in Reference Example 24 was examined in a manner similar to that described in Reference Example 20.

WR1SL12a cells were cultured in RPMI 1640 medium with 10% v/v FCS (Gibco BRL) at 37° C. for 3 days under 5% v/v $CO_2$, and 50 µl ($1 \times 10^5$ cells) of the resulting culture were then dispensed into each well of a 96-well microplate (Sumitomo Bakelite). The culture supernatants obtained in Reference Example 24 were adjusted to a final concentration of antibody of 100 ng/ml in RPMI 1640 medium containing 10% v/v FCS. Concentrations were estimated by the method of Reference Example 17. Each of the adjusted solutions of the expression products was used to produce serial dilutions by serial 2-fold dilution with RPMI 1640 containing 10% v/v FCS. Each of the resulting dilutions of each expression product solution was added to individual wells, at 50 µl per well, and the plate was incubated at 37° C. for 1 hour. After this time, the cells in each well were washed once with RPMI 1640 containing 10% v/v FCS and then the washed cells were suspended in 100 µl per well of 0.5 µg/ml goat anti-human IgG Fc specific polyclonal antibody (Kappel) in RPMI 1640 containing 10% v/v FCS.

The plate was allowed to stand at 37° C. for 12 hours, and then 50 µl of 25 µM PMS (phenazine methosulfate; Sigma Chemical Co.), containing 1 mg/ml XTT [2,3-bis(2-methoxy-4-nitro-5-sulfophenyl)-2H-tetrazolium-5-carboxyanilide inner salt; Sigma Chemical Co.] to final concentrations of 333 µg/ml for XTT and 8.3 µM for PMS, were added to each well. The plate was then incubated for 3 hours at 37° C., and the absorbance at 450 nm of each well was measured, to calculate cell viability, using the reducing power of the mitochondria as the index.

The viability of the cells in each well was calculated according to the following formula:

$$\text{Viability } (\%) = 100 \times (a-b)/(c-b)$$

wherein "a" is the absorbance of a test well, "b" is the absorbance of a well with no cells, and "c" is the absorbance of a well with no antibody added.

Figure 47:
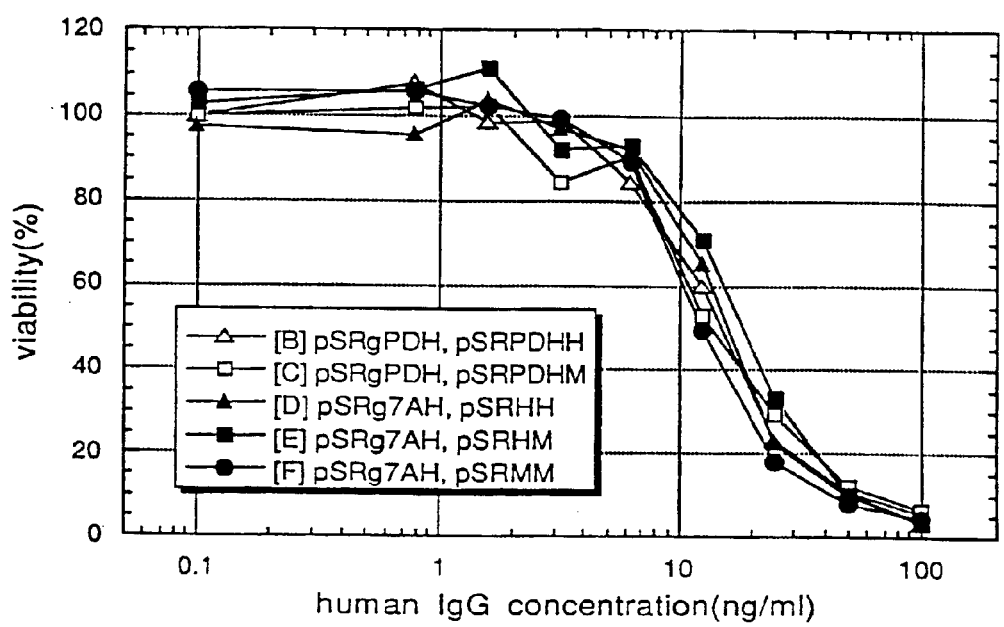
FIG. 47 shows the results of inducing apoptosis in T cells by culture supernatant fluids of Example 12.

As expected, each of the expression products of the culture supernatant fluids (B), (C), (D), (E) and (F) obtained in Reference Example 24 above were demonstrated to induce apoptosis in T cells of this lymphoma cell line expressing human Fas antigen (FIG. 47).

EXAMPLE 1

Designing an Eu Type Humanized HFE7A Antibody

In the above Reference Examples, the human antibody 8E10'CL was chosen as an acceptor. In an alternative aspect of the present invention, the human Eu antibody was selected as an acceptor instead, in order to prepare the humanized antibody (hereinafter the humanized antibody, or a subunit thereof, as prepared in the Reference Examples, is referred to as "8E10 type", while the humanized HFE7A antibody, or subunit thereof, having Eu as the acceptor, is referred to as "Eu type").

(1) Molecular Modeling of the Variable Regions of HFE7A

Molecular modeling of the variable regions of HFE7A was performed by the method generally known as homology modeling [c.f. Methods in Enzymology, 203, 121–153, (1991)].

The primary sequences of variable regions of human immunoglobulins registered in the Protein Data Bank (hereinafter referred to as the "PDB"; Chemistry Department, Building 555, Brookhaven National Laboratory, P.O. Box 5000, Upton, N.Y. 11973-5000, USA), for which X-ray crystallography had been performed, were compared with the framework regions of HFE7A determined above. As a result, 1GGI and 2HFL were selected as having the highest homologies of the three-dimensional structures of the framework regions for the light and heavy chains, respectively. Three-dimensional structures of the framework regions were generated by combining the properties of 1GGI and 2HFL and by calculating the properties of the regions of HFE7A, as described below, thereby to obtain the "framework model".

Using the classification described by Chothia et al., the CDR's of HFE7A were classified as follows: $CDRL_2$, $CDRL_3$ and $CDRH_1$ all belonged to canonical class 1, while $CDRL_1$, $CDRH_2$ and $CDRH_3$ did not appear to belong to any specific canonical class. The CDR loops of $CDRL_2$, $CDRL_3$ and $CDRH_1$ were ascribed the conformations inherent to their respective canonical classes, and then integrated into the framework model. $CDRL_1$ was assigned the conformation of cluster 15B, in accordance with the classification of Thornton et al. [c.f. J. Mol. Biol., 263, 800–815, (1996)]. For $CDRH_2$ and $CDRH_3$, conformations of sequences with high homologies were selected from the PDB and then these were combined with the results of energy calculations. The conformations of the CDR loops with the highest probabilities were then taken and integrated into the framework model.

Finally, energy calculations were carried out to eliminate undesirable contact between inappropriate atoms, in terms of energy, in order to obtain a molecular model of HFE7A. The above procedure was performed using the commercially available common molecular modeling system, AbM (Oxford Molecular Limited, Inc.), although any other appropriate system could have been used.

The accuracy of the structure of the molecular model obtained was further evaluated using PROCHECK software [J. Appl. Cryst., (1993), 26, 283–291], and the degree of surface exposure of each residue was calculated to determine which surface atoms and groups interacted.

(2) Selection of the Acceptor

The subgroups of the light and heavy chains of HFE7A shared identities of 79% with the subgroup κIV and 79% with the subgroup I, respectively, by comparison with the consensus sequences of the respective subgroups of human antibodies. However, there was no human antibody having such a combination of these subgroups. Human antibody Eu was selected as an antibody in which the light chain and heavy chain were from the same antibody and which had the highest possible homology with HFE7A.

The antibody Eu has commonly been used to humanize antibodies (for the amino acid sequence of Eu, c.f. Kabat, E. A., et al., ibid.). The light chain and the heavy chain of Eu belong to subgroup κI and subgroup I respectively.

(3) Selection of donor residues to be grafted onto the acceptor

The amino acid sequence of each of the light and heavy chains of HFE7A was aligned with that of the corresponding chain of the acceptor, and humanized sequences of the variable regions, as described in the following Examples, were designed in accordance with the general guidelines set out in a) to d) above.

Plasmids were constructed which could serve as recombinant vectors comprising DNA nucleotide sequences encoding Eu type, humanized, anti-Fas antibodies. Specifically, the vectors comprising DNA encoding 8E10 type humanized light chain and heavy chains, prepared in Reference Examples 14 and 15, were used as templates and modified so that the amino acid sequence in the FR was of the Eu type (FIGS. 48 and 49).

DNA encoding the constant region of the light chain, obtained by cloning, was ligated with DNA encoding the variable region. The constant region of the 8E10 type heavy chain was used without modification, as it was the same as that of the Eu type heavy chain.

EXAMPLE 2

Construction of Expression Vector of Light Chain of Eu Type Humanized HFE7A (1) Cloning of cDNA Encoding a Human Light Chain (κ Chain Subgroup Type I)

Prior to preparation of the light chain of Eu type humanized HFE7A, cloning of cDNA of a human light chain κ chain subgroup, type I, was performed.

1) Synthesis of Primer

Synthesis of a cDNA primer encoding the human light chain (κ chain subgroup type I) was carried out by PCR. For the PCR, the following oligonucleotide primer was synthesized:

5'-AAGCTTATGG ACATGAGGGT CCCCGCTCTG CTCC-3' (FHKI: SEQ ID No. 124 of the Sequence Listing), and used in combination with 7ALCN (SEQ ID No. 64 of the Sequence Listing).

2) Construction of a Plasmid

An SpHE fragment encoding a full-length of human immunoglobulin light chain, having κ chain subgroup type I in the variable region, was prepared under the following conditions:

Composition of the PCR Reaction Solution:
  human spleen cDNA library (Life Technologies), 25 ng;
  primer FHKI (10 μM), 5 μl;
  primer 7ALCN (10 μM), 5 μl;
  2.5 mM dNTP cocktail, 5 μl;
  25 mM Tris-HCl buffer (pH 8.2), 5 μl;
  1 M potassium chloride, 2.5 μl;
  25 mM magnesium chloride, 5 μl;
  Taq DNA polymerase, 1 unit; and
  Redistilled water to a total volume of 50 μl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The thus prepared SpHE-DNA fragment was inserted into plasmid pCR3.1 using a eukaryote TA Cloning Kit (Invitrogen), following the manufacturer's protocol, and introduced into competent E. coli TOP10F' contained in the kit. Plasmid pKISp35 was thereby obtained, carrying the SpHE-DNA fragment, which is a cDNA of a human immunoglobulin light chain having κ chain subgroup type I in the variable region.

3) Nucleotide Sequence Analysis

The nucleotide sequences of the SpHE-DNA fragment carried by the plasmids pKISp35, obtained in (2) above, were determined by the dideoxy method [c.f. Sanger, F. S., et al., (1977), Proc. Natl. Acad. Sci. USA, 74: 5463–5467] using a gene sequence analyzer (Model 310 Genetic Analyzer; Perkin Elmer Japan). As a result, the nucleotide sequence of SEQ ID No. 125 of the Sequence Listing was obtained. The sequence corresponded to the nucleotide sequence of cDNA encoding a human Ig light chain having κ chain subgroup type I in the variable region.

(2) Construction of Expression Plasmid Vectors for Eu Type Humanized HFE7A Light Chain cDNA's were prepared encoding three types of Eu-type humanized light chain amino acid sequences, modified so that FR's of the humanized HFE7A light chain resembled those of an Eu type molecule (subgroup type I) as shown in FIG. 48 (hereinafter referred to as "LEU1 type", "LEU2 type" and "LEU3 type"). The cDNA's were prepared according to the following method, and each of them was inserted into a plasmid.

(1) Synthesis of Primers

PCR was used to construct the following DNA sequences, each of which comprised the variable region of the light chain of Eu type humanized HFE7A and the constant region of the human immunoglobulin light chain (κ chain):

DNA (SEQ ID No. 126 of the Sequence Listing) encoding the LEU1 type polypeptide chain (SEQ ID No. 127 of the Sequence Listing)

DNA (SEQ ID No. 128 of the Sequence Listing) encoding the LEU2 type polypeptide chain (SEQ ID No. 129 of the Sequence Listing); and DNA (SEQ ID No. 130 of the Sequence Listing) encoding the LEU3 type polypeptide chain (SEQ Sequence No. 131 of the Sequence Listing).

The following 10 oligonucleotide PCR primers were synthesized in addition to primer 7ALCN (SEQ ID No. 64 of the Sequence Listing) and primer 7AL1P (SEQ ID No. 55 of the Sequence Listing):

5'-AGGGAGGATG GAGATTGGGT GAGCACAATG TCACCAGTGG A-3' (7ALR2; SEQ ID No. 132);

5'-ATTGTGCTCA CCCAATCTCC ATCCTCCCTG TCTGCATCT-3' (7ALF12; SEQ ID No. 133);

5'-ATCAACACTT TGGCTGGCCT TGCAAGTGAT GGTGACTCTG TC-3' (7ALR33; SEQ ID No. 134);

5'-CCATCACTTG CAAGGCCAGC CAAAGTGTTG ATTATGATGG-3' (7ALF2; SEQ ID No. 135);

5'-AGTTTCGAGA TTGGATGCAG CATAGATGAG GAGTTTGGGT GCCTTTCC-3' (7ALR45; SEQ ID No. 136);

5'-CCCAAGCTCC TCATCTATGC TGCATCCAAT TTGGAAAGTG GGGTC-3' (7ALF33; SEQ ID No. 137);

5'-TTGGCCGAAC GTTCGAGGAT CCTCGTTACT CTGTTGACAG TAGT-3' (7ALR53; SEQ ID No. 138);

5'-ACTACTGTCA ACAGAGTAAC GAGGATCCTC GAACGTTCGG CCAA-3' (7ALF53; SEQ ID No. 139);

5'-CTCATCTATG CTGCATCCAA TTTGGAAAGT GGGATCCCAT CAAGG-3' (7ALF34; SEQ ID No. 140); and 5'-ATTGGATGCA GCATAGATGA GGAGCTTGGG TGCCTGTCCT GGTTT-3' (7ALR44; SEQ ID No. 141).

(2) Preparation of DNA Encoding LEU1 Type Light Chain

1) Preparation of LEU1 DNA Fragment

The LEU1-DNA fragment (SEQ ID No. 126 of the Sequence Listing), encoding the amino acid sequence of SEQ ID No. 127 of the Sequence Listing, was prepared by 2-stage PCR, and was then inserted into a plasmid vector and cloned into *E. coli*.

First Stace PCR

Figure 50:
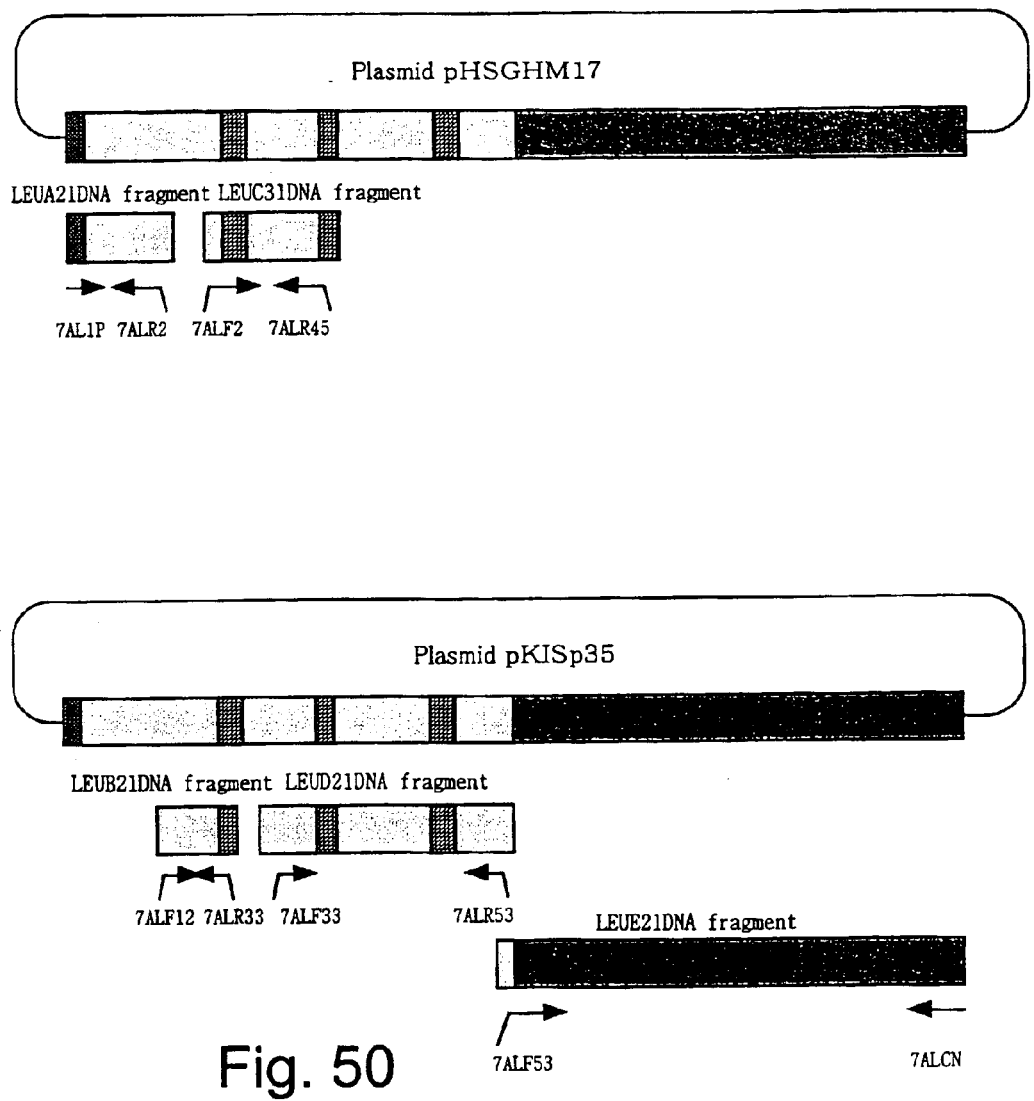
FIG. 50 is a summary of the first step PCR for the production of LEU1-DNA.

The outline of the first stage PCR for the preparation of LEU1-DNA is shown in FIG. 50.

The LEUA21-DNA fragment, encoding a secretion signal sequence and a portion of the $FRL_1$ region altered to contain a Hind III restriction enzyme cleavage site at the 5'-end, was prepared as follows. The plasmid pHSGHM17 prepared in Reference Example 14 was used as a template for PCR.

Composition of the PCR Reaction Solution:
plasmid pHSGHM17 DNA, 25 ng;
primer 7AL1P, 5 pmol;
primer 7ALR2, 5 pmol;
2.5 mM dNTP cocktail, 5 µl;
10×Pfu buffer, 5 µl;
Pfu DNA polymerase, 1 unit; and
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The LEUB21-DNA fragment, encoding a portion of the $FRL_1$ region and a portion of the $CDRL_1$ region, was prepared as follows.

Composition of the PCR Reaction Solution:
plasmid pKISp35 DNA, 25 ng;
primer 7ALF12, 5 pmol;
primer 7ALR33, 5 pmol
2.5 mM dNTP cocktail, 5 µl;
10×Pfu buffer, 5 µl;
Pfu DNA polymerase, 1 unit; and
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes was repeated 30 times. After completion of this procedure, the reaction solution was heated at 72° C. for 10 minutes.

The LEUC31 DNA fragment, encoding a portion of the $FRL_1$ region, the $CDRL_1$ region, the $FRL_2$ region and the $CDRL_2$ region was prepared as follows.

Composition of the PCR Reaction Solution:
plasmid pHSGHM17 DNA, 25 ng;
primer 7ALF2, 5 pmol,
primer 7ALR45 5 pmol,
2.5 mM dNTP cocktail, 5 µl;
10×Pfu buffer, 5 µl;
Pfu DNA polymerase, 1 unit;
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The LEUD21-DNA fragment, encoding a portion of the $FRL_2$ region, the $CDRL_2$ region, the $FRL_3$ region, the $CDRL_3$ region and a portion of the $FRL_4$ region was prepared as follows.

Composition of the PCR Reaction Solution:
plasmid pKISp35 DNA 25 ng;
primer 7ALF33, 5 pmol;
primer 7ALR53, 5 pmol;
2.5 mM dNTP cocktail, 5 µl;
10×Pfu buffer, 5 µl;
Pfu DNA polymerase 1 unit; and
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes was repeated 30 times. After completion of this procedure, the reaction solution was heated at 72° C. for 10 minutes.

The LEUE21-DNA fragment, encoding a portion of the $FRL_3$ region, the $CDRL_3$ region, the $FRL_4$ region and the constant region, altered to have an EcoRI restriction enzyme cleavage site at the 3'-end, was prepared as follows.

Composition of the PCR Reaction Solution:
plasmid pKISp35 DNA, 50 ng;
primer 7ALF53, 5 pmol;
primer 7ALCN, 5 pmol;
2.5 mM dNTP cocktail, 5 µl;
10×Pfu buffer, 50 µl;
Pfu DNA polymerase, 1 unit; and
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After phenol extraction and ethanol precipitation of each of the PCR-amplified products, each resulting DNA precipitate was separated by 5% w/v polyacrylamide gel electrophoresis. After electrophoresis, the acrylamide gel was stained with a 1 μg/ml of ethidium bromide to allow detection of DNA under UV light. The DNA bands corresponding to LEUA21-DNA, LEUB21-DNA, LEUC31-DNA, LEUD21-DNA and LEUE21-DNA were excised with a razor blade.

Second Stage PCR

Figure 51:
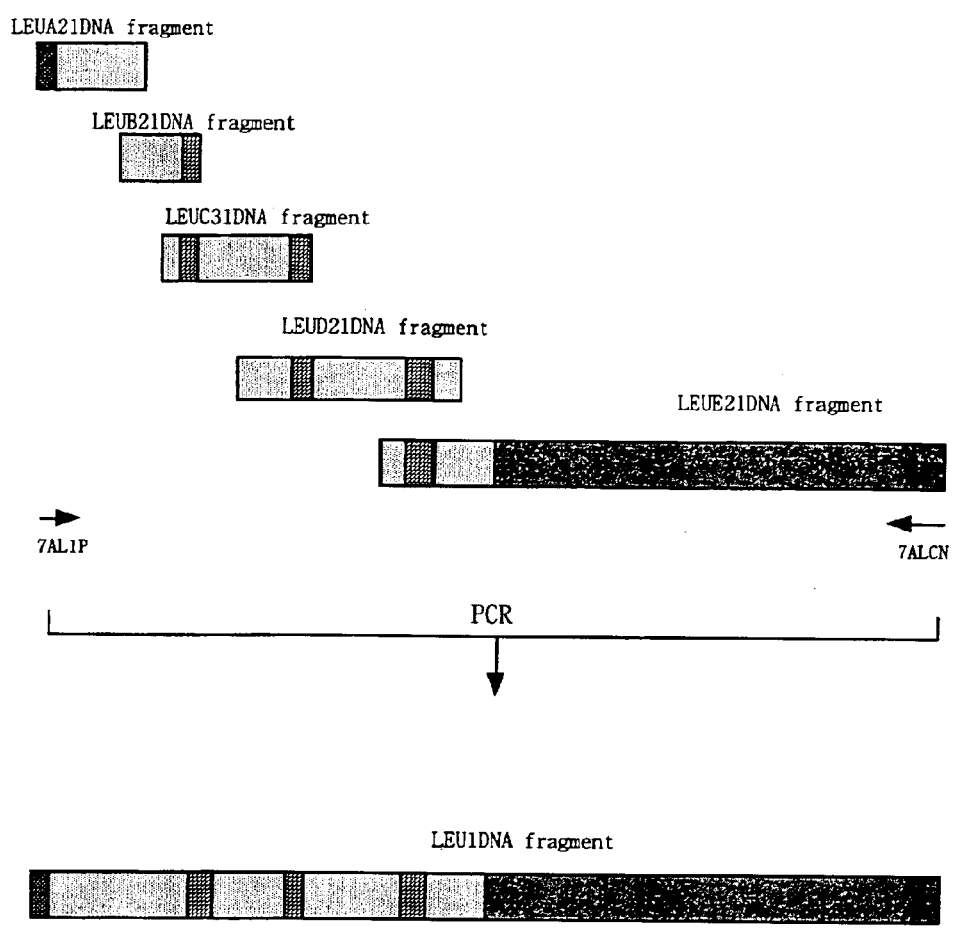
FIG. 51 is a summary of the second step PCR for the production of LEU1-DNA.

The outline of the second stage PCR for the production of LEU1-DNA is shown in FIG. 51.

LEU1-DNA, in which the LEUA21-DNA, LEUB21-DNA, LEUC31-DNA, LEUD21-DNA and LEUE21-DNA fragments described above were fused, was prepared as follows.

The electrophoresed gel excised in the first stage PCR was added to the reaction solution without extraction.

Composition of the PCR Reaction:
  gel piece containing LEUA21-DNA;
  gel piece containing LEUB21-DNA;
  gel piece containing LEUC31-DNA;
  gel piece containing LEUD21-DNA;
  gel piece containing LEUE21-DNA;
  primer 7AL1P, 10 pmol;
  primer 7ALCN, 10 pmol;
  dNTP cocktail, 10 μl;
  10×Pfu buffer, 10 μl;
  Pfu DNA polymerase, 2 units; and
  redistilled water to a final volume of 100 μl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

Phenol extraction followed by ethanol precipitation were performed on the amplified PCR fragments, and these fragments were then separated by 5% w/v polyacrylamide gel electrophoresis. After electrophoresis, the gel was stained with 1 μg/ml of ethidium bromide, and viewed under UV light. The band corresponding to LEU1-DNA was excised with a razor blade from the gel, and DNA was eluted from the excised band using Centricon and a Centriruter. The thus eluted DNA was concentrated, first by centrifugation at 7,500×g and then by ethanol precipitation, after which it was dissolved in 50 μl of distilled water.

2) Preparation of Plasmid

The LEU1-DNA fragment obtained in 1) above was further purified by phenol extraction followed by ethanol precipitation, and was then digested with the restriction enzymes Hind III and EcoRI. One μg of cloning plasmid pHSG399 DNA (Takara Shuzo Co., Ltd.) was digested with the restriction enzymes Hind III and EcoRI, and then dephosphorylated with CIP. The resulting, dephosphorylated plasmid pHSG399 DNA and the digested LEU1-DNA fragment were ligated using a DNA Ligation Kit Version 2.0 (Takara Shuzo Co., Ltd.). The ligated DNA was then used to transform *E. coli* JM 109 (Takara Shuzo Co., Ltd.). Cells were plated onto LB agar medium containing final concentrations of 0.1 mM IPTG, 0.1% X-Gal and 50 μg/ml chloramphenicol, and the plates were incubated at 37° C. overnight to obtain *E. coli* transformants. Any white transformants obtained were cultured in 2 ml of liquid LB medium containing 50 μg/ml chloramphenicol at 37° C. overnight, and plasmid DNA was extracted from the resulting cultures by the alkaline-SDS method [c.f. Sambrook et al., supra].

The resulting, extracted plasmid DNA was digested with the restriction enzymes Hind III and EcoRI, and a clone carrying the LEU1-DNA fragment was then identified and selected by 1% w/v agarose gel electrophoresis, stained with ethidium bromide.

Plasmid pHSGLEU15-29-1, carrying DNA encoding a fusion polypeptide of the variable region of the LEU1 type humanized light chain and the constant region of human immunoglobulin κ chain, was obtained accordingly. The transformant *E. coli* pHSGLEU15-29-1 SANK 72598 harboring plasmid pHSGLEU15-29-1 was deposited with the Kogyo Gijutsuin Seimei-Kogaku Kogyo Gijutsu Kenkyujo on Sep. 18, 1998, in accordance with the Budapest Treaty, and was accorded the accession number FERM BP-6512.

3) Construction of Expression Vector

Figure 56:
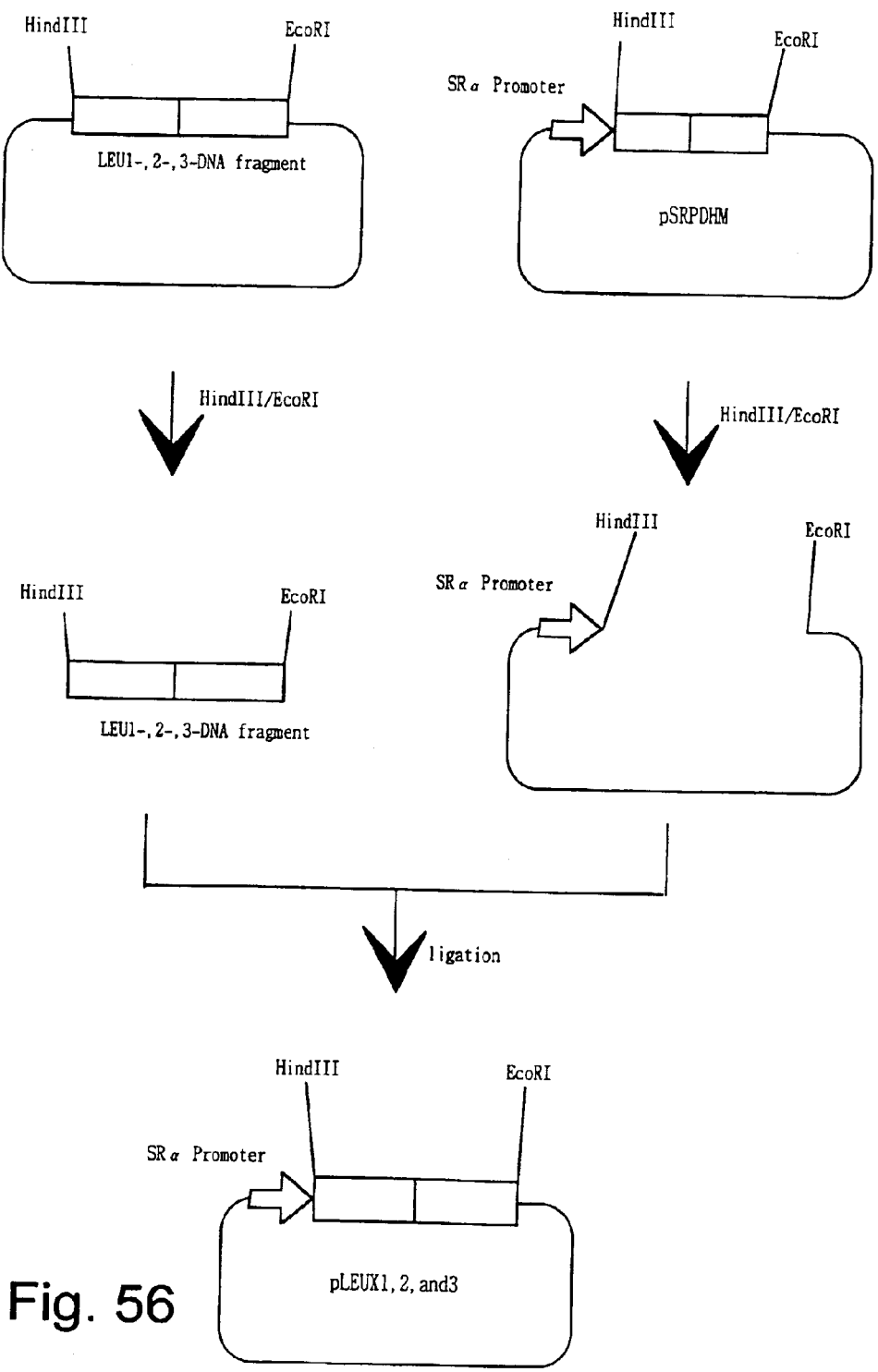
FIG. 56 shows the outline of the construction of expression plasmid carrying DNA encoding Eu type humanized light chain.

The outline of the method of construction of the expression vector plasmid carrying the DNA encoding the LEU-1 type humanized light polypeptide obtained in the above 2) is shown in FIG. 56.

One μg of the plasmid pSRPDHM prepared in Reference Example 23 was digested with the restriction enzymes Hind III and EcoRI, and then dephosphorylated using CIP. The resulting dephosphorylated pSRPDHM DNA (100 ng) was ligated with 10 μg of the pHSGLEU15-29-1 DNA fragment which had also been digested with Hind III and EcoRI, using a DNA Ligation Kit, and then used to transform *E. coli* JM109. Cells were then plated on LB agar plates containing 50 μg/ml ampicillin and incubated at 37° C.

The transformants obtained by this method were cultured in 2 ml of liquid LB medium containing 50 μg/ml ampicillin, and plasmid DNA was subsequently extracted from the resulting culture by the alkaline-SDS method [Sambrook et al., supra]. The extracted plasmid DNA was digested with Hind III and EcoRI, and subjected to 1% w/v agarose gel electrophoresis to confirm the presence or absence of the insert of interest, by staining with ethidium bromide. This enabled the identification and isolation of the plasmid pLEUX15-29-5, containing DNA encoding the LEU1 type humanized light chain located downstream of the S*a* promoter in the correct orientation.

(3) Preparation of DNA Encoding LEU2 Type Light Chain

1) Preparation of LEU2-DNA Fragment

The LEU2-DNA fragment (SEQ ID No. 128 of the Sequence Listing), encoding the amino acid sequence of SEQ ID No. 129 of the Sequence Listing, was prepared by two step PCR. The resulting PCR product was then inserted into a plasmid vector and cloned into *E. coli*. The plasmid pHSGHM17, constructed in Reference Example 14, was used as a template for PCR.

First Stage PCR

The outline of the first stage PCR for the preparation of LEU2-DNA is shown in FIG. 52.

The LEUA21-DNA fragment, LEUB21-DNA fragment, LEUD21-DNA fragment and LEUE21-DNA fragment were each amplified by performing PCR in accordance with the procedure described (1) above, respectively.

The LEUC211-DNA fragment, encoding a portion of the $FRL_1$ region, the $CDRL_2$ region, the $FRL_2$ region and a portion of the $CDRL_2$ region was prepared as follows.

Composition of the PCR Reaction Solution:
  plasmid pHSGHM17 DNA, 25 ng;
  primer 7ALF2, 5 pmol;
  primer 7ALR44, 5 pmol;

2.5 mM dNTP cocktail, 5 µl;
10×Pfu buffer, 5 µl;
Pfu DNA polymerase, 1 unit; and
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After phenol extraction and ethanol precipitation of each PCR-amplified product, the resulting DNA precipitate was separated by 5% w/v polyacrylamide gel electrophoresis. After electrophoresis, the acrylamide gel was stained with 1 µg/ml of ethidium bromide to allow detection of DNA under UV light. The DNA bands corresponding to LEUA21-DNA, LEUB21-DNA, LEUC211-DNA, LEUD21-DNA and LEUE21-DNA were excised using a razor blade.

Second Stage PCR

Figure 53:
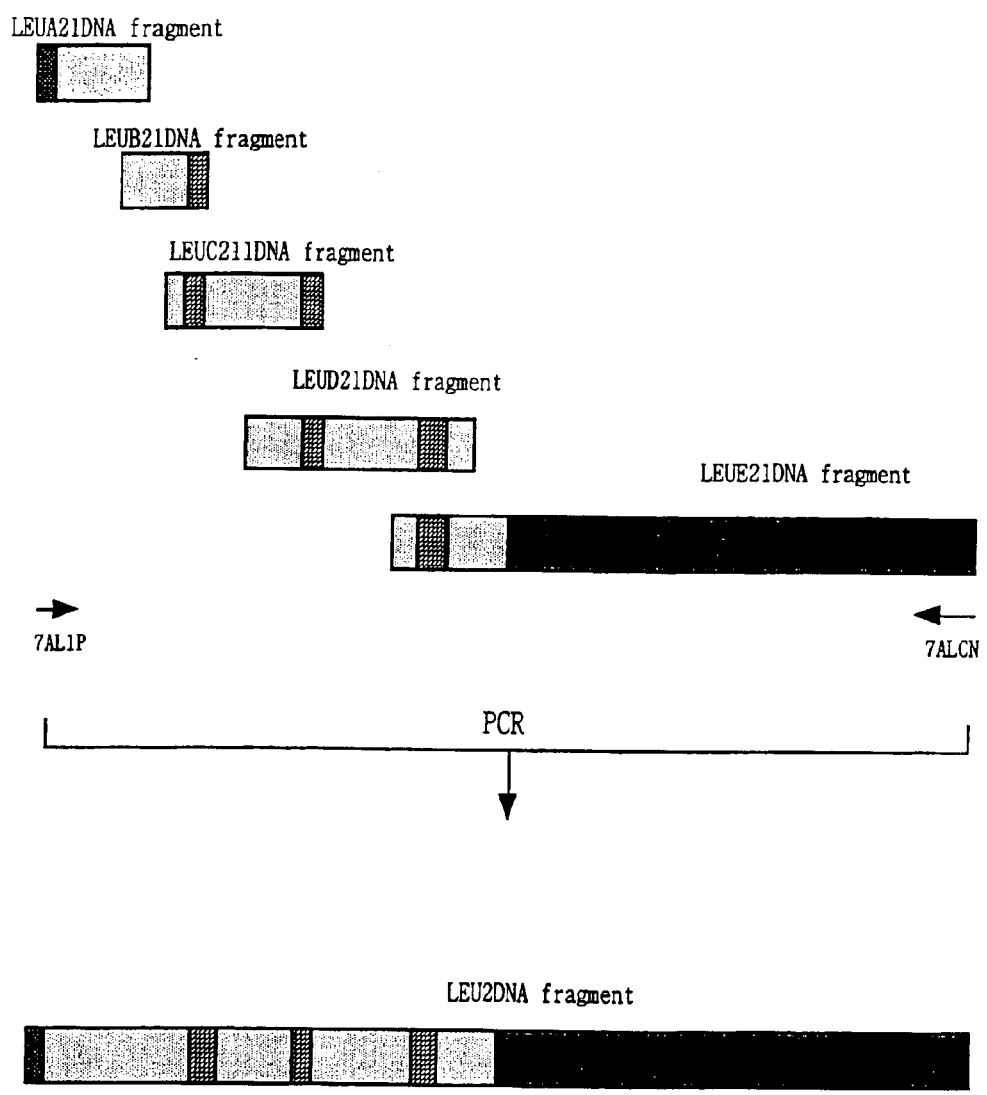
FIG. 53 is a summary of the second step PCR for the production of LEU2-DNA.

The outline of the second stage PCR for the production of LEU2-DNA fragment is shown in FIG. 53.

The LEU2-DNA fragment, in which the LEUA21-DNA, LEUB21-DNA, LEUC211-DNA, LEUD21-DNA and LEUE21-DNA fragment were fused, was prepared as follows.

The electrophoresed gel excised in the first stage PCR was added to the reaction solution without extraction.

The Composition of the PCR Reaction was as Follows:
gel piece containing LEUA21-DNA;
gel piece containing LEUB21-DNA;
gel piece containing LEUC211-DNA;
gel piece containing LEUD21-DNA;
gel piece containing LEUE21-DNA;
primer 7AL1P, 10 pmol;
primer 7ALCN, 10 pmol;
dNTP cocktail, 10 µl;
10×Pfu buffer, 10 µl;
Pfu DNA polymerase, 2 units; and
redistilled water to a final volume of 100 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

Phenol extraction and then ethanol precipitation were performed on the amplified PCR fragments, and these fragments were then separated by 5% w/v polyacrylamide gel electrophoresis. a After electrophoresis, the acrylamide gel was stained with 1 µg/ml of ethidium bromide, and analyzed under UV light. The gel at the band corresponding to LEU2-DNA was excised using a razor blade, and DNA was eluted from the gel using Centricon and a Centriruter. The eluted DNA was concentrated first by centrifugation at 7,500×g, precipitated with ethanol, then dissolved in 50 µl of distilled water.

2) Preparation of Plasmid

The LEU2-DNA fragment obtained in 1) above was further purified by phenol extraction followed by ethanol precipitation, and it was then digested with the restriction enzymes Hind III and EcoRI. One µg of cloning plasmid pHSG399 DNA was digested with the restriction enzymes Hind III and EcoRI, before being dephosphorylated with CIP. The resulting, dephosphorylated plasmid pHSG399 DNA and the digested LEU2-DNA fragment were ligated using a DNA Ligation Kit. The ligated DNA was then used to transform E. coli JM 109. The cells were plated onto LB agar medium containing final concentrations of 0.1 mM IPTG, 0.1% X-Gal and 50 µg/ml chloramphenicol. Any white transformants obtained were cultured in 2 ml of liquid LB medium containing 50 µg/ml chloramphenicol, and plasmid DNA was extracted from the resulting culture by the alkaline-SDS method. The resulting plasmid DNA was digested with the restriction enzymes Hind III and EcoRI, and a clone carrying the LEU2-DNA fragment was then selected after analysis by 1% w/v agarose gel electrophoresis, stained with ethidium bromide.

Plasmid pHSGLEU21-28-8 carrying DNA, encoding a fusion polypeptide of the variable region of the LEU2 type humanized light chain and the constant region of human immunoglobulin κ chain, was obtained accordingly. The transformant E. coli pHSGLEU21-28-8 SANK 72698, harboring plasmid pHSGLEU21-28-8, was deposited with the Kogyo Gijutsuin Seimei-Kogaku Kogyo Gijutsu Kenkyujo on Sep. 18, 1998, in accordance with the Budapest Treaty, and was accorded the accession number PERM BP-6511.

3) Construction of Expression Vector

The outline of the method of construction of the expression vector plasmid carrying the DNA encoding the LEU-2 type humanized light polypeptide obtained in the above (2) is shown in FIG. 56.

One µg of the plasmid pSRPDHM prepared in Reference Example 23 was digested with the restriction enzymes Hind III and EcoRI, and then dephosphorylated using CIP. The resulting dephosphorylated plasmid DNA (100 ng) was ligated with 10 µg of the pHSGLEU21-28-8 DNA fragment which had also been digested with Hind III and EcoRI, using a DNA Ligation Kit. The resulting ligated DNA was then used to transform E. coli JM109. Cells were then plated on LB agar plates containing 50 µg/ml ampicillin, followed by incubation at 37° C.

The transformants obtained by this method were cultured in liquid LB medium containing 50 µg/ml ampicillin, and plasmid DNA was subsequently extracted from the resulting culture by the alkaline-SDS method. The extracted plasmid DNA was digested with Hind III and EcoRI, and subjected to analysis on a 1% w/v agarose gel and, after electrophoresis, to confirm the presence or absence of the insert of interest by staining with ethidium bromide and observation under UV light. This enabled the isolation of the plasmid pLEUX22-7-1, which contains DNA encoding the LEU2 type humanized light chain located downstream of the SRα promoter in the correct orientation.

(4) Preparation of DNA Encoding LEU3 Type Light Chain

1) Preparation of LEU3-DNA Fragment

The LEU3-DNA fragment (SEQ ID No. 130 of the Sequence Listing), encoding the amino acid sequence of SEQ ID No. 131 of the Sequence Listing, was prepared by performing a two step PCR. The product thus obtained was then inserted into a plasmid vector and cloned into E. coli. The plasmid pHSGHM17 constructed in Reference Example 14 was used as a template for PCR.

First Stage PCR

The outline of the first stage PCR for the preparation of LEU3-DNA fragment is shown in FIG. 54.

The LEUA21-DNA fragment, the LEUB21-DNA fragment, the LEUC31-DNA fragment and the LEUE21-DNA fragment were amplified by performing PCR in accordance with the procedure as described (1), respectively.

The LEUD31-DNA fragment, encoding a portion of the $FRL_2$ region, the $CDRL_2$ region, the $FRL_3$ region, the $CDRL_3$ region and a portion of the $FRL_4$ region was prepared as follows:

Composition of the PCR Reaction Solution:
  plasmid pKISp35 DNA, 25 ng;
  primer 7ALF34, 5pmol;
  primer 7ALR53, 5 pmol;
  2.5 mM dNTP cocktail, 5 µl;
  10×Pfu buffer, 5 µl;
  Pfu DNA polymerase, 1 unit; and
  redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After phenol extraction and ethanol precipitation of each PCR-amplified product, the resulting DNA precipitate was separated by 5% w/v polyacrylamide gel electrophoresis. After electrophoresis, the acrylamide gel was stained with 1 µg/ml of ethidium bromide to allow detection of DNA under UV light. The gel at the bands corresponding to LEUA21-DNA, LEUB21-DNA, LEUC31-DNA, LEUD31-DNA and LEUE21-DNA was excised, using a razor blade.

Second Stage PCR

Figure 55:
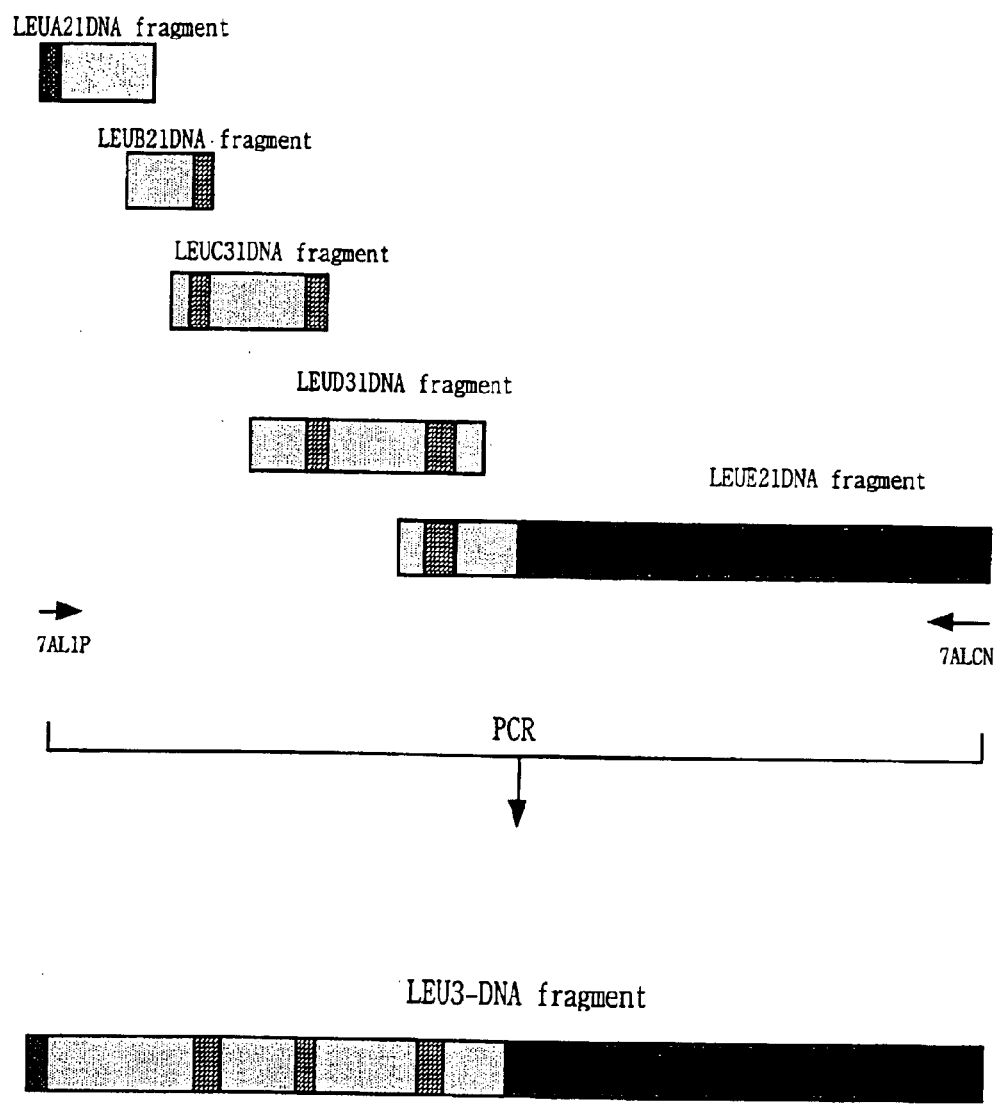
FIG. 55 is a summary of the second step PCR for the production of LEU3-DNA.

The outline of the second stage PCR for the production of LEU3-DNA fragment is shown in FIG. 55.

The LEU3-DNA fragment, in which the LEUA21-DNA, LEUB21-DNA, LEUC31-DNA, LEUD31-DNA and LEUE21-DNA fragments, were fused, was prepared as follows.

The electrophoresed gel excised in the first stage PCR was added to the reaction solution without extraction.

Composition of the PCR Reaction:
  gel piece containing LEUA21-DNA;
  gel piece containing LEUB21-DNA;
  gel piece containing LEUC31-DNA;
  gel piece containing LEUD31-DNA;
  gel piece containing LEUE21-DNA;
  primer 7AL1P, 10 pmol;
  primer 7ALCN, 10 pmol;
  dNTP cocktail, 10 µl;
  10×Pfu buffer, 10 µl;
  Pfu DNA polymerase, 2 units; and
  redistilled water to a final volume of 100 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

Phenol extraction and then ethanol precipitation were performed on the amplified PCR fragments, and these fragments were then separated by 5% w/v polyacrylamide gel electrophoresis. After electrophoresis, the gel was stained with 1 µg/ml of ethidium bromide, and analyzed under UV light. The gel at the band corresponding to LEU3-DNA was excised, using a razor blade, and DNA was eluted from the gel using Centricon and a Centriruter. The eluted DNA was concentrated first by centrifugation at 7,500×g, then precipitated with ethanol, after which it was dissolved in 50 µl of distilled water.

2) Preparation of Plasmid

The LEU3-DNA fragment obtained in 1) above was further purified by phenol extraction followed by ethanol precipitation, and it was then digested with the restriction enzymes Hind III and EcoRI. One µg of cloning plasmid pHSG399 DNA was digested with the restriction enzymes Hind III and EcoRI, and then dephosphorylated with CIP. The resulting, dephosphorylated plasmid pHSG399. DNA and the digested LEU3-DNA fragment were ligated using a DNA Ligation Kit (Version 2.0, Takara Shuzo Co., Ltd.).

The ligated DNA was then used to transform E. coli JM 109. The cells were plated onto LB agar medium containing final concentrations of 0.1 mM IPTG, 0.1% X-Gal and 50 µg/ml chloramphenicol, and the plates were incubated at 37° C. to obtain E. coli transformants. Any white transformants obtained were cultured in a liquid LB medium containing 50 µg/ml chloramphenicol, and plasmid DNA was extracted from the resulting culture by the alkaline-SDS method [Sambrook et al., supra]. The resulting, extracted plasmid DNA was digested with the restriction enzymes Hind III and EcoRI, and a clone carrying the LEU3-DNA fragment was then identified and selected by 1% w/v agarose gel electrophoresis, stained with ethidium bromide.

Plasmid pHSGLEU31-6-2 carrying DNA, encoding a fusion polypeptide of the variable region-of the LEU3 type humanized light chain and the constant region of human immunoglobulin κ chain, was obtained accordingly. The transformant E. coli pHSGLEU31-6-2 SANK 72798, harboring plasmid pHSGLEU31-6-2, was deposited with the Kogyo Gijutsuin Seimei-Kogaku Kogyo Gijutsu Kenkyujo on Sep. 18, 1998, in accordance with the Budapest Treaty, and was accorded the accession number FERM BP-6513.

3) Construction of Expression Vector

The outline of the method of construction of the expression vector plasmid, carrying the DNA encoding the LEU-3 type humanized light polypeptide, obtained in 2) above, is shown in FIG. 56.

One µg of the plasmid pSRPDHM, prepared in Reference Example 23, was digested with the restriction enzymes Hind III and EcoRI, and then dephosphorylated using CIP. 100 ng of the dephosphorylated pSRPDHM DNA was ligated with LEU3-DNA which had also been digested with Hind III and EcoRI, using a DNA Ligation Kit, and the ligation product was then used to transform E. coli JM109. Cells were then plated on LB agar plates containing 50 µg/ml ampicillin and cultured at 37 ° C.

The transformants obtained by this method were cultured in liquid LB medium containing 50 µg/ml ampicillin, and plasmid DNA was subsequently extracted from the resulting culture by the alkaline-SDS method. The extracted plasmid DNA was digested with Hind III and EcoRI, and subjected to 1% w/v agarose gel electrophoresis, stained with ethidium bromide, to confirm the presence or absence of the insert of interest. This enabled the isolation of the plasmid pLEUX31-6-2, which contains DNA encoding the LEU3 type humanized light chain, located downstream of the SRα promoter in the correct orientation.

(5) Verification of the Nucleotide Sequences

To verify that the DNA inserts of plasmids obtained in the above (2) to (4) have the desired nucleotide sequences, their DNA inserts were analyzed to determine the nucleotide sequences, using primers 7AL1P and 7ALCN as sequencing primers.

As a result, it was established that the plasmids pLEUX15-29-5, pLEUX22-7-1 and pLEUX31-6-2 had the nucleotide sequences SEQ ID No. 126, SEQ ID No. 128; and SEQ ID No. 130, respectively, of the Sequence Listing.

EXAMPLE 3

Construction of Expression Vector of Eu Type Humanized Heavy Chain

The heavy chain of the HFE7A antibody, humanized using 8E10 prepared in Reference Example 15 as an acceptor, was modified by using PCR primers so that the 8E10 FR region was substituted by the Eu type, in order to prepare an Eu type humanized heavy chain as described below (FIG. 49).

The 44th amino acid (Arg) and the 76th amino acid (Ala) from the N-terminus of the amino acid sequence of the heavy chain of the humanized HFE7A were replaced with Gly and Thr respectively, which are present in Eu. The 113th amino acid (Glu) was replaced with Gln which is conserved in the human Ig heavy chain subgroup I. The resulting amino acid sequence was designated as "HEU1 type".

The 44th amino acid (Arg) and the 76th amino acid (Ala) from the N-terminus were replaced with Gly and Thr, respectively, and the 113th amino acid (Glu) was replaced with Gln, which is conserved in the human H chain subgroup I. The 70th amino acid (Leu) was replaced with Ile which is present in Eu. The resulting amino acid sequence is referred to as "HEU2 type".

The 44th amino acid (Arg) and the 76th amino acid (Ala) from the N-terminus of the amino acid sequence of the heavy chain of the humanized HFE7A prepared in Reference Example 15 (SEQ ID No. 89 of the Sequence Listing) were replaced with Gly and Thr, respectively, the 113th amino acid (Glu) was replaced with Gln and the 38th amino acid (Lys) was replaced with Arg, which is present in Eu. The resulting amino acid sequence is referred to as "HEU3 type".

Expression plasmids, respectively carrying these 3 types of HEU type humanized heavy chain amino acid sequences from the anti-Fas antibody, were constructed as follows.

(1) Synthesis of Primers

PCR was used to construct the following DNA sequences encoding each type of HEU type humanized heavy chains designed above:

DNA (SEQ ID No. 142 of the Sequence Listing) encoding the HEU1 type heavy chain (SEQ ID No. 143 of the Sequence Listing);

DNA (SEQ ID No. 144 of the Sequence Listing) encoding the HEU2 type heavy chain (SEQ ID No. 145 of the Sequence Listing); and DNA (SEQ ID No. 146 of the Sequence Listing) encoding the HEU3 type heavy chain (SEQ Sequence No. 147 of the Sequence Listing).

The following oligonucleotide PCR primers were synthesized:

5'-CCAAGCTTGG CTTGACCTCA CCATGGGATG GAGCTGTA-3' (7AH1P; SEQ ID No. 148);

5'-AGTGGGTAAA ACAGGCCCCT GGACAGGGAC TTGAGTGGAT-3' (HEU16F; SEQ ID No. 149);

5'-ATCCACTCAA GTCCCTGTCC AGGGGCCTGT TTTACCCACT-3' (HEU16R; SEQ ID No. 150);

5'-AAGACCGATG GGCCCTTGGT GGAGGCTGAG GAGACGGTGA CCAGTGTACC TTGGCCCCAG ACAT-3' (HEU28R; SEQ ID No. 151);

5'-GTTCAAGGGC AAGGCCACAA TAACTGTAGA CACATCCGC-3' (HEU25F; SEQ ID No. 152);

5'-GCGGATGTGT CTACAGTTAT TGTGGCCTTG CCCTTGAAC-3' (HEU25R; SEQ ID No. 153);

5'-AGTGGGTACG ACAGGCCCCT GGACAAGGAC TTGAGTGGAT-3' (HEU36F; SEQ ID No. 154); and

5'-ATCCACTCAA GTCCTTGTCC AGGGGCCTGT CGTACCCACT-3' (HEU36R; SEQ ID No. 155).

(2) Preparation of DNA Encoding HEU1 Type Heavy Chain

1)Preparation of HEU1-DNA Fragment

The HEU1HA-DNA fragment, containing the nucleotide sequence encoding the amino acids 1 to 125 of SEQ ID No. 143 of the Sequence Listing, was prepared by two step PCR. The product was then inserted into a plasmid vector and cloned into *E. coli*. The plasmid pgHSL7A62, prepared in Reference Example 15, was used as the template for PCR.

First Stage PCR

Figure 57:
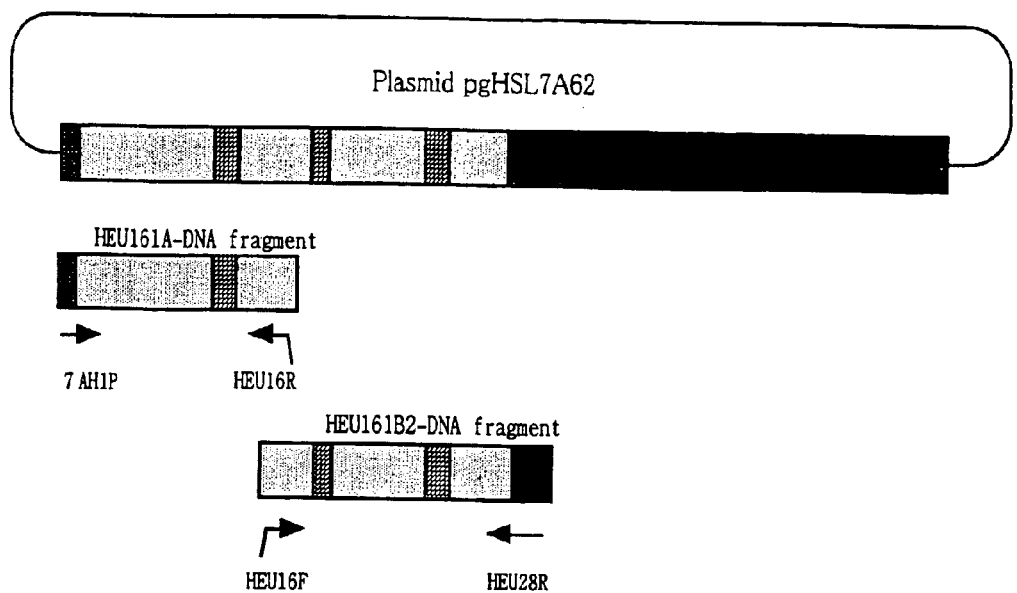
FIG. 57 is a summary of the first step PCR for the production of HEU1HA-DNA.

The outline of the first stage PCR for the preparation of HEU1HA-DNA is shown in FIG. 57.

The HEU161A-DNA fragment, encoding a secretion signal sequence, the $FRH_1$ region, the $CDRH_1$ region and a portion of the $FRH_2$ region altered to contain a Hind III restriction enzyme cleavage site at the 5'-end, was prepared as follows.

Composition of the PCR Reaction Solution:
  plasmid pgHSL7A62 DNA, 50 ng;
  primer 7AH1P, 5 pmol;
  primer HEU16R, 5 pmol;
  2.5 mM dNTP cocktail, 5 µl;
  10×Pfu buffer, 5 µl;
  Pfu DNA polymerase, 1 unit; and
  redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The HEU161B2-DNA fragment, encoding the $FRH_2$ region, the $CDRH_2$ region, the $FRH_3$ region, the $CDRH_3$ region, the $FRH_4$ region and apportion of the constant region of human Ig heavy chain was prepared as follows.

Composition of the PCR Reaction Solution:
  plasmid pgHSL7A62 DNA, 50 ng;
  primer HEU16F, 5 pmol;
  primer HEU28R, 5 pmol;
  2.5 mM dNTP cocktail, 5 µl;
  10×Pfu buffer, 5 µl;
  Pfu DNA polymerase, 1 unit; and
  redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After phenol extraction and ethanol precipitation of each PCR-amplified product, the resulting DNA precipitate was separated by 5% w/v polyacrylamide gel electrophoresis. After electrophoresis, the acrylamide gel was stained with a 1 µg/ml solution of ethidium bromide to allow detection of DNA under UV light. The DNA bands corresponding to HEU161A-DNA and HEU161B2-DNA were excised using a razor blade.

Second Stage PCR

Figure 58:
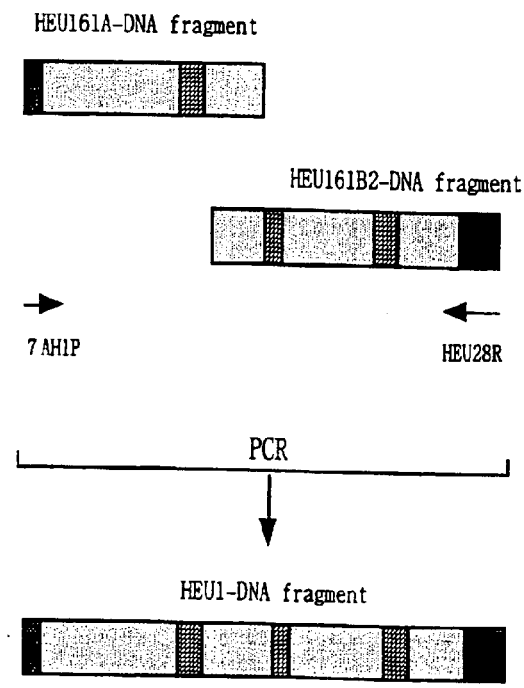
FIG. 58 is a summary of the second step PCR for the production of HEU1HA-DNA.

The outline of the second stage PCR for the production of HEU1HA-DNA is shown in FIG. 58.

HEU1HA-DNA fragment, in which the HEU161A-DNA and HEU161B2-DNA fragments described above were fused, was prepared as follows. The electrophoresed gel excised in the first stage PCR was added to the reaction solution without extraction.

Composition of the PCR Reaction:
  gel piece containing HEU161A-DNA
  gel piece containing HEU161B2-DNA
  primer 7AH1P, 5 pmol;
  primer HEU28R, 5 pmol;
  2.5 mM dNTP cocktail, 5 µl;
  10×Pfu buffer, 5 µl;
  Pfu DNA polymerase, 10 units; and
  redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

Phenol extraction and then ethanol precipitation were performed on the amplified PCR fragments, and these fragments were then separated by 5% w/v polyacrylamide gel electrophoresis. After electrophoresis, the gel was stained with 1 µg/ml of ethidium bromide, and analyzed under UV light. The gel at the position of the band corresponding to HEU1HA-DNA was excised, using a razor blade, and DNA was eluted from the gel using Centricon and a Centriruter. The eluted DNA was concentrated first by centrifugation at 7,500×g, precipitated with ethanol, then dissolved in 50 µl of distilled water.

2) Preparation of Plasmid

The HEU1HA-DNA fragment, obtained in 1) above, was further purified by phenol extraction followed by ethanol precipitation, and it was then digested with the restriction enzymes Hind III and ApaI. One µg of plasmid pgHSL7A62 DNA was digested with the restriction enzymes Hind III and ApaI, and then dephosphorylated with CIP. The resulting, dephosphorylated plasmid pgHSL7A62 DNA and the digested HEU1HA-DNA fragment were ligated using a DNA Ligation Kit (Version 2.0, Takara Shuzo Co., Ltd.). The ligated DNA was then used to transform *E. coli* JM 109.

The cells were plated onto LB agar medium containing final concentrations of 50 µg/ml chloramphenicol, and the plates were incubated at 37° C. to obtain *E. coli* transformants. The transformants obtained were cultured in liquid LB medium containing 50 µg/ml chloramphenicol, and plasmid DNA was extracted from the resulting culture by the alkaline-SDS method [Sambrook et al., supra]. The resulting, extracted plasmid DNA was digested with the restriction enzymes Hind III and ApaI, and a clone carrying the HEU1HA-DNA fragment was then selected by agarose gel electrophoresis, stained with ethidium bromide.

Plasmid pHSGAB580-3-21, carrying DNA encoding a fusion polypeptide of the variable region of the HEU1 type humanized heavy chain and the constant region of human IgG1 was obtained accordingly. The transformant *E. coli* pHSGAB580-3-21 SANK 72898, harboring plasmid pHSGAB580-3-21, was deposited with the Kogyo Gijutsuin Seimei-Kogaku Kogyo Gijutsu Kenkyujo on Sep. 18, 1998, in accordance with the Budapest Treaty, and was accorded the accession number FERM BP-6515.

3) Construction of Expression Vector

Figure 63:
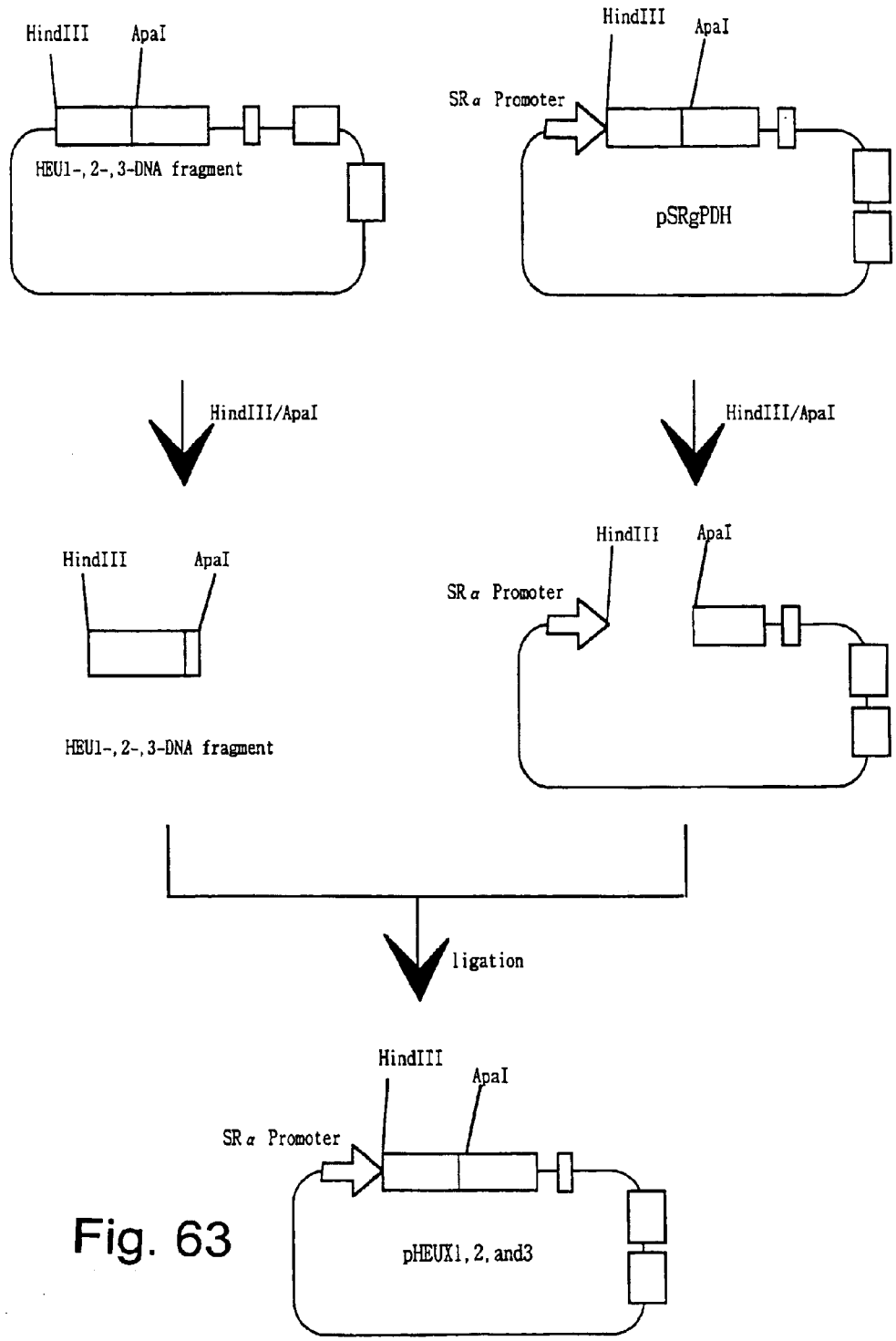
FIG. 63 shows the outline of the construction of expression plasmid carrying DNA encoding Eu type humanized heavy chain.

The outline of the method of construction of the expression vector plasmid carrying the DNA encoding the HEU1 type humanized heavy polypeptide obtained in 2) above was shown in FIG. 63.

Ten µg of pHSGAB580-3-21 DNA was digested with the restriction enzymes Hind III and ApaI. One µg of the plasmid pSRgPDH prepared in Reference Example 23 was digested with the restriction enzymes Hind III and ApaI, and then dephosphorylated using CIP. 100 ng of the resulting dephosphorylated pSRgPDH was ligated with 10 µg of the HEU1-DNA fragment digested with the restriction enzymes Hind III and ApaI, using a DNA Ligation Kit (Version 2.0, Takara Shuzo Co., Ltd.), and then used to transform *E. coli* JM109. Cells were then plated on LB agar plates containing 50 µg/ml, ampicillin, and cultured at 37° C.

The transformants obtained by this method were cultured in liquid LB medium containing 50 µg/ml ampicillin, and plasmid DNA was subsequently extracted from the resulting culture by the alkaline-SDS method [Sambrook et al., supra]. The extracted plasmid DNA was digested with Hind III and ApaI, and subjected to 1% w/v agarose gel electrophoresis, stained with ethidium bromide, to confirm the presence or absence of the insert of interest. This enabled the isolation of the plasmid pHEUX 580-3-23, which contains DNA encoding the HEU1 type humanized heavy chain located downstream of the SRα promoter, and in the correct orientation.

(3) Preparation of DNA Encoding HEU2 Type Heavy Chain

1) Preparation of HEU2-DNA Fragment

The HEU2HA-DNA fragment containing the nucleotide sequence encoding amino acids 1–125 of SEQ ID No. 145 of the Sequence Listing was prepared by performing a two step PCR. The product was then inserted into a plasmid vector and cloned into *E. coli*. The plasmid pgHSL7A62 constructed in Reference Example 15 was used as a template for PCR.

First Stage PCR

Figure 59:
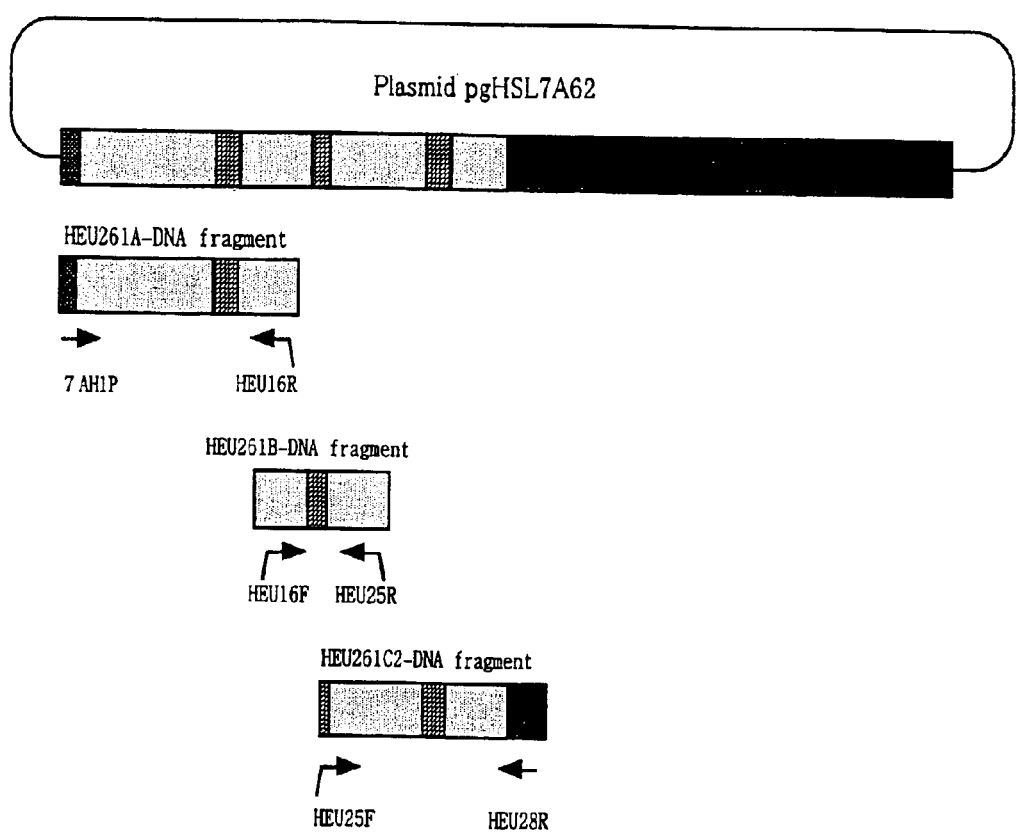
FIG. 59 is a summary of the first step PCR for the production of HEU2HA-DNA.

The outline of the first stage PCR for the preparation of HEU2HA-DNA fragment is shown in FIG. 59.

The HEU261A-DNA fragment, encoding a secretion signal sequence, the $FRH_1$ region, the $CDRH_1$ region and a portion of the $FRH_2$ region altered to contain a Hind III restriction enzyme cleavage site at the 5'-end, was prepared as follows.

Composition of the PCR Reaction Solution:
    plasmid pgHSL7A62 DNA, 50 ng;
    primer 7AH1P, 5 pmol;
    primer HEU16R, 5 pmol;
    2.5 mM dNTP cocktail, 5 µl;
    10×Pfu buffer, 5 µl;
    Pfu DNA polymerase, 1 unit; and
    redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The HEU261B-DNA fragment, encoding the $FRH_2$ region, the $CDRH_2$ region and a portion of the $FRH_3$ region was prepared as follows.

Composition of the PCR Reaction Solution:
    plasmid pgHSL7A62 DNA, 50 ng;
    primer HEU16F, 5 pmol;
    primer KEU25R, 5 pmol;
    2.5 mM dNTP cocktail, 5 µl;
    10×Pfu buffer, 5 µl;
    Pfu DNA polymerase, 1 unit; and
    redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The HEU261C2-DNA fragment, encoding a portion of the $CDRH_2$ region, the $FRH_3$ region, the $CDRH_3$ region, the $FRH_4$ region and a portion of constant region of human Ig heavy chain was prepared as follows.

Composition of the PCR Reaction Solution:
    plasmid pgHSL7A62 DNA, 50 ng;
    primer HEU25F, 5 pmol;
    primer HEU28R, 5 pmol;
    2.5 mM dNTP cocktail, 5 µl;
    10×Pfu buffer, 5 µl;

Pfu DNA polymerase (Stratagene), 1 unit; and
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After phenol extraction and ethanol precipitation of each PCR-amplified product, the resulting DNA precipitate was separated by 5% w/v polyacrylamide gel electrophoresis. After electrophoresis, the acrylamide gel was stained with 1 µg/ml of ethidium bromide to allow detection of DNA under UV light. The DNA bands corresponding to HEU261A-DNA, HEU261B-DNA and HEU261C2-DNA were excised, using a razor blade.

Second Stage PCR

Figure 60:
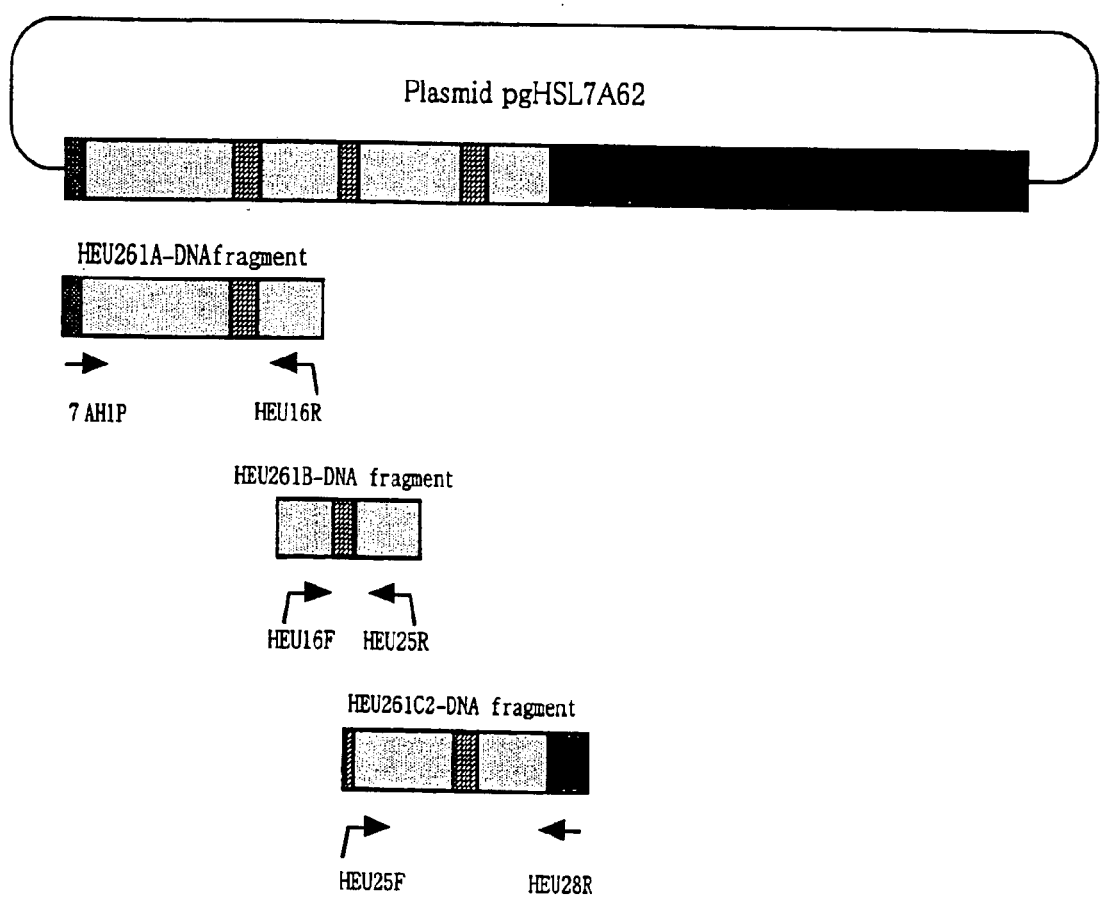
FIG. 60 is a summary of the second step PCR for the production of HEU2HA-DNA.

The outline of the second stage PCR for the production of HEU2HA-DNA fragment is shown in FIG. 60. HEU2HA-DNA fragment, in which the HEU261A-DNA, HEM261B-DNA and HEU261C2-DNA fragments were fused, was prepared as follows. The electrophoresed gel excised in the first stage PCR was added to the reaction solution without extraction.

Composition of the PCR Reaction:
gel piece containing HEU261A-DNA;
gel piece containing HEU261B-DNA;
gel piece containing HEU261C2-DNA;
primer 7AH1P, 5 pmol;
primer HEU28R, 5 pmol;
2.5 mN dNTP cocktail, 5 µl;
10×Pfu buffer, 5 µl;
Pfu DNA polymerase, 10 units; and
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

Phenol extraction and then ethanol precipitation were performed on the amplified PCR fragments, and these fragments were then separated by 5% w/v polyacrylamide gel electrophoresis. After electrophoresis, the gel was stained with 1 µg/ml of ethidium bromide, and observed under UV light. The gel at the position of the band corresponding to HEU2HA-DNA was excised, using a razor blade, and DNA was eluted from the gel using Centricon and a Centriruter. The eluted DNA was concentrated first-by centrifugation at 7,500×g, then precipitated with ethanol, and finally dissolved in 50 µl of distilled water.

2) Preparation of Plasmid

The HEU2HA-DNA fragment obtained above 1) was further purified by phenol extraction followed by ethanol precipitation, and it was then digested with the restriction enzymes Hind III and ApaI. One µg of plasmid pgHSL7A62 DNA was digested with the restriction enzymes Hind III and ApaI, and then dephosphorylated with CIP. The resulting, dephosphorylated plasmid pgHSL7A62 DNA and the HEU2HA-DNA fragment, digested with the restriction enzymes, were ligated using a DNA Ligation Kit (Version 2.0, Takara Shuzo Co., Ltd.). The ligated DNA then used to transform E. coli JM 109. The cells were plated onto LB agar medium containing final concentrations of 50 µg/ml chloramphenicol, and were cultured at 37° C. The resulting transformants were cultured in liquid LB medium containing 50 µg/ml chloramphenicol, and plasmid DNA was extracted from the resulting culture by the alkaline-SDS method [Sambrook et al., supra]. The resulting, extracted plasmid DNA was digested with the restriction enzymes Hind III and ApaI, and a clone carrying the HEU2HA-DNA fragment was then selected by agarose gel electrophoresis with ethidium bromide staining.

There was thus obtained plasmid pHSGHEU223-30-1, carrying the fragment of DNA encoding the polypeptide in which the variable region of the HEU2 type humanized heavy chain and DNA encoding the constant region of human IgG1, are ligated. The transformant E. coli pHSGHEU223-30-1 SANK 72998, harboring plasmid pHSGHEU223-30-1, was deposited with the Kogyo Gijutsuin Seimei-Togaku Kogyo Gijutsu Kenkyujo on Sep. 18, 1998, in accordance with the Budapest Treaty, and was accorded the accession number FERM BP-6516.

3) Construction of Expression Vector

The outline of the method of construction of the expression vector plasmid carrying the DNA encoding the HEU2 type humanized heavy polypeptide obtained in 2) above is shown in FIG. 63.

Ten µg of the pHSGHEU223-30-1 was digested with the restriction enzymes Hind III and ApaI. One µg of the plasmid pSRgPDH, prepared in Reference Example 23, was digested with the restriction enzymes Hind III and ApaI, and then dephosphorylated using CIP. 100 ng of the resulting dephosphorylated plasmid DNA was ligated with 10 µg of the HEU2-DNA fragment digested with Hind III and ApaI, using a DNA Ligation Kit, and then used to transform E. coli JM109. Cells were then plated on LB agar plates containing 50 µg/ml ampicillin, and incubated at 37° C.

The transformants obtained by this method were cultured in liquid LB medium containing 50 µg/ml ampicillin, and plasmid DNA was subsequently extracted from the resulting culture by the alkaline-SDS method [Sambrook et al., supral]. The extracted plasmid DNA was digested with Hind III and ApaI, and subjected to 1% w/v agarose gel electrophoresis, with ethidium bromide staining, to confirm the presence or absence of the insert of interest. This enabled the isolation of the plasmid pHEUX222-1-4, which contains DNA encoding the HEU2 type humanized heavy chain, located downstream of the SRα promoter, in the correct orientation.

(4) Preparation of DNA Encoding HEU3 Type Heavy Chain

1) Preparation of HEU3-DNA Fragment

The HEU3HA-DNA fragment, containing the nucleotide sequence encoding amino acids 1 to 125 sequence of SEQ ID No. 147 of the Sequence Listing, was prepared by performing two stage PCR. The product was then inserted into a plasmid vector and cloned into E. coli. The plasmid pgHSL7A62, constructed in Reference Example 15, was used as a template for PCR.

First Stage PCR

Figure 61:
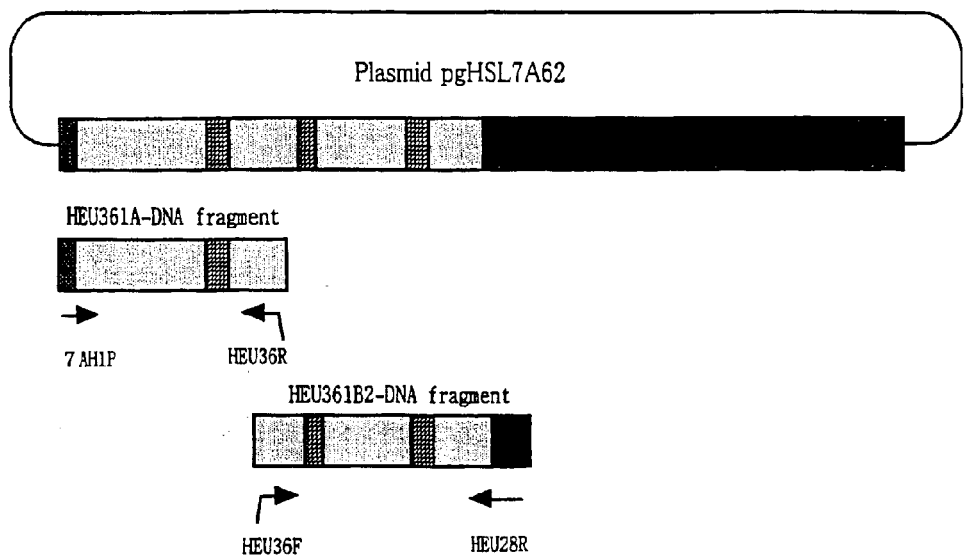
FIG. 61 is a summary of the first step PCR for the production of HEU3HA-DNA.

The outline of the first stage PCR for the preparation of HEU3HA-DNA is shown in FIG. 61.

The HEU361A-DNA fragment, encoding a secretion signal sequence, the $FRH_1$ region, the $CDRH_1$ region and a portion of the $FRH_2$ region altered to contain a Hind III restriction enzyme cleavage site at the 5'-end, was prepared as follows.

Composition of the PCR Reaction Solution:
plasmid pgHSL7A62 DNA, 50 ng;
primer 7AH1P, 5 pmol;
primer HEU36R, 5 pmol;
2.5 mM dNTP cocktail, 5 µl;
10×Pfu buffer, 5 µl;
Pfu DNA polymerase, 1 unit; and
redistilled water to a final volume of 50 µl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

The HEU361B2-DNA fragment, encoding the $FRH_2$ region, the $CDRH_2$ region, the $FRH_3$ region, the $CDRH_3$ region, the $FRH_4$ region and a portion of the constant region of the human Ig heavy chain was prepared as follows.
Composition of the PCR Reaction Solution:
  plasmid pgHSL7A62 DNA, 50 ng;
  primer HEU36F, 5 pmol;
  primer HEU28R, 5 pmol;
  2.5 mM dNTP cocktail, 5 μl;
  10×Pfu buffer, 5 μl;
  Pfu DNA polymerase, 1 unit; and
  redistilled water to a final volume of 50 μl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

After phenol extraction and ethanol precipitation of each PCR-amplified product, the resulting DNA precipitate was separated by 5% w/v polyacrylamide gel electrophoresis. After electrophoresis, the acrylamide gel was stained with 1 μg/ml of ethidium bromide to allow detection of DNA under UV light. The gel at the bands corresponding to HEU361A-DNA and HEU361B2-DNA was excised, using a razor blade.

Second Stage PCR

Figure 62:
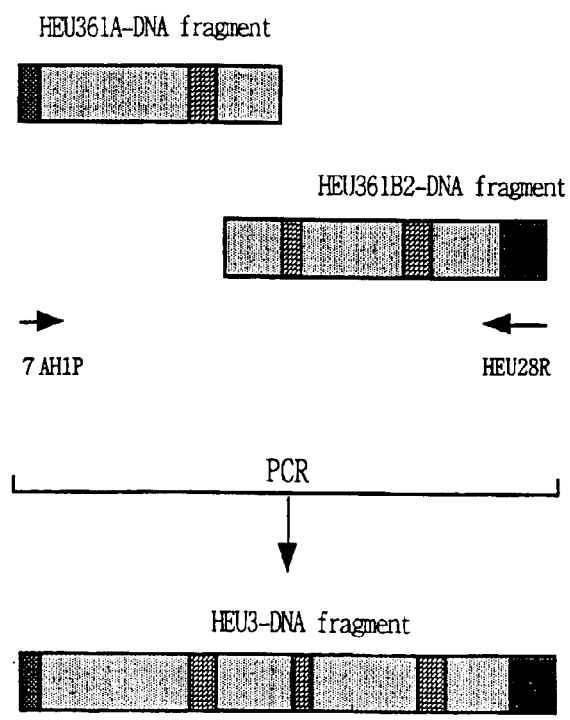
FIG. 62 is a summary of the second step PCR for the production of HEU3HA-DNA.

The outline of the second stage PCR for the production of HEU3HA-DNA fragment is shown in FIG. 62.

The HEU3HA-DNA fragment, in which the HEU361A-DNA and HEU361B2-DNA were fused, was prepared as follows. The electrophoresed gel excised in the first stage PCR was added to the reaction solution without extraction.
Composition of the PCR Reaction:
  gel piece containing HEU361A-DNA;
  gel piece containing HEU361B2A-DNA;
  primer 7AH1P, 5 pmol;
  primer HEU28R, 5 pmol;
  2.5 mM dNTP cocktail, 5 μl;
  10×Pfu buffer, 5 μl;
  IPfu DNA polymerase, 10 units; and
  redistilled water to a final volume of 50 μl.

PCR was conducted as follows. The solution was first heated at 94° C. for 2 minutes, after which a cycle of heating to 94° C. for 1 minute, 55° C. for 1 minute and 72° C. for 2 minutes, was repeated 30 times. After completion of this procedure, the reaction solution was heated at 72° C. for 10 minutes.

Phenol extraction and then ethanol precipitation were performed on the amplified PCR fragments, and these fragments were then separated by 5% w/v polyacrylamide gel electrophoresis. After electrophoresis, the gel was stained with 1 μg/ml of ethidium bromide, and analyzed under UV light. The gel at the position of the band corresponding to HEU3HA-DNA was excised, using a razor blade, and DNA was eluted from the gel using Centricon and a Centriruter. The eluted DNA was concentrated first by centrifugation at 7,500×g, then precipitated with ethanol, and finally dissolved in 50 μg of distilled water.

2) Preparation of Plasmid

The HEU3HA-DNA fragment obtained in 1) above was further purified by phenol extraction, followed by ethanol precipitation. The purified fragment was then digested with the restriction enzymes Hind III and ApaI. One μg of plasmid pgHSL7A62 DNA was digested with the restriction enzymes Hind III and ApaI, and then dephosphorylated with CIP. The resulting, dephosphorylated plasmid pgHSL7A62 DNA and the digested HEU3HA-DNA fragment were then ligated using a DNA Ligation Kit (Version 2.0, Takara Shuzo Co., Ltd.). The ligated DNA was then used to transform *E. coli* JM 109. The cells were plated onto LB agar medium containing final concentrations of 50 μg/ml chloramphenicol, and were incubated at 37° C. Resulting transformants were cultured in liquid LB medium containing 50 μg/ml chloramphenicol, and plasmid DNA was extracted from the resulting culture by the alkaline-SDS method [Sambrook et al., supra]. The resulting, extracted plasmid DNA was digested with the restriction enzymes Hind III and ApaI, and a clone carrying the HEU3HA-DNA fragment was then selected by agarose gel electrophoresis.

Plasmid pHGHEU222-1-2 was thus obtained, carrying DNA encoding a polypeptide wherein the variable region of the HEU3 type humanized heavy chain and the constant region of human IgG1 are ligated. The transformant *E. coli* pHSGHEU222-1-2 SANK 73098, harboring plasmid pHSGHEU222-1-2, was deposited with the Kogyo Gijutsuin Seimei-Kogaku Kogyo Gijutsu Kenkyujo on Sep. 18, 1998, in accordance with the Budapest Treaty, and was accorded the accession number FERM BP-6514.

3) Construction of Expression Vector

The outline of the method of construction of the expression vector plasmid carrying the DNA encoding the HEU3 type humanized heavy polypeptide obtained in 2) above is shown in FIG. 63.

Ten μg of the plasmid pHSGHEU222-1-2 was digested with the restriction enzymes Hind III and ApaI. One μg of the plasmid pSRgPDH, prepared in Reference Example 23, was digested with the restriction enzymes Hind III and ApaI, and then dephosphorylated using CIP. 100 ng of the dephosphorylated pSRgPDH was ligated with HEU3-DNA which had also been digested with Hind III and ApaI, using a DNA Ligation Kit, and then used to transform *E. coli* JM109. Cells were then plated on LB agar plates containing 50 μg/ml ampicillin and cultured at 37 ° C.

Any transformants were cultured in liquid LB medium containing 50 μg/ml ampicillin, and plasmid DNA was subsequently extracted from the resulting culture by the alkaline-SDS method. The extracted plasmid DNA was digested with Hind III and ApaI, and subjected to 1% w/v agarose gel electrophoresis, with ethidium bromide staining, to confirm the presence or absence of the insert of interest. This enabled the isolation of the plasmid pHEUX 322-22-5, which contains DNA, encoding the HEU3 type humanized heavy chain located downstream of the SRα promoter, in the correct orientation.

(5) Verification of the Nucleotide Sequences

To verify that the DNA inserts of plasmids obtained in (2) to (4) above had the desired nucleotide sequences, their DNA inserts were analyzed, in order to determine the nucleotide sequences, using primers 7AH1P and HEU28R as sequencing primers.

As a result, it was established that the DNA inserts of plasmids pHEUX580-3-23, pHEUX222-1-4 and pHEUX322-22-5 had the nucleotide sequences: SEQ ID No.142, SEQ ID No. 144; and SEQ ID No. 146, respectively, of the Sequence Listing.

EXAMPLE 4

Expression of Eu Type Humanized Antibody in COS-7. Cells

Transfection of COS-7 cells with each of the plasmids prepared above, for expression of Eu type humanized heavy chain and Eu type humanized light chains, constructed in Examples 2 and 3, was effected by a transfection method using the transfection reagent FuGENE6 (Transfection reagent, Boehringer Mannheim).

$2 \times 10^5$ COS-7 cells were grown to semi-confluence in a petri dish for cell culture (diameter: 90 mm; culture area: 57 cm$^2$; Sumitomo Bakelite, K. K.) containing DMEM (Nissui pharmaceuticals K. K.) supplemented with 10% v/v fetal calf serum (FCS) (Moregate).

Six μl of the transfection reagent was added into 200 μl of DMEM which did not contain FCS, and allowed to stand at room temperature for 5 minutes (hereinafter referred to as "transfection reagent/DMEM").

2 μg of HEU type humanized heavy chain expression plasmid (pHEUX580-3-23, pHEUX222-1-4 or pHEUX322-22-5) DNA and 2 μg of LEU type humanized light chain expression plasmid (pLEUX15-29-5, pLEUX22-7-1 or pLEUX31-6-2) prepared with a large-scale plasmid preparation kit (Withered MaxiPrep DNA Purification System; Promega) were mixed, subjected to ethanol precipitation in the same tube, and then suspended in 5 μl of distilled water. 206 μl of the transfection reagent/DMEM was then added to the suspension. After 15 minutes, the transfection reagent/DMEM, containing the DNA, was layered over the COS-7 cells in the dish. The cells were then cultured at 37° C. for 72 hours under an atmosphere of 5% v/v gaseous $CO_2$, after which time the supernatant was recovered.

Using the above method, COS-7 cells were variously transfected and cultured with each of the following plasmid or plasmid combinations, after which the supernatant was recovered:
(A): no plasmid DNA
(B): cotransfection with pHEUX580-3-23 and pLEUX15-29-5
(C): cotransfection with pHEUX222-1-4 and pLEUX15-29-5
(D): cotransfection with pHEUX322-22-5 and pLEUX15-29-5
(E): cotransfection with pHEUX580-3-23 and pLEUX22-7-1
(F): cotransfection with pHEUX222-1-4 and pLEUX22-7-1
(G): cotransfection with pHEUX322-22-5 and pLEUX22-7-1
(H): cotransfection with pHEUX580-3-23 and pLEUX31-6-2
(I): cotransfection with pHEUX222-1-4 and pLEUX31-6-2
(J): cotransfection with pHEUX322-22-5 and pLEUX31-6-2

EXAMPLE 5

Quantification of Expressed Products by ELISA

Expression of humanized antibody in the culture supernatant prepared in Example 4 was verified, and quantification of the expressed products was performed in accordance with a method similar to that described in Reference Example 17, but wherein DMEM was used as a diluent. Accordingly, it was verified that each of the expression products of culture supernatants [B], [C], [D], [E], [F], [G], [H], [I] and [J], prepared in Example 4 above, was specifically detected by the anti-human IgG antibody.

EXAMPLE 6

Assay for Human Fas-Binding Activity

Figure 64:
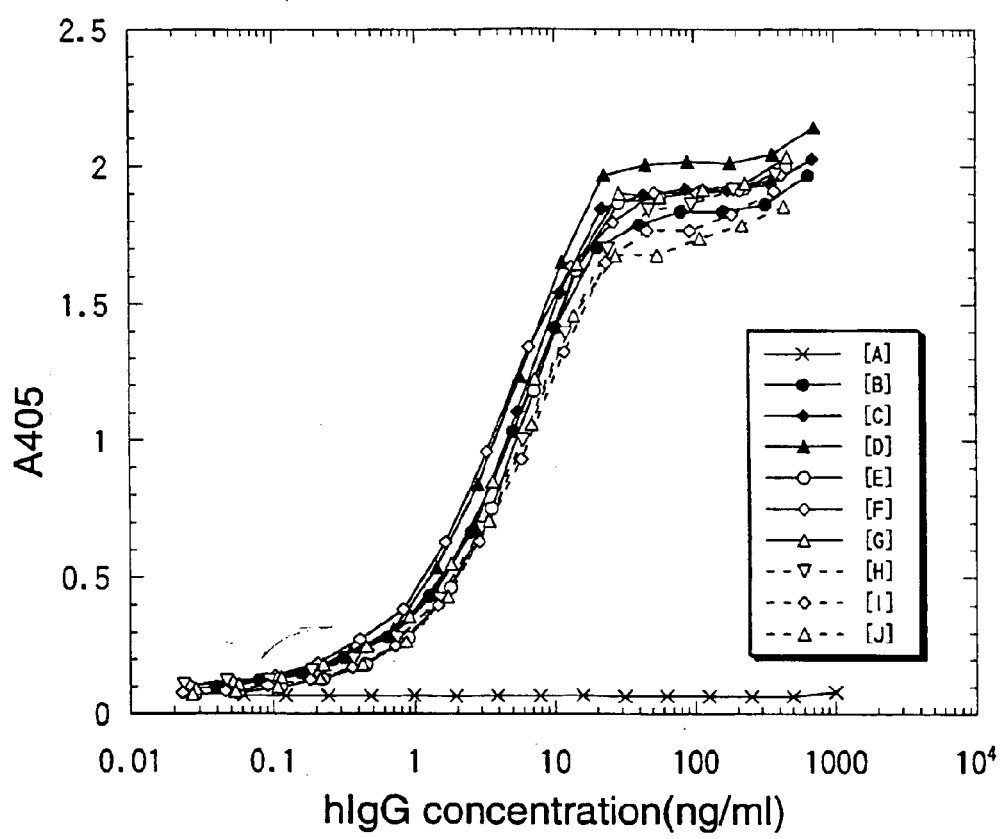
FIG. 64 shows the binding activity of the human Fas fusion protein for the supernatants of culture of transformed COS-7 cells.

The assay for Fas-binding activity in the cell culture supernatant fluids prepared in Example 4 was performed using a similar method to that described in Reference Example 18, but wherein DMEM was used as a diluent. Binding activity for the human Fas fusion protein was demonstrated for the expressed products of culture supernatants of categories (B), (C), (D), (E), (F), (G), (H), (I) and (J), prepared in Example 4, (FIG. 64).

EXAMPLE 7

Competitive Inhibition of the Binding of HFE7A to Fas

The expression products of Example 4 were evaluated for their ability to competitively inhibit the binding of HFE7A to the human Fas fusion protein, by a similar method to that described in Reference Example 19, but wherein DMEM was used as a diluent.

Figure 65:
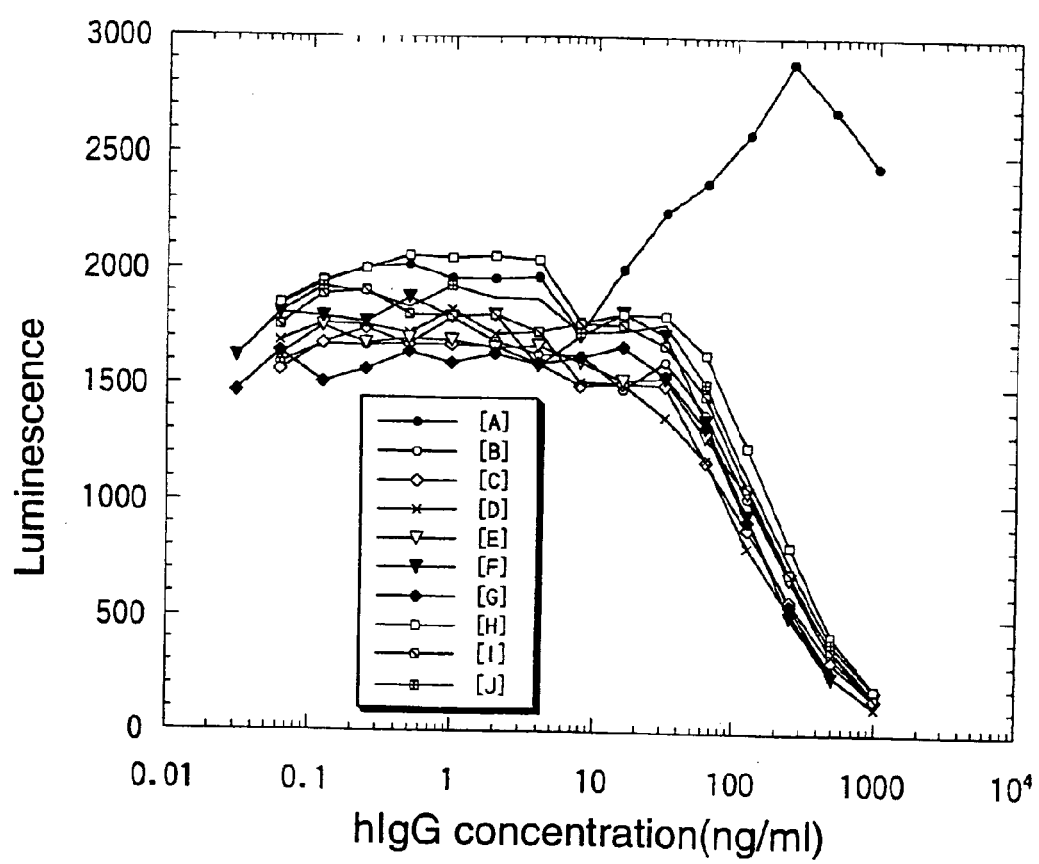
FIG. 65 shows the results of competitive inhibition of HFE7A antibody by the supernatants of culture of transformed COS-7 cells.

It was verified that each of the expression products of supernatants (B), (C), (D), (E), (F), (G), (H), (I) and (J) of Example 4 above specifically inhibited the binding of HFE7A prepared from a mouse hybridoma to the human Fas fusion protein (FIG. 65).

EXAMPLE 8

Apoptosis-Inducing Activity

The apoptosis-inducing activity of each of the expression products in the culture supernatant fluids obtained in Example 4 was evaluated by the method described in Reference Example 20.

Figure 66:
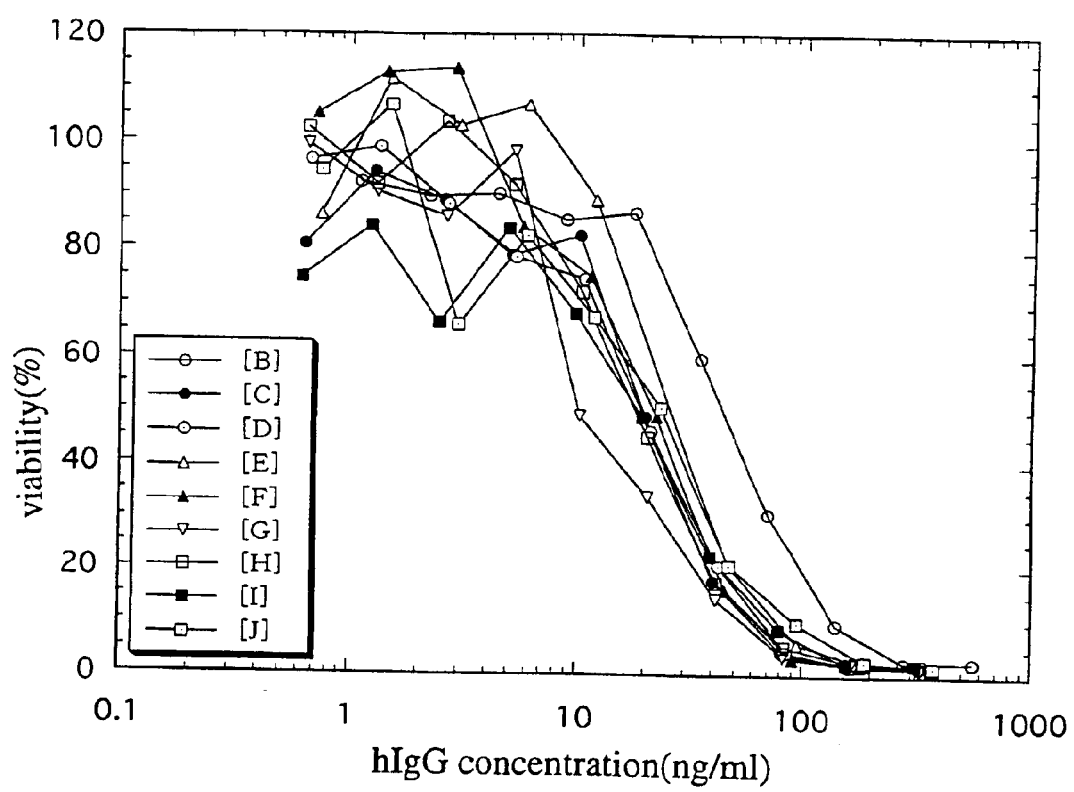
FIG. 66 shows the results of inducing apoptosis in WR19L12a by culture supernatant fluid of culture of transformed COS-7 cells.

Each of the expression products of the culture supernatant fluids (B), (C), (D), (E), (F), (G), (H), (I) and (J), obtained in Example 4, were demonstrated to induce apoptosis in T cells of the lymphoma cell line expressing human Fas antigen (FIG. 66).

EXAMPLE 9

Construction of Expression Vector of Heavy Chain of Humanized HFE7A

DNA was prepared encoding a humanized heavy chain, in which the CDR's of the HFE7A heavy chain, but not the FR, were grafted into the human antibody 8E10 heavy chain (hereinafter referred to as "HHH type humanized heavy chain"). The DNA and an expression vector plasmid having such DNA was prepared as follows:
1) Synthesis of Primer Synthesis of DNA (SEQ ID No. 156 of the Sequence Listing) encoding HHH type humanized heavy chain (SEQ ID No. 157 of the Sequence Listing) was carried out by PCR. The protein encoded by the DNA comprises a variable region (wherein each of CDR's of HFE7A heavy chain is grafted into the human monoclonal antibody 8E10 at the position corresponding thereto) and a constant region of human Ig heavy chain (γ-chain). For PCR, the following four oligonucleotide primers were synthesized in addition to the above mentioned 7AH1P (SEQ ID No. 76 of the Sequence Listing) and H5-(SEQ ID No. 103 of the Sequence Listing):
5'-GATGCAGTGG GTACGACAGG CCCCTGGAC-3' (HFR1F : SEQ ID No. 158 of the Sequence Listing);
5'-GTCCHGGGGC CTGTCGTACC CACTGCATC-3' (HFR1B : SEQ ID No. 159 of the Sequence Listing);
5'-CAAGGGCCGG GTCACAATCA CTCGAGACAC ATC- 3' (HFR2F : SEQ ID No. 160 of the Sequence Listing); and
5'-GATGTGTCTC GAGTGATTGT GACCCGGCCC TTG-3' (HFR2B SEQ ID No. 161 of the Sequence Listing).

2) Preparation of DNA Encoding HHH Type Humanized Heavy Chain

The HHH-DNA fragment (SEQ ID No. 156 of the Sequence Listing), encoding the amino acid sequence of SEQ ID No. 157 of the Sequence Listing, was prepared by PCR, then inserted into a plasmid and cloned into E. coli. The plasmid pgHPDHV3, constructed in Reference Example 23, was used as a template for PCR.

The heavy chain encoded by the plasmid pgHPDHV3 has the same amino acid sequence as the FR's of the 8E10 heavy chain, except that the 38th amino acid (Arg), the 66th amino acid (Arg), the 67th amino acid (Val), the 69th amino acid (Ile) and the 71st amino acid (Arg) are, instead, Lys, Lys, Ala, Leu and Val, respectively (hereinafter, the amino acid numbering is defined in accordance with Kabat et al., supra). Other amino acids in the FR and amino acids in the constant region are not replaced.

The CDR's in the amino acid sequence of the heavy chain encoded by pgRPDHV3 are the same as the CDR's in murine HFE7A. Accordingly, in the following steps, pgHPDHV3 (encoding a heavy chain amino acid sequence) was modified so that amino acids at the above mentioned positions were the same as those in the FR's of the 8E10 heavy chain.

a) First Stage PCR

Figure 67:
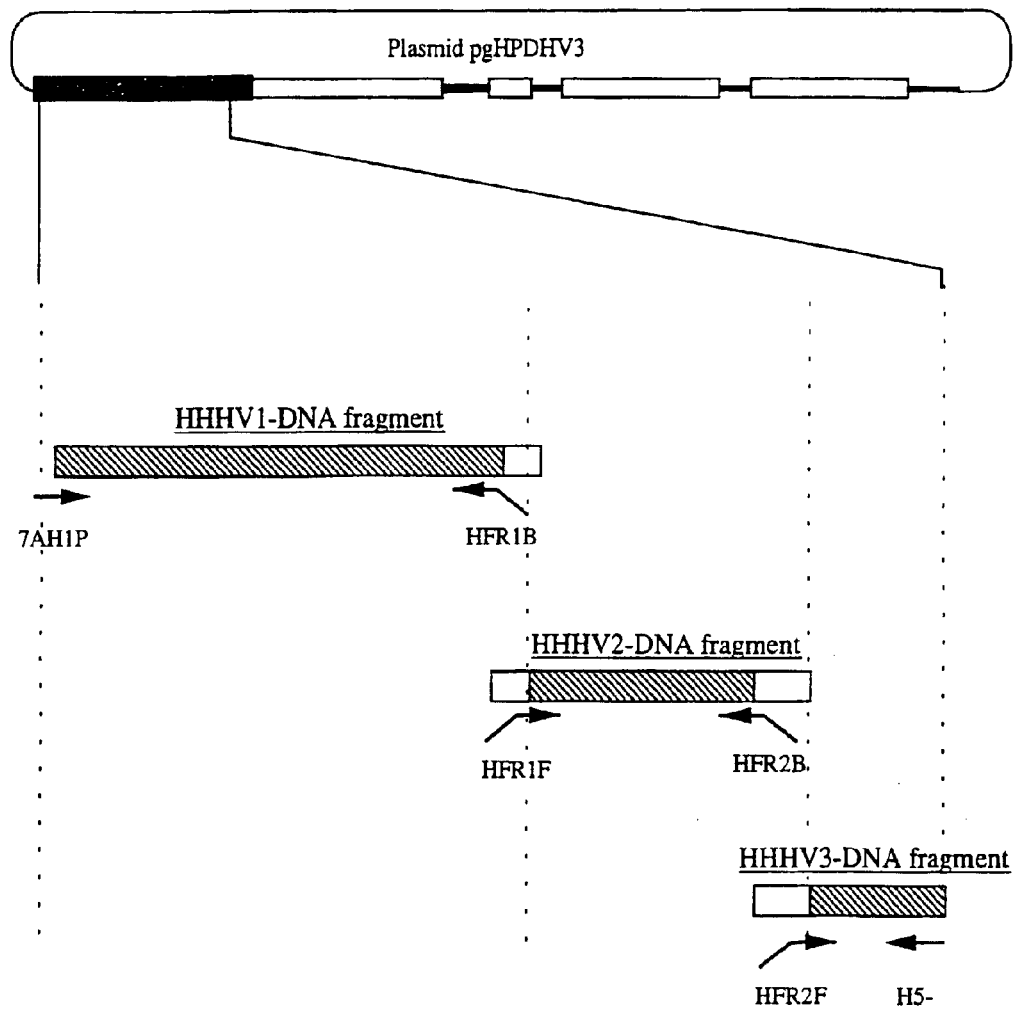
FIG. 67 is a summary of the first step PCR for the production of HHHV-DNA.

The outline of the first stage PCR for the preparation of HHHV-DNA is shown in FIG. 67.

The HHHV1-DNA fragment, encoding a secretion signal sequence, the $FRH_1$ region, the $CDRH_1$ region, and a portion of the $FRH_2$ region altered to contain a Hind III restriction enzyme cleavage site at the 5'-end, was prepared as follows.

Composition of the PCR solution:
- plasmid pgHPDHV3 DNA, 200 ng;
- primer 7AH1P, 80 pmol;
- primer HFR1B, 80 pmol;
- dNTP cocktail, 20 µl;
- 10×Pfu buffer, 20 µl;
- Pfu DNA polymerase, 10 units; and
- redistilled water was added so that final volume of composition was 200 µl.

PCR was conducted as follows. The solution was first heated at 94° C. for 2 minutes, and then a cycle of heating to 94° C. for 1 minute, 55° C. for 1 minute and 72° C. for 2 minutes, was repeated 30 times. After this procedure, the reaction solution was heated at 72° C. for 10 minutes.

The HHHV2-DNA fragment, encoding a portion of the $FRH_2$ region, the $CDRH_2$ region, and a portion of the $FRH_3$ region, was prepared as follows.

Composition of the PCR Reaction Solution:.
- plasmid pgHPDHV3 DNA, 200 ng;
- primer HFR1F, 80 pmol;
- primer HFR2B, 80 pmol;
- dNTP cocktail, 20 µl;
- 10×Pfu buffer, 20 µl;
- Pfu DNA polymerase, 10 units; and
- redistilled water to a final volume of 200 µl.

PCR was conducted as follows. The solution was first heated at 94° C. for 2 minutes, and then a cycle of heating to 94° C. for 1 minute, 55° C. for 1 minute and 72° C. for 2 minutes was repeated 30 times. After this procedure, the reaction solution was heated at 72° C. for 10 minutes.

The HHHV3-DNA fragment, encoding a portion of the $CDRH_2$ region and a portion of the $FRH_3$ region, was prepared as follows.

Composition of the PCR Reaction Solution:
- plasmid pgHPDHV3 DNA, 200 ng;
- primer HFR2F, 80 pmol;
- primer H5-, 80 pmol;
- dNTP cocktail, 20 µl;
- 10×Pfu buffer, 20 µl;
- Pfu DNA polymerase, 10 units; and
- redistilled water to a final volume of 200 µl.

PCR was conducted as follows. The solution was first heated at 94° C. for 2 minutes, and then a cycle of heating to 94° C. for 1 minute, 55° C. for 1 minute and 72° C. for 2 minutes was repeated 30 times. After completion of this procedure, the reaction solution was heated at 72° C. for 10 minutes.

After extraction with phenol and precipitation with ethanol, the resulting DNA precipitate was subjected to 5% w/v polyacrylamide gel electrophoresis. After electrophoresis, the acrylamide gel was stained with a 1 µg/ml of ethidium bromide to allow detection of DNA band under UV light. The DNA bands corresponding to HHHV1-DNA, HHHV2-DNA and HHHV3-DNA were excised, using a razor blade, and DNA was eluted from the gel using Centricon and Centriruter. The eluted DNA was concentrated first by centrifugation at 7,500×g, then precipitated with ethanol, and finally dissolved in 50 µl of distilled water.

b) Second Stage PCR

Figure 68:
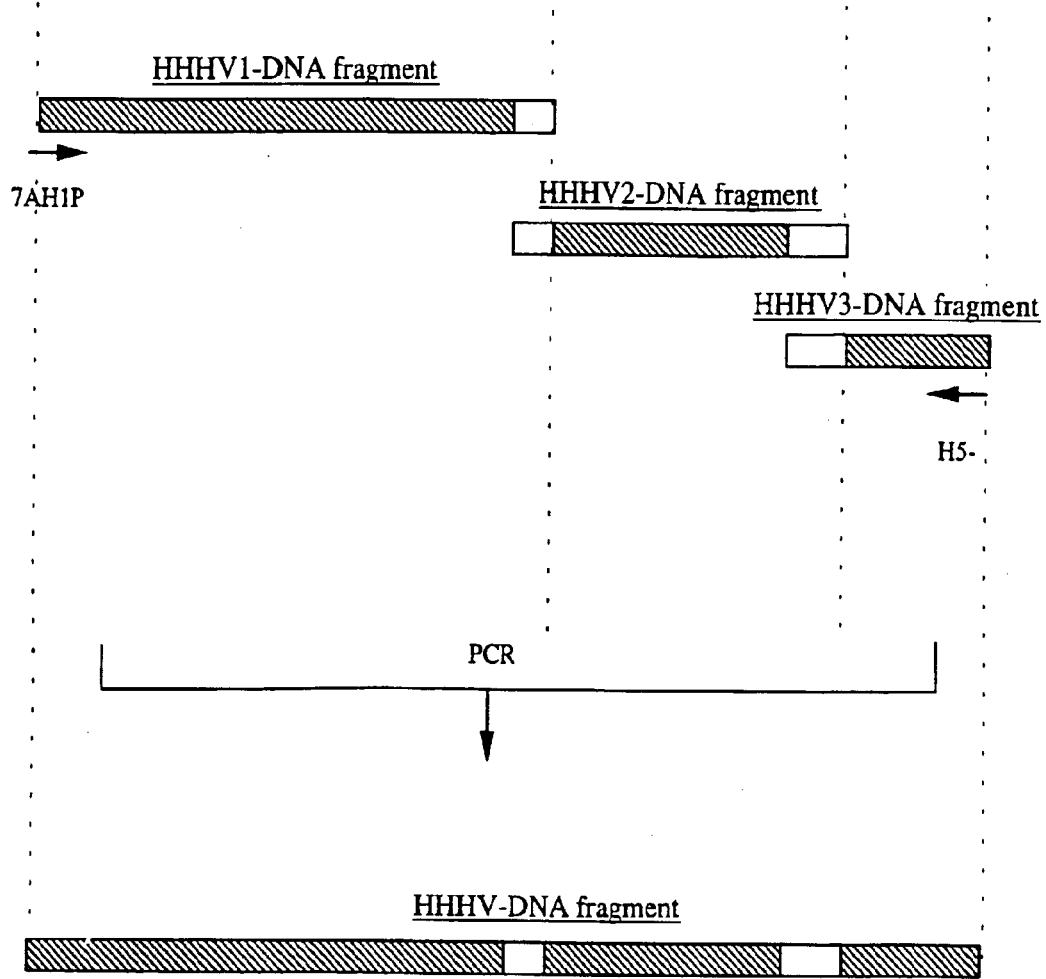
FIG. 68 is a summary of the second step PCR for the production of HHHV-DNA.

The outline of the second stage PCR for the production of HHHV-DNA is shown in FIG. 68.

HHHV-DNA, in which the HHHV1-DNA, HHHV2-DNA and HHHV3-DNA fragments described above were fused, was prepared as follows.

Composition of the PCR Reaction:
- HHHV1-DNA solution prepared in the first stage PC, 10 µl;
- HHHV2-DNA solution prepared in the first stage PCR, 10 µl;
- HHHV3-DNA solution prepared in the first stage PCR, 10 µl,
- primer 7AH1P, 80 pmol;
- primer H5-, 80 pmol;
- dNTP cocktail, 20 µl;
- 10×Pfu buffer, 20 µl;
- Pfu DNA polymerase, 10 units; and
- redistilled water to a final volume of 200 µl.

PCR was conducted as follows. The solution was first heated at 94° C. for 2 minutes, and then a cycle of heating to 94° C. for 1 minute, 55° C. for 1 minute and 72° C. for 2 minutes, was repeated 30 times. After this procedure, the reaction solution was heated at 72° C. for 10 minutes.

After extraction with phenol and precipitation with ethanol, the resulting DNA precipitate was subjected to 5% w/v polyacrylamide gel electrophoresis. After electrophoresis, the acrylamide gel was stained with a 1 µg/ml of ethidium bromide to allow detection of DNA band under UV light. The DNA band corresponding to HHHV-DNA was excised, using a razor blade, and DNA was eluted from the gel using Centricon and Centriruter. The eluted DNA was concentrated first by centrifugation at 7,500×g, precipitated with ethanol, then dissolved in 50 µl of distilled water.

c) Construction of Plasmid pgHSHHH1

Figure 69:
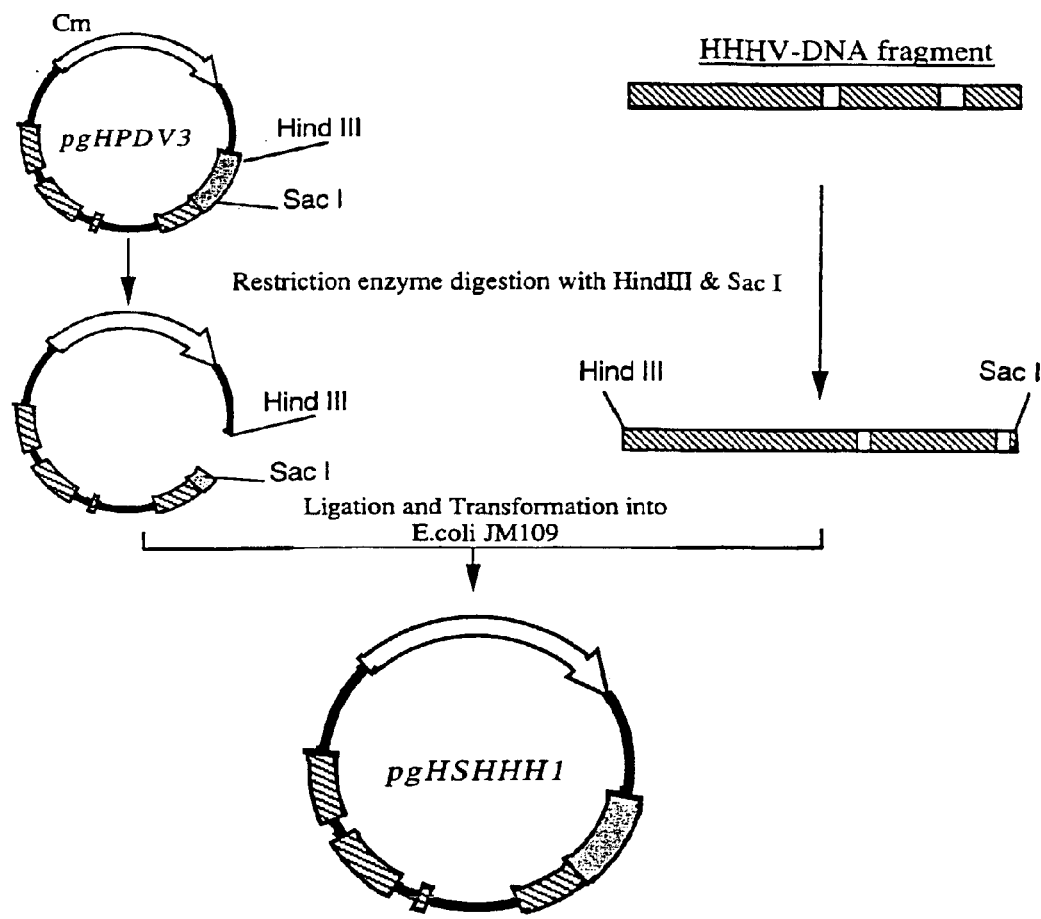
FIG. 69 shows the outline of the construction of plasmid carrying HHHV-DNA.

The outline of the method of construction of the plasmid pgHSHHH1 carrying the HHHV-DNA fragment is shown in FIG. 69.

The HHHV-DNA fragment, obtained above, was further purified by extraction with phenol and precipitation with ethanol, after which it was digested with the restriction enzymes Hind III and SacI. One μg of plasmid pgHPDHV3 was digested with the restriction enzymes Hind III and SacI, and then dephosphorylated with CIP. The resulting dephosphorylated plasmid pgHPDHV3 DNA and the digested HHHV-DNA fragment were ligated using a DNA Ligation Kit (Version 2.0, Takara Shuzo Co., Ltd.). The ligated DNA was then used to transform E. coli JM 109. The cells were plated onto LB agar medium containing final concentrations of 50 μg/ml of chloramphenicol, and were cultured at 37° C.

Transformants thus obtained were cultured in liquid LB medium containing 50 μg/ml of chloramphenicol, and the plasmid DNA was extracted from the resulting culture by the alkaline-SDS method [Sambrook et al., supra]. The resulting, extracted plasmid DNA was digested with the restriction enzymes Hind III and SacI, and a clone carrying the HHHV-DNA fragment was then selected by 1% w/v agarose gel electrophoresis and ethidium bromide staining.

Plasmid pgHSHHH1 carrying DNA encoding a fusion polypeptide of the variable region of the HHH type humanized heavy chain and the constant region of human IgG1 γ chain was obtained accordingly.

3) Verification of the Nucleotide Sequences

In order to verify whether the DNA inserts of plasmid pgHSHHH1 obtained in the above 2) had the desired nucleotide sequence, its sequence was determined. The following oligonucleotides were used to determine the sequence as a primer for sequencing: the commercially available oligonucleotide primer RV (Takara Shuzo. Co. Ltd.); the above-mentioned 7AH1P (SEQ ID No. 76 of the Sequence Listing), HFR1F (SEQ ID No. 158 of the Sequence Listing), HFR1B (SEQ ID No. 159 of the Sequence Listing), HFR2F (SEQ ID No. 160 of the Sequence Listing), HFR2B (SEQ ID No. 161 of the Sequence Listing), H5-(SEQ ID No. 103 of the Sequence Listing) and the following four newly synthesized primers:

5'-CTACAATCAA AAGTTCAAGG-3' (SACF; SEQ ID No. 162);

5'-GACTATAGTA ACAACTGGTA C-3' (APAF; SEQ ID No. 163);

5'-GTACCAGTTG TTACTATAGT C-3' (SACB; SEQ ID No. 164); and

5'-GCAGCCCAGG GCCGCTGTGC-3' (APAB; SEQ ID No. 165).

Figure 70:
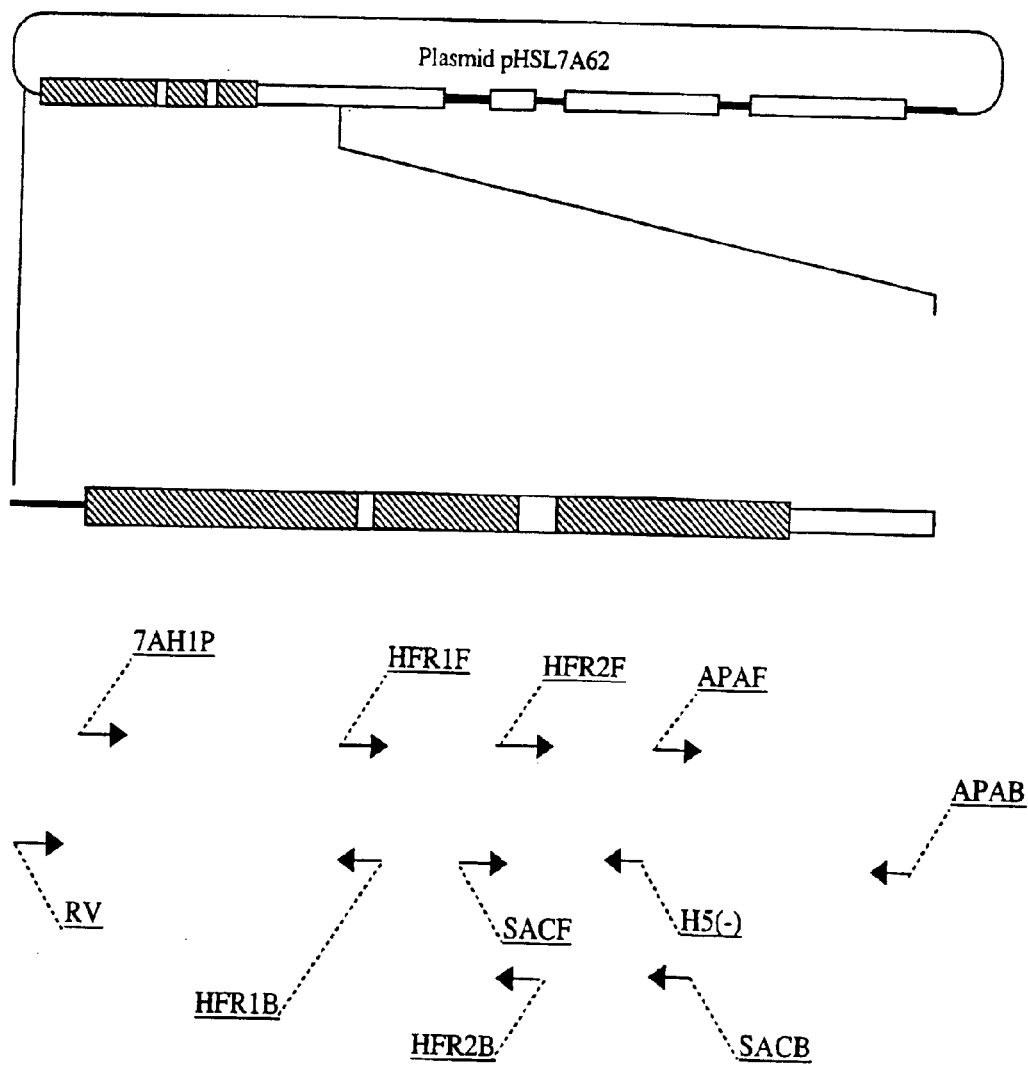
FIG. 70 shows the position to which sequencing primers for the HHH type humanized heavy chain is bound.

The positions to which each primer binds are shown in FIG. 70.

As a result, it was established that the plasmid pgHSHHH1 had the nucleotide sequences of SEQ ID No. 156 of the Sequence Listing encoding the polypeptide of SEQ ID No. 157 of the Sequence Listing. The transformant E. coli pgHSHHH1 SANK 72198, harboring plasmid pgHSHHH1, was deposited in the Kogyo Gijutsuin Seimei-Kogaku Kogyo Gijutsu Kenkyujo on Sep. 18, 1998, in accordance with the Budapest Treaty, and was accorded the accession number FERM BP-6510.

4) Construction of Expression Plasmid

Figure 71:
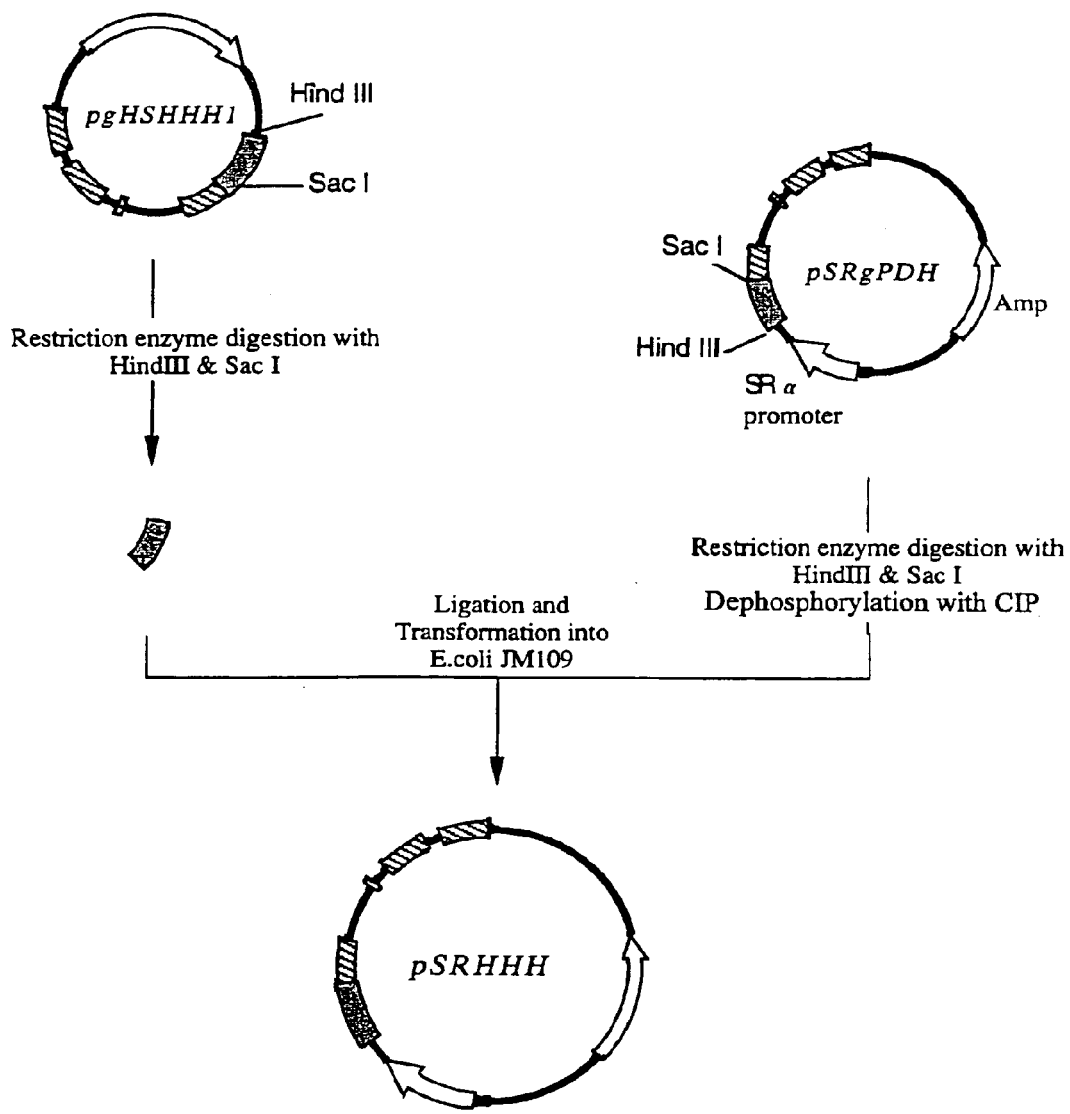
FIG. 71 shows the outline of the construction of expression plasmid carrying HHHV-DNA.

The expression plasmid vector pSRHHH, carrying the DNA encoding HHH type humanized heavy chain polypeptide (SEQ ID No. 156 of the Sequence Listing), was constructed using the plasmid pgHSHHH1 obtained in 3) above. The procedure for construction of the plasmid pSRHHH is outlined in FIG. 71.

One μg of plasmid pSRgPDH DNA (c.f. Reference Example 23) was digested with the restriction enzymes Hind III and SacI, and then dephosphorylated using CIP. The resulting dephosphorylated pSRgPDH DNA (100 ng) was ligated with 10 μg of the pgHSHHH1 DNA fragment which had also been digested with Hind III and SacI, using a DNA Ligation Kit (Version 2.0, Takara Shuzo Co., Ltd.). The ligation mix was then used to transform E. coli JM109, cells of which were then plated on LB agar plates containing 50 μg/ml of ampicillin, and cultured at 37° C.

All resulting transformants were cultured in liquid LB medium containing 50 μg/ml of ampicillin, and the plasmid DNA was extracted from the culture by the alkaline-SDS method [Sambrook et al., supra]. After the plasmid DNA was digested with Hind III and SacI, the presence or absence of the desired insert fragment was confirmed by 1% w/v agarose gel electrophoresis, stained with ethidium bromide. The plasmid pSRHHH, which contains DNA encoding the HHH type humanized heavy chain was inserted downstream of the SRα promoter in the correct orientation was, thus, obtained.

EXAMPLE 10

Construction of Expression Vector of Light Chain of Humanized HFE7A pLPDHH75, prepared in Reference Example 21, was used as an expression plasmid vector carrying DNA (SEQ ID No. 107 of the Sequence Listing) encoding a humanized light chain (SEQ ID No. 106 of the Sequence Listing). In this construction, CDR's of HFE7A light chain are grafted into the human antibody 8E10'CL light chain, but no FR's.

EXAMPLE 11

Expression in COS-1 Cells

COS-1 cells were grown to semi-confluence in α(+)MEM containing 10% v/v FCS (Moregate) in a culture flask (culture area: 225 cm$^2$). The medium was then discarded, and 3 ml of trypsin-EDTA solution (Sigma) was added to the flask, which was then incubated at 37° C. for 3 minutes to detach the cells from the flask. The detached cells were then harvested by centrifugation at 800 r.p.m. for 2 minutes, and washed twice with PBS(−) The COS-1 cells were then suspended so that cell density was 1×10$^8$ cells/ml in PBS(−) buffer.

In parallel, 10 μg of humanized HFE7A heavy chain expression plasmid DNA were mixed with 10 μg of humanized HFE7A light chain expression plasmid DNA, each of which was prepared by the alkaline-SDS method and cesium chloride density gradient centrifugation [Sambrook et al., supra]. Ethanol was added to the mixture to precipitate the DNA and the precipitate was suspended in 20 μl of PBS(−). The resulting plasmid suspension (20 μl) was mixed with 20 μl of the previously prepared COS-1 cell suspension (2×10$^6$ cells) and the mixture was transferred to an FCT-13 chamber (Shimadzu Seisakusho, K. K.) having electrodes set 2 mm apart, and the chamber was then loaded into gene transfection apparatus GTE-1 (Shimadzu Seisakusho, K. K.). The desired plasmid DNA was transformed into the COS-1 cells by applying pulses of 600 V, 50 μF twice with a one second interval.

After this time, the solution of cell-DNA mixture in the chamber was suspended in 5 ml of α(+) MEM containing 10% v/v FCS and transferred to a culture flask (culture area 25 cm$^2$). After incubating under 5% v/v CO$_2$ at 37° C. for 72 hours, the culture supernatant was recovered.

Using the above method, COS-1 cells were variously transfected with each of the following plasmid combinations, and the supernatant thereof was recovered:

[A]: no plasmid DNA
[B]; cotransfection with pSRgPDH and pSRPDHH
[C]; cotransfection with pSRHHH and pSRPDHH

EXAMPLE 12

Quantification of Expressed Products by ELISA Method

The expression of humanized antibody in the culture supernatant prepared in Example 11 was verified and the quantification of the expressed products was performed in accordance with the method described in Reference Example 17. As a result, it was verified that each of the expressed products of culture supernatants prepared in Example 11 using [B] and [C] was specifically detected by the anti-human IgG antibody.

EXAMPLE 13

Determination of Binding Activity to Fas

The culture supernatants obtained in Example 11 were adjusted to final concentrations of 100 ng/ml of the desired humanized antibody product, in α(+) MEM containing 10% v/v FCS. Concentrations were calculated by the method described in Reference Example 17. When the concentration of the desired product was less than 100 ng/ml, the culture supernatant was first concentrated by Centriprep-10 (Amicon, Co. Ltd.). That is, 5 ml of the culture supernatant was transferred into the Centriprep-10 followed by concentrating by centrifugation at 3,000×g, and again the concentration of the desired product was calculated by the method described in Reference Example 17.

Each of the resulting solutions, adjusted to 100 ng/ml, was then diluted by serial 2-fold dilution with α(+) MEM containing 10% v/v FCS. The binding activity to human Fas fusion protein was determined by the ELISA method described in Reference Example 18.

Figure 72:
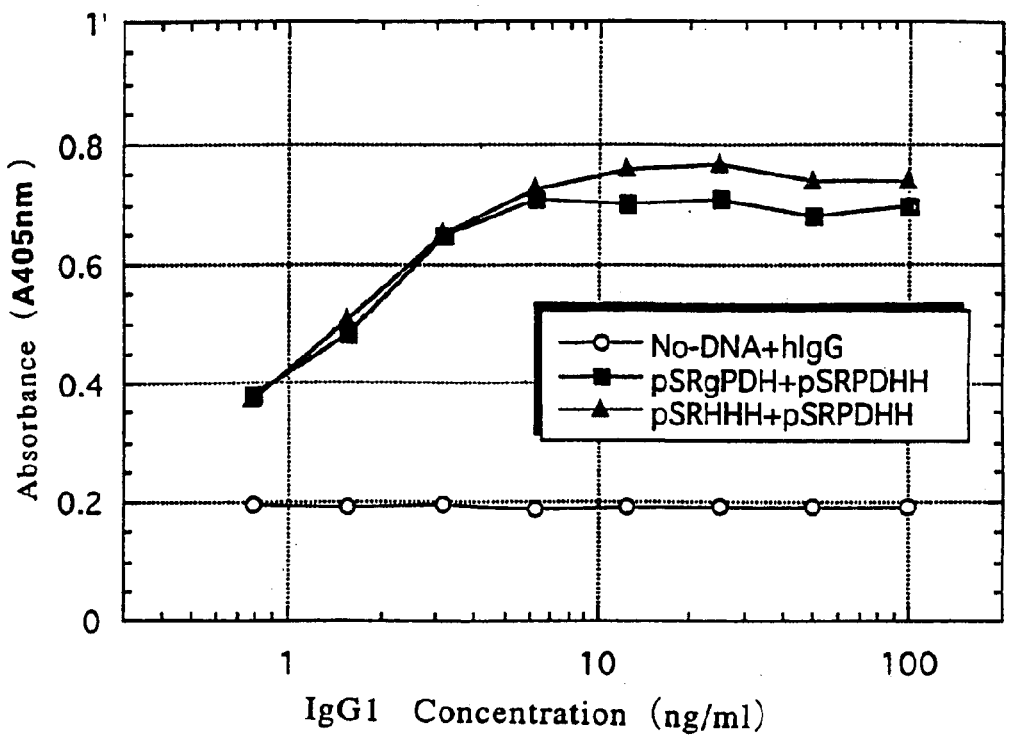
FIG. 72 shows the binding activity in the human Fas fusion protein for the supernatants of culture of transformed COS-1 cells.

The binding activity to the human Fas fusion protein was verified for the supernatants prepared in Example 11 using [B] and [C] and is shown in FIG. 72.

EXAMPLE 14

Competitive Inhibition of the Binding of HFE7A to Fas

The competitive inhibitory activity of each of the expressed products prepared in Example 11 against the human Fas fusion protein, along with that of HFE7A, was determined by a similar method to that described in Reference Example 26.

Figure 73:
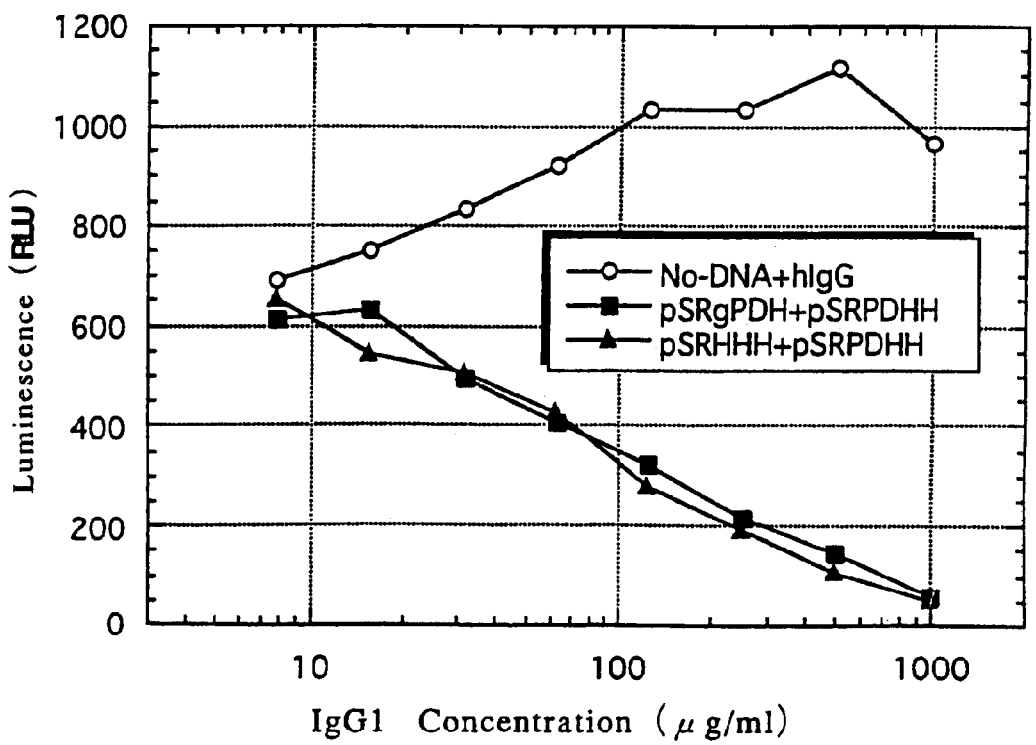
FIG. 73 shows the results of competitive inhibition of binding of human Fas fusion protein with HFE7A antibody by the supernatants of cultures of transformed COS-1 cells.

It was verified that each of the expression products prepared in Example 11 specifically inhibited the binding of HFE7A prepared from a mouse hybridoma to the human Fas fusion protein (FIG. 73).

EXAMPLE 15

Apoptosis-Inducing Activity

The culture supernatants obtained in Example 11 were adjusted so that the final concentration of antibody was 100 ng/ml, by a similar method to that described in Reference Example 22 (RPMI 1640 medium containing 10% v/v FCS was used as diluent, as necessary). Each of the solutions of the expression products was then diluted in serial 2-fold dilution with RPMI 1640 containing 10% v/v FCS. The cytotoxic activity of each sample to WR19L12a cells was determined by the method described in Reference Example 20.

As expected, each of the expression products of the culture supernatant obtained in Example 11 using [B] and [C] were demonstrated to induce apoptosis in T cells of this lymphoma cell line expressing human Fas antigen, in a similar manner to HFE7A prepared from the hybridoma cultures.

What is claimed is:

1. An antibody produced by the hybridoma HFE7A having the accession number FERM BP-5828.

2. An antibody comprising a light polypeptide chain and a heavy polypeptide chain, the heavy chain having the following formula (I):

$$-FRH_1-CDRH_1-FRH_2-CDRH_2-FRH_3-CDRH_3-FRH_4- \quad (I)$$

wherein $FRH_1$ represents amino acid sequence having 18 to 30 amino acids, $CDRH_1$ represent the sequence of SEQ ID NO: 2, $FRH_2$ represents an amino acid sequence having 14 amino acids, $CDRH_2$ represents the sequence of SEQ ID NO: 3, $FRH_3$ represents an amino acid sequence having 32 amino acids, $CDRH_3$ represents the sequence of SEQ ID NO: 4, $FRH_4$ represents an amino acid sequence having 11 amino acids, light chain having the following formula (II):

$$-FRL_1-CDRL_1-FRL_2-CDRL_2-FRL_3-CDRL_3-FRL_4- \quad (II)$$

wherein $FFL_1$ represents an amino acid sequence having 23 amino acids, $CDRL_1$ represents the sequence of SEQ ID NO: 5, $FRL_2$ represents an amino acid sequence having 15 amino acids, $CDRL_2$ represents the sequence of SEQ ID NO: 6, $FRL_3$ represent an amino acid sequence having 32 amino acids, $CDRL_3$ represents the sequence of SEQ ID NO: 7, $FRL_4$ represents an amino acid sequence having 10 amino acids, wherein said antibody binds Fas.

3. The antibody of claim 2, which is humanized.

4. The antibody of claim 1, which is humanized.

5. An isolated antibody that comprises a light chain polypeptide protein selected from the group consisting of (i) the amino acid sequence 1 to 218 of SEQ ID NO: 50, (ii) the amino acid sequence 1 to 218 of SEQ ID NO: 52, (iii) the amino acid sequence 1 to 218 of SEQ ID NO: 54, (iv) the amino acid sequence 1 to 218 of SEQ ID NO: 107 and (v) the amino acid sequence 1 to 218 of SE; ID NO: 109, wherein said antibody binds Fas.

6. An isolated antibody that comprises a heavy chain polypeptide protein selected from the group consisting of (i) the amino acid sequence 1 to 451 of SEQ ID NO: 89 and (ii) the amino acid sequence 1 to 451 of SEQ ID NO: 117, wherein said antibody binds Fas.

7. An isolated antibody that comprises a light chain polypeptide protein having the amino acid sequence 1 to 218 of SEQ ID NO: 50, and a heavy chain polypeptide protein having the amino acid sequence 1 to 451 of SEQ ID NO: 89, wherein said antibody binds Fas.

8. An isolated antibody that comprises a light chain polypeptide protein having the amino acid sequence 1 to 218 of SEQ ID NO: 107, and a heavy chain polypeptide protein having the amino acid sequence 1 to 451 of SEQ ID NO: 117, wherein said antibody binds Fas.

9. An isolated antibody molecule comprising one or more heavy chain subunits having an amino acid sequence selected from the group consisting of:

the amino acid sequence 1 to 451 of SEQ ID NO: 143;

the amino acid sequence 1 to 451 of SEQ ID NO: 145;

the amino acid sequence 1 to 451 of SEQ ID NO: 147; and the amino acid sequence 1 to 451 of SEQ ID NO: 157, wherein said antibody binds Fas.

10. The isolated antibody of claim 9 which has one or more light chain subunits having an amino acid sequence selected from the group consisting of:

the amino acid sequence 1 to 218 of SEQ ID NO: 107;

the amino acid sequence 1 to 218 of SEQ ID NO: 127;

the amino acid sequence 1 to 218 of SEQ ID NO: 129; and the amino acid sequence 1 to 218 of SEQ ID NO: 131, wherein said antibody binds Fas.

11. The antibody of claim 9, wherein the heavy chain consists essentially of the amino acid sequence 1 to 451 of SEQ ID NO: 157.

12. The antibody of claim 11, wherein the light chain consists essentially of the amino acid sequence 1 to 218 of SEQ ID NO: 107.

13. The antibody of claim 9, which consists essentially of two heavy chains and two light chain.

14. The antibody of claim 9, which consists of two heavy chains and two light chains, said heavy chains each consisting essentially of the amino acid sequence 1 to 451 of SEQ ID NO: 157, and said light chains each consisting essentially of the amino acid sequence 1 to 218 of SEQ ID NO: 107.

15. An isolated antibody molecule, wherein one or more light chain subunits have an amino acid sequence selected from the group consisting of:

the amino acid sequence 1 to 218 of SEQ ID NO: 127;

the amino acid sequence 1 to 218 of SEQ ID NO: 129; and the amino acid sequence 1 to 218 of SEQ ID NO: 131, and one or more heavy chain subunits having an amino acid sequence selected from the group consisting of:

the amino acid sequence 1 to 451 of SEQ ID NO: 143;

the amino acid sequence 1 to 451 of SEQ ID NO: 145; and the amino acid sequence 1 to 451 of SEQ ID NO: 147, wherein said antibody binds Fas.

16. The antibody of claim 15, wherein said light chain subunits have the amino acid sequence 1 to 218 of SEQ ID NO: 127, and one or more heavy chain subunits have the amino acid sequence 1 to 451 of SEQ ID NO: 143.

17. The antibody of claim 15, wherein said light chain subunits have the amino acid sequence 1 to 218 of SEQ ID NO: 127, and one or more heavy chain subunits have the amino acid sequence 1 to 451 of SEQ ID NO: 145.

18. The antibody of claim 15, wherein said light chain subunits have the amino acid sequence 1 to 214 of SEQ ID NO: 127, and one or more heavy chain subunits have the amino acid sequence 1 to 451 of SEQ ID NO: 147.

19. The antibody of claim 15, wherein said light chain subunits have the amino acid sequence 1 to 218 of SEQ ID NO: 129, and one or more heavy chain subunits have the amino acid sequence 1 to 451 of SEQ ID NO: 143.

20. The antibody of claim 15, wherein said light chain subunits have the amino acid sequence 1 to 218 of SEQ ID NO: 129, and one or more heavy chain subunits have the amino acid sequence 1 to 451 of SEQ ID NO: 145.

21. The antibody of claim 15, wherein said light chain subunits have the amino acid sequence 1 to 218 of SEQ ID NO: 129, and one or more heavy chain subunits have the amino acid sequence 1 to 451 of SEQ ID NO: 147.

22. The antibody of claim 15, wherein said light chain subunits have the amino acid sequence 1 to 218 of SEQ ID NO: 131, and one or more heavy chain subunits have the amino acid sequence 1 to 451 of SEQ ID NO: 143.

23. The antibody of claim 15, wherein said light chain subunits have the amino acid sequence 1 to 218 of SEQ ID NO: 131, and one or more heavy chain subunits have the amino acid sequence 1 to 451 of SEQ ID NO: 145.

24. The antibody of claim 15, wherein said light chain subunits have the amino acid sequence 1 to 218 of SEQ ID NO: 131, and one or more heavy chain subunits have the amino acid sequence 1 to 451 of SEQ ID NO: 147.

25. The antibody of claim 15, which consists essentially of two heavy chains and two light chains.

26. The antibody of claim 9 that binds a peptide comprising the amino acid sequence of SEQ ID NO: 1.

27. The antibody of claim 14 that binds a peptide comprising the amino acid sequence at SEQ ID NO: 1.

28. The antibody of claim 15 that binds a peptide comprising the amino acid sequence of SEQ ID NO: 1.

29. An isolated Fas-specific antibody comprising a first polypeptide protein having an amino acid sequence 1 to 218 of SEQ ID NO: 127, the amino acid sequence 1 to 218 of SEQ ID NO: 129 and the amino acid sequence 1 to 218 of SEQ ID NO: 131, together with a second polypeptide protein having an amino acid sequence selected from the group consisting of the amino acid sequence 1 to 451 of SEQ ID NO: 143, the amino acid sequence 1 to 451 of SEQ ID NO: 145 and the amino acid sequence 1 to 451 of SEQ ID NO: 147.

30. The isolated antibody of claim 5, wherein said protein comprises the amino acid sequence 1 to 218 of SEQ ID NO: 50.

31. The isolated antibody of claim 5, wherein said protein comprises the amino acid sequence 1 to 218 of SEQ ID NO: 52.

32. The isolated antibody of claim 5, wherein said protein comprises the amino acid sequence 1 to 218 of SEQ ID NO: 54.

33. The isolated antibody of claim 5, wherein said protein comprises the amino acid sequence 1 to 218 of SEQ ID NO: 107.

34. The isolated antibody of claim 5, wherein said protein comprises the amino acid sequence 1 to 218 of SEQ ID NO: 109.

35. The isolated antibody of claim 6, wherein said protein comprises the amino acid sequence 1 to 218 of SEQ ID NO: 89.

36. The isolated antibody of claim 6, wherein said protein comprises the amino acid sequence 1 to 218 of SEQ ID NO: 117.

* * * * *

SEQUENCE LISTING

<160> NUMBER OF SEQ ID NOS: 165

<210> SEQ ID NO 1
<211> LENGTH: 10
<212> TYPE: PRT
<213> ORGANISM: Homo sapiens

<400> SEQUENCE: 1

Arg Thr Gln Asn Thr Lys Cys Arg Cys Lys
 1               5                  10

<210> SEQ ID NO 2
<211> LENGTH: 5
<212> TYPE: PRT
<213> ORGANISM: Mus musculus

<400> SEQUENCE: 2

Ser Tyr Trp Met Gln
 1               5

<210> SEQ ID NO 3
<211> LENGTH: 17
<212> TYPE: PRT

<213> ORGANISM: Mus musculus

<400> SEQUENCE: 3

Glu Ile Asp Pro Ser Asp Ser Tyr Thr Asn Tyr Asn Gln Lys Phe Lys
 1               5                  10                  15
Gly

<210> SEQ ID NO 4
<211> LENGTH: 12
<212> TYPE: PRT
<213> ORGANISM: Mus musculus

<400> SEQUENCE: 4

Asn Arg Asp Tyr Ser Asn Asn Trp Tyr Phe Asp Val
 1               5                  10

<210> SEQ ID NO 5
<211> LENGTH: 15
<212> TYPE: PRT
<213> ORGANISM: Mus musculus

<400> SEQUENCE: 5

Lys Ala Ser Gln Ser Val Asp Tyr Asp Gly Asp Ser Tyr Met Asn
 1               5                  10                  15

<210> SEQ ID NO 6
<211> LENGTH: 7
<212> TYPE: PRT
<213> ORGANISM: Mus musculus

<400> SEQUENCE: 6

Ala Ala Ser Asn Leu Glu Ser
 1               5

<210> SEQ ID NO 7
<211> LENGTH: 9
<212> TYPE: PRT
<213> ORGANISM: Mus musculus

<400> SEQUENCE: 7

Gln Gln Ser Asn Glu Asp Pro Arg Thr
 1               5

<210> SEQ ID NO 8
<211> LENGTH: 1392
<212> TYPE: DNA
<213> ORGANISM: Mus musculus
<220> FEATURE:
<221> NAME/KEY: CDS
<222> LOCATION: (1)..(1392)
<220> FEATURE:
<221> NAME/KEY: mat peptide
<222> LOCATION: (58)..(1392)
<220> FEATURE:
<221> NAME/KEY: sig peptide
<222> LOCATION: (1)..(57)

<400> SEQUENCE: 8

```
atg gga tgg agc tgt atc atc ctc ttc ttg gta gca aca gct aca ggt       48
Met Gly Trp Ser Cys Ile Ile Leu Phe Leu Val Ala Thr Ala Thr Gly
            -15                 -10                 -5 gtc cat tct cag gtc caa ctg cag cag cct ggg gct gag ctt gtg aag       96
Val His Ser Gln Val Gln Leu Gln Gln Pro Gly Ala Glu Leu Val Lys
     -1   1               5                  10 cct ggg gct tca gtg aag ctg tcc tgc aag gct tct ggc tac acc ttc      144
```

|   |   |   |   |   |   |   |   |   |   |   |   |   |   |   |   |
|---|---|---|---|---|---|---|---|---|---|---|---|---|---|---|---|
| Pro | Gly | Ala | Ser | Val | Lys | Leu | Ser | Cys | Lys | Ala | Ser | Gly | Tyr | Thr | Phe |
|  | 15 |  |  |  | 20 |  |  |  | 25 |  |  |  |  |  |  |

```
acc agc tac tgg atg cag tgg gta aaa cag agg cct gga cag ggc ctt     192
Thr Ser Tyr Trp Met Gln Trp Val Lys Gln Arg Pro Gly Gln Gly Leu
 30              35                  40                  45 gag tgg atc gga gag att gat cct tct gat agc tat act aac tac aat     240
Glu Trp Ile Gly Glu Ile Asp Pro Ser Asp Ser Tyr Thr Asn Tyr Asn
                 50                  55                  60 caa aag ttc aag ggc aag gcc aca ttg act gta gac aca tcc tcc agc     288
Gln Lys Phe Lys Gly Lys Ala Thr Leu Thr Val Asp Thr Ser Ser Ser
             65                  70                  75 aca gcc tac atg cag ctc agc agc ctg aca tct gag gac tct gcg gtc     336
Thr Ala Tyr Met Gln Leu Ser Ser Leu Thr Ser Glu Asp Ser Ala Val
         80                  85                  90 tat tac tgt gca aga aat agg gac tat agt aac aac tgg tac ttc gat     384
Tyr Tyr Cys Ala Arg Asn Arg Asp Tyr Ser Asn Asn Trp Tyr Phe Asp
     95                 100                 105 gtc tgg ggc aca ggg acc acg gtc acc gtc tca gcc aaa acg aca         432
Val Trp Gly Thr Gly Thr Thr Val Thr Val Ser Ala Lys Thr Thr
110             115                 120                 125 ccc cca tct gtc tat cca ctg gcc cct gga tct gct gcc caa act aac     480
Pro Pro Ser Val Tyr Pro Leu Ala Pro Gly Ser Ala Ala Gln Thr Asn
             130                 135                 140 tcc atg gtg acc ctg gga tgc ctg gtc aag ggc tat ttc cct gag cca     528
Ser Met Val Thr Leu Gly Cys Leu Val Lys Gly Tyr Phe Pro Glu Pro
         145                 150                 155 gtg aca gtg acc tgg aac tct gga tcc ctg tcc agc ggt gtg cac acc     576
Val Thr Val Thr Trp Asn Ser Gly Ser Leu Ser Ser Gly Val His Thr
     160                 165                 170 ttc cca gct gtc ctg cag tct gac ctc tac act ctg agc agc tca gtg     624
Phe Pro Ala Val Leu Gln Ser Asp Leu Tyr Thr Leu Ser Ser Ser Val
175             180                 185 act gtc ccc tcc agc acc tgg ccc agc cag acc gtc acc tgc aac gtt     672
Thr Val Pro Ser Ser Thr Trp Pro Ser Gln Thr Val Thr Cys Asn Val
190                 195                 200                 205 gcc cac ccg gcc agc agc acc aag gtg gac aag aaa att gtg ccc agg     720
Ala His Pro Ala Ser Ser Thr Lys Val Asp Lys Lys Ile Val Pro Arg
             210                 215                 220 gat tgt ggt tgt aag cct tgc ata tgt aca gtc cca gaa gta tca tct     768
Asp Cys Gly Cys Lys Pro Cys Ile Cys Thr Val Pro Glu Val Ser Ser
         225                 230                 235 gtc ttc atc ttc ccc cca aag ccc aag gat gtg ctc acc att act ctg     816
Val Phe Ile Phe Pro Pro Lys Pro Lys Asp Val Leu Thr Ile Thr Leu
     240                 245                 250 act cct aag gtc acg tgt gtt gtg gta gac atc agc aag gat gat ccc     864
Thr Pro Lys Val Thr Cys Val Val Val Asp Ile Ser Lys Asp Asp Pro
255                 260                 265 gag gtc cag ttc agc tgg ttt gta gat gat gtg gag gtg cac aca gct     912
Glu Val Gln Phe Ser Trp Phe Val Asp Asp Val Glu Val His Thr Ala
270                 275                 280                 285 cag acg caa ccc cgg gag gag cag ttc aac agc act ttc cgc tca gtc     960
Gln Thr Gln Pro Arg Glu Glu Gln Phe Asn Ser Thr Phe Arg Ser Val
             290                 295                 300 agt gaa ctt ccc atc atg cac cag aac tgg ctc aat ggc aag gag ttc    1008
Ser Glu Leu Pro Ile Met His Gln Asn Trp Leu Asn Gly Lys Glu Phe
         305                 310                 315 aaa tgc agg gtc aac agt gca gct ttc cct gcc ccc atc gag aaa acc    1056
Lys Cys Arg Val Asn Ser Ala Ala Phe Pro Ala Pro Ile Glu Lys Thr
     320                 325                 330
```

-continued

```
atc tcc aaa acc aaa ggc aga ccg aag gct cca cag gtg tac acc att    1104
Ile Ser Lys Thr Lys Gly Arg Pro Lys Ala Pro Gln Val Tyr Thr Ile
335             340             345 cca cct ccc aag gag cag atg gcc aag gat aaa gtc agt ctg acc tgc    1152
Pro Pro Pro Lys Glu Gln Met Ala Lys Asp Lys Val Ser Leu Thr Cys
350             355             360             365 atg ata aca gac ttc ttc cct gaa gac att act gtg gag tgg cag tgg    1200
Met Ile Thr Asp Phe Phe Pro Glu Asp Ile Thr Val Glu Trp Gln Trp
            370             375             380 aat ggg cag cca gcg gag aac tac aag aac act cag ccc atc atg aac    1248
Asn Gly Gln Pro Ala Glu Asn Tyr Lys Asn Thr Gln Pro Ile Met Asn
            385             390             395 acg aat ggc tct tac ttc gtc tac agc aag ctc aat gtg cag aag agc    1296
Thr Asn Gly Ser Tyr Phe Val Tyr Ser Lys Leu Asn Val Gln Lys Ser
            400             405             410 aac tgg gag gca gga aat act ttc acc tgc tct gtg tta cat gag ggc    1344
Asn Trp Glu Ala Gly Asn Thr Phe Thr Cys Ser Val Leu His Glu Gly
415             420             425 ctg cac aac cac cat act gag aag agc ctc tcc cac tct cct ggt aaa    1392
Leu His Asn His His Thr Glu Lys Ser Leu Ser His Ser Pro Gly Lys
430             435             440             445

<210> SEQ ID NO 9
<211> LENGTH: 464
<212> TYPE: PRT
<213> ORGANISM: Mus musculus

<400> SEQUENCE: 9

Met Gly Trp Ser Cys Ile Ile Leu Phe Leu Val Ala Thr Ala Thr Gly
                -15             -10                  -5

Val His Ser Gln Val Gln Leu Gln Gln Pro Gly Ala Glu Leu Val Lys
         -1   1               5                  10

Pro Gly Ala Ser Val Lys Leu Ser Cys Lys Ala Ser Gly Tyr Thr Phe
             15                  20                  25

Thr Ser Tyr Trp Met Gln Trp Val Lys Gln Arg Pro Gly Gln Gly Leu
 30                  35                  40                  45

Glu Trp Ile Gly Glu Ile Asp Pro Ser Asp Ser Tyr Thr Asn Tyr Asn
                 50                  55                  60

Gln Lys Phe Lys Gly Lys Ala Thr Leu Thr Val Asp Thr Ser Ser Ser
             65                  70                  75

Thr Ala Tyr Met Gln Leu Ser Ser Leu Thr Ser Glu Asp Ser Ala Val
 80                  85                  90

Tyr Tyr Cys Ala Arg Asn Arg Asp Tyr Ser Asn Asn Trp Tyr Phe Asp
 95                 100                 105

Val Trp Gly Thr Gly Thr Thr Val Thr Val Ser Ser Ala Lys Thr Thr
110                 115                 120                 125

Pro Pro Ser Val Tyr Pro Leu Ala Pro Gly Ser Ala Ala Gln Thr Asn
                130                 135                 140

Ser Met Val Thr Leu Gly Cys Leu Val Lys Gly Tyr Phe Pro Glu Pro
                145                 150                 155

Val Thr Val Thr Trp Asn Ser Gly Ser Leu Ser Ser Gly Val His Thr
                160                 165                 170

Phe Pro Ala Val Leu Gln Ser Asp Leu Tyr Thr Leu Ser Ser Ser Val
175                 180                 185

Thr Val Pro Ser Ser Thr Trp Pro Ser Gln Thr Val Thr Cys Asn Val
190                 195                 200                 205

Ala His Pro Ala Ser Ser Thr Lys Val Asp Lys Lys Ile Val Pro Arg
```

-continued

```
                        210                 215                 220
Asp Cys Gly Cys Lys Pro Cys Ile Cys Thr Val Pro Glu Val Ser Ser
                225                 230                 235
Val Phe Ile Phe Pro Pro Lys Pro Lys Asp Val Leu Thr Ile Thr Leu
                240                 245                 250
Thr Pro Lys Val Thr Cys Val Val Asp Ile Ser Lys Asp Asp Pro
        255                 260                 265
Glu Val Gln Phe Ser Trp Phe Val Asp Asp Val Glu Val His Thr Ala
270                 275                 280                 285
Gln Thr Gln Pro Arg Glu Glu Gln Phe Asn Ser Thr Phe Arg Ser Val
                290                 295                 300
Ser Glu Leu Pro Ile Met His Gln Asn Trp Leu Asn Gly Lys Glu Phe
                305                 310                 315
Lys Cys Arg Val Asn Ser Ala Ala Phe Pro Ala Pro Ile Glu Lys Thr
                320                 325                 330
Ile Ser Lys Thr Lys Gly Arg Pro Lys Ala Pro Gln Val Tyr Thr Ile
        335                 340                 345
Pro Pro Pro Lys Glu Gln Met Ala Lys Asp Lys Val Ser Leu Thr Cys
350                 355                 360                 365
Met Ile Thr Asp Phe Phe Pro Glu Asp Ile Thr Val Glu Trp Gln Trp
                370                 375                 380
Asn Gly Gln Pro Ala Glu Asn Tyr Lys Asn Thr Gln Pro Ile Met Asn
                385                 390                 395
Thr Asn Gly Ser Tyr Phe Val Tyr Ser Lys Leu Asn Val Gln Lys Ser
                400                 405                 410
Asn Trp Glu Ala Gly Asn Thr Phe Thr Cys Ser Val Leu His Glu Gly
        415                 420                 425
Leu His Asn His His Thr Glu Lys Ser Leu Ser His Ser Pro Gly Lys
430                 435                 440                 445

<210> SEQ ID NO 10
<211> LENGTH: 714
<212> TYPE: DNA
<213> ORGANISM: Mus musculus
<220> FEATURE:
<221> NAME/KEY: CDS
<222> LOCATION: (1)..(714)
<220> FEATURE:
<221> NAME/KEY: mat peptide
<222> LOCATION: (61)..(714)
<220> FEATURE:
<221> NAME/KEY: sig peptide
<222> LOCATION: (1)..(60)

<400> SEQUENCE: 10 atg gag aca gac aca atc ctg cta tgg gtg atg atg ctc tgg att cca      48
Met Glu Thr Asp Thr Ile Leu Leu Trp Val Met Met Leu Trp Ile Pro
-20                 -15                 -10                 -5 ggc tcc act ggt gac att gtg ctg acc caa tct cca gct tct ttg gct      96
Gly Ser Thr Gly Asp Ile Val Leu Thr Gln Ser Pro Ala Ser Leu Ala
            -1   1               5                  10 gtg tct cta ggg cag agg gcc acc atc tcc tgc aag gcc agc caa agt     144
Val Ser Leu Gly Gln Arg Ala Thr Ile Ser Cys Lys Ala Ser Gln Ser
        15                  20                  25 gtt gat tat gat ggt gat agt tat atg aac tgg tac caa cag aaa cca     192
Val Asp Tyr Asp Gly Asp Ser Tyr Met Asn Trp Tyr Gln Gln Lys Pro
    30                  35                  40 gga cag cca ccc aaa ctc ctc atc tat gct gca tcc aat cta gaa tct     240
Gly Gln Pro Pro Lys Leu Leu Ile Tyr Ala Ala Ser Asn Leu Glu Ser
```

```
                45                  50                  55                  60
ggg atc cca gcc agg ttt agt ggc agt ggg tct ggg aca gac ttc acc              288
Gly Ile Pro Ala Arg Phe Ser Gly Ser Gly Ser Gly Thr Asp Phe Thr
                65                  70                  75 ctc aac atc cat cct gtg gag gag gag gat gct gca acc tat tac tgt              336
Leu Asn Ile His Pro Val Glu Glu Glu Asp Ala Ala Thr Tyr Tyr Cys
                80                  85                  90 cag caa agt aat gag gat cct cgg acg ttc ggt gga ggc acc aag ctg              384
Gln Gln Ser Asn Glu Asp Pro Arg Thr Phe Gly Gly Gly Thr Lys Leu
                95                 100                 105 gaa atc aaa cgg gct gat gct gca cca act gta tcc atc ttc cca cca              432
Glu Ile Lys Arg Ala Asp Ala Ala Pro Thr Val Ser Ile Phe Pro Pro
    110                 115                 120 tcc agt gag cag tta aca tct gga ggt gcc tca gtc gtg tgc ttc ttg              480
Ser Ser Glu Gln Leu Thr Ser Gly Gly Ala Ser Val Val Cys Phe Leu
125                 130                 135                 140 aac aac ttc tac ccc aaa gac atc aat gtc aag tgg aag att gat ggc              528
Asn Asn Phe Tyr Pro Lys Asp Ile Asn Val Lys Trp Lys Ile Asp Gly
                145                 150                 155 agt gaa cga caa aat ggc gtc ctg aac agt tgg act gat cag gac agc              576
Ser Glu Arg Gln Asn Gly Val Leu Asn Ser Trp Thr Asp Gln Asp Ser
                160                 165                 170 aaa gac agc acc tac agc atg agc agc acc ctc acg ttg acc aag gac              624
Lys Asp Ser Thr Tyr Ser Met Ser Ser Thr Leu Thr Leu Thr Lys Asp
                175                 180                 185 gag tat gaa cga cat aac agc tat acc tgt gag gcc act cac aag aca              672
Glu Tyr Glu Arg His Asn Ser Tyr Thr Cys Glu Ala Thr His Lys Thr
    190                 195                 200 tca act tca ccc att gtc aag agc ttc aac agg aat gag tgt                      714
Ser Thr Ser Pro Ile Val Lys Ser Phe Asn Arg Asn Glu Cys
205                 210                 215

<210> SEQ ID NO 11
<211> LENGTH: 238
<212> TYPE: PRT
<213> ORGANISM: Mus musculus

<400> SEQUENCE: 11

Met Glu Thr Asp Thr Ile Leu Leu Trp Val Met Leu Trp Ile Pro
-20                 -15                 -10                  -5

Gly Ser Thr Gly Asp Ile Val Leu Thr Gln Ser Pro Ala Ser Leu Ala
                 -1   1               5                  10

Val Ser Leu Gly Gln Arg Ala Thr Ile Ser Cys Lys Ala Ser Gln Ser
            15                  20                  25

Val Asp Tyr Asp Gly Asp Ser Tyr Met Asn Trp Tyr Gln Gln Lys Pro
        30                  35                  40

Gly Gln Pro Pro Lys Leu Leu Ile Tyr Ala Ala Ser Asn Leu Glu Ser
45                  50                  55                  60

Gly Ile Pro Ala Arg Phe Ser Gly Ser Gly Ser Gly Thr Asp Phe Thr
                65                  70                  75

Leu Asn Ile His Pro Val Glu Glu Glu Asp Ala Ala Thr Tyr Tyr Cys
                80                  85                  90

Gln Gln Ser Asn Glu Asp Pro Arg Thr Phe Gly Gly Gly Thr Lys Leu
                95                 100                 105

Glu Ile Lys Arg Ala Asp Ala Ala Pro Thr Val Ser Ile Phe Pro Pro
    110                 115                 120

Ser Ser Glu Gln Leu Thr Ser Gly Gly Ala Ser Val Val Cys Phe Leu
125                 130                 135                 140
```

```
Asn Asn Phe Tyr Pro Lys Asp Ile Asn Val Lys Trp Lys Ile Asp Gly
                145                 150                 155

Ser Glu Arg Gln Asn Gly Val Leu Asn Ser Trp Thr Asp Gln Asp Ser
            160                 165                 170

Lys Asp Ser Thr Tyr Ser Met Ser Ser Thr Leu Thr Leu Thr Lys Asp
        175                 180                 185

Glu Tyr Glu Arg His Asn Ser Tyr Thr Cys Glu Ala Thr His Lys Thr
    190                 195                 200

Ser Thr Ser Pro Ile Val Lys Ser Phe Asn Arg Asn Glu Cys
205             210                 215

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: PCR
      primer to amplify a DNA encoding the extracellular region of
      human Fas antigen

<400> SEQUENCE: 12
ggggaattcc agtacggagt tggggaagct cttt                           34

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: PCR
      primer to amplify a DNA encoding the extracellular region of
      human Fas antigen

<400> SEQUENCE: 13
gtttcttctg cctctgtcac caagttagat ctgga                          35

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: PCR
      primer to amplify a DNA encoding the extracellular region of
      mouse IL-3 receptor

<400> SEQUENCE: 14
tccagatcta acttggtgac agaggcagaa gaaac                          35

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: PCR
      primer to amplify a DNA encoding the extracellular region of
      mouse IL-3 receptor

<400> SEQUENCE: 15
ccctctagac gcgtcacgtg ggcatcac                                  28

<210> SEQ ID NO 16
<211> LENGTH: 11
<212> TYPE: PRT
<213> ORGANISM: Mus musculus
<220> FEATURE:
<221> NAME/KEY: Unsure
```

```
<222> LOCATION: 2
<223> OTHER INFORMATION: Unidentified amino acid

<400> SEQUENCE: 16

Gln Xaa Gln Leu Gln Gln Pro Gly Ala Glu Leu
  1               5                  10

<210> SEQ ID NO 17
<211> LENGTH: 22
<212> TYPE: PRT
<213> ORGANISM: Mus musculus

<400> SEQUENCE: 17

Asp Ile Val Leu Thr Gln Ser Pro Ala Ser Leu Ala Val Ser Leu Gly
  1               5                  10                  15

Gln Arg Ala Thr Ile Ser
             20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: PCR primer
      to amplify a DNA encoding mouse immunoglobulin heavy
      chain gamma 1 subtype 2b

<400> SEQUENCE: 18
gacctcacca tgggatgga                                             19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: PCR primer
      to amplify a DNA encoding mouse immunoglobulin heavy
      chain gamma 1 subtype 2b

<400> SEQUENCE: 19
tttaccagga gagtgggaga                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: PCR primer
      to amplify a DNA encoding mouse immunoglobulin light
      chain kappa subtype 3

<400> SEQUENCE: 20
aagaagcatc ctctcatcta                                            20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: PCR primer
      to amplify a DNA encoding mouse immunoglobulin light
      chain kappa subtype 3

<400> SEQUENCE: 21
acactcattc ctgttgaagc                                            20
```

```
<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Adaptor
      primer to subclone a cDNA encoding the heavy chain of
      anti-human Fas antibody HFE7A

<400> SEQUENCE: 22
ggggaattcg acctcaccat gggatgga                                28

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Adaptor
      primer to subclone a cDNA encoding the heavy chain of
      anti-human Fas antibody HFE7A

<400> SEQUENCE: 23
gggtctagac tatttaccag gagagtggga ga                           32

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Adaptor
      primer to subclone a cDNA encoding the light chain of
      anti-human Fas antibody HFE7A

<400> SEQUENCE: 24
ggggaattca agaagcatcc tctcatcta                               29

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Adaptor
      primer to subclone a cDNA encoding the light chain of
      anti-human Fas antibody HFE7A

<400> SEQUENCE: 25
ggggcggccg cttactaaca ctcattcctg ttgaagc                      37

<210> SEQ ID NO 26
<211> LENGTH: 19
<212> TYPE: PRT
<213> ORGANISM: Homo sapiens

<400> SEQUENCE: 26

Arg Leu Ser Ser Lys Ser Val Asn Ala Gln Val Thr Asp Ile Asn Ser
 1               5                  10                  15

Lys Gly Leu

<210> SEQ ID NO 27
<211> LENGTH: 19
<212> TYPE: PRT
<213> ORGANISM: Homo sapiens

<400> SEQUENCE: 27

Val Thr Asp Ile Asn Ser Lys Gly Leu Glu Leu Arg Lys Thr Val Thr
 1               5                  10                  15
```

-continued

Thr Val Glu

<210> SEQ ID NO 28
<211> LENGTH: 20
<212> TYPE: PRT
<213> ORGANISM: Homo sapiens

<400> SEQUENCE: 28

Glu Leu Arg Lys Thr Val Thr Thr Val Glu Thr Gln Asn Leu Glu Gly
 1               5                  10                  15

Leu His His Asp
            20

<210> SEQ ID NO 29
<211> LENGTH: 20
<212> TYPE: PRT
<213> ORGANISM: Homo sapiens

<400> SEQUENCE: 29

Thr Gln Asn Leu Glu Gly Leu His His Asp Gly Gln Phe Cys His Lys
 1               5                  10                  15

Pro Cys Pro Pro
            20

<210> SEQ ID NO 30
<211> LENGTH: 20
<212> TYPE: PRT
<213> ORGANISM: Homo sapiens

<400> SEQUENCE: 30

Gly Gln Phe Cys His Lys Pro Cys Pro Pro Gly Glu Arg Lys Ala Arg
 1               5                  10                  15

Asp Cys Thr Val
            20

<210> SEQ ID NO 31
<211> LENGTH: 21
<212> TYPE: PRT
<213> ORGANISM: Homo sapiens

<400> SEQUENCE: 31

Gly Glu Arg Lys Ala Arg Asp Cys Thr Val Asn Gly Asp Glu Pro Asp
 1               5                  10                  15

Cys Val Pro Cys Gln
            20

<210> SEQ ID NO 32
<211> LENGTH: 20
<212> TYPE: PRT
<213> ORGANISM: Homo sapiens

<400> SEQUENCE: 32

Asn Gly Asp Glu Pro Asp Cys Val Pro Cys Gln Glu Gly Lys Glu Tyr
 1               5                  10                  15

Thr Asp Lys Ala
            20

<210> SEQ ID NO 33
<211> LENGTH: 19
<212> TYPE: PRT
<213> ORGANISM: Homo sapiens

<400> SEQUENCE: 33

```
Glu Gly Lys Glu Tyr Thr Asp Lys Ala His Phe Ser Ser Lys Cys Arg
 1               5                  10                  15

Arg Cys Arg
```

<210> SEQ ID NO 34
<211> LENGTH: 20
<212> TYPE: PRT
<213> ORGANISM: Homo sapiens

<400> SEQUENCE: 34

```
His Phe Ser Ser Lys Cys Arg Arg Cys Arg Leu Cys Asp Glu Gly His
 1               5                  10                  15

Gly Leu Glu Val
            20
```

<210> SEQ ID NO 35
<211> LENGTH: 20
<212> TYPE: PRT
<213> ORGANISM: Homo sapiens

<400> SEQUENCE: 35

```
Leu Cys Asp Glu Gly His Gly Leu Glu Val Glu Ile Asn Cys Thr Arg
 1               5                  10                  15

Thr Gln Asn Thr
            20
```

<210> SEQ ID NO 36
<211> LENGTH: 20
<212> TYPE: PRT
<213> ORGANISM: Homo sapiens

<400> SEQUENCE: 36

```
Glu Ile Asn Cys Thr Arg Thr Gln Asn Thr Lys Cys Arg Cys Lys Pro
 1               5                  10                  15

Asn Phe Phe Cys
            20
```

<210> SEQ ID NO 37
<211> LENGTH: 20
<212> TYPE: PRT
<213> ORGANISM: Homo sapiens

<400> SEQUENCE: 37

```
Lys Cys Arg Cys Lys Pro Asn Phe Phe Cys Asn Ser Thr Val Cys Glu
 1               5                  10                  15

His Cys Asp Pro
            20
```

<210> SEQ ID NO 38
<211> LENGTH: 20
<212> TYPE: PRT
<213> ORGANISM: Homo sapiens

<400> SEQUENCE: 38

```
Asn Ser Thr Val Cys Glu His Cys Asp Pro Cys Thr Lys Cys Glu His
 1               5                  10                  15

Gly Ile Ile Lys
            20
```

<210> SEQ ID NO 39
<211> LENGTH: 20

```
<212> TYPE: PRT
<213> ORGANISM: Homo sapiens

<400> SEQUENCE: 39

Cys Thr Lys Cys Glu His Gly Ile Ile Lys Glu Cys Thr Leu Thr Ser
  1               5                  10                  15

Asn Thr Lys Cys
            20

<210> SEQ ID NO 40
<211> LENGTH: 18
<212> TYPE: PRT
<213> ORGANISM: Homo sapiens

<400> SEQUENCE: 40

Glu Cys Thr Leu Thr Ser Asn Thr Lys Cys Lys Glu Glu Gly Ser Arg
  1               5                  10                  15

Ser Asn

<210> SEQ ID NO 41
<211> LENGTH: 20
<212> TYPE: PRT
<213> ORGANISM: Homo sapiens

<400> SEQUENCE: 41

Ser Ser Gly Lys Tyr Glu Gly Gly Asn Ile Tyr Thr Lys Lys Glu Ala
  1               5                  10                  15

Phe Asn Val Glu
            20

<210> SEQ ID NO 42
<211> LENGTH: 10
<212> TYPE: PRT
<213> ORGANISM: Homo sapiens

<400> SEQUENCE: 42

His Gly Leu Glu Val Glu Ile Asn Cys Thr
  1               5                  10

<210> SEQ ID NO 43
<211> LENGTH: 10
<212> TYPE: PRT
<213> ORGANISM: Homo sapiens

<400> SEQUENCE: 43

Glu Ile Asn Cys Thr Arg Thr Gln Asn Thr
  1               5                  10

<210> SEQ ID NO 44
<211> LENGTH: 10
<212> TYPE: PRT
<213> ORGANISM: Homo sapiens

<400> SEQUENCE: 44

Lys Cys Arg Cys Lys Pro Asn Phe Phe Cys
  1               5                  10

<210> SEQ ID NO 45
<211> LENGTH: 14
<212> TYPE: PRT
<213> ORGANISM: Homo sapiens

<400> SEQUENCE: 45
```

```
Pro Asn Phe Phe Cys Asn Ser Thr Val Cys Glu His Cys Asp
 1               5                  10
```

<210> SEQ ID NO 46
<211> LENGTH: 10
<212> TYPE: PRT
<213> ORGANISM: Homo sapiens

<400> SEQUENCE: 46

```
Gly Lys Ile Ala Ser Cys Leu Asn Asp Asn
 1               5                  10
```

<210> SEQ ID NO 47
<211> LENGTH: 34
<212> TYPE: DNA
<213> ORGANISM: Homo sapiens

<400> SEQUENCE: 47
gcgaattctg ccttgactga tcagagtttc ctca                               34

<210> SEQ ID NO 48
<211> LENGTH: 32
<212> TYPE: DNA
<213> ORGANISM: Homo sapiens

<400> SEQUENCE: 48
gctctagatg aggtgaaaga tgagctggag ga                                 32

<210> SEQ ID NO 49
<211> LENGTH: 768
<212> TYPE: DNA
<213> ORGANISM: Artificial Sequence
<220> FEATURE:
<221> NAME/KEY: CDS
<222> LOCATION: (40)..(753)
<220> FEATURE:
<221> NAME/KEY: mat peptide
<222> LOCATION: (100)..(753)
<220> FEATURE:
<221> NAME/KEY: sig peptide
<222> LOCATION: (40)..(99)
<220> FEATURE:
<223> OTHER INFORMATION: Description of Artificial Sequence: Designed
      DNA encoding the light chain of humanized anti-human
      Fas antibody

<400> SEQUENCE: 49

```
cccaagctta agaagcatcc tctcatctag ttctcagag atg gag aca gac aca      54
                                            Met Glu Thr Asp Thr
                                                -20 atc ctg cta tgg gtg ctg ctg ctc tgg gtt cca ggc tcc act ggt gac   102
Ile Leu Leu Trp Val Leu Leu Leu Trp Val Pro Gly Ser Thr Gly Asp
-15                 -10                 -5                  -1  1 att gtg ctc acc caa tct cca ggt act ttg tct ctg tct cca ggg gag   150
Ile Val Leu Thr Gln Ser Pro Gly Thr Leu Ser Leu Ser Pro Gly Glu
                5                   10                  15 agg gcc acc ctc tcc tgc aag gcc agc caa agt gtt gat tat gat ggt   198
Arg Ala Thr Leu Ser Cys Lys Ala Ser Gln Ser Val Asp Tyr Asp Gly
         20                  25                  30 gat agt tat atg aac tgg tac caa cag aaa cca gga cag gca ccc aga   246
Asp Ser Tyr Met Asn Trp Tyr Gln Gln Lys Pro Gly Gln Ala Pro Arg
     35                  40                  45 ctc ctc atc tat gct gca tcc aat ctc gaa tct ggg atc cca gac agg   294
Leu Leu Ile Tyr Ala Ala Ser Asn Leu Glu Ser Gly Ile Pro Asp Arg
 50                  55                  60                  65
```

-continued

```
ttt agt ggc agt ggg tct ggg aca gac ttc acc ctc acc atc tct cgt      342
Phe Ser Gly Ser Gly Ser Gly Thr Asp Phe Thr Leu Thr Ile Ser Arg
         70                      75                      80 ctg gag ccg gcg gat ttt gca gtc tat tac tgt cag caa agt aat gag      390
Leu Glu Pro Ala Asp Phe Ala Val Tyr Tyr Cys Gln Gln Ser Asn Glu
                 85                      90                  95 gat cct cgg acg ttc ggt caa ggc acc agg ctg gaa atc aaa cgg act      438
Asp Pro Arg Thr Phe Gly Gln Gly Thr Arg Leu Glu Ile Lys Arg Thr
             100                     105                     110 gtg gct gca cca tct gtc ttc atc ttc ccg cca tct gat gag cag ttg      486
Val Ala Ala Pro Ser Val Phe Ile Phe Pro Pro Ser Asp Glu Gln Leu
         115                     120                     125 aaa tct gga act gcc tct gtt gtg tgc ctg ctg aat aac ttc tat ccc      534
Lys Ser Gly Thr Ala Ser Val Val Cys Leu Leu Asn Asn Phe Tyr Pro
130                     135                     140                 145 aga gag gcc aaa gta cag tgg aag gtg gat aac gcc ctc caa tcg ggt      582
Arg Glu Ala Lys Val Gln Trp Lys Val Asp Asn Ala Leu Gln Ser Gly
                 150                     155                 160 aac tcc cag gag agt gtc aca gag cag gac agc aag gac agc acc tac      630
Asn Ser Gln Glu Ser Val Thr Glu Gln Asp Ser Lys Asp Ser Thr Tyr
             165                     170                     175 agc ctc agc agc acc ctg acg ctg agc aaa gca gac tac gag aaa cac      678
Ser Leu Ser Ser Thr Leu Thr Leu Ser Lys Ala Asp Tyr Glu Lys His
         180                     185                     190 aaa gtc tac gcc tgc gaa gtc acc cat cag ggc ctg agc tcg ccc gtc      726
Lys Val Tyr Ala Cys Glu Val Thr His Gln Gly Leu Ser Ser Pro Val
195                     200                     205 aca aag agc ttc aac agg gga gag tgt tagtaagaat tcggg                 768
Thr Lys Ser Phe Asn Arg Gly Glu Cys
210                     215
```

<210> SEQ ID NO 50
<211> LENGTH: 238
<212> TYPE: PRT
<213> ORGANISM: Artificial Sequence
<220> FEATURE:
<223> OTHER INFORMATION: Description of Artificial Sequence: Designed
      light chain of humanized anti-Fas antibody

<400> SEQUENCE: 50

```
Met Glu Thr Asp Thr Ile Leu Leu Trp Val Leu Leu Leu Trp Val Pro
-20                 -15                 -10                  -5

Gly Ser Thr Gly Asp Ile Val Leu Thr Gln Ser Pro Gly Thr Leu Ser
             -1   1               5                      10

Leu Ser Pro Gly Glu Arg Ala Thr Leu Ser Cys Lys Ala Ser Gln Ser
         15                  20                  25

Val Asp Tyr Asp Gly Asp Ser Tyr Met Asn Trp Tyr Gln Gln Lys Pro
     30                  35                  40

Gly Gln Ala Pro Arg Leu Leu Ile Tyr Ala Ala Ser Asn Leu Glu Ser
45                  50                  55                  60

Gly Ile Pro Asp Arg Phe Ser Gly Ser Gly Ser Gly Thr Asp Phe Thr
                 65                  70                  75

Leu Thr Ile Ser Arg Leu Glu Pro Ala Asp Phe Ala Val Tyr Tyr Cys
             80                  85                  90

Gln Gln Ser Asn Glu Asp Pro Arg Thr Phe Gly Gln Gly Thr Arg Leu
         95                     100                     105

Glu Ile Lys Arg Thr Val Ala Ala Pro Ser Val Phe Ile Phe Pro Pro
     110                     115                     120

Ser Asp Glu Gln Leu Lys Ser Gly Thr Ala Ser Val Val Cys Leu Leu
```

```
                125                 130                 135                 140
         Asn Asn Phe Tyr Pro Arg Glu Ala Lys Val Gln Trp Lys Val Asp Asn
                         145                 150                 155

Ala Leu Gln Ser Gly Asn Ser Gln Glu Ser Val Thr Glu Gln Asp Ser
                         160                 165                 170

Lys Asp Ser Thr Tyr Ser Leu Ser Ser Thr Leu Thr Leu Ser Lys Ala
                     175                 180                 185

Asp Tyr Glu Lys His Lys Val Tyr Ala Cys Glu Val Thr His Gln Gly
                 190                 195                 200

Leu Ser Ser Pro Val Thr Lys Ser Phe Asn Arg Gly Glu Cys
         205                 210                 215

<210> SEQ ID NO 51
<211> LENGTH: 768
<212> TYPE: DNA
<213> ORGANISM: Artificial Sequence
<220> FEATURE:
<221> NAME/KEY: CDS
<222> LOCATION: (40)..(753)
<220> FEATURE:
<221> NAME/KEY: mat peptide
<222> LOCATION: (100)..(753)
<220> FEATURE:
<221> NAME/KEY: sig peptide
<222> LOCATION: (40)..(99)
<220> FEATURE:
<223> OTHER INFORMATION: Description of Artificial Sequence: Designed
      DNA encoding the light chain of humanized anti-human
      Fas antibody

<400> SEQUENCE: 51
cccaagctta agaagcatcc tctcatctag ttctcagag atg gag aca gac aca          54
                                            Met Glu Thr Asp Thr
                                                -20 atc ctg cta tgg gtg ctg ctc tgg gtt cca ggc tcc act ggt gac           102
Ile Leu Leu Trp Val Leu Leu Trp Val Pro Gly Ser Thr Gly Asp
-15                 -10                  -5                 -1   1 att gtg ctc acc caa tct cca ggt act ttg tct ctg tct cca ggg gag       150
Ile Val Leu Thr Gln Ser Pro Gly Thr Leu Ser Leu Ser Pro Gly Glu
             5                  10                  15 agg gcc acc ctc tcc tgc aag gcc agc caa agt gtt gat tat gat ggt       198
Arg Ala Thr Leu Ser Cys Lys Ala Ser Gln Ser Val Asp Tyr Asp Gly
         20                  25                  30 gat agt tat atg aac tgg tac caa cag aaa cca gga cag gca ccc aga       246
Asp Ser Tyr Met Asn Trp Tyr Gln Gln Lys Pro Gly Gln Ala Pro Arg
     35                  40                  45 ctc ctc atc tat gct gca tcc aat ctc gaa tct ggg atc cca gac agg       294
Leu Leu Ile Tyr Ala Ala Ser Asn Leu Glu Ser Gly Ile Pro Asp Arg
 50                  55                  60                  65 ttt agt ggc agt ggg tct ggg aca gac ttc acc ctc acc atc cat cct       342
Phe Ser Gly Ser Gly Ser Gly Thr Asp Phe Thr Leu Thr Ile His Pro
                 70                  75                  80 gtg gag gag gag gat gct gca acc tat tac tgt cag caa agt aat gag       390
Val Glu Glu Glu Asp Ala Ala Thr Tyr Tyr Cys Gln Gln Ser Asn Glu
             85                  90                  95 gat cct cgg acg ttc ggt caa ggc acc agg ctg gaa atc aaa cgg act       438
Asp Pro Arg Thr Phe Gly Gln Gly Thr Arg Leu Glu Ile Lys Arg Thr
         100                 105                 110 gtg gct gca cca tct gtc ttc atc ttc ccg cca tct gat gag cag ttg       486
Val Ala Ala Pro Ser Val Phe Ile Phe Pro Pro Ser Asp Glu Gln Leu
     115                 120                 125 aaa tct gga act gcc tct gtt gtg tgc ctg ctg aat aac ttc tat ccc       534
```

-continued

```
Lys Ser Gly Thr Ala Ser Val Val Cys Leu Leu Asn Asn Phe Tyr Pro
130             135                 140                 145 aga gag gcc aaa gta cag tgg aaa gtg gat aac gcc ctc caa tcg ggt        582
Arg Glu Ala Lys Val Gln Trp Lys Val Asp Asn Ala Leu Gln Ser Gly
            150                 155                 160 aac tcc cag gag agt gtc aca gag cag gac agc aag gac agc acc tac        630
Asn Ser Gln Glu Ser Val Thr Glu Gln Asp Ser Lys Asp Ser Thr Tyr
                165                 170                 175 agc ctc agc agc acc ctg acg ctg agc aaa gca gac tac gag aaa cac        678
Ser Leu Ser Ser Thr Leu Thr Leu Ser Lys Ala Asp Tyr Glu Lys His
            180                 185                 190 aaa gtc tac gcc tgc gaa gtc acc cat cag ggc ctg agc tcg ccc gtc        726
Lys Val Tyr Ala Cys Glu Val Thr His Gln Gly Leu Ser Ser Pro Val
    195                 200                 205 aca aag agc ttc aac agg gga gag tgt tagtaagaat tcggg                   768
Thr Lys Ser Phe Asn Arg Gly Glu Cys
210             215
```

<210> SEQ ID NO 52
<211> LENGTH: 238
<212> TYPE: PRT
<213> ORGANISM: Artificial Sequence
<220> FEATURE:
<223> OTHER INFORMATION: Description of Artificial Sequence: Designed
    light chain of humanized anti-Fas antibody

<400> SEQUENCE: 52

```
Met Glu Thr Asp Thr Ile Leu Leu Trp Val Leu Leu Leu Trp Val Pro
-20                 -15                 -10                  -5

Gly Ser Thr Gly Asp Ile Val Leu Thr Gln Ser Pro Gly Thr Leu Ser
            -1   1               5                  10

Leu Ser Pro Gly Glu Arg Ala Thr Leu Ser Cys Lys Ala Ser Gln Ser
        15                  20                  25

Val Asp Tyr Asp Gly Asp Ser Tyr Met Asn Trp Tyr Gln Gln Lys Pro
    30                  35                  40

Gly Gln Ala Pro Arg Leu Leu Ile Tyr Ala Ala Ser Asn Leu Glu Ser
45                  50                  55                  60

Gly Ile Pro Asp Arg Phe Ser Gly Ser Gly Ser Gly Thr Asp Phe Thr
                65                  70                  75

Leu Thr Ile His Pro Val Glu Glu Asp Ala Ala Thr Tyr Tyr Cys
            80                  85                  90

Gln Gln Ser Asn Glu Asp Pro Arg Thr Phe Gly Gln Gly Thr Arg Leu
        95                  100                 105

Glu Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu Leu
125                 130                 135                 140

Asn Asn Phe Tyr Pro Arg Glu Ala Lys Val Gln Trp Lys Val Asp Asn
                145                 150                 155

Ala Leu Gln Ser Gly Asn Ser Gln Glu Ser Val Thr Glu Gln Asp Ser
            160                 165                 170

Lys Asp Ser Thr Tyr Ser Leu Ser Ser Thr Leu Thr Leu Ser Lys Ala
        175                 180                 185

Asp Tyr Glu Lys His Lys Val Tyr Ala Cys Glu Val Thr His Gln Gly
    190                 195                 200

Leu Ser Ser Pro Val Thr Lys Ser Phe Asn Arg Gly Glu Cys
205                 210                 215
```

<210> SEQ ID NO 53
<211> LENGTH: 768
<212> TYPE: DNA
<213> ORGANISM: Artificial Sequence
<220> FEATURE:
<221> NAME/KEY: CDS
<222> LOCATION: (40)..(753)
<220> FEATURE:
<221> NAME/KEY: mat peptide
<222> LOCATION: (100)..(753)
<220> FEATURE:
<221> NAME/KEY: sig peptide
<222> LOCATION: (40)..(99)
<220> FEATURE:
<223> OTHER INFORMATION: Description of Artificial Sequence: Designed DNA encoding the light chain of humanized anti-human Fas antibody

<400> SEQUENCE: 53

| | | | | | | | | | | | | | | | |
|---|---|---|---|---|---|---|---|---|---|---|---|---|---|---|---|
| cccaagctta agaagcatcc tctcatctag ttctcagag atg gag aca gac aca | | | | | | | | | | | | | | | 54 |
| | | | | | | | | | | Met | Glu | Thr | Asp | Thr | |
| | | | | | | | | | | | | | -20 | | |
| atc | ctg | cta | tgg | gtg | ctg | ctg | ctc | tgg | gtt | cca | ggc | tcc | act | ggt gac | 102 |
| Ile | Leu | Leu | Trp | Val | Leu | Leu | Leu | Trp | Val | Pro | Gly | Ser | Thr | Gly Asp | |
| -15 | | | | -10 | | | | | -5 | | | | | -1  1 | |
| att | gtg | ctc | acc | caa | tct | cca | ggt | act | ttg | tct | ctg | tct | cca | ggg gag | 150 |
| Ile | Val | Leu | Thr | Gln | Ser | Pro | Gly | Thr | Leu | Ser | Leu | Ser | Pro | Gly Glu | |
| | | | 5 | | | | | 10 | | | | | 15 | | |
| agg | gcc | acc | ctc | tcc | tgc | aag | gcc | agc | caa | agt | gtt | gat | tat | gat ggt | 198 |
| Arg | Ala | Thr | Leu | Ser | Cys | Lys | Ala | Ser | Gln | Ser | Val | Asp | Tyr | Asp Gly | |
| | | 20 | | | | | 25 | | | | | 30 | | | |
| gat | agt | tat | atg | aac | tgg | tac | caa | cag | aaa | cca | gga | cag | cca | ccc aaa | 246 |
| Asp | Ser | Tyr | Met | Asn | Trp | Tyr | Gln | Gln | Lys | Pro | Gly | Gln | Pro | Pro Lys | |
| | 35 | | | | | 40 | | | | | 45 | | | | |
| ctc | ctc | atc | tat | gct | gca | tcc | aat | ctc | gaa | tct | ggg | atc | cca | gac agg | 294 |
| Leu | Leu | Ile | Tyr | Ala | Ala | Ser | Asn | Leu | Glu | Ser | Gly | Ile | Pro | Asp Arg | |
| 50 | | | | | 55 | | | | | 60 | | | | | 65 |
| ttt | agt | ggc | agt | ggg | tct | ggg | aca | gac | ttc | acc | ctc | acc | atc | cat cct | 342 |
| Phe | Ser | Gly | Ser | Gly | Ser | Gly | Thr | Asp | Phe | Thr | Leu | Thr | Ile | His Pro | |
| | | | 70 | | | | | 75 | | | | | 80 | | |
| gtg | gag | gag | gag | gat | gct | gca | acc | tat | tac | tgt | cag | caa | agt | aat gag | 390 |
| Val | Glu | Glu | Glu | Asp | Ala | Ala | Thr | Tyr | Tyr | Cys | Gln | Gln | Ser | Asn Glu | |
| | | | | 85 | | | | | 90 | | | | | 95 | |
| gat | cct | cgg | acg | ttc | ggt | caa | ggc | acc | agg | ctg | gaa | atc | aaa | cgg act | 438 |
| Asp | Pro | Arg | Thr | Phe | Gly | Gln | Gly | Thr | Arg | Leu | Glu | Ile | Lys | Arg Thr | |
| | | | 100 | | | | | 105 | | | | | 110 | | |
| gtg | gct | gca | cca | tct | gtc | ttc | atc | ttc | ccg | cca | tct | gat | gag | cag ttg | 486 |
| Val | Ala | Ala | Pro | Ser | Val | Phe | Ile | Phe | Pro | Pro | Ser | Asp | Glu | Gln Leu | |
| | 115 | | | | | 120 | | | | | 125 | | | | |
| aaa | tct | gga | act | gcc | tct | gtt | gtg | tgc | ctg | ctg | aat | aac | ttc | tat ccc | 534 |
| Lys | Ser | Gly | Thr | Ala | Ser | Val | Val | Cys | Leu | Leu | Asn | Asn | Phe | Tyr Pro | |
| 130 | | | | | 135 | | | | | 140 | | | | | 145 |
| aga | gag | gcc | aaa | gta | cag | tgg | aaa | gtg | gat | aac | gcc | ctc | caa | tcg ggt | 582 |
| Arg | Glu | Ala | Lys | Val | Gln | Trp | Lys | Val | Asp | Asn | Ala | Leu | Gln | Ser Gly | |
| | | | | 150 | | | | | 155 | | | | | 160 | |
| aac | tcc | cag | gag | agt | gtc | aca | gag | cag | gac | agc | aag | gac | agc | acc tac | 630 |
| Asn | Ser | Gln | Glu | Ser | Val | Thr | Glu | Gln | Asp | Ser | Lys | Asp | Ser | Thr Tyr | |
| | | | | 165 | | | | | 170 | | | | | 175 | |
| agc | ctc | agc | agc | acc | ctg | acg | ctg | agc | aaa | gca | gac | tac | gag | aaa cac | 678 |
| Ser | Leu | Ser | Ser | Thr | Leu | Thr | Leu | Ser | Lys | Ala | Asp | Tyr | Glu | Lys His | |
| | | 180 | | | | | 185 | | | | | 190 | | | |
| aaa | gtc | tac | gcc | tgc | gaa | gtc | acc | cat | cag | ggc | ctg | agc | tcg | ccc gtc | 726 |

-continued

```
Lys Val Tyr Ala Cys Glu Val Thr His Gln Gly Leu Ser Ser Pro Val
    195                 200                 205 aca aag agc ttc aac agg gga gag tgt tagtaagaat tcggg              768
Thr Lys Ser Phe Asn Arg Gly Glu Cys
210                 215
```

<210> SEQ ID NO 54
<211> LENGTH: 238
<212> TYPE: PRT
<213> ORGANISM: Artificial Sequence
<220> FEATURE:
<223> OTHER INFORMATION: Description of Artificial Sequence: Designed
      light chain of humanized anti-Fas antibody

<400> SEQUENCE: 54

```
Met Glu Thr Asp Thr Ile Leu Leu Trp Val Leu Leu Leu Trp Val Pro
-20                 -15                 -10                  -5

Gly Ser Thr Gly Asp Ile Val Leu Thr Gln Ser Pro Gly Thr Leu Ser
            -1   1               5                  10

Leu Ser Pro Gly Glu Arg Ala Thr Leu Ser Cys Lys Ala Ser Gln Ser
        15                  20                  25

Val Asp Tyr Asp Gly Asp Ser Tyr Met Asn Trp Tyr Gln Gln Lys Pro
    30                  35                  40

Gly Gln Pro Pro Lys Leu Leu Ile Tyr Ala Ala Ser Asn Leu Glu Ser
45                  50                  55                  60

Gly Ile Pro Asp Arg Phe Ser Gly Ser Gly Ser Gly Thr Asp Phe Thr
                65                  70                  75

Leu Thr Ile His Pro Val Glu Glu Glu Asp Ala Ala Thr Tyr Tyr Cys
            80                  85                  90

Gln Gln Ser Asn Glu Asp Pro Arg Thr Phe Gly Gln Gly Thr Arg Leu
        95                  100                 105

Glu Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu Leu
125                 130                 135                 140

Asn Asn Phe Tyr Pro Arg Glu Ala Lys Val Gln Trp Lys Val Asp Asn
                145                 150                 155

Ala Leu Gln Ser Gly Asn Ser Gln Glu Ser Val Thr Glu Gln Asp Ser
            160                 165                 170

Lys Asp Ser Thr Tyr Ser Leu Ser Ser Thr Leu Thr Leu Ser Lys Ala
        175                 180                 185

Asp Tyr Glu Lys His Lys Val Tyr Ala Cys Glu Val Thr His Gln Gly
    190                 195                 200

Leu Ser Ser Pro Val Thr Lys Ser Phe Asn Arg Gly Glu Cys
205                 210                 215
```

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 55
cccaagctta agaagcatcc tctcatctag ttct                             34

<210> SEQ ID NO 56

```
<211> LENGTH: 44
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 56
gagagggtgg ccctctcccc tggagacaga gacaaagtac ctgg              44

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 57
ccaggtactt tgtctctgtc tccaggggag agggccaccc tctc              44

<210> SEQ ID NO 58
<211> LENGTH: 44
<212> TYPE: DNA
<213> ORGANISM: Artificial Sequence
<220> FEATURE:
<223> OTHER INFORMATION: Description of Artificial Sequence: PCR primer
      to      amplify a fragment of DNA encoding the light
      chain of humanized anti-Fas antibody

<400> SEQUENCE: 58
gattcgagat tggatgcagc atagatgagg agtctgggtg cctg              44

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 59
gctgcatcca atctcgaatc tgggatccca gacaggttta gtggc             45

<210> SEQ ID NO 60
<211> LENGTH: 52
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 60
aaaatccgcc ggctccagac gagagatggt gagggtgaag tctgtcccag ac     52

<210> SEQ ID NO 61
<211> LENGTH: 58
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 61
```
ctcgtctgga gccggcggat tttgcagtct attactgtca gcaaagtaat gaggatcc        58

<210> SEQ ID NO 62
<211> LENGTH: 55
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 62
tgaagacaga tggtgcagcc acagtccgtt tgatttccag cctggtgcct tgacc          55

<210> SEQ ID NO 63
<211> LENGTH: 55
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 63
ggtcaaggca ccaggctgga aatcaaacgg actgtggctg caccatctgt cttca          55

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 64
cccgaattct tactaacact ctcccctgtt gaagctcttt gtgac                     45

<210> SEQ ID NO 65
<211> LENGTH: 55
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 65
tctgtcccag acccactgcc actaaacctg tctgggatcc cagattcgag attgg          55

<210> SEQ ID NO 66
<211> LENGTH: 55
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light
      chain of humanized anti-Fas antibody

<400> SEQUENCE: 66
gtttagtggc agtgggtctg ggacagactt cacctctacc atccatcctg tggag          55

<210> SEQ ID NO 67
<211> LENGTH: 55
<212> TYPE: DNA
<213> ORGANISM: Artificial Sequence
<220> FEATURE:

```
<223> OTHER INFORMATION: Description of Artificial Sequence: PCR primer
      to amplify a fragment of DNA encoding the light
      chain of humanized anti-Fas antibody

<400> SEQUENCE: 67
atggtgcagc cacagtccgt ttgatttcca gcctggtgcc ttgaccgaac gtccg            55

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for DNAs encoding the light chains of
      humanized anti-Fas antibodies

<400> SEQUENCE: 68
cccaagctta agaagcatcc                                                   20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for DNAs encoding the light chains of
      humanized anti-Fas antibodies

<400> SEQUENCE: 69
atctatgctg catccaatct                                                   20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for DNAs encoding the light chains of
      humanized anti-Fas antibodies

<400> SEQUENCE: 70
gttgtgtgcc tgctgaataa                                                   20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for DNAs encoding the light chains of
      humanized anti-Fas antibodies

<400> SEQUENCE: 71
cccgaattct tactaacact                                                   20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for DNAs encoding the light chains of
      humanized anti-Fas antibodies

<400> SEQUENCE: 72
ttattcagca ggcacacaac                                                   20
```

```
<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for DNAs encoding the light chains of
      humanized anti-Fas antibodies

<400> SEQUENCE: 73
agattggatg cagcatagat                                                    20

<210> SEQ ID NO 74
<211> LENGTH: 457
<212> TYPE: DNA
<213> ORGANISM: Artificial Sequence
<220> FEATURE:
<223> OTHER INFORMATION: Description of Artificial Sequence: DNA
      encoding the partial peptide of the heavy chain of a
      humanized anti-Fas antibody
<220> FEATURE:
<221> NAME/KEY: CDS
<222> LOCATION: (21)..(455)
<220> FEATURE:
<221> NAME/KEY: mat peptide
<222> LOCATION: (78)..(455)
<220> FEATURE:
<221> NAME/KEY: sig peptide
<222> LOCATION: (21)..(77)

<400> SEQUENCE: 74
aagcttggct tgacctcacc atg gga tgg agc tgt atc atc ctc ttc ttg gta      53
                     Met Gly Trp Ser Cys Ile Ile Leu Phe Leu Val
                                 -15                 -10 gca aca gct aca ggt gtc cac tct cag gtc caa ctg gtg cag tct ggg       101
Ala Thr Ala Thr Gly Val His Ser Gln Val Gln Leu Val Gln Ser Gly
             -5              -1   1               5 gct gag gtc aag aag cct ggg gct tca gtg aag gtg tcc tgc aag gct       149
Ala Glu Val Lys Lys Pro Gly Ala Ser Val Lys Val Ser Cys Lys Ala
        10                  15                  20 tct ggc tac acc ttc acc agc tac tgg atg cag tgg gta aaa cag gcc       197
Ser Gly Tyr Thr Phe Thr Ser Tyr Trp Met Gln Trp Val Lys Gln Ala
25                  30                  35                  40 cct gga cag agg ctt gag tgg atg gga gag att gat cct tct gat agc       245
Pro Gly Gln Arg Leu Glu Trp Met Gly Glu Ile Asp Pro Ser Asp Ser
                45                  50                  55 tat act aac tac aat caa aag ttc aag ggc aag gcc aca ttg act gta       293
Tyr Thr Asn Tyr Asn Gln Lys Phe Lys Gly Lys Ala Thr Leu Thr Val
            60                  65                  70 gac aca tcc gct agc aca gcc tac atg gag ctc agc agc ctg aga tct       341
Asp Thr Ser Ala Ser Thr Ala Tyr Met Glu Leu Ser Ser Leu Arg Ser
        75                  80                  85 gag gac acg gcg gtc tat tac tgt gca aga aat agg gac tat agt aac       389
Glu Asp Thr Ala Val Tyr Tyr Cys Ala Arg Asn Arg Asp Tyr Ser Asn
    90                  95                  100 aac tgg tac ttc gat gtc tgg ggc gaa ggg acc ctg gtc acc gtc tcc       437
Asn Trp Tyr Phe Asp Val Trp Gly Glu Gly Thr Leu Val Thr Val Ser
105                 110                 115                 120 tca gcc tcc acc aag ggc cc                                            457
Ser Ala Ser Thr Lys Gly
                125

<210> SEQ ID NO 75
<211> LENGTH: 145
<212> TYPE: PRT
<213> ORGANISM: Artificial Sequence
```

```
<220> FEATURE:
<223> OTHER INFORMATION: Description of Artificial Sequence: Designed
      partial peptide of the heavy chain of humanized anti-human
      Fas antibody

<400> SEQUENCE: 75

Met Gly Trp Ser Cys Ile Ile Leu Phe Leu Val Ala Thr Ala Thr Gly
                -15                 -10                  -5
Val His Ser Gln Val Gln Leu Val Gln Ser Gly Ala Glu Val Lys Lys
         -1   1               5                  10
Pro Gly Ala Ser Val Lys Val Ser Cys Lys Ala Ser Gly Tyr Thr Phe
             15                  20                  25
Thr Ser Tyr Trp Met Gln Trp Val Lys Gln Ala Pro Gly Gln Arg Leu
         30                  35                  40                  45
Glu Trp Met Gly Glu Ile Asp Pro Ser Asp Ser Tyr Thr Asn Tyr Asn
                 50                  55                  60
Gln Lys Phe Lys Gly Lys Ala Thr Leu Thr Val Asp Thr Ser Ala Ser
             65                  70                  75
Thr Ala Tyr Met Glu Leu Ser Ser Leu Arg Ser Glu Asp Thr Ala Val
         80                  85                  90
Tyr Tyr Cys Ala Arg Asn Arg Asp Tyr Ser Asn Asn Trp Tyr Phe Asp
     95                 100                 105
Val Trp Gly Glu Gly Thr Leu Val Thr Val Ser Ser Ala Ser Thr Lys
110                 115                 120                 125
Gly

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: PCR
      primer to amplify a fragment of the DNA encoding variable
      region in the heavy chain of a humanized anti-Fas
      antibody

<400> SEQUENCE: 76
gggaagcttg gcttgacctc accatgggat ggagctgtat                           40

<210> SEQ ID NO 77
<211> LENGTH: 48
<212> TYPE: DNA
<213> ORGANISM: Artificial Sequence
<220> FEATURE:
<223> OTHER INFORMATION: Description of Artificial Sequence: PCR
      primer to amplify a fragment of the DNA encoding variable
      region in the heavy chain of a humanized anti-Fas
      antibody

<400> SEQUENCE: 77
tgaagcccca ggcttcttga cctcagcccc agactgcacc agttggac                  48

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding variable
      region in the heavy chain of a humanized anti-Fas
      antibody

<400> SEQUENCE: 78
```

```
tccactcaag cctctgtcca ggggcctgtt ttaccc                              36
```

<210> SEQ ID NO 79
<211> LENGTH: 52
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding variable
      region in the heavy chain of a humanized anti-Fas
      antibody

<400> SEQUENCE: 79

```
gtctggggct gaggtcaaga agcctggggc ttcagtgaag gtgtcctgca ag            52
```

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding variable
      region in the heavy chain of a humanized anti-Fas
      antibody

<400> SEQUENCE: 80

```
caggcccctg gacagaggct tgagtggatg ggagagatt                           39
```

<210> SEQ ID NO 81
<211> LENGTH: 50
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding variable
      region in the heavy chain of a humanized anti-Fas
      antibody

<400> SEQUENCE: 81

```
tcagatctca ggctgctgag ctccatgtag gctgtgctag cggatgtgtc               50
```

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding variable
      region in the heavy chain of a humanized anti-Fas
      antibody

<400> SEQUENCE: 82

```
tggagctcag cagcctgaga tctgaggaca cggcggtcta ttac                     44
```

<210> SEQ ID NO 83
<211> LENGTH: 55
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding variable
      region in the heavy chain of a humanized anti-Fas
      antibody

<400> SEQUENCE: 83

```
gatgggccct tggtggaggc tgaggagacg gtgaccaggg tcccttcgcc ccagt         55
```

<210> SEQ ID NO 84

```
<211> LENGTH: 39
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding the
      constant region of human immunoglobulin G1 heavy
      chain

<400> SEQUENCE: 84
gggaagcttc cgcggtcaca tggcaccacc tctcttgca                          39

<210> SEQ ID NO 85
<211> LENGTH: 35
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding the
      constant region of human immunoglobulin G1 heavy
      chain

<400> SEQUENCE: 85
gctctgcaga gagaagattg ggagttactg gaatc                              35

<210> SEQ ID NO 86
<211> LENGTH: 35
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding the
      constant region of human immunoglobulin G1 heavy
      chain

<400> SEQUENCE: 86
tctctgcaga gcccaaatct tgtgacaaaa ctcac                              35

<210> SEQ ID NO 87
<211> LENGTH: 39
<212> TYPE: DNA
<213> ORGANISM: Artificial Sequence
<220> FEATURE:
<223> OTHER INFORMATION: Description of Artificial Sequence: PCR primer
      to amplify a fragment of the DNA encoding the
      constant region of human immunoglobulin G1 heavy
      chain

<400> SEQUENCE: 87
ggggaattcg ggagcggggc ttgccggccg tcgcactca                          39

<210> SEQ ID NO 88
<211> LENGTH: 2077
<212> TYPE: DNA
<213> ORGANISM: Artificial Sequence
<220> FEATURE:
<223> OTHER INFORMATION: Description of Artificial Sequence: Designed
      DNA encoding the heavy chain of a humanized anti-Fas
      antibody
<220> FEATURE:
<221> NAME/KEY: sig peptide
<222> LOCATION: (27)..(83)
<220> FEATURE:
<221> NAME/KEY: intron
<222> LOCATION: (741)..(1131)
<220> FEATURE:
<221> NAME/KEY: intron
<222> LOCATION: (1177)..(1294)
<220> FEATURE:
<221> NAME/KEY: intron
<222> LOCATION: (1625)..(1721)
```

```
<220> FEATURE:
<221> NAME/KEY: exon
<222> LOCATION: (27)..(740)
<220> FEATURE:
<221> NAME/KEY: exon
<222> LOCATION: (1132)..(1176)
<220> FEATURE:
<221> NAME/KEY: exon
<222> LOCATION: (1295)..(1624)
<220> FEATURE:
<221> NAME/KEY: exon
<222> LOCATION: (1722)..(2042)
<220> FEATURE:
<221> NAME/KEY: mat peptide
<222> LOCATION: (84)..(740)
<220> FEATURE:
<221> NAME/KEY: mat peptide
<222> LOCATION: (1132)..(1176)
<220> FEATURE:
<221> NAME/KEY: mat peptide
<222> LOCATION: (1295)..(1624)
<220> FEATURE:
<221> NAME/KEY: mat peptide
<222> LOCATION: (1722)..(2042)
<220> FEATURE:
<221> NAME/KEY: CDS
<222> LOCATION: (27)..(740)
<220> FEATURE:
<221> NAME/KEY: CDS
<222> LOCATION: (1132)..(1176)
<220> FEATURE:
<221> NAME/KEY: CDS
<222> LOCATION: (1295)..(1624)
<220> FEATURE:
<221> NAME/KEY: CDS
<222> LOCATION: (1722)..(2042)

<400> SEQUENCE: 88
```

```
gggcgaaagc ttggcttgac ctcacc atg gga tgg agc tgt atc atc ctc ttc      53
                              Met Gly Trp Ser Cys Ile Ile Leu Phe
                                                    -15 ttg gta gca aca gct aca ggt gtc cac tct cag gtc caa ctg gtg cag      101
Leu Val Ala Thr Ala Thr Gly Val His Ser Gln Val Gln Leu Val Gln
-10                 -5              -1   1               5 tct ggg gct gag gtc aag aag cct ggg gct tca gtg aag gtg tcc tgc      149
Ser Gly Ala Glu Val Lys Lys Pro Gly Ala Ser Val Lys Val Ser Cys
                10              15              20 aag gct tct ggc tac acc ttc acc agc tac tgg atg cag tgg gta aaa      197
Lys Ala Ser Gly Tyr Thr Phe Thr Ser Tyr Trp Met Gln Trp Val Lys
            25              30              35 cag gcc cct gga cag agg ctt gag tgg atg gga gag att gat cct tct      245
Gln Ala Pro Gly Gln Arg Leu Glu Trp Met Gly Glu Ile Asp Pro Ser
    40              45              50 gat agc tat act aac tac aat caa aag ttc aag ggc aag gcc aca ttg      293
Asp Ser Tyr Thr Asn Tyr Asn Gln Lys Phe Lys Gly Lys Ala Thr Leu
55              60              65              70 act gta gac aca tcc gct agc aca gcc tac atg gag ctc agc agc ctg      341
Thr Val Asp Thr Ser Ala Ser Thr Ala Tyr Met Glu Leu Ser Ser Leu
                75              80              85 aga tct gag gac acg gcg gtc tat tac tgt gca aga aat agg gac tat      389
Arg Ser Glu Asp Thr Ala Val Tyr Tyr Cys Ala Arg Asn Arg Asp Tyr
            90              95              100 agt aac aac tgg tac ttc gat gtc tgg ggc gaa ggg acc ctg gtc acc      437
Ser Asn Asn Trp Tyr Phe Asp Val Trp Gly Glu Gly Thr Leu Val Thr
        105             110             115 gtc tcc tca gcc tcc acc aag ggc cca tcg gtc ttc ccc ctg gca ccc      485
Val Ser Ser Ala Ser Thr Lys Gly Pro Ser Val Phe Pro Leu Ala Pro
120             125             130
```

-continued

| | |
|---|---|
| tcc tcc aag agc acc tct ggg ggc aca gcg gcc ctg ggc tgc ctg gtc<br>Ser Ser Lys Ser Thr Ser Gly Gly Thr Ala Ala Leu Gly Cys Leu Val<br>135              140              145              150 | 533 |
| aag gac tac ttc ccc gaa ccg gtg acg gtg tcg tgg aac tca ggc gcc<br>Lys Asp Tyr Phe Pro Glu Pro Val Thr Val Ser Trp Asn Ser Gly Ala<br>              155              160              165 | 581 |
| ctg acc agc ggc gtg cac acc ttc ccg gct gtc cta cag tcc tca gga<br>Leu Thr Ser Gly Val His Thr Phe Pro Ala Val Leu Gln Ser Ser Gly<br>170              175              180 | 629 |
| ctc tac tcc ctc agc agc gtg gtg acc gtg ccc tcc agc agc ttg ggc<br>Leu Tyr Ser Leu Ser Ser Val Val Thr Val Pro Ser Ser Ser Leu Gly<br>              185              190              195 | 677 |
| acc cag acc tac atc tgc aac gtg aat cac aag ccc agc aac acc aag<br>Thr Gln Thr Tyr Ile Cys Asn Val Asn His Lys Pro Ser Asn Thr Lys<br>200              205              210 | 725 |
| gtg gac aag aga gtt ggtgagaggc cagcacaggg agggagggtg tctgctggaa<br>Val Asp Lys Arg Val<br>215 | 780 |
| gccaggctca gcgctcctgc ctggacgcat cccggctatg cagtcccagt ccagggcagc | 840 |
| aaggcaggcc ccgtctgcct cttcacccgg aggcctctgc ccgccccact catgctcagg | 900 |
| gagagggtct tctggctttt tccccaggct ctgggcaggc acaggctagg tgcccctaac | 960 |
| ccaggccctg cacacaaagg gcaggtgctg ggctcagac ctgccaagag ccatatccgg | 1020 |
| gaggaccctg ccctgacct aagcccaccc caaaggccaa actctccact ccctcagctc | 1080 |
| ggacaccttc tctcctccca gattccagta actcccaatc ttctctctgc a gag ccc<br>                                                                                                                                         Glu Pro<br>                                                                                                                                          220 | 1137 |
| aaa tct tgt gac aaa act cac aca tgc cca ccg tgc cca ggtaagccag<br>Lys Ser Cys Asp Lys Thr His Thr Cys Pro Pro Cys Pro<br>                      225                      230 | 1186 |
| cccaggcctc gccctccagc tcaaggcggg acaggtgccc tagagtagcc tgcatccagg | 1246 |
| gacaggcccc agccgggtgc tgacacgtcc acctccatct cttcctca gca cct gaa<br>                                                                                                                                                        Ala Pro Glu<br>                                                                                                                                                                  235 | 1303 |
| ctc ctg ggg gga ccg tca gtc ttc ctc ttc ccc cca aaa ccc aag gac<br>Leu Leu Gly Gly Pro Ser Val Phe Leu Phe Pro Pro Lys Pro Lys Asp<br>            240              245              250 | 1351 |
| acc ctc atg atc tcc cgg acc cct gag gtc aca tgc gtg gtg gtg gac<br>Thr Leu Met Ile Ser Arg Thr Pro Glu Val Thr Cys Val Val Val Asp<br>255              260              265 | 1399 |
| gtg agc cac gaa gac cct gag gtc aag ttc aac tgg tac gtg gac ggc<br>Val Ser His Glu Asp Pro Glu Val Lys Phe Asn Trp Tyr Val Asp Gly<br>270              275              280              285 | 1447 |
| gtg gag gtg cat aat gcc aag aca aag ccg cgg gag gag cag tac aac<br>Val Glu Val His Asn Ala Lys Thr Lys Pro Arg Glu Glu Gln Tyr Asn<br>              290              295              300 | 1495 |
| agc acg tac cgt gtg gtc agc gtc ctc acc gtc ctg cac cag gac tgg<br>Ser Thr Tyr Arg Val Val Ser Val Leu Thr Val Leu His Gln Asp Trp<br>305              310              315 | 1543 |
| ctg aat ggc aag gag tac aag tgc aag gtc tcc aac aaa gcc ctc cca<br>Leu Asn Gly Lys Glu Tyr Lys Cys Lys Val Ser Asn Lys Ala Leu Pro<br>320              325              330 | 1591 |
| gcc ccc atc gag aaa acc atc tcc aaa gcc aaa gtgggaccc gtggggtgcg<br>Ala Pro Ile Glu Lys Thr Ile Ser Lys Ala Lys<br>335              340 | 1644 |
| agggccacat ggacagaggc cggctcggcc caccctctgc cctgagagtg accgctgtac | 1704 |
| caacctctgt ccctaca ggg cag ccc cga gaa cca cag gtg tac acc ctg | 1754 |

-continued

```
            Gly Gln Pro Arg Glu Pro Gln Val Tyr Thr Leu
            345                 350                 355 ccc cca tcc cgg gag gag atg acc aag aac cag gtc agc ctg acc tgc    1802
Pro Pro Ser Arg Glu Glu Met Thr Lys Asn Gln Val Ser Leu Thr Cys
            360                 365                 370 ctg gtc aaa ggc ttc tat ccc agc gac atc gcc gtg gag tgg gag agc    1850
Leu Val Lys Gly Phe Tyr Pro Ser Asp Ile Ala Val Glu Trp Glu Ser
            375                 380                 385 aat ggg cag ccg gag aac aac tac aag acc acg cct ccc gtg ctg gac    1898
Asn Gly Gln Pro Glu Asn Asn Tyr Lys Thr Thr Pro Pro Val Leu Asp
            390                 395                 400 tcc gac ggc tcc ttc ttc ctc tat agc aag ctc acc gtg gac aag agc    1946
Ser Asp Gly Ser Phe Phe Leu Tyr Ser Lys Leu Thr Val Asp Lys Ser
405                 410                 415 agg tgg cag cag ggg aac gtc ttc tca tgc tcc gtg atg cat gag gct    1994
Arg Trp Gln Gln Gly Asn Val Phe Ser Cys Ser Val Met His Glu Ala
420                 425                 430                 435 ctg cac aac cac tac acg cag aag agc ctc tcc ctg tcc ccg ggt aaa    2042
Leu His Asn His Tyr Thr Gln Lys Ser Leu Ser Leu Ser Pro Gly Lys
            440                 445                 450 tgagtgcgac ggccggcaag ccccgctccc gaatt                              2077
```

<210> SEQ ID NO 89
<211> LENGTH: 470
<212> TYPE: PRT
<213> ORGANISM: Artificial Sequence
<220> FEATURE:
<223> OTHER INFORMATION: Description of Artificial Sequence: Designed
      heavy chain of humanized anti-Fas antibody

<400> SEQUENCE: 89

```
Met Gly Trp Ser Cys Ile Ile Leu Phe Leu Val Ala Thr Ala Thr Gly
                -15                 -10                  -5

Val His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
        15                  20                  25

Thr Ser Tyr Trp Met Gln Trp Val Lys Gln Ala Pro Gly Gln Arg Leu
 30                  35                  40                  45

Glu Trp Met Gly Glu Ile Asp Pro Ser Asp Ser Tyr Thr Asn Tyr Asn
                 50                  55                  60

Gln Lys Phe Lys Gly Lys Ala Thr Leu Thr Val Asp Thr Ser Ala Ser
             65                  70                  75

Thr Ala Tyr Met Glu Leu Ser Ser Leu Arg Ser Glu Asp Thr Ala Val
             80                  85                  90

Tyr Tyr Cys Ala Arg Asn Arg Asp Tyr Ser Asn Asn Trp Tyr Phe Asp
         95                 100                 105

Val Trp Gly Glu Gly Thr Leu Val Thr Val Ser Ser Ala Ser Thr Lys
110                 115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
            145                 150                 155

Val Thr Val Ser Trp Asn Ser Gly Ala Leu Thr Ser Gly Val His Thr
            160                 165                 170

Phe Pro Ala Val Leu Gln Ser Ser Gly Leu Tyr Ser Leu Ser Ser Val
    175                 180                 185
```

```
Val Thr Val Pro Ser Ser Leu Gly Thr Gln Thr Tyr Ile Cys Asn
190                 195                 200                 205

Val Asn His Lys Pro Ser Asn Thr Lys Val Asp Lys Arg Val Glu Pro
                210                 215                 220

Lys Ser Cys Asp Lys Thr His Thr Cys Pro Pro Cys Pro Ala Pro Glu
            225                 230                 235

Leu Leu Gly Gly Pro Ser Val Phe Leu Phe Pro Pro Lys Pro Lys Asp
        240                 245                 250

Thr Leu Met Ile Ser Arg Thr Pro Glu Val Thr Cys Val Val Val Asp
    255                 260                 265

Val Ser His Glu Asp Pro Glu Val Lys Phe Asn Trp Tyr Val Asp Gly
270                 275                 280                 285

Val Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu Pro
        320                 325                 330

Ala Pro Ile Glu Lys Thr Ile Ser Lys Ala Lys Gly Gln Pro Arg Glu
    335                 340                 345

Pro Gln Val Tyr Thr Leu Pro Pro Ser Arg Glu Glu Met Thr Lys Asn
350                 355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
            385                 390                 395

Thr Pro Pro Val Leu Asp Ser Asp Gly Ser Phe Phe Leu Tyr Ser Lys
        400                 405                 410

Leu Thr Val Asp Lys Ser Arg Trp Gln Gln Gly Asn Val Phe Ser Cys
    415                 420                 425

Ser Val Met His Glu Ala Leu His Asn His Tyr Thr Gln Lys Ser Leu
430                 435                 440                 445

Ser Leu Ser Pro Gly Lys
            450

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 90
acagccggga aggtgtgcac                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 91
agacaccctc cctccctgtg                                              20
```

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 92
gtgcagggcc tgggttaggg                                         20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 93
gcacggtggg catgtgtgag                                         20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 94
gttttggggg gaagaggaag                                         20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 95
ccagtcctgg tgcaggacgg                                         20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 96
cctgtggttc tcggggctgc                                         20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

```
<400> SEQUENCE: 97
cgtggtcttg tagttgttct                                              20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 98
cttcctcttc cccccaaaac                                              20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 99
ccgtcctgca ccaggactgg                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 100
gcagccccga gaaccacagg                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 101
agaacaacta caagaccacg                                              20

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 102
gcctgacatc tgaggactc                                               19

<210> SEQ ID NO 103
<211> LENGTH: 19
<212> TYPE: DNA
```

-continued

<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 103
gagtcctcag atgtcaggc                                                  19

<210> SEQ ID NO 104
<211> LENGTH: 34
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 104
gagcagtact cgttgctgcc gcgcgcgcca ccag                                 34

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of a
      humanized anti-Fas antibody

<400> SEQUENCE: 105
ggtatggctg attaatgatc aatg                                            24

<210> SEQ ID NO 106
<211> LENGTH: 768
<212> TYPE: DNA
<213> ORGANISM: Artificial Sequence
<220> FEATURE:
<223> OTHER INFORMATION: Description of Artificial Sequence: Designed
      DNA encoding the light chain of a humanized anti-Fas
      antibody
<220> FEATURE:
<221> NAME/KEY: CDS
<222> LOCATION: (40)..(753)
<220> FEATURE:
<221> NAME/KEY: mat peptide
<222> LOCATION: (100)..(753)
<220> FEATURE:
<221> NAME/KEY: sig peptide
<222> LOCATION: (40)..(99)

<400> SEQUENCE: 106
cccaagctta agaagcatcc tctcatctag ttctcagag atg gag aca gac aca        54
                                            Met Glu Thr Asp Thr
                                                        -20 atc ctg cta tgg gtg ctg ctg ctc tgg gtt cca ggc tcc act ggt gag      102
Ile Leu Leu Trp Val Leu Leu Leu Trp Val Pro Gly Ser Thr Gly Glu
-15                 -10                 -5                  -1   1 att gtg ctc acc caa tct cca ggt act ttg tct ctg tct cca ggg gag      150
Ile Val Leu Thr Gln Ser Pro Gly Thr Leu Ser Leu Ser Pro Gly Glu
                5                   10                  15 agg gcc acc ctc tcc tgc aag gcc agc caa agt gtt gat tat gat ggt      198
Arg Ala Thr Leu Ser Cys Lys Ala Ser Gln Ser Val Asp Tyr Asp Gly
            20                  25                  30 gat agt tat atg aac tgg tac caa cag aaa cca gga cag gca ccc aga      246
Asp Ser Tyr Met Asn Trp Tyr Gln Gln Lys Pro Gly Gln Ala Pro Arg
        35                  40                  45

```
ctc ctc atc tat gct gca tcc aat ctc gaa tct ggg atc cca gac agg    294
Leu Leu Ile Tyr Ala Ala Ser Asn Leu Glu Ser Gly Ile Pro Asp Arg
 50                  55                  60                  65 ttt agt ggc agt ggg tct ggg aca gac ttc acc ctc acc atc tct cgt    342
Phe Ser Gly Ser Gly Ser Gly Thr Asp Phe Thr Leu Thr Ile Ser Arg
             70                  75                  80 ctg gag ccg gag gat ttt gca gtc tat tac tgt cag caa agt aat gag    390
Leu Glu Pro Glu Asp Phe Ala Val Tyr Tyr Cys Gln Gln Ser Asn Glu
                 85                  90                  95 gat cct cgg acg ttc ggt caa ggc acc aag ctg gaa atc aaa cgg act    438
Asp Pro Arg Thr Phe Gly Gln Gly Thr Lys Leu Glu Ile Lys Arg Thr
            100                 105                 110 gtg gct gca cca tct gtc ttc atc ttc ccg cca tct gat gag cag ttg    486
Val Ala Ala Pro Ser Val Phe Ile Phe Pro Pro Ser Asp Glu Gln Leu
        115                 120                 125 aaa tct gga act gcc tct gtt gtg tgc ctg ctg aat aac ttc tat ccc    534
Lys Ser Gly Thr Ala Ser Val Val Cys Leu Leu Asn Asn Phe Tyr Pro
130                 135                 140                 145 aga gag gcc aaa gta cag tgg aag gtg gat aac gcc ctc caa tcg ggt    582
Arg Glu Ala Lys Val Gln Trp Lys Val Asp Asn Ala Leu Gln Ser Gly
                150                 155                 160 aac tcc cag gag agt gtc aca gag cag gac agc aag gac agc acc tac    630
Asn Ser Gln Glu Ser Val Thr Glu Gln Asp Ser Lys Asp Ser Thr Tyr
            165                 170                 175 agc ctc agc agc acc ctg acg ctg agc aaa gca gac tac gag aaa cac    678
Ser Leu Ser Ser Thr Leu Thr Leu Ser Lys Ala Asp Tyr Glu Lys His
        180                 185                 190 aaa gtc tac gcc tgc gaa gtc acc cat cag ggc ctg agc tcg ccc gtc    726
Lys Val Tyr Ala Cys Glu Val Thr His Gln Gly Leu Ser Ser Pro Val
195                 200                 205 aca aag agc ttc aac agg gga gag tgt tagtaagaat tcggg              768
Thr Lys Ser Phe Asn Arg Gly Glu Cys
210                 215

<210> SEQ ID NO 107
<211> LENGTH: 238
<212> TYPE: PRT
<213> ORGANISM: Artificial Sequence
<220> FEATURE:
<223> OTHER INFORMATION: Description of Artificial Sequence: Designed
      light chain of humanized anti-Fas antibody

<400> SEQUENCE: 107

Met Glu Thr Asp Thr Ile Leu Leu Trp Val Leu Leu Leu Trp Val Pro
-20                 -15                 -10                 -5

Gly Ser Thr Gly Glu Ile Val Leu Thr Gln Ser Pro Gly Thr Leu Ser
             -1  1                   5                  10

Leu Ser Pro Gly Glu Arg Ala Thr Leu Ser Cys Lys Ala Ser Gln Ser
         15                  20                  25

Val Asp Tyr Asp Gly Asp Ser Tyr Met Asn Trp Tyr Gln Gln Lys Pro
     30                  35                  40

Gly Gln Ala Pro Arg Leu Leu Ile Tyr Ala Ala Ser Asn Leu Glu Ser
 45                  50                  55                  60

Gly Ile Pro Asp Arg Phe Ser Gly Ser Gly Ser Gly Thr Asp Phe Thr
                 65                  70                  75

Leu Thr Ile Ser Arg Leu Glu Pro Glu Asp Phe Ala Val Tyr Tyr Cys
             80                  85                  90

Gln Gln Ser Asn Glu Asp Pro Arg Thr Phe Gly Gln Gly Thr Lys Leu
         95                 100                 105
```

```
Glu Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu Leu
125                 130                 135                 140

Asn Asn Phe Tyr Pro Arg Glu Ala Lys Val Gln Trp Lys Val Asp Asn
                145                 150                 155

Ala Leu Gln Ser Gly Asn Ser Gln Glu Ser Val Thr Glu Gln Asp Ser
                160                 165                 170

Lys Asp Ser Thr Tyr Ser Leu Ser Ser Thr Leu Thr Leu Ser Lys Ala
            175                 180                 185

Asp Tyr Glu Lys His Lys Val Tyr Ala Cys Glu Val Thr His Gln Gly
    190                 195                 200

Leu Ser Ser Pro Val Thr Lys Ser Phe Asn Arg Gly Glu Cys
205                 210                 215

<210> SEQ ID NO 108
<211> LENGTH: 768
<212> TYPE: DNA
<213> ORGANISM: Artificial Sequence
<220> FEATURE:
<221> NAME/KEY: CDS
<222> LOCATION: (40)..(753)
<220> FEATURE:
<221> NAME/KEY: mat peptide
<222> LOCATION: (100)..(753)
<220> FEATURE:
<221> NAME/KEY: sig peptide
<222> LOCATION: (40)..(99)
<220> FEATURE:
<223> OTHER INFORMATION: Description of Artificial Sequence: Designed
      DNA encoding the light chain of a humanized anti-Fas
      antibody

<400> SEQUENCE: 108
cccaagctta agaagcatcc tctcatctag ttctcagag atg gag aca gac aca         54
                                           Met Glu Thr Asp Thr
                                               -20 atc ctg cta tgg gtg ctg ctg ctc tgg gtt cca ggc tcc act ggt gag      102
Ile Leu Leu Trp Val Leu Leu Leu Trp Val Pro Gly Ser Thr Gly Glu
-15                 -10                 -5                  -1   1 att gtg ctc acc caa tct cca ggt act ttg tct ctg tct cca ggg gag      150
Ile Val Leu Thr Gln Ser Pro Gly Thr Leu Ser Leu Ser Pro Gly Glu
                5                   10                  15 agg gcc acc ctc tcc tgc aag gcc agc caa agt gtt gat tat gat ggt      198
Arg Ala Thr Leu Ser Cys Lys Ala Ser Gln Ser Val Asp Tyr Asp Gly
            20                  25                  30 gat agt tat atg aac tgg tac caa cag aaa cca gga cag gca ccc aga      246
Asp Ser Tyr Met Asn Trp Tyr Gln Gln Lys Pro Gly Gln Ala Pro Arg
        35                  40                  45 ctc ctc atc tat gct gca tcc aat ctc gaa tct ggg atc cca gac agg      294
Leu Leu Ile Tyr Ala Ala Ser Asn Leu Glu Ser Gly Ile Pro Asp Arg
 50                  55                  60                   65 ttt agt ggc agt ggg tct ggg aca gac ttc acc ctc acc atc cat cct      342
Phe Ser Gly Ser Gly Ser Gly Thr Asp Phe Thr Leu Thr Ile His Pro
                70                  75                  80 gtg gag gag gag gat gct gca acc tat tac tgt cag caa agt aat gag      390
Val Glu Glu Glu Asp Ala Ala Thr Tyr Tyr Cys Gln Gln Ser Asn Glu
            85                  90                  95 gat cct cgg acg ttc ggt caa ggc acc aag ctg gaa atc aaa cgg act      438
Asp Pro Arg Thr Phe Gly Gln Gly Thr Lys Leu Glu Ile Lys Arg Thr
        100                 105                 110 gtg gct gca cca tct gtc ttc atc ttc ccg cca tct gat gag cag ttg      486
```

```
Val Ala Ala Pro Ser Val Phe Ile Phe Pro Pro Ser Asp Glu Gln Leu
    115                 120                 125 aaa tct gga act gcc tct gtt gtg tgc ctg ctg aat aac ttc tat ccc        534
Lys Ser Gly Thr Ala Ser Val Val Cys Leu Leu Asn Asn Phe Tyr Pro
130                 135                 140                 145 aga gag gcc aaa gta cag tgg aaa gtg gat aac gcc ctc caa tcg ggt        582
Arg Glu Ala Lys Val Gln Trp Lys Val Asp Asn Ala Leu Gln Ser Gly
                150                 155                 160 aac tcc cag gag agt gtc aca gag cag gac agc aag gac agc acc tac        630
Asn Ser Gln Glu Ser Val Thr Glu Gln Asp Ser Lys Asp Ser Thr Tyr
            165                 170                 175 agc ctc agc agc acc ctg acg ctg agc aaa gca gac tac gag aaa cac        678
Ser Leu Ser Ser Thr Leu Thr Leu Ser Lys Ala Asp Tyr Glu Lys His
        180                 185                 190 aaa gtc tac gcc tgc gaa gtc acc cat cag ggc ctg agc tcg ccc gtc        726
Lys Val Tyr Ala Cys Glu Val Thr His Gln Gly Leu Ser Ser Pro Val
    195                 200                 205 aca aag agc ttc aac agg gga gag tgt tagtaagaat tcggg                   768
Thr Lys Ser Phe Asn Arg Gly Glu Cys
210                 215
```

<210> SEQ ID NO 109
<211> LENGTH: 238
<212> TYPE: PRT
<213> ORGANISM: Artificial Sequence
<220> FEATURE:
<223> OTHER INFORMATION: Description of Artificial Sequence: Designed
      light chain of humanized anti-Fas antibody

<400> SEQUENCE: 109

```
Met Glu Thr Asp Thr Ile Leu Leu Trp Val Leu Leu Leu Trp Val Pro
-20                 -15                 -10                 -5

Gly Ser Thr Gly Glu Ile Val Leu Thr Gln Ser Pro Gly Thr Leu Ser
            -1   1               5                  10

Leu Ser Pro Gly Glu Arg Ala Thr Leu Ser Cys Lys Ala Ser Gln Ser
        15                  20                  25

Val Asp Tyr Asp Gly Asp Ser Tyr Met Asn Trp Tyr Gln Gln Lys Pro
    30                  35                  40

Gly Gln Ala Pro Arg Leu Leu Ile Tyr Ala Ala Ser Asn Leu Glu Ser
45                  50                  55                  60

Gly Ile Pro Asp Arg Phe Ser Gly Ser Gly Ser Gly Thr Asp Phe Thr
                65                  70                  75

Leu Thr Ile His Pro Val Glu Glu Glu Asp Ala Ala Thr Tyr Tyr Cys
            80                  85                  90

Gln Gln Ser Asn Glu Asp Pro Arg Thr Phe Gly Gln Gly Thr Lys Leu
        95                  100                 105

Glu Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu Leu
125                 130                 135                 140

Asn Asn Phe Tyr Pro Arg Glu Ala Lys Val Gln Trp Lys Val Asp Asn
                145                 150                 155

Ala Leu Gln Ser Gly Asn Ser Gln Glu Ser Val Thr Glu Gln Asp Ser
            160                 165                 170

Lys Asp Ser Thr Tyr Ser Leu Ser Ser Thr Leu Thr Leu Ser Lys Ala
        175                 180                 185

Asp Tyr Glu Lys His Lys Val Tyr Ala Cys Glu Val Thr His Gln Gly
    190                 195                 200
```

```
Leu Ser Ser Pro Val Thr Lys Ser Phe Asn Arg Gly Glu Cys
205                 210                 215
```

```
<210> SEQ ID NO 110
<211> LENGTH: 29
<212> TYPE: DNA
<213> ORGANISM: Artificial Sequence
<220> FEATURE:
<223> OTHER INFORMATION: Description of Artificial Sequence: PCR primer
      to amplify a fragment of a DNA encoding the light
      chain of a humanized anti-Fas antibody

<400> SEQUENCE: 110
ggtgagattg tgctcaccca atctccagg                                      29

<210> SEQ ID NO 111
<211> LENGTH: 29
<212> TYPE: DNA
<213> ORGANISM: Artificial Sequence
<220> FEATURE:
<223> OTHER INFORMATION: Description of Artificial Sequence: PCR primer
      to amplify a fragment of a DNA encoding the light
      chain of a humanized anti-Fas antibody

<400> SEQUENCE: 111
cctggagatt gggtgagcac aatctcacc                                      29

<210> SEQ ID NO 112
<211> LENGTH: 31
<212> TYPE: DNA
<213> ORGANISM: Artificial Sequence
<220> FEATURE:
<223> OTHER INFORMATION: Description of Artificial Sequence: PCR primer
      to amplify a fragment of a DNA encoding the light
      chain of a humanized anti-Fas antibody

<400> SEQUENCE: 112
ccatctctcg tctggagccg gaggattttg c                                   31

<210> SEQ ID NO 113
<211> LENGTH: 31
<212> TYPE: DNA
<213> ORGANISM: Artificial Sequence
<220> FEATURE:
<223> OTHER INFORMATION: Description of Artificial Sequence: PCR primer
      to amplify a fragment of a DNA encoding the light
      chain of a humanized anti-Fas antibody

<400> SEQUENCE: 113
gcaaaatcct ccggctccag acgagagatg g                                   31

<210> SEQ ID NO 114
<211> LENGTH: 31
<212> TYPE: DNA
<213> ORGANISM: Artificial Sequence
<220> FEATURE:
<223> OTHER INFORMATION: Description of Artificial Sequence: PCR primer
      to amplify a fragment of a DNA encoding the light
      chain of a humanized anti-Fas antibody

<400> SEQUENCE: 114
caaggcacca agctggaaat caaacggact g                                   31

<210> SEQ ID NO 115
<211> LENGTH: 31
<212> TYPE: DNA
<213> ORGANISM: Artificial Sequence
```

```
<220> FEATURE:
<223> OTHER INFORMATION: Description of Artificial Sequence: PCR primer
      to amplify a fragment of a DNA encoding the light
      chain of a humanized anti-Fas antibody

<400> SEQUENCE: 115
cagtccgttt gatttccagc ttggtgcctt g                                     31

<210> SEQ ID NO 116
<211> LENGTH: 2071
<212> TYPE: DNA
<213> ORGANISM: Artificial Sequence
<220> FEATURE:
<223> OTHER INFORMATION: Description of Artificial Sequence: Designed
      DNA encoding the heavy chain of a humanized anti-Fas
      antibody
<220> FEATURE:
<221> NAME/KEY: sig peptide
<222> LOCATION: (21)..(77)
<220> FEATURE:
<221> NAME/KEY: intron
<222> LOCATION: (735)..(1125)
<220> FEATURE:
<221> NAME/KEY: intron
<222> LOCATION: (1171)..(1288)
<220> FEATURE:
<221> NAME/KEY: intron
<222> LOCATION: (1619)..(1715)
<220> FEATURE:
<221> NAME/KEY: exon
<222> LOCATION: (21)..(734)
<220> FEATURE:
<221> NAME/KEY: exon
<222> LOCATION: (1126)..(1170)
<220> FEATURE:
<221> NAME/KEY: exon
<222> LOCATION: (1289)..(1618)
<220> FEATURE:
<221> NAME/KEY: exon
<222> LOCATION: (1716)..(2036)
<220> FEATURE:
<221> NAME/KEY: mat peptide
<222> LOCATION: (78)..(734)
<220> FEATURE:
<221> NAME/KEY: mat peptide
<222> LOCATION: (1126)..(1170)
<220> FEATURE:
<221> NAME/KEY: mat peptide
<222> LOCATION: (1289)..(1618)
<220> FEATURE:
<221> NAME/KEY: mat peptide
<222> LOCATION: (1716)..(2036)
<220> FEATURE:
<221> NAME/KEY: CDS
<222> LOCATION: (21)..(734)
<220> FEATURE:
<221> NAME/KEY: CDS
<222> LOCATION: (1126)..(1170)
<220> FEATURE:
<221> NAME/KEY: CDS
<222> LOCATION: (1289)..(1618)
<220> FEATURE:
<221> NAME/KEY: CDS
<222> LOCATION: (1716)..(2036)

<400> SEQUENCE: 116
aagcttggct tgacctcacc atg gga tgg agc tgt atc atc ctc ttc ttg gta        53
                     Met Gly Trp Ser Cys Ile Ile Leu Phe Leu Val
                         -15                 -10 gca aca gct aca ggt gtc cac tct cag gtc caa ctg gtg cag tct ggg        101
Ala Thr Ala Thr Gly Val His Ser Gln Val Gln Leu Val Gln Ser Gly
        -5              -1   1               5 gct gag gtc aag aag cct ggg gct tca gtg aag gtg tcc tgc aag gct        149
Ala Glu Val Lys Lys Pro Gly Ala Ser Val Lys Val Ser Cys Lys Ala
```

```
               10                  15                  20
tct ggc tac acc ttc acc agc tac tgg atg cag tgg gta aaa cag gcc    197
Ser Gly Tyr Thr Phe Thr Ser Tyr Trp Met Gln Trp Val Lys Gln Ala
 25                  30                  35                  40 cct gga cag ggc ctt gag tgg atg gga gag att gat cct tct gat agc    245
Pro Gly Gln Gly Leu Glu Trp Met Gly Glu Ile Asp Pro Ser Asp Ser
                 45                  50                  55 tat act aac tac aat caa aag ttc aag ggc aag gcc aca ttg act gta    293
Tyr Thr Asn Tyr Asn Gln Lys Phe Lys Gly Lys Ala Thr Leu Thr Val
                 60                  65                  70 gac aca tcc act agc aca gcc tac atg gag ctc agc agc ctg aga tct    341
Asp Thr Ser Thr Ser Thr Ala Tyr Met Glu Leu Ser Ser Leu Arg Ser
             75                  80                  85 gag gac acg gcg gtc tat tac tgt gca aga aat agg gac tat agt aac    389
Glu Asp Thr Ala Val Tyr Tyr Cys Ala Arg Asn Arg Asp Tyr Ser Asn
         90                  95                 100 aac tgg tac ttc gat gtc tgg ggc gaa ggg acc ctg gtc acc gtc tcc    437
Asn Trp Tyr Phe Asp Val Trp Gly Glu Gly Thr Leu Val Thr Val Ser
105                 110                 115                 120 tca gcc tcc acc aag ggc cca tcg gtc ttc ccc ctg gca ccc tcc tcc    485
Ser Ala Ser Thr Lys Gly Pro Ser Val Phe Pro Leu Ala Pro Ser Ser
                125                 130                 135 aag agc acc tct ggg ggc aca gcg gcc ctg ggc tgc ctg gtc aag gac    533
Lys Ser Thr Ser Gly Gly Thr Ala Ala Leu Gly Cys Leu Val Lys Asp
                140                 145                 150 tac ttc ccc gaa ccg gtg acg gtg tcg tgg aac tca ggc gcc ctg acc    581
Tyr Phe Pro Glu Pro Val Thr Val Ser Trp Asn Ser Gly Ala Leu Thr
            155                 160                 165 agc ggc gtg cac acc ttc ccg gct gtc cta cag tcc tca gga ctc tac    629
Ser Gly Val His Thr Phe Pro Ala Val Leu Gln Ser Ser Gly Leu Tyr
        170                 175                 180 tcc ctc agc agc gtg gtg acc gtg ccc tcc agc agc ttg ggc acc cag    677
Ser Leu Ser Ser Val Val Thr Val Pro Ser Ser Ser Leu Gly Thr Gln
185                 190                 195                 200 acc tac atc tgc aac gtg aat cac aag ccc agc aac acc aag gtg gac    725
Thr Tyr Ile Cys Asn Val Asn His Lys Pro Ser Asn Thr Lys Val Asp
                205                 210                 215 aag aga gtt ggtgagaggc cagcacaggg agggagggtg tctgctggaa             774
Lys Arg Val gccaggctca gcgctcctgc ctggacgcat cccggctatg cagtcccagt ccagggcagc    834
aaggcaggcc ccgtctgcct cttcacccgg aggcctctgc ccgccccact catgctcagg    894
gagagggtct tctggctttt tccccaggct ctgggcaggc acaggctagg tgcccctaac    954
ccaggccctg cacacaaagg ggcaggtgct gggctcagac ctgccaagag ccatatccgg   1014
gaggaccctg cccctgacct aagcccaccc caaaggccaa actctccact ccctcagctc   1074
ggacaccttc tctcctccca gattccagta actcccaatc ttctctctgc a gag ccc   1131
                                                      Glu Pro
                                                          220 aaa tct tgt gac aaa act cac aca tgc cca ccg tgc cca ggtaagccag      1180
Lys Ser Cys Asp Lys Thr His Thr Cys Pro Pro Cys Pro
            225                 230 cccaggcctc gccctccagc tcaaggcggg acaggtgccc tagagtagcc tgcatccagg   1240
gacaggcccc agccgggtgc tgacacgtcc acctccatct cttcctca gca cct gaa    1297
                                                     Ala Pro Glu
                                                             235 ctc ctg ggg gga ccg tca gtc ttc ctc ttc ccc cca aaa ccc aag gac    1345
Leu Leu Gly Gly Pro Ser Val Phe Leu Phe Pro Pro Lys Pro Lys Asp
```

-continued

```
                  240                 245                 250
acc ctc atg atc tcc cgg acc cct gag gtc aca tgc gtg gtg gtg gac      1393
Thr Leu Met Ile Ser Arg Thr Pro Glu Val Thr Cys Val Val Val Asp
    255                 260                 265 gtg agc cac gaa gac cct gag gtc aag ttc aac tgg tac gtg gac ggc      1441
Val Ser His Glu Asp Pro Glu Val Lys Phe Asn Trp Tyr Val Asp Gly
270                 275                 280                 285 gtg gag gtg cat aat gcc aag aca aag ccg cgg gag gag cag tac aac      1489
Val Glu Val His Asn Ala Lys Thr Lys Pro Arg Glu Glu Gln Tyr Asn
                290                 295                 300 agc acg tac cgt gtg gtc agc gtc ctc acc gtc ctg cac cag gac tgg      1537
Ser Thr Tyr Arg Val Val Ser Val Leu Thr Val Leu His Gln Asp Trp
            305                 310                 315 ctg aat ggc aag gag tac aag tgc aag gtc tcc aac aaa gcc ctc cca      1585
Leu Asn Gly Lys Glu Tyr Lys Cys Lys Val Ser Asn Lys Ala Leu Pro
        320                 325                 330 gcc ccc atc gag aaa acc atc tcc aaa gcc aaa ggtgggaccc gtgggtgcg     1638
Ala Pro Ile Glu Lys Thr Ile Ser Lys Ala Lys
    335                 340 agggccacat ggacagaggc cggctcggcc caccctctgc cctgagagtg accgctgtac    1698
caacctctgt ccctaca ggg cag ccc cga gaa cca cag gtg tac acc ctg      1748
                Gly Gln Pro Arg Glu Pro Gln Val Tyr Thr Leu
                                345                 350                 355 ccc cca tcc cgg gag gag atg acc aag aac cag gtc agc ctg acc tgc      1796
Pro Pro Ser Arg Glu Glu Met Thr Lys Asn Gln Val Ser Leu Thr Cys
                360                 365                 370 ctg gtc aaa ggc ttc tat ccc agc gac atc gcc gtg gag tgg gag agc      1844
Leu Val Lys Gly Phe Tyr Pro Ser Asp Ile Ala Val Glu Trp Glu Ser
            375                 380                 385 aat ggg cag ccg gag aac aac tac aag acc acg cct ccc gtg ctg gac      1892
Asn Gly Gln Pro Glu Asn Asn Tyr Lys Thr Thr Pro Pro Val Leu Asp
        390                 395                 400 tcc gac ggc tcc ttc ttc ctc tat agc aag ctc acc gtg gac aag agc      1940
Ser Asp Gly Ser Phe Phe Leu Tyr Ser Lys Leu Thr Val Asp Lys Ser
    405                 410                 415 agg tgg cag cag ggg aac gtc ttc tca tgc tcc gtg atg cat gag gct      1988
Arg Trp Gln Gln Gly Asn Val Phe Ser Cys Ser Val Met His Glu Ala
420                 425                 430                 435 ctg cac aac cac tac acg cag aag agc ctc tcc ctg tcc ccg ggt aaa      2036
Leu His Asn His Tyr Thr Gln Lys Ser Leu Ser Leu Ser Pro Gly Lys
                440                 445                 450 tgagtgcgac ggccggcaag ccccgctccc gaatt                                2071
```

<210> SEQ ID NO 117
<211> LENGTH: 470
<212> TYPE: PRT
<213> ORGANISM: Artificial Sequence
<220> FEATURE:
<223> OTHER INFORMATION: Description of Artificial Sequence: Designed heavy chain of humanized anti-Fas antibody

<400> SEQUENCE: 117

Met Gly Trp Ser Cys Ile Ile Leu Phe Leu Val Ala Thr Ala Thr Gly
              -15                 -10                  -5

Val His Ser Gln Val Gln Leu Val Gln Ser Gly Ala Glu Val Lys Lys
         -1   1                   5                  10

Pro Gly Ala Ser Val Lys Val Ser Cys Lys Ala Ser Gly Tyr Thr Phe
         15                  20                  25

Thr Ser Tyr Trp Met Gln Trp Val Lys Gln Ala Pro Gly Gln Gly Leu

-continued

```
            30                  35                  40                  45
Glu Trp Met Gly Glu Ile Asp Pro Ser Asp Ser Tyr Thr Asn Tyr Asn
                50                  55                  60
Gln Lys Phe Lys Gly Lys Ala Thr Leu Thr Val Asp Thr Ser Thr Ser
                65                  70                  75
Thr Ala Tyr Met Glu Leu Ser Ser Leu Arg Ser Glu Asp Thr Ala Val
                80                  85                  90
Tyr Tyr Cys Ala Arg Asn Arg Asp Tyr Ser Asn Asn Trp Tyr Phe Asp
        95                 100                 105
Val Trp Gly Glu Gly Thr Leu Val Thr Val Ser Ser Ala Ser Thr Lys
110                 115                 120                 125
Gly Pro Ser Val Phe Pro Leu Ala Pro Ser Ser Lys Ser Thr Ser Gly
                130                 135                 140
Gly Thr Ala Ala Leu Gly Cys Leu Val Lys Asp Tyr Phe Pro Glu Pro
                145                 150                 155
Val Thr Val Ser Trp Asn Ser Gly Ala Leu Thr Ser Gly Val His Thr
                160                 165                 170
Phe Pro Ala Val Leu Gln Ser Ser Gly Leu Tyr Ser Leu Ser Ser Val
                175                 180                 185
Val Thr Val Pro Ser Ser Leu Gly Thr Gln Thr Tyr Ile Cys Asn
190                 195                 200                 205
Val Asn His Lys Pro Ser Asn Thr Lys Val Asp Lys Arg Val Glu Pro
                210                 215                 220
Lys Ser Cys Asp Lys Thr His Thr Cys Pro Pro Cys Pro Ala Pro Glu
                225                 230                 235
Leu Leu Gly Gly Pro Ser Val Phe Leu Phe Pro Pro Lys Pro Lys Asp
                240                 245                 250
Thr Leu Met Ile Ser Arg Thr Pro Glu Val Thr Cys Val Val Val Asp
                255                 260                 265
Val Ser His Glu Asp Pro Glu Val Lys Phe Asn Trp Tyr Val Asp Gly
270                 275                 280                 285
Val Glu Val His Asn Ala Lys Thr Lys Pro Arg Glu Glu Gln Tyr Asn
                290                 295                 300
Ser Thr Tyr Arg Val Val Ser Val Leu Thr Val Leu His Gln Asp Trp
                305                 310                 315
Leu Asn Gly Lys Glu Tyr Lys Cys Lys Val Ser Asn Lys Ala Leu Pro
                320                 325                 330
Ala Pro Ile Glu Lys Thr Ile Ser Lys Ala Lys Gly Gln Pro Arg Glu
                335                 340                 345
Pro Gln Val Tyr Thr Leu Pro Pro Ser Arg Glu Glu Met Thr Lys Asn
350                 355                 360                 365
Gln Val Ser Leu Thr Cys Leu Val Lys Gly Phe Tyr Pro Ser Asp Ile
                370                 375                 380
Ala Val Glu Trp Glu Ser Asn Gly Gln Pro Glu Asn Asn Tyr Lys Thr
                385                 390                 395
Thr Pro Pro Val Leu Asp Ser Asp Gly Ser Phe Phe Leu Tyr Ser Lys
                400                 405                 410
Leu Thr Val Asp Lys Ser Arg Trp Gln Gln Gly Asn Val Phe Ser Cys
                415                 420                 425
Ser Val Met His Glu Ala Leu His Asn His Tyr Thr Gln Lys Ser Leu
430                 435                 440                 445
Ser Leu Ser Pro Gly Lys
                450
```

<210> SEQ ID NO 118
<211> LENGTH: 30
<212> TYPE: DNA
<213> ORGANISM: Artificial Sequence
<220> FEATURE:
<223> OTHER INFORMATION: Description of Artificial Sequence: PCR primer
      to amplify a fragment of a DNA encoding the heavy
      chain of a humanized anti-Fas antibody

<400> SEQUENCE: 118
caggcccctg gacagggcct tgagtggatg                                        30

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: PCR primer
      to amplify a fragment of a DNA encoding the heavy
      chain of a humanized anti-Fas antibody

<400> SEQUENCE: 119
catccactca aggccctgtc caggggcctg                                        30

<210> SEQ ID NO 120
<211> LENGTH: 39
<212> TYPE: DNA
<213> ORGANISM: Artificial Sequence
<220> FEATURE:
<223> OTHER INFORMATION: Description of Artificial Sequence: PCR primer
      to amplify a fragment of a DNA encoding the heavy
      chain of a humanized anti-Fas antibody

<400> SEQUENCE: 120
gctgagctcc atgtaggctg tgctagtgga tgtgtctac                              39

<210> SEQ ID NO 121
<211> LENGTH: 33
<212> TYPE: DNA
<213> ORGANISM: Artificial Sequence
<220> FEATURE:
<223> OTHER INFORMATION: Description of Artificial Sequence: PCR primer
      to amplify a DNA fragment including SR alpha promoter

<400> SEQUENCE: 121
tgcacgcgtg gctgtggaat gtgtgtcagt tag                                    33

<210> SEQ ID NO 122
<211> LENGTH: 31
<212> TYPE: DNA
<213> ORGANISM: Artificial Sequence
<220> FEATURE:
<223> OTHER INFORMATION: Description of Artificial Sequence: PCR primer
      to amplify a DNA fragment including SR alpha promoter

<400> SEQUENCE: 122
tccgaagctt ttagagcaga agtaacactt c                                      31

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: PCR primer
      to amplify a DNA fragment including SR alpha promoter

<400> SEQUENCE: 123

-continued aaagcggccg ctgctagctt ggctgtggaa tgtgtg                                36

<210> SEQ ID NO 124
<211> LENGTH: 34
<212> TYPE: DNA
<213> ORGANISM: Artificial Sequence
<220> FEATURE:
<223> OTHER INFORMATION: Description of Artificial Sequence: PCR primer
      to amplify a DNA encoding the kappa light chain of
      human immunoglobulin

<400> SEQUENCE: 124
aagcttatgg acatgagggt ccccgctctg ctcc                                  34

<210> SEQ ID NO 125
<211> LENGTH: 729
<212> TYPE: DNA
<213> ORGANISM: Homo sapiens

<400> SEQUENCE: 125
aagcttatgg acatgagggt ccccgctctg ctcctggggc tcctgctact ctggctccga      60
ggtgccagat gtgacatcca gatgacccag tctccatcct ccctgtctgc atctgtagga     120
gacagagtca ccatcacttg ccgggcaagt cagagcatta gcagctattt aaattggtat     180
cagcagaaac agggaaagc ccctaagctc ctgatctatg ctgcatccag tttgcaaagt      240
ggggtcccat caaggttcag tgcagtgga tctgggacag atttcactct caccatcagc      300
agtctgcaac tgaagatt tgcaacttac tactgtcaac agagttacag taccctcga      360 acgttcggcc aagggaccaa ggtggaaatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt tacagagcag gacagcaagg acagcaccta cagcctcagc     600
agcaccctga cgctgagcaa agcagactac gagaaacaca agtctacgc ctgcgaagtc     660 acccatcagg gcctgagctc gcccgtcaca aagagcttca caggggaga gtgttagtaa     720 gaattcggg                                                             729

<210> SEQ ID NO 126
<211> LENGTH: 767
<212> TYPE: DNA
<213> ORGANISM: Artificial Sequence
<220> FEATURE:
<223> OTHER INFORMATION: Description of Artificial Sequence: Designed
      DNA encoding the light chain of a humanized anti-Fas
      antibody
<220> FEATURE:
<221> NAME/KEY: CDS
<222> LOCATION: (39)..(752)
<220> FEATURE:
<221> NAME/KEY: mat peptide
<222> LOCATION: (99)..(752)
<220> FEATURE:
<221> NAME/KEY: sig peptide
<222> LOCATION: (39)..(98)

<400> SEQUENCE: 126
ccaagcttaa gaagcatcct ctcatctagt tctcagag atg gag aca gac aca atc      56
                                         Met Glu Thr Asp Thr Ile
                                             -20             -15 ctg cta tgg gtg ctg ctc tgg gtt cca ggc tcc act ggt gac att          104
Leu Leu Trp Val Leu Leu Trp Val Pro Gly Ser Thr Gly Asp Ile
         -10              -5               -1   1

-continued

```
gtg ctc acc caa tct cca tcc tcc ctg tct gca tct gta gga gac aga        152
Val Leu Thr Gln Ser Pro Ser Ser Leu Ser Ala Ser Val Gly Asp Arg
         5                  10                  15 gtc acc atc act tgc aag gcc agc caa agt gtt gat tat gat ggt gat        200
Val Thr Ile Thr Cys Lys Ala Ser Gln Ser Val Asp Tyr Asp Gly Asp
 20                  25                  30 agt tat atg aac tgg tac caa cag aaa cca gga aag gca ccc aag ctc        248
Ser Tyr Met Asn Trp Tyr Gln Gln Lys Pro Gly Lys Ala Pro Lys Leu
 35                  40                  45                  50 ctc atc tat gct gca tcc aat ttg gaa agt ggg gtc cca tca agg ttc        296
Leu Ile Tyr Ala Ala Ser Asn Leu Glu Ser Gly Val Pro Ser Arg Phe
                 55                  60                  65 agt gga agt gga tct ggg aca gat ttt act ctc acc atc agc agc ctg        344
Ser Gly Ser Gly Ser Gly Thr Asp Phe Thr Leu Thr Ile Ser Ser Leu
                 70                  75                  80 cag cct gaa gat ttt gca acc tac tac tgt cag caa agt aac gag gat        392
Gln Pro Glu Asp Phe Ala Thr Tyr Tyr Cys Gln Gln Ser Asn Glu Asp
             85                  90                  95 cct cgg acg ttc ggc caa ggc acc aag gtg gaa atc aaa cgg act gtg        440
Pro Arg Thr Phe Gly Gln Gly Thr Lys Val Glu Ile Lys Arg Thr Val
100                 105                 110 gct gca cca tct gtc ttc atc ttc ccg cca tct gat gag cag ttg aaa        488
Ala Ala Pro Ser Val Phe Ile Phe Pro Pro Ser Asp Glu Gln Leu Lys
115                 120                 125                 130 tct gga act gcc tct gtt gtg tgc ctg ctg aat aac ttc tat ccc aga        536
Ser Gly Thr Ala Ser Val Val Cys Leu Leu Asn Asn Phe Tyr Pro Arg
                135                 140                 145 gag gcc aaa gta cag tgg aaa gtg gat aac gcc ctc caa tcg ggt aac        584
Glu Ala Lys Val Gln Trp Lys Val Asp Asn Ala Leu Gln Ser Gly Asn
                150                 155                 160 tcc cag gag agt gtc aca gag cag gac agc aag gac agc acc tac agc        632
Ser Gln Glu Ser Val Thr Glu Gln Asp Ser Lys Asp Ser Thr Tyr Ser
165                 170                 175 ctc agc agc acc ctg acg ctg agc aaa gca gac tac gag aaa cac aaa        680
Leu Ser Ser Thr Leu Thr Leu Ser Lys Ala Asp Tyr Glu Lys His Lys
180                 185                 190 gtc tac gcc tgc gaa gtc acc cat cag ggc ctg agc tcg ccc gtc aca        728
Val Tyr Ala Cys Glu Val Thr His Gln Gly Leu Ser Ser Pro Val Thr
195                 200                 205                 210 aag agc ttc aac agg gga gag tgt tagtaagaat tcggg                       767
Lys Ser Phe Asn Arg Gly Glu Cys
                215
```

<210> SEQ ID NO 127
<211> LENGTH: 238
<212> TYPE: PRT
<213> ORGANISM: Artificial Sequence
<220> FEATURE:
<223> OTHER INFORMATION: Description of Artificial Sequence: Designed light chain of humanized anti-Fas antibody

<400> SEQUENCE: 127

```
Met Glu Thr Asp Thr Ile Leu Leu Trp Val Leu Leu Leu Trp Val Pro
-20                 -15                 -10                  -5

Gly Ser Thr Gly Asp Ile Val Leu Thr Gln Ser Pro Ser Ser Leu Ser
            -1   1                   5                  10

Ala Ser Val Gly Asp Arg Val Thr Ile Thr Cys Lys Ala Ser Gln Ser
            15                  20                  25

Val Asp Tyr Asp Gly Asp Ser Tyr Met Asn Trp Tyr Gln Gln Lys Pro
         30                  35                  40
```

```
Gly Lys Ala Pro Lys Leu Leu Ile Tyr Ala Ala Ser Asn Leu Glu Ser
 45                  50                  55                  60

Gly Val Pro Ser Arg Phe Ser Gly Ser Gly Ser Gly Thr Asp Phe Thr
                 65                  70                  75

Leu Thr Ile Ser Ser Leu Gln Pro Glu Asp Phe Ala Thr Tyr Tyr Cys
             80                  85                  90

Gln Gln Ser Asn Glu Asp Pro Arg Thr Phe Gly Gln Gly Thr Lys Val
             95                 100                 105

Glu Ile Lys Arg Thr Val Ala Ala Pro Ser Val Phe Ile Phe Pro Pro
        110                 115                 120

Ser Asp Glu Gln Leu Lys Ser Gly Thr Ala Ser Val Val Cys Leu Leu
125                 130                 135                 140

Asn Asn Phe Tyr Pro Arg Glu Ala Lys Val Gln Trp Lys Val Asp Asn
                145                 150                 155

Ala Leu Gln Ser Gly Asn Ser Gln Glu Ser Val Thr Glu Gln Asp Ser
            160                 165                 170

Lys Asp Ser Thr Tyr Ser Leu Ser Ser Thr Leu Thr Leu Ser Lys Ala
        175                 180                 185

Asp Tyr Glu Lys His Lys Val Tyr Ala Cys Glu Val Thr His Gln Gly
    190                 195                 200

Leu Ser Ser Pro Val Thr Lys Ser Phe Asn Arg Gly Glu Cys
205                 210                 215

<210> SEQ ID NO 128
<211> LENGTH: 767
<212> TYPE: DNA
<213> ORGANISM: Artificial Sequence
<220> FEATURE:
<223> OTHER INFORMATION: Description of Artificial Sequence: Designed
      DNA encoding the light chain of a humanized anti-Fas
      antibody
<220> FEATURE:
<221> NAME/KEY: CDS
<222> LOCATION: (39)..(752)
<220> FEATURE:
<221> NAME/KEY: mat peptide
<222> LOCATION: (99)..(752)
<220> FEATURE:
<221> NAME/KEY: sig peptide
<222> LOCATION: (39)..(98)

<400> SEQUENCE: 128
ccaagcttaa gaagcatcct ctcatctagt tctcagag atg gag aca gac aca atc      56
                                          Met Glu Thr Asp Thr Ile
                                                 -20             -15 ctg cta tgg gtg ctg ctg ctc tgg gtt cca ggc tcc act ggt gac att     104
Leu Leu Trp Val Leu Leu Leu Trp Val Pro Gly Ser Thr Gly Asp Ile
             -10                  -5                  -1   1 gtg ctc acc caa tct cca tcc tcc ctg tct gca tct gta gga gac aga     152
Val Leu Thr Gln Ser Pro Ser Ser Leu Ser Ala Ser Val Gly Asp Arg
          5                  10                  15 gtc acc atc act tgc aag gcc agc caa agt gtt gat tat gat ggt gat     200
Val Thr Ile Thr Cys Lys Ala Ser Gln Ser Val Asp Tyr Asp Gly Asp
     20                  25                  30 agt tat atg aac tgg tac caa cag aaa cca gga cag gca ccc aag ctc     248
Ser Tyr Met Asn Trp Tyr Gln Gln Lys Pro Gly Gln Ala Pro Lys Leu
 35                  40                  45                  50 ctc atc tat gct gca tcc aat ttg gaa agt ggg gtc cca tca agg ttc     296
Leu Ile Tyr Ala Ala Ser Asn Leu Glu Ser Gly Val Pro Ser Arg Phe
             55                  60                  65
```

-continued

```
agt gga agt gga tct ggg aca gat ttt act ctc acc atc agc agc ctg          344
Ser Gly Ser Gly Ser Gly Thr Asp Phe Thr Leu Thr Ile Ser Ser Leu
             70                  75                  80 cag cct gaa gat ttt gca acc tac tac tgt caa cag agt aac gag gat          392
Gln Pro Glu Asp Phe Ala Thr Tyr Tyr Cys Gln Gln Ser Asn Glu Asp
         85                  90                  95 cct cga acg ttc ggc caa ggc acc aag gtg gaa atc aaa cgg act gtg          440
Pro Arg Thr Phe Gly Gln Gly Thr Lys Val Glu Ile Lys Arg Thr Val
100                 105                 110 gct gca cca tct gtc ttc atc ttc ccg cca tct gat gag cag ttg aaa          488
Ala Ala Pro Ser Val Phe Ile Phe Pro Pro Ser Asp Glu Gln Leu Lys
115                 120                 125                 130 tct gga act gcc tct gtt gtg tgc ctg ctg aat aac ttc tat ccc aga          536
Ser Gly Thr Ala Ser Val Val Cys Leu Leu Asn Asn Phe Tyr Pro Arg
                135                 140                 145 gag gcc aaa gta cag tgg aaa gtg gat aac gcc ctc caa tcg ggt aac          584
Glu Ala Lys Val Gln Trp Lys Val Asp Asn Ala Leu Gln Ser Gly Asn
            150                 155                 160 tcc cag gag agt gtc aca gag cag gac agc aag gac agc acc tac agc          632
Ser Gln Glu Ser Val Thr Glu Gln Asp Ser Lys Asp Ser Thr Tyr Ser
        165                 170                 175 ctc agc agc acc ctg acg ctg agc aaa gca gac tac gag aaa cac aaa          680
Leu Ser Ser Thr Leu Thr Leu Ser Lys Ala Asp Tyr Glu Lys His Lys
    180                 185                 190 gtc tac gcc tgc gaa gtc acc cat cag ggc ctg agc tcg ccc gtc aca          728
Val Tyr Ala Cys Glu Val Thr His Gln Gly Leu Ser Ser Pro Val Thr
195                 200                 205                 210 aag agc ttc aac agg gga gag tgt tagtaagaat tcggg                         767
Lys Ser Phe Asn Arg Gly Glu Cys
                215
```

<210> SEQ ID NO 129
<211> LENGTH: 238
<212> TYPE: PRT
<213> ORGANISM: Artificial Sequence
<220> FEATURE:
<223> OTHER INFORMATION: Description of Artificial Sequence: Designed
      light chain of humanized anti-Fas antibody

<400> SEQUENCE: 129

```
Met Glu Thr Asp Thr Ile Leu Leu Trp Val Leu Leu Leu Trp Val Pro
-20                 -15                 -10                 -5

Gly Ser Thr Gly Asp Ile Val Leu Thr Gln Ser Pro Ser Ser Leu Ser
            -1  1                   5                  10

Ala Ser Val Gly Asp Arg Val Thr Ile Thr Cys Lys Ala Ser Gln Ser
        15                  20                  25

Val Asp Tyr Asp Gly Asp Ser Tyr Met Asn Trp Tyr Gln Gln Lys Pro
    30                  35                  40

Gly Gln Ala Pro Lys Leu Leu Ile Tyr Ala Ala Ser Asn Leu Glu Ser
45                  50                  55                  60

Gly Val Pro Ser Arg Phe Ser Gly Ser Gly Ser Gly Thr Asp Phe Thr
                65                  70                  75

Leu Thr Ile Ser Ser Leu Gln Pro Glu Asp Phe Ala Thr Tyr Tyr Cys
            80                  85                  90

Gln Gln Ser Asn Glu Asp Pro Arg Thr Phe Gly Gln Gly Thr Lys Val
        95                 100                 105

Glu Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu Leu
```

```
                125                 130                 135                 140
Asn Asn Phe Tyr Pro Arg Glu Ala Lys Val Gln Trp Lys Val Asp Asn
                145                 150                 155

Ala Leu Gln Ser Gly Asn Ser Gln Glu Ser Val Thr Glu Gln Asp Ser
            160                 165                 170

Lys Asp Ser Thr Tyr Ser Leu Ser Ser Thr Leu Thr Leu Ser Lys Ala
        175                 180                 185

Asp Tyr Glu Lys His Lys Val Tyr Ala Cys Glu Val Thr His Gln Gly
    190                 195                 200

Leu Ser Ser Pro Val Thr Lys Ser Phe Asn Arg Gly Glu Cys
205                 210                 215

<210> SEQ ID NO 130
<211> LENGTH: 778
<212> TYPE: DNA
<213> ORGANISM: Artificial Sequence
<220> FEATURE:
<223> OTHER INFORMATION: Description of Artificial Sequence: Designed
      DNA encoding the light chain of a humanized anti-Fas
      antibody
<220> FEATURE:
<221> NAME/KEY: CDS
<222> LOCATION: (39)..(752)
<220> FEATURE:
<221> NAME/KEY: mat peptide
<222> LOCATION: (99)..(752)
<220> FEATURE:
<221> NAME/KEY: sig peptide
<222> LOCATION: (39)..(98)

<400> SEQUENCE: 130
ccaagcttaa gaagcatcct ctcatctagt tctcagag atg gag aca gac aca atc        56
                                         Met Glu Thr Asp Thr Ile
                                             -20             -15 ctg cta tgg gtg ctg ctg ctc tgg gtt cca ggc tcc act ggt gac att        104
Leu Leu Trp Val Leu Leu Leu Trp Val Pro Gly Ser Thr Gly Asp Ile
            -10                 -5                  -1  1 gtg ctc acc caa tct cca tcc tcc ctg tct gca tct gta gga gac aga        152
Val Leu Thr Gln Ser Pro Ser Ser Leu Ser Ala Ser Val Gly Asp Arg
         5                  10                  15 gtc acc atc act tgc aag gcc agc caa agt gtt gat tat gat ggt gat        200
Val Thr Ile Thr Cys Lys Ala Ser Gln Ser Val Asp Tyr Asp Gly Asp
     20                  25                  30 agt tat atg aac tgg tac caa cag aaa cca gga aag gca ccc aaa ctc        248
Ser Tyr Met Asn Trp Tyr Gln Gln Lys Pro Gly Lys Ala Pro Lys Leu
 35                  40                  45                  50 ctc atc tac gct gca tcc aat ttg gaa tca ggg atc cca tca agg ttc        296
Leu Ile Tyr Ala Ala Ser Asn Leu Glu Ser Gly Ile Pro Ser Arg Phe
             55                  60                  65 agt gga agt gga tct ggg aca gat ttt act ctc acc atc agc agc ctg        344
Ser Gly Ser Gly Ser Gly Thr Asp Phe Thr Leu Thr Ile Ser Ser Leu
         70                  75                  80 cag cct gag gat ttt gca acc tat tac tgt cag caa agt aat gag gat        392
Gln Pro Glu Asp Phe Ala Thr Tyr Tyr Cys Gln Gln Ser Asn Glu Asp
     85                  90                  95 cct cgg acg ttc ggt caa ggc acc aag gtg gaa atc aaa cgg act gtg        440
Pro Arg Thr Phe Gly Gln Gly Thr Lys Val Glu Ile Lys Arg Thr Val
100                 105                 110 gct gca cca tct gtc ttc atc ttc ccg cca tct gat gag cag ttg aaa        488
Ala Ala Pro Ser Val Phe Ile Phe Pro Pro Ser Asp Glu Gln Leu Lys
115                 120                 125                 130 tct gga act gcc tct gtt gtg tgc ctg ctg aat aac ttc tat ccc aga        536
```

```
Ser Gly Thr Ala Ser Val Val Cys Leu Leu Asn Asn Phe Tyr Pro Arg
            135                 140                 145 gag gcc aaa gta cag tgg aag gtg gat aac gcc ctc caa tcg ggt aac     584
Glu Ala Lys Val Gln Trp Lys Val Asp Asn Ala Leu Gln Ser Gly Asn
            150                 155                 160 tcc cag gag agt gtc aca gag cag gac agc aag gac agc acc tac agc     632
Ser Gln Glu Ser Val Thr Glu Gln Asp Ser Lys Asp Ser Thr Tyr Ser
            165                 170                 175 ctc agc agc acc ctg acg ctg agc aaa gca gac tac gag aaa cac aaa     680
Leu Ser Ser Thr Leu Thr Leu Ser Lys Ala Asp Tyr Glu Lys His Lys
        180                 185                 190 gtc tac gcc tgc gaa gtc acc cat cag ggc ctg agc tcg ccc gtc aca     728
Val Tyr Ala Cys Glu Val Thr His Gln Gly Leu Ser Ser Pro Val Thr
195                 200                 205                 210 aag agc ttc aac agg gga gag tgt tagtaagaat tcgggaagcc gaattc        778
Lys Ser Phe Asn Arg Gly Glu Cys
            215

<210> SEQ ID NO 131
<211> LENGTH: 238
<212> TYPE: PRT
<213> ORGANISM: Artificial Sequence
<220> FEATURE:
<223> OTHER INFORMATION: Description of Artificial Sequence: Designed
      light chain of humanized anti-Fas antibody

<400> SEQUENCE: 131

Met Glu Thr Asp Thr Ile Leu Leu Trp Val Leu Leu Leu Trp Val Pro
-20                 -15                 -10                  -5

Gly Ser Thr Gly Asp Ile Val Leu Thr Gln Ser Pro Ser Ser Leu Ser
            -1  1                   5                  10

Ala Ser Val Gly Asp Arg Val Thr Ile Thr Cys Lys Ala Ser Gln Ser
            15                  20                  25

Val Asp Tyr Asp Gly Asp Ser Tyr Met Asn Trp Tyr Gln Gln Lys Pro
        30                  35                  40

Gly Lys Ala Pro Lys Leu Leu Ile Tyr Ala Ala Ser Asn Leu Glu Ser
45                  50                  55                  60

Gly Ile Pro Ser Arg Phe Ser Gly Ser Gly Ser Gly Thr Asp Phe Thr
            65                  70                  75

Leu Thr Ile Ser Ser Leu Gln Pro Glu Asp Phe Ala Thr Tyr Tyr Cys
            80                  85                  90

Gln Gln Ser Asn Glu Asp Pro Arg Thr Phe Gly Gln Gly Thr Lys Val
        95                  100                 105

Glu Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu Leu
125                 130                 135                 140

Asn Asn Phe Tyr Pro Arg Glu Ala Lys Val Gln Trp Lys Val Asp Asn
            145                 150                 155

Ala Leu Gln Ser Gly Asn Ser Gln Glu Ser Val Thr Glu Gln Asp Ser
            160                 165                 170

Lys Asp Ser Thr Tyr Ser Leu Ser Ser Thr Leu Thr Leu Ser Lys Ala
        175                 180                 185

Asp Tyr Glu Lys His Lys Val Tyr Ala Cys Glu Val Thr His Gln Gly
        190                 195                 200

Leu Ser Ser Pro Val Thr Lys Ser Phe Asn Arg Gly Glu Cys
205                 210                 215
```

<210> SEQ ID NO 132
<211> LENGTH: 41
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light chain
      of a humanized anti-Fas antibody

<400> SEQUENCE: 132
agggaggatg gagattgggt gagcacaatg tcaccagtgg a                 41

<210> SEQ ID NO 133
<211> LENGTH: 39
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light chain
      of a humanized anti-Fas antibody

<400> SEQUENCE: 133
attgtgctca cccaatctcc atcctccctg tctgcatct                    39

<210> SEQ ID NO 134
<211> LENGTH: 42
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light chain
      of a humanized anti-Fas antibody

<400> SEQUENCE: 134
atcaacactt tggctggcct tgcaagtgat ggtgactctg tc                42

<210> SEQ ID NO 135
<211> LENGTH: 40
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light chain
      of a humanized anti-Fas antibody

<400> SEQUENCE: 135
ccatcacttg caaggccagc caaagtgttg attatgatgg                   40

<210> SEQ ID NO 136
<211> LENGTH: 48
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light chain
      of a humanized anti-Fas antibody

<400> SEQUENCE: 136
agtttcgaga ttggatgcag catagatgag gagtttgggt gcctttcc          48

<210> SEQ ID NO 137
<211> LENGTH: 45
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light chain
      of a humanized anti-Fas antibody

```
<400> SEQUENCE: 137
cccaagctcc tcatctatgc tgcatccaat ttggaaagtg gggtc                    45

<210> SEQ ID NO 138
<211> LENGTH: 44
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light chain
      of a humanized anti-Fas antibody

<400> SEQUENCE: 138
ttggccgaac gttcgaggat cctcgttact ctgttgacag tagt                     44

<210> SEQ ID NO 139
<211> LENGTH: 44
<212> TYPE: DNA
<213> ORGANISM: Artificial Sequence
<220> FEATURE:
<223> OTHER INFORMATION: Description of Artificial Sequence:  PCR primer
      to amplify a fragment of DNA encoding the light chain
      of a humanized anti-Fas antibody

<400> SEQUENCE: 139
actactgtca acagagtaac gaggatcctc gaacgttcgg ccaa                     44

<210> SEQ ID NO 140
<211> LENGTH: 45
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the light chain
      of a humanized anti-Fas antibody

<400> SEQUENCE: 140
ctcatctatg ctgcatccaa tttggaaagt gggatcccat caagg                    45

<210> SEQ ID NO 141
<211> LENGTH: 45
<212> TYPE: DNA
<213> ORGANISM: Artificial Sequence
<220> FEATURE:
<223> OTHER INFORMATION: Description of Artificial Sequence:  PCR primer
      to amplify a fragment of DNA encoding the light chain
      of a humanized anti-Fas antibody

<400> SEQUENCE: 141
attggatgca gcatagatga ggagcttggg tgcctgtcct ggttt                    45

<210> SEQ ID NO 142
<211> LENGTH: 2073
<212> TYPE: DNA
<213> ORGANISM: Artificial Sequence
<220> FEATURE:
<223> OTHER INFORMATION: Description of Artificial Sequence: Designed
      DNA encoding the heavy chain of a humanized anti-Fas
      antibody
<220> FEATURE:
<221> NAME/KEY: sig peptide
<222> LOCATION: (23)..(79)
<220> FEATURE:
<221> NAME/KEY: intron
<222> LOCATION: (737)..(1127)
<220> FEATURE:
<221> NAME/KEY: intron
<222> LOCATION: (1173)..(1290)
```

```
<220> FEATURE:
<221> NAME/KEY: intron
<222> LOCATION: (1621)..(1717)
<220> FEATURE:
<221> NAME/KEY: exon
<222> LOCATION: (23)..(736)
<220> FEATURE:
<221> NAME/KEY: exon
<222> LOCATION: (1128)..(1172)
<220> FEATURE:
<221> NAME/KEY: exon
<222> LOCATION: (1291)..(1620)
<220> FEATURE:
<221> NAME/KEY: exon
<222> LOCATION: (1718)..(2038)
<220> FEATURE:
<221> NAME/KEY: mat peptide
<222> LOCATION: (80)..(736)
<220> FEATURE:
<221> NAME/KEY: mat peptide
<222> LOCATION: (1128)..(1172)
<220> FEATURE:
<221> NAME/KEY: mat peptide
<222> LOCATION: (1291)..(1620)
<220> FEATURE:
<221> NAME/KEY: mat peptide
<222> LOCATION: (1718)..(2038)
<220> FEATURE:
<221> NAME/KEY: CDS
<222> LOCATION: (23)..(736)
<220> FEATURE:
<221> NAME/KEY: CDS
<222> LOCATION: (1128)..(1172)
<220> FEATURE:
<221> NAME/KEY: CDS
<222> LOCATION: (1291)..(1620)
<220> FEATURE:
<221> NAME/KEY: CDS
<222> LOCATION: (1718)..(2038)

<400> SEQUENCE: 142
```

```
ccaagcttgg cttgacctca cc atg gga tgg agc tgt atc atc ctc ttc ttg       52
                         Met Gly Trp Ser Cys Ile Ile Leu Phe Leu
                             -15                         -10 gta gca aca gct aca ggt gtc cat tct cag gtc caa ctg gtg cag tct       100
Val Ala Thr Ala Thr Gly Val His Ser Gln Val Gln Leu Val Gln Ser
             -5                  -1   1               5 ggg gct gag gtc aag aag cct ggg gct tca gtg aag gtg tcc tgc aag       148
Gly Ala Glu Val Lys Lys Pro Gly Ala Ser Val Lys Val Ser Cys Lys
         10                  15                  20 gct tct ggc tac acc ttc acc agc tac tgg atg cag tgg gta aaa cag       196
Ala Ser Gly Tyr Thr Phe Thr Ser Tyr Trp Met Gln Trp Val Lys Gln
     25                  30                  35 gcc cct gga cag gga ctt gag tgg atg gga gag att gat cct tct gat       244
Ala Pro Gly Gln Gly Leu Glu Trp Met Gly Glu Ile Asp Pro Ser Asp
 40                  45                  50                  55 agc tat act aac tac aat caa aag ttc aag ggc aag gcc aca ttg act       292
Ser Tyr Thr Asn Tyr Asn Gln Lys Phe Lys Gly Lys Ala Thr Leu Thr
                 60                  65                  70 gta gac aca tcc act agc aca gcc tac atg gag ctc agc agc ctg aga       340
Val Asp Thr Ser Thr Ser Thr Ala Tyr Met Glu Leu Ser Ser Leu Arg
             75                  80                  85 tct gag gac acg gcg gtc tat tac tgt gca aga aat agg gac tat agt       388
Ser Glu Asp Thr Ala Val Tyr Tyr Cys Ala Arg Asn Arg Asp Tyr Ser
         90                  95                  100 aac aac tgg tac ttc gat gtc tgg ggc caa ggt aca ctg gtc acc gtc       436
Asn Asn Trp Tyr Phe Asp Val Trp Gly Gln Gly Thr Leu Val Thr Val
     105                 110                 115 tcc tca gcc tcc acc aag ggc cca tcg gtc ttc ccc ctg gca ccc tcc       484
```

```
Ser Ser Ala Ser Thr Lys Gly Pro Ser Val Phe Pro Leu Ala Pro Ser
120             125                 130                 135 tcc aag agc acc tct ggg ggc aca gcg gcc ctg ggc tgc ctg gtc aag        532
Ser Lys Ser Thr Ser Gly Gly Thr Ala Ala Leu Gly Cys Leu Val Lys
                140                 145                 150 gac tac ttc ccc gaa ccg gtg acg gtg tcg tgg aac tca ggc gcc ctg        580
Asp Tyr Phe Pro Glu Pro Val Thr Val Ser Trp Asn Ser Gly Ala Leu
                155                 160                 165 acc agc ggc gtg cac acc ttc ccg gct gtc cta cag tcc tca gga ctc        628
Thr Ser Gly Val His Thr Phe Pro Ala Val Leu Gln Ser Ser Gly Leu
            170                 175                 180 tac tcc ctc agc agc gtg gtg acc gtg ccc tcc agc agc ttg ggc acc        676
Tyr Ser Leu Ser Ser Val Val Thr Val Pro Ser Ser Ser Leu Gly Thr
        185                 190                 195 cag acc tac atc tgc aac gtg aat cac aag ccc agc aac acc aag gtg        724
Gln Thr Tyr Ile Cys Asn Val Asn His Lys Pro Ser Asn Thr Lys Val
200                 205                 210                 215 gac aag aga gtt ggtgagaggc cagcacaggg agggaggtg tctgctggaa             776
Asp Lys Arg Val gccaggctca gcgctcctgc ctggacgcat cccggctatg cagtcccagt ccagggcagc     836
aaggcaggcc ccgtctgcct cttcacccgg aggcctctgc ccgccccact catgctcagg     896
gagagggtct tctggctttt tccccaggct ctgggcaggc acaggctagg tgcccctaac     956
ccaggccctg cacacaaagg ggcaggtgct gggctcagac ctgccaagag ccatatccgg    1016
gaggaccctg ccctgacct aagcccaccc caaaggccaa actctccact ccctcagctc    1076
ggacaccttc tctcctccca gattccagta actcccaatc ttctctctgc a gag ccc    1133
                                                        Glu Pro
                                                        220 aaa tct tgt gac aaa act cac aca tgc cca ccg tgc cca ggtaagccag       1182
Lys Ser Cys Asp Lys Thr His Thr Cys Pro Pro Cys Pro
            225                 230 cccaggcctc gccctccagc tcaaggcggg acaggtgccc tagagtagcc tgcatccagg    1242
gacaggcccc agccgggtgc tgacacgtcc acctccatct cttcctca gca cct gaa    1299
                                                     Ala Pro Glu
                                                             235 ctc ctg ggg gga ccg tca gtc ttc ctc ttc ccc cca aaa ccc aag gac        1347
Leu Leu Gly Gly Pro Ser Val Phe Leu Phe Pro Pro Lys Pro Lys Asp
            240                 245                 250 acc ctc atg atc tcc cgg acc cct gag gtc aca tgc gtg gtg gtg gac        1395
Thr Leu Met Ile Ser Arg Thr Pro Glu Val Thr Cys Val Val Val Asp
        255                 260                 265 gtg agc cac gaa gac cct gag gtc aag ttc aac tgg tac gtg gac ggc        1443
Val Ser His Glu Asp Pro Glu Val Lys Phe Asn Trp Tyr Val Asp Gly
270                 275                 280                 285 gtg gag gtg cat aat gcc aag aca aag ccg cgg gag gag cag tac aac        1491
Val Glu Val His Asn Ala Lys Thr Lys Pro Arg Glu Glu Gln Tyr Asn
                290                 295                 300 agc acg tac cgt gtg gtc agc gtc ctc acc gtc ctg cac cag gac tgg        1539
Ser Thr Tyr Arg Val Val Ser Val Leu Thr Val Leu His Gln Asp Trp
                305                 310                 315 ctg aat ggc aag gag tac aag tgc aag gtc tcc aac aaa gcc ctc cca        1587
Leu Asn Gly Lys Glu Tyr Lys Cys Lys Val Ser Asn Lys Ala Leu Pro
            320                 325                 330 gcc ccc atc gag aaa acc atc tcc aaa gcc aaa ggtgggaccc gtggggtgcg     1640
Ala Pro Ile Glu Lys Thr Ile Ser Lys Ala Lys
        335                 340
```

-continued

```
agggccacat ggacagaggc cggctcggcc caccctctgc cctgagagtg accgctgtac    1700
caacctctgt ccctaca ggg cag ccc cga gaa cca cag gtg tac acc ctg       1750
                Gly Gln Pro Arg Glu Pro Gln Val Tyr Thr Leu
                345                 350                 355 ccc cca tcc cgg gag gag atg acc aag aac cag gtc agc ctg acc tgc      1798
Pro Pro Ser Arg Glu Glu Met Thr Lys Asn Gln Val Ser Leu Thr Cys
            360                 365                 370 ctg gtc aaa ggc ttc tat ccc agc gac atc gcc gtg gag tgg gag agc      1846
Leu Val Lys Gly Phe Tyr Pro Ser Asp Ile Ala Val Glu Trp Glu Ser
        375                 380                 385 aat ggg cag ccg gag aac aac tac aag acc acg cct ccc gtg ctg gac      1894
Asn Gly Gln Pro Glu Asn Asn Tyr Lys Thr Thr Pro Pro Val Leu Asp
            390                 395                 400 tcc gac ggc tcc ttc ttc ctc tat agc aag ctc acc gtg gac aag agc      1942
Ser Asp Gly Ser Phe Phe Leu Tyr Ser Lys Leu Thr Val Asp Lys Ser
    405                 410                 415 agg tgg cag cag ggg aac gtc ttc tca tgc tcc gtg atg cat gag gct      1990
Arg Trp Gln Gln Gly Asn Val Phe Ser Cys Ser Val Met His Glu Ala
420                 425                 430                 435 ctg cac aac cac tac acg cag aag agc ctc tcc ctg tcc ccg ggt aaa      2038
Leu His Asn His Tyr Thr Gln Lys Ser Leu Ser Leu Ser Pro Gly Lys
                440                 445                 450 tgagtgcgac ggccggcaag ccccgctccc gaatt                                2073
```

<210> SEQ ID NO 143
<211> LENGTH: 470
<212> TYPE: PRT
<213> ORGANISM: Artificial Sequence
<220> FEATURE:
<223> OTHER INFORMATION: Description of Artificial Sequence: Designed
      heavy chain of humanized anti-Fas antibody

<400> SEQUENCE: 143

```
Met Gly Trp Ser Cys Ile Ile Leu Phe Leu Val Ala Thr Ala Thr Gly
              -15                 -10                  -5

Val His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
     15                  20                  25

Thr Ser Tyr Trp Met Gln Trp Val Lys Gln Ala Pro Gly Gln Gly Leu
 30                  35                  40                  45

Glu Trp Met Gly Glu Ile Asp Pro Ser Asp Ser Tyr Thr Asn Tyr Asn
                 50                  55                  60

Gln Lys Phe Lys Gly Lys Ala Thr Leu Thr Val Asp Thr Ser Thr Ser
             65                  70                  75

Thr Ala Tyr Met Glu Leu Ser Ser Leu Arg Ser Glu Asp Thr Ala Val
         80                  85                  90

Tyr Tyr Cys Ala Arg Asn Arg Asp Tyr Ser Asn Asn Trp Tyr Phe Asp
     95                 100                 105

Val Trp Gly Gln Gly Thr Leu Val Thr Val Ser Ser Ala Ser Thr Lys
110                 115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
            145                 150                 155

Val Thr Val Ser Trp Asn Ser Gly Ala Leu Thr Ser Gly Val His Thr
        160                 165                 170
```

```
Phe Pro Ala Val Leu Gln Ser Ser Gly Leu Tyr Ser Leu Ser Ser Val
    175                 180                 185

Val Thr Val Pro Ser Ser Ser Leu Gly Thr Gln Thr Tyr Ile Cys Asn
190             195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
                225                 230                 235

Leu Leu Gly Gly Pro Ser Val Phe Leu Phe Pro Pro Lys Pro Lys Asp
            240                 245                 250

Thr Leu Met Ile Ser Arg Thr Pro Glu Val Thr Cys Val Val Val Asp
    255                 260                 265

Val Ser His Glu Asp Pro Glu Val Lys Phe Asn Trp Tyr Val Asp Gly
270             275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
                305                 310                 315

Leu Asn Gly Lys Glu Tyr Lys Cys Lys Val Ser Asn Lys Ala Leu Pro
            320                 325                 330

Ala Pro Ile Glu Lys Thr Ile Ser Lys Ala Lys Gly Gln Pro Arg Glu
    335                 340                 345

Pro Gln Val Tyr Thr Leu Pro Pro Ser Arg Glu Glu Met Thr Lys Asn
350             355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
                385                 390                 395

Thr Pro Pro Val Leu Asp Ser Asp Gly Ser Phe Phe Leu Tyr Ser Lys
            400                 405                 410

Leu Thr Val Asp Lys Ser Arg Trp Gln Gln Gly Asn Val Phe Ser Cys
    415                 420                 425

Ser Val Met His Glu Ala Leu His Asn His Tyr Thr Gln Lys Ser Leu
430             435                 440                 445

Ser Leu Ser Pro Gly Lys
                450

<210> SEQ ID NO 144
<211> LENGTH: 2073
<212> TYPE: DNA
<213> ORGANISM: Artificial Sequence
<220> FEATURE:
<223> OTHER INFORMATION: Description of Artificial Sequence: Designed
      DNA encoding the heavy chain of a humanized anti-Fas
      antibody
<220> FEATURE:
<221> NAME/KEY: sig peptide
<222> LOCATION: (23)..(79)
<220> FEATURE:
<221> NAME/KEY: intron
<222> LOCATION: (737)..(1127)
<220> FEATURE:
<221> NAME/KEY: intron
<222> LOCATION: (1173)..(1290)
<220> FEATURE:
<221> NAME/KEY: intron
<222> LOCATION: (1621)..(1717)
<220> FEATURE:
<221> NAME/KEY: exon
<222> LOCATION: (23)..(736)
<220> FEATURE:
```

```
<221> NAME/KEY: exon
<222> LOCATION: (1128)..(1172)
<220> FEATURE:
<221> NAME/KEY: exon
<222> LOCATION: (1291)..(1620)
<220> FEATURE:
<221> NAME/KEY: exon
<222> LOCATION: (1718)..(2038)
<220> FEATURE:
<221> NAME/KEY: mat peptide
<222> LOCATION: (80)..(736)
<220> FEATURE:
<221> NAME/KEY: mat peptide
<222> LOCATION: (1128)..(1172)
<220> FEATURE:
<221> NAME/KEY: mat peptide
<222> LOCATION: (1291)..(1620)
<220> FEATURE:
<221> NAME/KEY: mat peptide
<222> LOCATION: (1718)..(2038)
<220> FEATURE:
<221> NAME/KEY: CDS
<222> LOCATION: (23)..(736)
<220> FEATURE:
<221> NAME/KEY: CDS
<222> LOCATION: (1128)..(1172)
<220> FEATURE:
<221> NAME/KEY: CDS
<222> LOCATION: (1291)..(1620)
<220> FEATURE:
<221> NAME/KEY: CDS
<222> LOCATION: (1718)..(2038)

<400> SEQUENCE: 144
ccaagcttgg cttgacctca cc atg gga tgg agc tgt atc atc ctc ttc ttg        52
                         Met Gly Trp Ser Cys Ile Ile Leu Phe Leu
                             -15                         -10 gta gca aca gct aca ggt gtc cat tct cag gtc caa ctg gtg cag tct       100
Val Ala Thr Ala Thr Gly Val His Ser Gln Val Gln Leu Val Gln Ser
                -5              -1   1               5 ggg gct gag gtc aag aag cct ggg gct tca gtg aag gtg tcc tgc aag       148
Gly Ala Glu Val Lys Lys Pro Gly Ala Ser Val Lys Val Ser Cys Lys
            10                  15                  20 gct tct ggc tac acc ttc acc agc tac tgg atg cag tgg gta aaa cag       196
Ala Ser Gly Tyr Thr Phe Thr Ser Tyr Trp Met Gln Trp Val Lys Gln
        25                  30                  35 gcc cct gga cag gga ctt gag tgg atg gga gag att gat cct tct gat       244
Ala Pro Gly Gln Gly Leu Glu Trp Met Gly Glu Ile Asp Pro Ser Asp
    40                  45                  50                  55 agc tat act aac tac aat caa aag ttc aag ggc aag gcc aca ata act       292
Ser Tyr Thr Asn Tyr Asn Gln Lys Phe Lys Gly Lys Ala Thr Ile Thr
                60                  65                  70 gta gac aca tcc act agc aca gcc tac atg gag ctc agc agc ctg aga       340
Val Asp Thr Ser Thr Ser Thr Ala Tyr Met Glu Leu Ser Ser Leu Arg
            75                  80                  85 tct gag gac acg gcg gtc tat tac tgt gca aga aat agg gac tat agt       388
Ser Glu Asp Thr Ala Val Tyr Tyr Cys Ala Arg Asn Arg Asp Tyr Ser
        90                  95                 100 aac aac tgg tac ttc gat gtc tgg ggc caa ggt aca ctg gtc acc gtc       436
Asn Asn Trp Tyr Phe Asp Val Trp Gly Gln Gly Thr Leu Val Thr Val
    105                 110                 115 tcc tca gcc tcc acc aag ggc cca tcg gtc ttc ccc ctg gca ccc tcc       484
Ser Ser Ala Ser Thr Lys Gly Pro Ser Val Phe Pro Leu Ala Pro Ser
120                 125                 130                 135 tcc aag agc acc tct ggg ggc aca gcg gcc ctg ggc tgc ctg gtc aag       532
Ser Lys Ser Thr Ser Gly Gly Thr Ala Ala Leu Gly Cys Leu Val Lys
                140                 145                 150
```

-continued

```
gac tac ttc ccc gaa ccg gtg acg gtg tcg tgg aac tca ggc gcc ctg      580
Asp Tyr Phe Pro Glu Pro Val Thr Val Ser Trp Asn Ser Gly Ala Leu
                155                 160                 165 acc agc ggc gtg cac acc ttc ccg gct gtc cta cag tcc tca gga ctc      628
Thr Ser Gly Val His Thr Phe Pro Ala Val Leu Gln Ser Ser Gly Leu
            170                 175                 180 tac tcc ctc agc agc gtg gtg acc gtg ccc tcc agc agc ttg ggc acc      676
Tyr Ser Leu Ser Ser Val Val Thr Val Pro Ser Ser Ser Leu Gly Thr
        185                 190                 195 cag acc tac atc tgc aac gtg aat cac aag ccc agc aac acc aag gtg      724
Gln Thr Tyr Ile Cys Asn Val Asn His Lys Pro Ser Asn Thr Lys Val
200                 205                 210                 215 gac aag aga gtt ggtgagaggc cagcacaggg agggagggtg tctgctggaa          776
Asp Lys Arg Val gccaggctca gcgctcctgc ctggacgcat cccggctatg cagtcccagt ccagggcagc    836
aaggcaggcc ccgtctgcct cttcacccgg aggcctctgc ccgccccact catgctcagg    896
gagagggtct tctggctttt tccccaggct ctgggcaggc acaggctagg tgcccctaac    956
ccaggccctg cacacaaagg ggcaggtgct gggctcagac ctgccaagag ccatatccgg   1016
gaggaccctg cccctgacct aagcccaccc caaaggccaa actctccact ccctcagctc   1076
ggacaccttc tcctcccca gattccagta actcccaatc ttctctctgc a gag ccc     1133
                                                        Glu Pro
                                                        220 aaa tct tgt gac aaa act cac aca tgc cca ccg tgc cca ggtaagccag      1182
Lys Ser Cys Asp Lys Thr His Thr Cys Pro Pro Cys Pro
                225                 230 cccaggcctc gccctccagc tcaaggcggg acaggtgccc tagagtagcc tgcatccagg   1242
gacaggcccc agccgggtgc tgacacgtcc acctccatct cttcctca gca cct gaa    1299
                                                    Ala Pro Glu
                                                            235 ctc ctg ggg gga ccg tca gtc ttc ctc ttc ccc cca aaa ccc aag gac     1347
Leu Leu Gly Gly Pro Ser Val Phe Leu Phe Pro Pro Lys Pro Lys Asp
        240                 245                 250 acc ctc atg atc tcc cgg acc cct gag gtc aca tgc gtg gtg gtg gac     1395
Thr Leu Met Ile Ser Arg Thr Pro Glu Val Thr Cys Val Val Val Asp
    255                 260                 265 gtg agc cac gaa gac cct gag gtc aag ttc aac tgg tac gtg gac ggc     1443
Val Ser His Glu Asp Pro Glu Val Lys Phe Asn Trp Tyr Val Asp Gly
270                 275                 280                 285 gtg gag gtg cat aat gcc aag aca aag ccg cgg gag gag cag tac aac     1491
Val Glu Val His Asn Ala Lys Thr Lys Pro Arg Glu Glu Gln Tyr Asn
                290                 295                 300 agc acg tac cgt gtg gtc agc gtc ctc acc gtc ctg cac cag gac tgg     1539
Ser Thr Tyr Arg Val Val Ser Val Leu Thr Val Leu His Gln Asp Trp
            305                 310                 315 ctg aat ggc aag gag tac aag tgc aag gtc tcc aac aaa gcc ctc cca     1587
Leu Asn Gly Lys Glu Tyr Lys Cys Lys Val Ser Asn Lys Ala Leu Pro
        320                 325                 330 gcc ccc atc gag aaa acc atc tcc aaa gcc aaa                         1640
Ala Pro Ile Glu Lys Thr Ile Ser Lys Ala Lys
    335                 340 agggccacat ggacagaggc cggctcggcc caccctctgc cctgagagtg accgctgtac   1700
caacctctgt ccctaca ggg cag ccc cga gaa cca cag gtg tac acc ctg     1750
                Gly Gln Pro Arg Glu Pro Gln Val Tyr Thr Leu
                        345                 350             355 ccc cca tcc cgg gag gag atg acc aag aac cag gtc agc ctg acc tgc    1798
```

```
Pro Pro Ser Arg Glu Glu Met Thr Lys Asn Gln Val Ser Leu Thr Cys
                360                 365                 370 ctg gtc aaa ggc ttc tat ccc agc gac atc gcc gtg gag tgg gag agc      1846
Leu Val Lys Gly Phe Tyr Pro Ser Asp Ile Ala Val Glu Trp Glu Ser
            375                 380                 385 aat ggg cag ccg gag aac aac tac aag acc acg cct ccc gtg ctg gac      1894
Asn Gly Gln Pro Glu Asn Asn Tyr Lys Thr Thr Pro Pro Val Leu Asp
        390                 395                 400 tcc gac ggc tcc ttc ttc ctc tat agc aag ctc acc gtg gac aag agc      1942
Ser Asp Gly Ser Phe Phe Leu Tyr Ser Lys Leu Thr Val Asp Lys Ser
    405                 410                 415 agg tgg cag cag ggg aac gtc ttc tca tgc tcc gtg atg cat gag gct      1990
Arg Trp Gln Gln Gly Asn Val Phe Ser Cys Ser Val Met His Glu Ala
420                 425                 430                 435 ctg cac aac cac tac acg cag aag agc ctc tcc ctg tcc ccg ggt aaa      2038
Leu His Asn His Tyr Thr Gln Lys Ser Leu Ser Leu Ser Pro Gly Lys
                440                 445                 450 tgagtgcgac ggccggcaag ccccgctccc gaatt                                2073
```

<210> SEQ ID NO 145
<211> LENGTH: 470
<212> TYPE: PRT
<213> ORGANISM: Artificial Sequence
<220> FEATURE:
<223> OTHER INFORMATION: Description of Artificial Sequence: Designed
      heavy chain of humanized anti-Fas antibody

<400> SEQUENCE: 145

```
Met Gly Trp Ser Cys Ile Ile Leu Phe Leu Val Ala Thr Ala Thr Gly
                -15                 -10                 -5

Val His Ser Gln Val Gln Leu Val Gln Ser Gly Ala Glu Val Lys Lys
        -1   1               5                  10

Pro Gly Ala Ser Val Lys Val Ser Cys Lys Ala Ser Gly Tyr Thr Phe
            15                  20                  25

Thr Ser Tyr Trp Met Gln Trp Val Lys Gln Ala Pro Gly Gln Gly Leu
 30                  35                  40                  45

Glu Trp Met Gly Glu Ile Asp Pro Ser Asp Ser Tyr Thr Asn Tyr Asn
                 50                  55                  60

Gln Lys Phe Lys Gly Lys Ala Thr Ile Thr Val Asp Thr Ser Thr Ser
             65                  70                  75

Thr Ala Tyr Met Glu Leu Ser Ser Leu Arg Ser Glu Asp Thr Ala Val
             80                  85                  90

Tyr Tyr Cys Ala Arg Asn Arg Asp Tyr Ser Asn Asn Trp Tyr Phe Asp
         95                 100                 105

Val Trp Gly Gln Gly Thr Leu Val Thr Val Ser Ser Ala Ser Thr Lys
110                 115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
                145                 150                 155

Val Thr Val Ser Trp Asn Ser Gly Ala Leu Thr Ser Gly Val His Thr
            160                 165                 170

Phe Pro Ala Val Leu Gln Ser Ser Gly Leu Tyr Ser Leu Ser Ser Val
        175                 180                 185

Val Thr Val Pro Ser Ser Leu Gly Thr Gln Thr Tyr Ile Cys Asn
190                 195                 200                 205

Val Asn His Lys Pro Ser Asn Thr Lys Val Asp Lys Arg Val Glu Pro
```

-continued

```
                   210                 215                 220
Lys Ser Cys Asp Lys Thr His Thr Cys Pro Pro Cys Pro Ala Pro Glu
                225                 230                 235
Leu Leu Gly Gly Pro Ser Val Phe Leu Phe Pro Pro Lys Pro Lys Asp
            240                 245                 250
Thr Leu Met Ile Ser Arg Thr Pro Glu Val Thr Cys Val Val Val Asp
        255                 260                 265
Val Ser His Glu Asp Pro Glu Val Lys Phe Asn Trp Tyr Val Asp Gly
270                 275                 280                 285
Val Glu Val His Asn Ala Lys Thr Lys Pro Arg Glu Glu Gln Tyr Asn
                290                 295                 300
Ser Thr Tyr Arg Val Val Ser Val Leu Thr Val Leu His Gln Asp Trp
            305                 310                 315
Leu Asn Gly Lys Glu Tyr Lys Cys Lys Val Ser Asn Lys Ala Leu Pro
        320                 325                 330
Ala Pro Ile Glu Lys Thr Ile Ser Lys Ala Lys Gly Gln Pro Arg Glu
        335                 340                 345
Pro Gln Val Tyr Thr Leu Pro Pro Ser Arg Glu Glu Met Thr Lys Asn
350                 355                 360                 365
Gln Val Ser Leu Thr Cys Leu Val Lys Gly Phe Tyr Pro Ser Asp Ile
                370                 375                 380
Ala Val Glu Trp Glu Ser Asn Gly Gln Pro Glu Asn Asn Tyr Lys Thr
            385                 390                 395
Thr Pro Pro Val Leu Asp Ser Asp Gly Ser Phe Phe Leu Tyr Ser Lys
        400                 405                 410
Leu Thr Val Asp Lys Ser Arg Trp Gln Gln Gly Asn Val Phe Ser Cys
    415                 420                 425
Ser Val Met His Glu Ala Leu His Asn His Tyr Thr Gln Lys Ser Leu
430                 435                 440                 445
Ser Leu Ser Pro Gly Lys
                450

<210> SEQ ID NO 146
<211> LENGTH: 2073
<212> TYPE: DNA
<213> ORGANISM: Artificial Sequence
<220> FEATURE:
<223> OTHER INFORMATION: Description of Artificial Sequence: Designed
      DNA encoding the heavy chain of a humanized anti-Fas
      antibody
<220> FEATURE:
<221> NAME/KEY: sig peptide
<222> LOCATION: (23)..(79)
<220> FEATURE:
<221> NAME/KEY: intron
<222> LOCATION: (737)..(1127)
<220> FEATURE:
<221> NAME/KEY: intron
<222> LOCATION: (1173)..(1290)
<220> FEATURE:
<221> NAME/KEY: intron
<222> LOCATION: (1621)..(1717)
<220> FEATURE:
<221> NAME/KEY: exon
<222> LOCATION: (23)..(736)
<220> FEATURE:
<221> NAME/KEY: exon
<222> LOCATION: (1128)..(1172)
<220> FEATURE:
<221> NAME/KEY: exon
<222> LOCATION: (1291)..(1620)
<220> FEATURE:
<221> NAME/KEY: exon
```

```
<222> LOCATION: (1718)..(2038)
<220> FEATURE:
<221> NAME/KEY: mat peptide
<222> LOCATION: (80)..(736)
<220> FEATURE:
<221> NAME/KEY: mat peptide
<222> LOCATION: (1128)..(1172)
<220> FEATURE:
<221> NAME/KEY: mat peptide
<222> LOCATION: (1291)..(1620)
<220> FEATURE:
<221> NAME/KEY: mat peptide
<222> LOCATION: (1718)..(2038)
<220> FEATURE:
<221> NAME/KEY: CDS
<222> LOCATION: (23)..(736)
<220> FEATURE:
<221> NAME/KEY: CDS
<222> LOCATION: (1128)..(1172)
<220> FEATURE:
<221> NAME/KEY: CDS
<222> LOCATION: (1291)..(1620)
<220> FEATURE:
<221> NAME/KEY: CDS
<222> LOCATION: (1718)..(2038)

<400> SEQUENCE: 146
```

| | | |
|---|---|---|
| ccaagcttgg cttgacctca cc atg gga tgg agc tgt atc atc ctc ttc ttg<br>Met Gly Trp Ser Cys Ile Ile Leu Phe Leu<br>-15               -10 | | 52 |
| gta gca aca gct aca ggt gtc cat tct cag gtc caa ctg gtg cag tct<br>Val Ala Thr Ala Thr Gly Val His Ser Gln Val Gln Leu Val Gln Ser<br>       -5                  -1 1               5 | | 100 |
| ggg gct gag gtc aag aag cct ggg gct tca gtg aag gtg tcc tgc aag<br>Gly Ala Glu Val Lys Lys Pro Gly Ala Ser Val Lys Val Ser Cys Lys<br>        10                  15                  20 | | 148 |
| gct tct ggc tac acc ttc acc agc tac tgg atg cag tgg gta cga cag<br>Ala Ser Gly Tyr Thr Phe Thr Ser Tyr Trp Met Gln Trp Val Arg Gln<br>    25                  30                  35 | | 196 |
| gcc cct gga caa gga ctt gag tgg atg gga gag att gat cct tct gat<br>Ala Pro Gly Gln Gly Leu Glu Trp Met Gly Glu Ile Asp Pro Ser Asp<br>40                  45                  50                  55 | | 244 |
| agc tat act aac tac aat caa aag ttc aag ggc aag gcc aca ttg act<br>Ser Tyr Thr Asn Tyr Asn Gln Lys Phe Lys Gly Lys Ala Thr Leu Thr<br>                60                  65                  70 | | 292 |
| gta gac aca tcc act agc aca gcc tac atg gag ctc agc agc ctg aga<br>Val Asp Thr Ser Thr Ser Thr Ala Tyr Met Glu Leu Ser Ser Leu Arg<br>            75                  80                  85 | | 340 |
| tct gag gac acg gcg gtc tat tac tgt gca aga aat agg gac tat agt<br>Ser Glu Asp Thr Ala Val Tyr Tyr Cys Ala Arg Asn Arg Asp Tyr Ser<br>        90                  95                  100 | | 388 |
| aac aac tgg tac ttc gat gtc tgg ggc caa ggt aca ctg gtc acc gtc<br>Asn Asn Trp Tyr Phe Asp Val Trp Gly Gln Gly Thr Leu Val Thr Val<br>    105                 110                 115 | | 436 |
| tcc tca gcc tcc acc aag ggc cca tcg gtc ttc ccc ctg gca ccc tcc<br>Ser Ser Ala Ser Thr Lys Gly Pro Ser Val Phe Pro Leu Ala Pro Ser<br>120                 125                 130                 135 | | 484 |
| tcc aag agc acc tct ggg ggc aca gcg gcc ctg ggc tgc ctg gtc aag<br>Ser Lys Ser Thr Ser Gly Gly Thr Ala Ala Leu Gly Cys Leu Val Lys<br>                140                 145                 150 | | 532 |
| gac tac ttc ccc gaa ccg gtg acg gtg tcg tgg aac tca ggc gcc ctg<br>Asp Tyr Phe Pro Glu Pro Val Thr Val Ser Trp Asn Ser Gly Ala Leu<br>            155                 160                 165 | | 580 |
| acc agc ggc gtg cac acc ttc ccg gct gtc cta cag tcc tca gga ctc<br>Thr Ser Gly Val His Thr Phe Pro Ala Val Leu Gln Ser Ser Gly Leu<br>        170                 175                 180 | | 628 |

-continued

| | |
|---|---|
| tac tcc ctc agc agc gtg gtg acc gtg ccc tcc agc agc ttg ggc acc<br>Tyr Ser Leu Ser Ser Val Val Thr Val Pro Ser Ser Ser Leu Gly Thr<br>185                             190                        195 | 676 |
| cag acc tac atc tgc aac gtg aat cac aag ccc agc aac acc aag gtg<br>Gln Thr Tyr Ile Cys Asn Val Asn His Lys Pro Ser Asn Thr Lys Val<br>200                         205                       210                    215 | 724 |
| gac aag aga gtt ggtgagaggc cagcacaggg agggaggtg tctgctggaa<br>Asp Lys Arg Val | 776 |
| gccaggctca gcgctcctgc ctggacgcat cccggctatg cagtcccagt ccagggcagc | 836 |
| aaggcaggcc ccgtctgcct cttcacccgg aggcctctgc ccgccccact catgctcagg | 896 |
| gagagggtct tctggctttt tccccaggct ctgggcaggc acaggctagg tgccctaac | 956 |
| ccaggccctg cacacaaagg ggcaggtgct gggctcagac ctgccaagag ccatatccgg | 1016 |
| gaggaccctg ccctgacct aagcccaccc caaaggccaa actctccact ccctcagctc | 1076 |
| ggacaccttc tctcctccca gattccagta actcccaatc ttctctctgc a gag ccc<br>                                                                                               Glu Pro<br>                                                                                                220 | 1133 |
| aaa tct tgt gac aaa act cac aca tgc cca ccg tgc cca ggtaagccag<br>Lys Ser Cys Asp Lys Thr His Thr Cys Pro Pro Cys Pro<br>                  225                       230 | 1182 |
| cccaggcctc gccctccagc tcaaggcggg acaggtgccc tagagtagcc tgcatccagg | 1242 |
| gacaggcccc agccgggtgc tgacacgtcc acctccatct cttcctca gca cct gaa<br>                                                                           Ala Pro Glu<br>                                                                                     235 | 1299 |
| ctc ctg ggg gga ccg tca gtc ttc ctc ttc ccc cca aaa ccc aag gac<br>Leu Leu Gly Gly Pro Ser Val Phe Leu Phe Pro Pro Lys Pro Lys Asp<br>          240                         245                       250 | 1347 |
| acc ctc atg atc tcc cgg acc cct gag gtc aca tgc gtg gtg gtg gac<br>Thr Leu Met Ile Ser Arg Thr Pro Glu Val Thr Cys Val Val Val Asp<br>255                           260                       265 | 1395 |
| gtg agc cac gaa gac cct gag gtc aag ttc aac tgg tac gtg gac ggc<br>Val Ser His Glu Asp Pro Glu Val Lys Phe Asn Trp Tyr Val Asp Gly<br>270                       275                       280                    285 | 1443 |
| gtg gag gtg cat aat gcc aag aca aag ccg cgg gag gag cag tac aac<br>Val Glu Val His Asn Ala Lys Thr Lys Pro Arg Glu Glu Gln Tyr Asn<br>                  290                       295                       300 | 1491 |
| agc acg tac cgt gtg gtc agc gtc ctc acc gtc ctg cac cag gac tgg<br>Ser Thr Tyr Arg Val Val Ser Val Leu Thr Val Leu His Gln Asp Trp<br>                  305                       310                       315 | 1539 |
| ctg aat ggc aag gag tac aag tgc aag gtc tcc aac aaa gcc ctc cca<br>Leu Asn Gly Lys Glu Tyr Lys Cys Lys Val Ser Asn Lys Ala Leu Pro<br>320                         325                       330 | 1587 |
| gcc ccc atc gag aaa acc atc tcc aaa gcc aaa ggtgggaccc gtggggtgcg<br>Ala Pro Ile Glu Lys Thr Ile Ser Lys Ala Lys<br>           335                       340 | 1640 |
| agggccacat ggacagaggc cggctcggcc caccctctgc cctgagagtg accgctgtac | 1700 |
| caacctctgt ccctaca ggg cag ccc cga gaa cca cag gtg tac acc ctg<br>                                  Gly Gln Pro Arg Glu Pro Gln Val Tyr Thr Leu<br>                                             345                       350                       355 | 1750 |
| ccc cca tcc cgg gag gag atg acc aag aac cag gtc agc ctg acc tgc<br>Pro Pro Ser Arg Glu Glu Met Thr Lys Asn Gln Val Ser Leu Thr Cys<br>                  360                       365                       370 | 1798 |
| ctg gtc aaa ggc ttc tat ccc agc gac atc gcc gtg gag tgg gag agc<br>Leu Val Lys Gly Phe Tyr Pro Ser Asp Ile Ala Val Glu Trp Glu Ser<br>                  375                       380                       385 | 1846 |
| aat ggg cag ccg gag aac aac tac aag acc acg cct ccc gtg ctg gac | 1894 |

-continued

```
Asn Gly Gln Pro Glu Asn Asn Tyr Lys Thr Thr Pro Pro Val Leu Asp
        390                 395                 400 tcc gac ggc tcc ttc ttc ctc tat agc aag ctc acc gtg gac aag agc    1942
Ser Asp Gly Ser Phe Phe Leu Tyr Ser Lys Leu Thr Val Asp Lys Ser
    405                 410                 415 agg tgg cag cag ggg aac gtc ttc tca tgc tcc gtg atg cat gag gct    1990
Arg Trp Gln Gln Gly Asn Val Phe Ser Cys Ser Val Met His Glu Ala
420                 425                 430                 435 ctg cac aac cac tac acg cag aag agc ctc tcc ctg tcc ccg ggt aaa    2038
Leu His Asn His Tyr Thr Gln Lys Ser Leu Ser Leu Ser Pro Gly Lys
                440                 445                 450 tgagtgcgac ggccggcaag ccccgctccc gaatt                             2073

<210> SEQ ID NO 147
<211> LENGTH: 470
<212> TYPE: PRT
<213> ORGANISM: Artificial Sequence
<220> FEATURE:
<223> OTHER INFORMATION: Description of Artificial Sequence: Designed
      heavy chain of humanized anti-Fas antibody

<400> SEQUENCE: 147

Met Gly Trp Ser Cys Ile Ile Leu Phe Leu Val Ala Thr Ala Thr Gly
            -15                 -10                  -5

Val His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
        15                  20                  25

Thr Ser Tyr Trp Met Gln Trp Val Arg Gln Ala Pro Gly Gln Gly Leu
 30                  35                  40                  45

Glu Trp Met Gly Glu Ile Asp Pro Ser Asp Ser Tyr Thr Asn Tyr Asn
                 50                  55                  60

Gln Lys Phe Lys Gly Lys Ala Thr Leu Thr Val Asp Thr Ser Thr Ser
             65                  70                  75

Thr Ala Tyr Met Glu Leu Ser Ser Leu Arg Ser Glu Asp Thr Ala Val
         80                  85                  90

Tyr Tyr Cys Ala Arg Asn Arg Asp Tyr Ser Asn Asn Trp Tyr Phe Asp
     95                 100                 105

Val Trp Gly Gln Gly Thr Leu Val Thr Val Ser Ser Ala Ser Thr Lys
110                 115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
            145                 150                 155

Val Thr Val Ser Trp Asn Ser Gly Ala Leu Thr Ser Gly Val His Thr
        160                 165                 170

Phe Pro Ala Val Leu Gln Ser Ser Gly Leu Tyr Ser Leu Ser Ser Val
    175                 180                 185

Val Thr Val Pro Ser Ser Ser Leu Gly Thr Gln Thr Tyr Ile Cys Asn
190                 195                 200                 205

Val Asn His Lys Pro Ser Asn Thr Lys Val Asp Lys Arg Val Glu Pro
                210                 215                 220

Lys Ser Cys Asp Lys Thr His Thr Cys Pro Pro Cys Pro Ala Pro Glu
            225                 230                 235

Leu Leu Gly Gly Pro Ser Val Phe Leu Phe Pro Pro Lys Pro Lys Asp
        240                 245                 250
```

```
Thr Leu Met Ile Ser Arg Thr Pro Glu Val Thr Cys Val Val Asp
    255                 260                 265
Val Ser His Glu Asp Pro Glu Val Lys Phe Asn Trp Tyr Val Asp Gly
270                 275                 280                 285
Val Glu Val His Asn Ala Lys Thr Lys Pro Arg Glu Glu Gln Tyr Asn
                290                 295                 300
Ser Thr Tyr Arg Val Val Ser Val Leu Thr Val Leu His Gln Asp Trp
            305                 310                 315
Leu Asn Gly Lys Glu Tyr Lys Cys Lys Val Ser Asn Lys Ala Leu Pro
        320                 325                 330
Ala Pro Ile Glu Lys Thr Ile Ser Lys Ala Lys Gly Gln Pro Arg Glu
    335                 340                 345
Pro Gln Val Tyr Thr Leu Pro Pro Ser Arg Glu Glu Met Thr Lys Asn
350                 355                 360                 365
Gln Val Ser Leu Thr Cys Leu Val Lys Gly Phe Tyr Pro Ser Asp Ile
                370                 375                 380
Ala Val Glu Trp Glu Ser Asn Gly Gln Pro Glu Asn Asn Tyr Lys Thr
            385                 390                 395
Thr Pro Pro Val Leu Asp Ser Asp Gly Ser Phe Leu Tyr Ser Lys
        400                 405                 410
Leu Thr Val Asp Lys Ser Arg Trp Gln Gln Gly Asn Val Phe Ser Cys
    415                 420                 425
Ser Val Met His Glu Ala Leu His Asn His Tyr Thr Gln Lys Ser Leu
430                 435                 440                 445
Ser Leu Ser Pro Gly Lys
                450

<210> SEQ ID NO 148
<211> LENGTH: 38
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of a humanized anti-Fas antibody

<400> SEQUENCE: 148
ccaagcttgg cttgacctca ccatgggatg gagctgta                              38

<210> SEQ ID NO 149
<211> LENGTH: 40
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of a humanized anti-Fas antibody

<400> SEQUENCE: 149
agtgggtaaa acaggcccct ggacagggac ttgagtggat                            40

<210> SEQ ID NO 150
<211> LENGTH: 40
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of a humanized anti-Fas antibody

<400> SEQUENCE: 150
```
atccactcaa gtccctgtcc aggggcctgt tttacccact        40

<210> SEQ ID NO 151
<211> LENGTH: 64
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of a humanized anti-Fas antibody

<400> SEQUENCE: 151
aagaccgatg ggcccttggt ggaggctgag gagacggtga ccagtgtacc ttggcccag        60 acat        64

<210> SEQ ID NO 152
<211> LENGTH: 39
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of a humanized anti-Fas antibody

<400> SEQUENCE: 152
gttcaagggc aaggccacaa taactgtaga cacatccgc        39

<210> SEQ ID NO 153
<211> LENGTH: 39
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of a humanized anti-Fas antibody

<400> SEQUENCE: 153
gcggatgtgt ctacagttat tgtggccttg cccttgaac        39

<210> SEQ ID NO 154
<211> LENGTH: 40
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of a humanized anti-Fas antibody

<400> SEQUENCE: 154
agtgggtacg acaggcccct ggacaaggac ttgagtggat        40

<210> SEQ ID NO 155
<211> LENGTH: 40
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of a humanized anti-Fas antibody

<400> SEQUENCE: 155
atccactcaa gtccttgtcc aggggcctgt cgtacccact        40

<210> SEQ ID NO 156
<211> LENGTH: 2077
<212> TYPE: DNA
<213> ORGANISM: Artificial Sequence

```
<220> FEATURE:
<221> NAME/KEY: sig peptide
<222> LOCATION: (27)..(83)
<220> FEATURE:
<221> NAME/KEY: intron
<222> LOCATION: (741)..(1131)
<220> FEATURE:
<221> NAME/KEY: intron
<222> LOCATION: (1177)..(1294)
<220> FEATURE:
<221> NAME/KEY: intron
<222> LOCATION: (1625)..(1725)
<220> FEATURE:
<221> NAME/KEY: exon
<222> LOCATION: (27)..(740)
<220> FEATURE:
<221> NAME/KEY: exon
<222> LOCATION: (1132)..(1176)
<220> FEATURE:
<221> NAME/KEY: exon
<222> LOCATION: (1295)..(1624)
<220> FEATURE:
<221> NAME/KEY: exon
<222> LOCATION: (1722)..(2042)
<220> FEATURE:
<221> NAME/KEY: mat peptide
<222> LOCATION: (84)..(740)
<220> FEATURE:
<221> NAME/KEY: mat peptide
<222> LOCATION: (1132)..(1176)
<220> FEATURE:
<221> NAME/KEY: mat peptide
<222> LOCATION: (1295)..(1624)
<220> FEATURE:
<221> NAME/KEY: mat peptide
<222> LOCATION: (1722)..(2042)
<220> FEATURE:
<221> NAME/KEY: CDS
<222> LOCATION: (27)..(740)
<220> FEATURE:
<221> NAME/KEY: CDS
<222> LOCATION: (1132)..(1176)
<220> FEATURE:
<221> NAME/KEY: CDS
<222> LOCATION: (1295)..(1624)
<220> FEATURE:
<221> NAME/KEY: CDS
<222> LOCATION: (1722)..(2042)
<220> FEATURE:
<223> OTHER INFORMATION: Description of Artificial Sequence: Designed
      DNA encoding the heavy chain of humanized anti-Fas
      antibody

<400> SEQUENCE: 156
gggcgaaagc ttggcttgac ctcacc atg gga tgg agc tgt atc atc ctc ttc        53
                             Met Gly Trp Ser Cys Ile Ile Leu Phe
                                                     -15 ttg gta gca aca gct aca ggt gtc cac tct cag gtc caa ctg gtg cag        101
Leu Val Ala Thr Ala Thr Gly Val His Ser Gln Val Gln Leu Val Gln
-10                  -5                  -1   1               5 tct ggg gct gag gtc aag aag cct ggg gct tca gtg aag gtg tcc tgc        149
Ser Gly Ala Glu Val Lys Lys Pro Gly Ala Ser Val Lys Val Ser Cys
             10                  15                  20 aag gct tct ggc tac acc ttc acc agc tac tgg atg cag tgg gta cga        197
Lys Ala Ser Gly Tyr Thr Phe Thr Ser Tyr Trp Met Gln Trp Val Arg
         25                  30                  35 cag gcc cct gga cag ggc ctt gag tgg atg gga gag att gat cct tct        245
Gln Ala Pro Gly Gln Gly Leu Glu Trp Met Gly Glu Ile Asp Pro Ser
     40                  45                  50 gat agc tat act aac tac aat caa aag ttc aag ggc cgg gtc aca atc        293
Asp Ser Tyr Thr Asn Tyr Asn Gln Lys Phe Lys Gly Arg Val Thr Ile
55                  60                  65                  70
```

-continued

| | |
|---|---|
| act cga gac aca tcc act agc aca gcc tac atg gag ctc agc agc ctg<br>Thr Arg Asp Thr Ser Thr Ser Thr Ala Tyr Met Glu Leu Ser Ser Leu<br>              75                        80                    85 | 341 |
| aga tct gag gac acg gcg gtc tat tac tgt gca aga aat agg gac tat<br>Arg Ser Glu Asp Thr Ala Val Tyr Tyr Cys Ala Arg Asn Arg Asp Tyr<br>              90                        95                    100 | 389 |
| agt aac aac tgg tac ttc gat gtc tgg ggc gaa ggg acc ctg gtc acc<br>Ser Asn Asn Trp Tyr Phe Asp Val Trp Gly Glu Gly Thr Leu Val Thr<br>            105                       110                    115 | 437 |
| gtc tcc tca gcc tcc acc aag ggc cca tcg gtc ttc ccc ctg gca ccc<br>Val Ser Ser Ala Ser Thr Lys Gly Pro Ser Val Phe Pro Leu Ala Pro<br>120                        125                      130 | 485 |
| tcc tcc aag agc acc tct ggg ggc aca gcg gcc ctg ggc tgc ctg gtc<br>Ser Ser Lys Ser Thr Ser Gly Gly Thr Ala Ala Leu Gly Cys Leu Val<br>135                        140                      145                    150 | 533 |
| aag gac tac ttc ccc gaa ccg gtg acg gtg tcg tgg aac tca ggc gcc<br>Lys Asp Tyr Phe Pro Glu Pro Val Thr Val Ser Trp Asn Ser Gly Ala<br>              155                       160                    165 | 581 |
| ctg acc agc ggc gtg cac acc ttc ccg gct gtc cta cag tcc tca gga<br>Leu Thr Ser Gly Val His Thr Phe Pro Ala Val Leu Gln Ser Ser Gly<br>            170                       175                    180 | 629 |
| ctc tac tcc ctc agc agc gtg gtg acc gtg ccc tcc agc agc ttg ggc<br>Leu Tyr Ser Leu Ser Ser Val Val Thr Val Pro Ser Ser Ser Leu Gly<br>              185                       190                    195 | 677 |
| acc cag acc tac atc tgc aac gtg aat cac aag ccc agc aac acc aag<br>Thr Gln Thr Tyr Ile Cys Asn Val Asn His Lys Pro Ser Asn Thr Lys<br>200                        205                      210 | 725 |
| gtg gac aag aga gtt ggtgagaggc cagcacaggg agggagggtg tctgctggaa<br>Val Asp Lys Arg Val<br>215 | 780 |
| gccaggctca gcgctcctgc ctggacgcat cccggctatg cagtcccagt ccagggcagc | 840 |
| aaggcaggcc ccgtctgcct cttcacccgg aggcctctgc ccgccccact catgctcagg | 900 |
| gagagggtct tctggctttt tccccaggct ctgggcaggc acaggctagg tgcccctaac | 960 |
| ccaggccctg cacacaaagg ggcaggtgct gggctcagac ctgccaagag ccatatccgg | 1020 |
| gaggaccctg cccctgacct aagcccaccc caaaggccaa actctccact ccctcagctc | 1080 |
| ggacaccttc tctcctccca gattccagta actcccaatc ttctctctgc a gag ccc<br>                                                                                                     Glu Pro<br>                                                                                                    220 | 1137 |
| aaa tct tgt gac aaa act cac aca tgc cca ccg tgc cca ggtaagccag<br>Lys Ser Cys Asp Lys Thr His Thr Cys Pro Pro Cys Pro<br>                  225                      230 | 1186 |
| cccaggcctc gccctccagc tcaaggcggg acaggtgccc tagagtagcc tgcatccagg | 1246 |
| gacaggcccc agccgggtgc tgacacgtcc acctccatct cttcctca gca cct gaa<br>                                                                                         Ala Pro Glu<br>                                                                                               235 | 1303 |
| ctc ctg ggg gga ccg tca gtc ttc ctc ttc ccc cca aaa ccc aag gac<br>Leu Leu Gly Gly Pro Ser Val Phe Leu Phe Pro Pro Lys Pro Lys Asp<br>            240                       245                      250 | 1351 |
| acc ctc atg atc tcc cgg acc cct gag gtc aca tgc gtg gtg gtg gac<br>Thr Leu Met Ile Ser Arg Thr Pro Glu Val Thr Cys Val Val Val Asp<br>255                        260                      265 | 1399 |
| gtg agc cac gaa gac cct gag gtc aag ttc aac tgg tac gtg gac ggc<br>Val Ser His Glu Asp Pro Glu Val Lys Phe Asn Trp Tyr Val Asp Gly<br>270                        275                      280                    285 | 1447 |
| gtg gag gtg cat aat gcc aag aca aag ccg cgg gag gag cag tac aac<br>Val Glu Val His Asn Ala Lys Thr Lys Pro Arg Glu Glu Gln Tyr Asn<br>              290                       295                    300 | 1495 |

-continued

```
agc acg tac cgt gtg gtc agc gtc ctc acc gtc ctg cac cag gac tgg     1543
Ser Thr Tyr Arg Val Val Ser Val Leu Thr Val Leu His Gln Asp Trp
            305                 310                 315 ctg aat ggc aag gag tac aag tgc aag gtc tcc aac aaa gcc ctc cca     1591
Leu Asn Gly Lys Glu Tyr Lys Cys Lys Val Ser Asn Lys Ala Leu Pro
        320                 325                 330 gcc ccc atc gag aaa acc atc tcc aaa gcc aaa ggtgggaccc gtggggtgcg   1644
Ala Pro Ile Glu Lys Thr Ile Ser Lys Ala Lys
335                 340 agggccacat ggacagaggc cggctcggcc caccctctgc cctgagagtg accgctgtac   1704
caacctctgt ccctaca ggg cag ccc cga gaa cca cag gtg tac acc ctg      1754
                    Gly Gln Pro Arg Glu Pro Gln Val Tyr Thr Leu
                                345                 350                 355 ccc cca tcc cgg gag gag atg acc aag aac cag gtc agc ctg acc tgc     1802
Pro Pro Ser Arg Glu Glu Met Thr Lys Asn Gln Val Ser Leu Thr Cys
                360                 365                 370 ctg gtc aaa ggc ttc tat ccc agc gac atc gcc gtg gag tgg gag agc     1850
Leu Val Lys Gly Phe Tyr Pro Ser Asp Ile Ala Val Glu Trp Glu Ser
            375                 380                 385 aat ggg cag ccg gag aac aac tac aag acc acg cct ccc gtg ctg gac     1898
Asn Gly Gln Pro Glu Asn Asn Tyr Lys Thr Thr Pro Pro Val Leu Asp
        390                 395                 400 tcc gac ggc tcc ttc ttc ctc tat agc aag ctc acc gtg gac aag agc     1946
Ser Asp Gly Ser Phe Phe Leu Tyr Ser Lys Leu Thr Val Asp Lys Ser
    405                 410                 415 agg tgg cag cag ggg aac gtc ttc tca tgc tcc gtg atg cat gag gct     1994
Arg Trp Gln Gln Gly Asn Val Phe Ser Cys Ser Val Met His Glu Ala
420                 425                 430                 435 ctg cac aac cac tac acg cag aag agc ctc tcc ctg tcc ccg ggt aaa     2042
Leu His Asn His Tyr Thr Gln Lys Ser Leu Ser Leu Ser Pro Gly Lys
                440                 445                 450 tgagtgcgac ggccggcaag ccccgctccc gaatt                              2077
```

<210> SEQ ID NO 157
<211> LENGTH: 470
<212> TYPE: PRT
<213> ORGANISM: Artificial Sequence
<220> FEATURE:
<223> OTHER INFORMATION: Description of Artificial Sequence: Designed
      heavy chain of humanized anti-Fas antibody

<400> SEQUENCE: 157

```
Met Gly Trp Ser Cys Ile Ile Leu Phe Leu Val Ala Thr Ala Thr Gly
                -15                 -10                  -5

Val His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
     15                  20                  25

Thr Ser Tyr Trp Met Gln Trp Val Arg Gln Ala Pro Gly Gln Gly Leu
 30                  35                  40                  45

Glu Trp Met Gly Glu Ile Asp Pro Ser Asp Ser Tyr Thr Asn Tyr Asn
                 50                  55                  60

Gln Lys Phe Lys Gly Arg Val Thr Ile Thr Arg Asp Thr Ser Thr Ser
             65                  70                  75

Thr Ala Tyr Met Glu Leu Ser Ser Leu Arg Ser Glu Asp Thr Ala Val
         80                  85                  90

Tyr Tyr Cys Ala Arg Asn Arg Asp Tyr Ser Asn Asn Trp Tyr Phe Asp
     95                 100                 105
```

Val Trp Gly Glu Gly Thr Leu Val Thr Val Ser Ser Ala Ser Thr Lys
110                 115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
            145                 150                 155

Val Thr Val Ser Trp Asn Ser Gly Ala Leu Thr Ser Gly Val His Thr
            160                 165                 170

Phe Pro Ala Val Leu Gln Ser Ser Gly Leu Tyr Ser Leu Ser Ser Val
            175                 180                 185

Val Thr Val Pro Ser Ser Ser Leu Gly Thr Gln Thr Tyr Ile Cys Asn
190                 195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
            225                 230                 235

Leu Leu Gly Gly Pro Ser Val Phe Leu Phe Pro Pro Lys Pro Lys Asp
            240                 245                 250

Thr Leu Met Ile Ser Arg Thr Pro Glu Val Thr Cys Val Val Val Asp
            255                 260                 265

Val Ser His Glu Asp Pro Glu Val Lys Phe Asn Trp Tyr Val Asp Gly
270                 275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu Pro
            320                 325                 330

Ala Pro Ile Glu Lys Thr Ile Ser Lys Ala Lys Gly Gln Pro Arg Glu
            335                 340                 345

Pro Gln Val Tyr Thr Leu Pro Pro Ser Arg Glu Glu Met Thr Lys Asn
350                 355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
            385                 390                 395

Thr Pro Pro Val Leu Asp Ser Asp Gly Ser Phe Phe Leu Tyr Ser Lys
            400                 405                 410

Leu Thr Val Asp Lys Ser Arg Trp Gln Gln Gly Asn Val Phe Ser Cys
            415                 420                 425

Ser Val Met His Glu Ala Leu His Asn His Tyr Thr Gln Lys Ser Leu
430                 435                 440                 445

Ser Leu Ser Pro Gly Lys
            450

<210> SEQ ID NO 158
<211> LENGTH: 29
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of humanized anti-Fas antibody

<400> SEQUENCE: 158

```
gatgcagtgg gtacgacagg cccctggac                                              29
```

<210> SEQ ID NO 159
<211> LENGTH: 29
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of humanized anti-Fas antibody

<400> SEQUENCE: 159

```
gtccaggggc ctgtcgtacc cactgcatc                                              29
```

<210> SEQ ID NO 160
<211> LENGTH: 33
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of humanized anti-Fas antibody

<400> SEQUENCE: 160

```
caagggccgg gtcacaatca ctcgagacac atc                                         33
```

<210> SEQ ID NO 161
<211> LENGTH: 33
<212> TYPE: DNA
<213> ORGANISM: Artificial Sequence
<220> FEATURE:
<223> OTHER INFORMATION: Description of Artificial Sequence: PCR primer
      to amplify a fragment of DNA encoding the heavy chain
      of humanized anti-Fas antibody

<400> SEQUENCE: 161

```
gatgtgtctc gagtgattgt gacccggccc ttg                                         33
```

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of
      humanized anti-Fas antibody

<400> SEQUENCE: 162

```
ctacaatcaa aagttcaagg                                                        20
```

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of
      humanized anti-Fas antibody

<400> SEQUENCE: 163

```
gactatagta acaactggta c                                                      21
```

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Sequencing -continued

```
      primer for a DNA encoding the heavy chain of
      humanized anti-Fas antibody

<400> SEQUENCE: 164
gtaccagttg ttactatagt c                                              21

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Sequencing
      primer for a DNA encoding the heavy chain of
      humanized anti-Fas antibody

<400> SEQUENCE: 165
gcagcccagg gccgctgtgc                                                20
```